(12) United States Patent
Yoshida et al.

(10) Patent No.: US 8,188,271 B2
(45) Date of Patent: May 29, 2012

(54) POLYCYCLIC CARBAMOYLPYRIDONE DERIVATIVE HAVING HIV INTEGRASE INHIBITORY ACTIVITY

(75) Inventors: Hiroshi Yoshida, Osaka (JP); Takashi Kawasuji, Osaka (JP); Teruhiko Taishi, Koka (JP); Yoshiyuki Taoda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 916 days.

(21) Appl. No.: 12/084,128

(22) PCT Filed: Oct. 26, 2006

(86) PCT No.: PCT/JP2006/321335
§ 371 (c)(1),
(2), (4) Date: Jun. 16, 2008

(87) PCT Pub. No.: WO2007/049675
PCT Pub. Date: May 3, 2007

(65) Prior Publication Data
US 2009/0143356 A1     Jun. 4, 2009

(30) Foreign Application Priority Data

Oct. 27, 2005  (JP) .................................. 2005-312076
Aug. 21, 2006  (JP) .................................. 2006-223875

(51) Int. Cl.
C07D 487/04    (2006.01)
C07D 471/04    (2006.01)
A61K 31/53     (2006.01)
A61P 31/18     (2006.01)

(52) U.S. Cl. ........................................ 544/183; 514/243
(58) Field of Classification Search .................. 544/183; 514/243
See application file for complete search history.

(56) References Cited

FOREIGN PATENT DOCUMENTS

| | | |
|---|---|---|
| EP | 1 422 218 A1 | 5/2004 |
| EP | 1 541 558 A1 | 6/2005 |
| EP | 1 544 199 A1 | 6/2005 |
| EP | 1 852 434 A1 | 11/2007 |
| JP | 02-096506 | 4/1990 |
| JP | 02-108668 | 4/1990 |
| JP | 02-108683 | 4/1990 |
| JP | 2004-244320 | 9/2004 |
| WO | 02/30931 A2 | 4/2002 |
| WO | 03/035076 A1 | 5/2003 |
| WO | 2004/004657 A2 | 1/2004 |
| WO | 2004/058756 A1 | 7/2004 |
| WO | 2005/087766 A1 | 9/2005 |
| WO | 2006/066414 A1 | 6/2006 |
| WO | 2006/116764 A1 | 11/2006 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48:3-26, 2001.*

* cited by examiner

*Primary Examiner* — Venkataraman Balasubramanian
(74) *Attorney, Agent, or Firm* — Wenderoth, Lind & Ponack, L.L.P.

(57) ABSTRACT

Is to provide a novel compound having an anti-viral activity, particularly a HIV integrase inhibitory activity, and a pharmaceutical composition, particularly an anti-HIV agent.

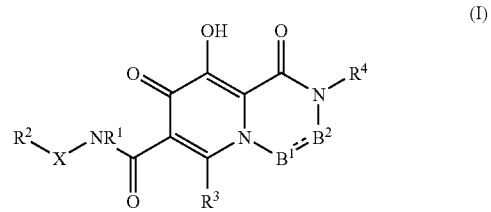

(I)

(wherein
  $R^1$ is hydrogen or lower alkyl;
  X is lower alkylene etc.;
  $R^2$ is optionally substituted aryl;
  $R^3$ is hydrogen, halogen, hydroxy, optionally substituted lower alkyl etc.;
  $R^4$ is hydrogen, optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocyclic lower alkyl etc.;
  A broken line indicates the presence or absence of a bond;
  $B^1$ and $B^2$ are such that any one of them is $CR^{20}R^{21}$, and the other is $NR^{22}$ and, in this case, there is no broken line.
When $B^2$ is $NR^{22}$, $R^4$ and $R^{22}$ may be connected together to form an optionally substituted heterocycle;
When $B^2$ is $CHR^{21}$, $R^4$ and $R^{21}$ may be connected together to form an optionally substituted heterocycle.
Alternatively, $B^1$ and $B^2$ are independently C, $CR^{23}$ or N and, in this case, $B^1$ and $B^2$ may be taken together to form a heterocycle.
$R^{20}$, $R^{21}$, $R^{22}$ and $R^{23}$ are independently hydrogen, optionally substituted lower alkyl, optionally substituted cycloalkyl, optionally substituted cycloalkyl lower alkyl etc.)

14 Claims, No Drawings

POLYCYCLIC CARBAMOYLPYRIDONE DERIVATIVE HAVING HIV INTEGRASE INHIBITORY ACTIVITY

TECHNICAL FIELD

The present invention relates to novel compounds possessing an antiviral activity, more particularly, polycyclic carbamoylpyridone derivatives having a HIV integrase inhibitory activity and a pharmaceutical composition, particularly an anti-HIV agent containing the same.

BACKGROUND TECHNIQUE

Among viruses, human immunodeficiency virus (hereafter, referred to as HIV), a kind of retrovirus, is known to cause acquired immunodeficiency syndrome (hereafter, referred to as AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, currently, a combination therapy is reported to be efficient in treatment for AIDS because of the frequent emergence of the resistant mutant. Two kinds of reverse transcriptase inhibitors and protease inhibitors are clinically used as an anti-HIV agent; however agents having the same mechanism of action often exhibit cross-resistance or only an additional activity. Therefore, development of anti-HIV agents having the other mechanism of action is desired.

Under the circumstances above, an integrase inhibitor has been focused on as an anti-HIV agent having a novel mechanism of action (Ref: Patent Documents 1 and 2). As an anti-HIV agent having such a mechanism of action, known are carbamoyl-substituted hydroxypyrimidinone derivative (Ref: Patent Documents 3 and 4) and carbamoyl-substituted hydroxypyrrolidione derivative (Ref: Patent Document 5). Further, a patent application concerning carbamoyl-substituted hydroxypyridone derivative has been filed (Ref: Patent Document 6, Example 8).

Other known carbamoylpyridone derivatives include 5-alkoxypyridine-3-carboxamide derivatives and γ-pyrone-3-carboxamide derivatives, which are a plant growth inhibitor or herbicide (Ref: Patent Documents 7-9).

Other HIV integrase inhibitors include N-containing condensed cyclic compounds (Ref: Patent Document 10).

In addition, the present applicant filed a dicyclic carbamoylpyridone derivative as a HIV integrase inhibiting agent (Ref: Patent Document 11).

[Patent Document 1] WO03/016275
[Patent Document 2] WO2004/024693
[Patent Document 3] WO03/035076
[Patent Document 4] WO03/035076
[Patent Document 5] WO2004/004657
[Patent Document 6] JP Patent Application 2003-32772
[Patent Document 7] JP Patent Publication 1990-108668
[Patent Document 8] JP Patent Publication 1990-108683
[Patent Document 9] JP Patent Publication 1990-96506
[Patent Document 10] WO2005/016927
[Patent Document 11] WO2006/088173

DISCLOSURE OF INVENTION

Problem to be Solved by the Invention

Under such the circumstances, the development of a novel integrase inhibitor has been desired.

Means to Solve the Problems

The present inventors intensively studied to find that a novel polycyclic carbamoylpyridone derivative possesses a potent HIV integrase inhibitory activity. Moreover, the present inventors have discovered that a compound of the present compound and a pharmaceutical composition containing the same are useful as an antiviral agent (e.g. antiretroviral agent, anti-HIV agent, anti-HTLV-1 (Human T cell leukemia virus type 1) agent, anti-FIV (Feline immunodeficiency virus) agent, anti-SIV (Simian immunodeficiency virus) agent), especially an anti-HIV agent, an anti-AIDS agent, or a therapeutic for associated diseases, to accomplish the present invention shown below.

(1) A compound of the formula:

[Chemical formula 1]

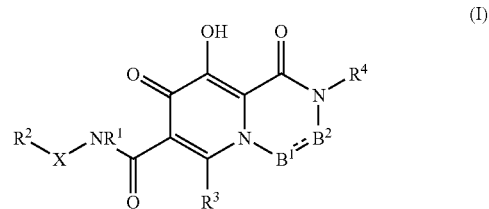

(wherein,
R1 is hydrogen or lower alkyl;
X is a single bond, a heteroatom group selected from O, S, SO, $SO_2$ and NH, or lower alkylene or lower alkenylene each may be intervened by the heteroatom group;
$R^2$ is optionally substituted aryl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino,
$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^a$ ($R^a$ is hydrogen or lower alkyl), —N= and =N—));
the broken line represents the presence or absence of a bond;
one of $B^1$ and $B^2$ is $CR^{20}R^{21}$ and another is $NR^{22}$, where the broken line represents the absence of a bond;
When $B^2$ is $NR^{22}$, $R^4$ and $R^{22}$ taken together may form optionally substituted heterocycle;
When $B^2$ is $CHR^{21}$, $R^4$ and $R^{21}$ taken together may form optionally substituted heterocycle; or $B^1$ and $B^2$ are each independently C, $CR^{23}$ or N, where $B^1$ and $B^2$ taken together may form optionally substituted heterocycle;

$R^{20}$, $R^{21}$, $R^{22}$ and $R^{23}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^5$ ($R^5$ is independently selected from the same substitution group as $R^4$), —N= and =N—), hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), a pharmaceutically acceptable salt, or a solvate thereof.

(2) A compound of the formula:

[Chemical formula 2]

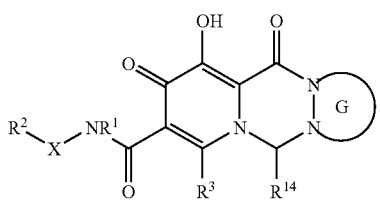

(I-10)

(wherein,

G ring is optionally substituted heterocycle $R^1$ is hydrogen or lower alkyl;

X is a single bond, a heteroatom group selected from O, S, SO, $SO_2$ and NH, or lower alkylene or lower alkenylene each may be intervened by the heteroatom group;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino, $R^{14}$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^5$ ($R^5$ is independently selected from the same substitution group as $R^4$), —N= and =N—), hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), according to (1), or a pharmaceutically acceptable salt, or a solvate thereof.

(3) A compound of the formula:

[Chemical formula 3]

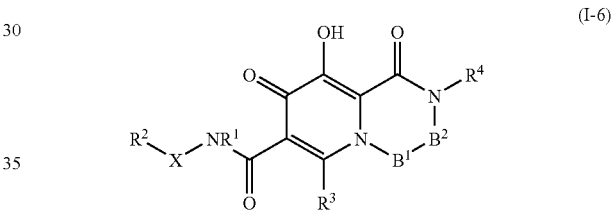

(I-6)

(wherein, $R^1$ is hydrogen or lower alkyl;

X is a single bond, a heteroatom group selected from O, S, SO, $SO_2$ and NH, or lower alkylene or lower alkenylene each may be intervened by the heteroatom group;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, SO$_2$, NR$^a$ (R$^a$ is selected hydrogen or lower alkyl), —N= and =N—));
one of B$^1$ and B$^2$ is CR$^{20}$R$^{21}$ and another is NR$^{22}$;
R$^{20}$, R$^{21}$ and R$^{22}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), according to (1), or a pharmaceutically acceptable salt, or a solvate thereof.

(4) A compound according to (3), pharmaceutically acceptable salt, or solvate thereof, wherein B$^1$ is CR$^{20}$R$^{21}$ and B$^2$ is NR$^{22}$ (R$^{20}$, R$^{21}$ and R$^{22}$ are the same as defined in (3)).

(5) A compound according to (3), pharmaceutically acceptable salt, or solvate thereof, wherein B$^1$ is NR$^{22}$ and B$^2$ is CR$^{20}$R$^{21}$ (R$^{20}$, R$^{21}$ and R$^{22}$ are the same as defined in (3)).

(6) A compound according to (3), pharmaceutically acceptable salt, or solvate thereof, wherein B$^1$ is NR$^{22}$ (R$^{22}$ is the same as defined in (3)) and B$^2$ is CH$_2$.

(7) A compound according to (3), pharmaceutically acceptable salt, or solvate thereof, wherein B$^1$ is NR$^{22}$ (R$^{22}$ is hydrogen, optionally substituted lower alkyl, lower alkenyl, optionally substituted cycloalkyl, optionally substituted cycloalkyl lower alkyl, optionally substituted aryl, optionally substituted aryl lower alkyl, optionally substituted heterocyclic group, optionally substituted heterocycle lower alkyl, optionally substituted lower alkylcarbonyl, optionally substituted aryl carbonyl, substituted thiourea or substituted sulfonyl), and B$^2$ is CH$_2$.

(8) A compound according to (3), pharmaceutically acceptable salt, or solvate thereof, wherein R$^4$ is optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocycle lower alkyl (9) A compound according to (3), pharmaceutically acceptable salt, or solvate thereof, wherein B$^1$ is NR$^{22}$ (R$^{22}$ is hydrogen, optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocycle lower alkyl, optionally substituted lower alkylcarbonyl, optionally substituted aryl carbonyl, substituted thiourea or substituted sulfonyl), B$^2$ is CH$_2$ and R$^4$ is optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocycle lower alkyl.

(10) A compound according to (3), pharmaceutically acceptable salt, or solvate thereof, wherein B$^1$ is NR$^{22}$ (R$^{22}$ is hydrogen, optionally substituted lower alkyl (substituent: amino, lower alkylamino, lower alkoxy, aryloxy, cyano, halogen, optionally substituted carbamoyl, acylamino lower alkynyl, hydroxy), cycloalkyl, cycloalkyl lower alkyl, optionally substituted phenyl, optionally substituted benzyl, optionally substituted 5- to 6-membered aromatic heterocyclic group, optionally substituted 5- to 6-membered heterocycle lower alkyl, optionally substituted lower alkylcarbonyl (substituent: lower alkoxy), optionally substituted benzoyl (substituent: lower alkoxy), substituted sulfonyl (substituent: lower alkyl, aryl, heterocyclic group)), B$^2$ is CH$_2$ and R$^4$ is optionally substituted lower alkyl (substituent: amino, lower alkylamino, lower alkoxy, aryloxy), cycloalkyl, cycloalkyl lower alkyl, phenyl, benzyl,
5- to 6-membered aromatic heterocyclic group, 5- to 6-membered heterocycle lower alkyl).

(11) A compound of the formula:

[Chemical formula 4]

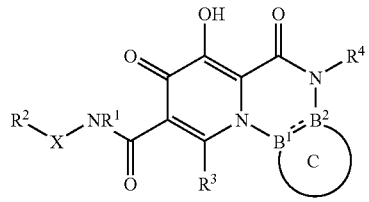

(wherein,
R$^1$ is hydrogen or lower alkyl;
X is a single bond, a heteroatom group selected from O, S, SO, SO$_2$ and NH, or lower alkylene or lower alkenylene each may be intervened by the heteroatom group;
R$^2$ is optionally substituted aryl;
R$^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino,
C ring is optionally substituted heterocycle or optionally substituted carbocycle;
B$^1$ and B$^2$ are independently C, CR$^{23}$ or N;
R$^{23}$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl),
the broken line represents the presence or absence of a bond;

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from CO, O, S, SO, $SO_2$, $NR^a$ ($R^a$ is selected hydrogen or lower alkyl), —N= and =N—));
according to (1), or a pharmaceutically acceptable salt, or solvate thereof.

(12) A compound of the formula:

[Chemical formula 5]

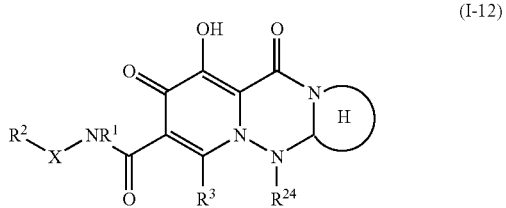

(I-12)

(wherein, $R^1$ is hydrogen or lower alkyl;

X is a single bond, a heteroatom group selected from O, S, SO, $SO_2$ and NH, or lower alkylene or lower alkenylene each may be intervened by the heteroatom group;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino, H ring is optionally substituted heterocycle;

$R^{24}$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), according to (1), or a pharmaceutically acceptable salt, or solvate thereof.

(13) A compound according to any one of (1) to (12), pharmaceutically acceptable salt, or solvate thereof, wherein $R^1$ is hydrogen or lower alkyl.

(14) A compound according to any one of (1) to (12), pharmaceutically acceptable salt, or solvate thereof, wherein X is lower alkylene; $R^2$ is phenyl or phenyl substituted with at least halogen.

(15) A compound according to any one of (1) to (12), pharmaceutically acceptable salt, or solvate thereof, wherein $R^3$ is hydrogen.

(16) A compound according to any one of (1) to (12), pharmaceutically acceptable salt, or solvate thereof, wherein $R^1$ is hydrogen or lower alkyl; X is lower alkylene; $R^2$ is phenyl or phenyl substituted with 1 to 2 halogen; $R^3$ is hydrogen.

(17) A pharmaceutical composition comprising a compound according to any one of (1) to (16), or a pharmaceutically acceptable salt, or solvate thereof.

(18) A pharmaceutical composition according to (17), which is an anti-HIV agent.

The present invention further provides a method for treating a virus infectious disease comprising administering the aforementioned compound. Further, the present invention provides a process for producing an agent for treating a virus infectious disease comprising the aforementioned compound.

Effect of the Invention

The present invention compounds possess an integrase inhibitory activity and/or a cell-growth inhibitory activity against virus, especially HIV. Accordingly, they are useful for the prevention or treatment of various diseases mediated by integrase or virus infection diseases (e.g., AIDS). A preferable compound is also effective to a resistant strain. In addition, a preferable compound has good pharmacokinetic in a body.

PREFERRED EMBODIMENT OF THE INVENTION

The terms used herein are explained below. Each term, alone or in combination with another term, means as follows.

"Lower alkylene" means a straight or branched C1 to C6 lower alkylene such as methylene, ethylene, trimethylene, propylene, tetramethylene, ethylethylene, pentamethylene, or hexamethylene, preferably C1 to C4 lower straight alkylene such as methylene, ethylene, trimethylene, and tetramethylene, more preferably methylene or ethylene.

"Lower alkenylene" means a straight or branched C2 to C6 lower alkenylene, which consists of the above "Lower alkylene" having one or more double bonds, such as vinylene, propylene, or butenylene, preferably a straight C2 to C3 lower alkenylene such as vinylene or propylene.

"Alkyl" means a straight or branched C1 to C10 alkyl such as methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, and n-decyl. Preferred is C1 to C6 lower alkyl, more preferred is C1 to C4 lower alkyl such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

When lower alkyl is intervened with "—N=" or "=N—", the lower alkyl may have a double bond to form —$CH_2$—N=$CH_2$, —CH=N—$CH_3$, etc.

"Alkenyl" means a straight or branched C2 to C8 alkenyl, which consists of the above "alkyl" having one or more double bonds, such as vinyl, 1-propenyl, 2-propenyl, 1-butenyl, 2-butenyl, 3-butenyl, 1,3-butadienyl, and 3-methyl-2-butenyl, preferably C2 to C6 lower alkenyl, and more preferably C2 to C4 lower alkenyl.

"Lower alkenyloxy" means oxy attached to the above "lower alkenyl", such as vinyloxy, 1-propenyloxy, 2-propenyloxy, 1-butenyloxy, 2-butenyloxy, 3-butenyloxy, 1,3-butadienyloxy, and 3-methyl-2-butenyloxy.

"Cycloalkyl" means C3 to C20, preferably C3 to C15, more preferably C3 to C10 cyclic saturated hydrocarbon, such as cyclopropyl, cyclobutyl, cyclopentyl, cyclohexyl, cyclopentyl, cyclooctyl, adamantyl, and polyhedron (e.g. cubane, dodecahedrane), further preferably C3 to C6 cycloalkyl.

"Cycloalkyl lower alkyl" means lower alkyl substituted with the above cycloalkyl, such as cyclopropylmethyl, cyclopropylethyl, cyclobutylmethyl, cyclopentylmethyl, cyclohexylmethyl, and cyclohexylethyl, and preferably C3 to C6 cycloalkyl lower alkyl.

"Aryl" means monocyclic aromatic hydrocarbon (phenyl) and polycyclic aromatic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.), preferably phenyl or naphthyl (e.g., 1-napthyl, 2-naphthyl).

"Aralkyl" or "aryl lower alkyl" means the above "lower alkyl" substituted with 1 to 3 of the above "aryl", such as benzyl, diphenylmethyl, triphenylmethyl, phenethyl, 1-napthylmethyl, 2-napthylmethyl, preferably benzyl.

"Aryloxy" means oxy attached to the above "aryl", such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, and 9-phenanthryloxy, preferably phenyloxy or naphthyloxy (e.g., 1-napthyloxy, 2-naphthyloxy).

"Heterocyclic group" means "heteroring" or "heteroaryl".

"Heteroring" means a non-aromatic heterocyclic group which has at least one of N, O, P and/or S in the ring and may be bonded at any substitutable position, preferably 5- to 7-membered ring, such as 1-pyrrolyl, 2-pyrrolyl, 3-pyrrolyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, and tetrahydropyranyl. The "non-aromatic heterocyclic group" may be saturated or unsaturated as far as it is non-aromatic.

"Heteroaryl" means monocyclic aromatic heterocyclic group or condensed aromatic heterocyclic group.

Monocyclic aromatic heterocyclic group means a group induced from a 5- to 8-membered aromatic ring optionally containing 1 to 4 of O, S, P and/or N in the ring wherein the group may be bonded at any substitutable position.

Condensed aromatic heterocyclic group means a group wherein a 5- to 8-membered aromatic ring optionally containing 1 to 4 of O, S, P and/or N in the ring is condensed with 1 to 4 of 5- to 8-membered aromatic carbocycle(s) or the other 5- to 8-membered aromatic heteroring(s), and may be bonded at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzoimidazolyl (e.g., 1-benzoimidazolyl, 2-benzoimidazolyl, 4-benzoimidazolyl, 5-benzoimidazolyl), dibenzofuryl, benzooxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenandinyl (e.g., 1-phenandinyl, 2-phenandinyl) or phenothiadinyl (e.g., 1-phenothiadinyl, 2-phenothiadinyl, 3-phenothiadinyl, 4-phenothiadinyl).

"Heterocycle lower alkyl" means lower alkyl substituted with the above "heterocyclic group".

"Heterocycleoxy" means an oxy attached to the above "heterocyclic group".

"Heterocycle" means a heterocycle which can form the heterocyclic group.

"Lower alkoxy" means oxy attached to the above "lower alkyl", such as methoxy, ethoxy, n-propoxy, isopropoxy, n-butoxy, isobutoxy, and tert-butoxy.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclecarbonyl", "heterocycle lower alkylcarbonyl", and "heterocycleoxy carbonyl", each means a carbonyl attached to the above "lower alkyl", "cycloalkyl", "cycloalkyl lower alkyl", "lower alkoxy", "aryl", "aryl lower alkyl", "aryloxy", "heterocyclic group", and "heterocycle lower alkyl", respectively.

When a substituent(s) is/are present on "optionally substituted lower alkyl", "optionally substituted cycloalkyl", "optionally substituted cycloalkyl lower alkyl", "optionally substituted lower alkenyl", "optionally substituted lower alkoxy", "optionally substituted aryl", "optionally substituted aryl lower alkyl", "optionally substituted aryloxy", "optionally substituted aryloxy lower alkyl", "optionally substituted heterocyle", "optionally substituted heterocyclic group", "optionally substituted heterocycle lower alkyl", "optionally substituted heterocycleoxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substituted heterocyclecarbonyl", "optionally substituted heterocycle lower alkylcarbonyl", "optionally substituted heterocycleoxy carbonyl", "optionally substituted lower alkylene", "optionally substituted lower alkenylene", "optionally substituted phosphoric acid residue", "optionally substituted carbocycle" or "optionally substituted heterocycle", each may be substituted with the same or different, 1 to 4 group(s) selected from Substituent group B at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetylamino, benzoylamino), aralkylamino (e.g., benzylamino, trithylamino), hydroxyamino)), azido, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethanesulfonyl), optionally substituted alkylsulfonylamino (e.g., methanesulfonylamino, ethanesulfonylamino, N-methylsulfonyl-N'-methylamino), optionally substituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, lower alkyl which is substituted with a phosphoric acid residue and may be intervened with a heteroatom group(s), aryl substituted with a phosphoric acid residue, aralkyl substituted with a phosphoric acid residue, and hydroxy lower alkyl, more preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), optionally substituted amino (e.g., alkylamino (e.g., methylamino, ethylamino, dimethylamino)), oxo, or phosphoric acid residue.

Examples of a substituent of "optionally substituted amino" or "optionally substituted carbamoyl" include mono- or di-lower alkyl, lower alkylcarbonyl, or lower alkylsulfonyl, optionally substituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxy lower alkyl, heteroring lower alkyl (e.g., morpholinoethyl, tetrahydropyranylethyl), alkoxycarbonyl lower alkyl (e.g., ethoxycarbonylmethyl, ethoxycarbonylethyl), mono- or di-lower alkylamino lower alkyl (e.g., dimethylaminoethyl)), lower alkoxy lower alkyl (e.g., methoxyethyl, ethoxymethyl, ethoxyethyl, isopropoxyethyl), acyl (e.g., formyl, optionally substituted lower alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally substituted with lower alkyl or halogen (e.g., benzenesulfonyl, toluenesulfonyl, 4-fluorobenzenesulfonyl), cycloalkyl (e.g., cyclopropyl), aryl optionally substituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heteroring (e.g., morpholino, tetrahydropyranyl), optionally substituted amino (e.g., mono- or di-alkylamino (e.g., dimethylamino), formylamino), and the like.

As to amino of "optionally substituted amino", "optionally substituted carbamoyl", or "optionally substituted carbamoylcarbonyl", two substituents on the amino together with the neighboring N atom may form an N-containing heteroring which optionally contains S and/or O in the ring (preferably 5- to 7-membered ring or saturated ring) and the ring is optionally substituted with oxo or hydroxy. The S atom forming the ring may be substituted with oxo. A 5- or 6-membered ring such as piperazinyl, piperidino, morpholino, pyrrolidino, thiadinan-2-yl, 2-oxopiperidino, 2-oxopyrrolidino, 1,1-dioxido-1,2-thiadinan-2-yl, and 4-hydroxymorpholino is preferable.

Phosphoric acid residue means a group shown of the formula: $-PO(OH)_2$. Optionally substituted phosphoric acid residue means a phosphoric acid residue wherein the OH part and/or hydrogen of the OH is optionally substituted with a phosphoric acid residue, preferably shown by the formula:

[Chemical formula 6]

(P-1)

(wherein, $R^A$ and $R^B$ each are independently $OR^C$ or $NR^D R^E$ (wherein $R^C$, $R^D$ and $R^E$ each are independently hydrogen, optionally substituted lower alkyl, optionally substituted cycloalkyl, optionally substituted aryl, optionally substituted heterocyclic group, or $R^D$ and $R^E$ taken together with the neighboring N atom may form an optionally substituted heterocycle (preferably 5- to 6-membered ring)) or $R^A$ and $R^B$ taken together with the neighboring P atom may form an optionally substituted heterocycle (preferably 5- to 6-membered ring)).

More preferably, $R^A$ and $R^B$ are both $OR^C$, or one of them is $OR^C$ and the other is $NR^D R^E$.

$R^C$, $R^D$ and $R^E$ each are preferably, independently, lower alkyl (e.g., methyl, ethyl).

The optionally substituted heterocycle formed by $R^A$ and $R^B$ taken together with the neighboring P atom may be the following structure:

[Chemical formula 7]

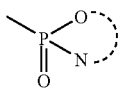

(wherein, the broken line means a part of the ring)

Hydroxy substituted with optionally substituted phosphoric acid residue is preferably hydroxy substituted with a phosphoric acid residue substituted with di lower alkyls, and more preferably a group of the following formula:

[Chemical formula 8]

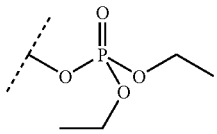

Amino substituted with optionally substituted phosphoric acid residue is preferably amino substituted with a phosphoric acid residue substituted with di lower alkyls, and more preferably a group of the following formula:

[Chemical formula 9]

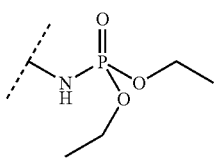

A ring is optionally substituted heterocycle. The heterocycle is preferably a 5- to 7-membered ring containing 1 to 3, preferably 2 to 3 of O, S and/or N atoms, and is more preferably selected from the above heterering. Optionally, 1 or 2 heteroatoms can be present on an arc of A ring, and a position thereof is not limited. One of preferable embodiments of A ring is the following ring which is optionally substituted.

[Chemical formula 10]

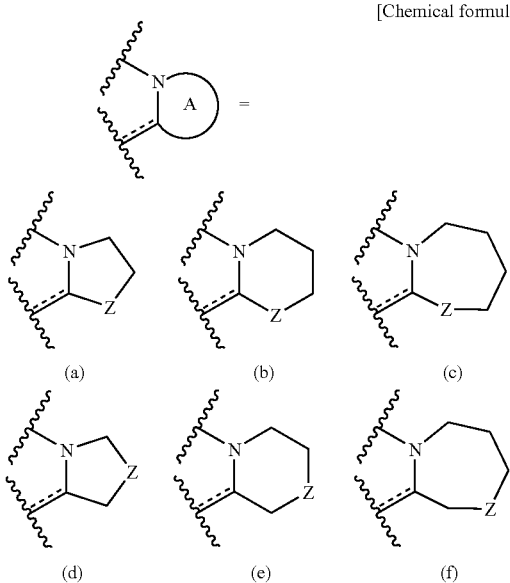

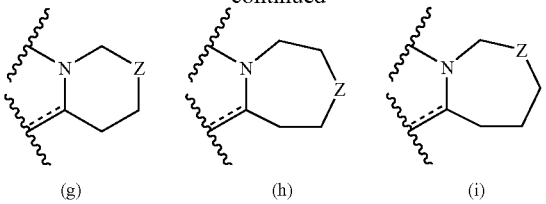

(Z is $Ch_2$, O, S, SO, $SO_2$ or $Nr^{19}$)

One of preferable embodiments of Z is Z=O or $NR^{19}$.

When Z=$NR^{19}$, $R^{19}$ is preferably 1) hydrogen, 2) optionally substituted lower alkyl (example of substituent: amino optionally substituted with mono- or di-lower alkyl, cycloalkyl, hydroxy, optionally substituted heterocyclic group (heterocycle is preferably 5- to 7-membered, e.g. furyl, thienyl, thiazolyl, pyridyl, morpholino, imidazole; example of substituent: lower alkyl, halogen), optionally substituted heterocyclecarbonyl (heterocycle is preferably 5- to 7-membered, e.g. morpholinocarbonyl), optionally substituted phenyl (substituent: lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, mono- or di-lower alkyl substituted carbamoyl, lower alkylsulfonylamino, lower alkoxy, carbonyl, halogen, thiol, lower alkylthio), 3) lower alkenyl, 4) acyl (e.g. lower alkylcarbonyl), 5) lower alkylsulfonyl.

As other substituent on the A ring, same or different one or more substituents selected from Substituent group S2 are exemplified, preferably lower alkyl and the like. Alternatively, a substituent part on A ring may be connected with a neighboring atom to further form a fused ring or a spiro ring, preferably an optionally substituted carbocylcle (preferably 5- to 6-membered ring) or an optionally substituted heterocycle (preferably 5- to 6-membered ring).

Substituent Group S2: hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocyclecarbonyl, optionally substituted heterocyclic lower alkylcarbonyl, optionally substituted heterocycleoxycarbonyl, optionally substituted aminocarbonyl, optionally substituted phosphoric acid residue, aryl substituted with optionally substituted phosphoric acid residue, aralkyl substituted optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^5$ ($R^5$ is selected independently from the same substituent group of $R^4$), —N= and =N—), oxo.

$R^1$ is hydrogen or lower alkyl, preferable hydrogen.

X is a single bond, a heteroatom group (hereinafter, referred to as M in some cases) selected from O, S, SO, $SO_2$ and NH, or lower alkylene or lower alkenylene, each may be intervened by the heteroatom. Herein, "intervene" means the case where the heteroatom 1) is present between carbon atoms constituting alkylene or alkenylene, 2) is bound to a N atom of carbamoyl group adjacent to X, and/or 3) is bound to $R^2$ adjacent to X. The heteroatom group (M) may be same or different one or more groups. For example, the case where lower alkylene is intervened by the heteroatom includes -M-CH$_2$—, —CH$_2$-M-CH$_2$—, —CH$_2$-M-, and —CH$_2$-M-M-CH$_2$—. X is preferably a spacer in which 1 to 3 atoms are connected. X is more preferably lower alkylene, or lower alkenylene which may be intervened by a heteroatom, or O, further preferably C1 to C3 lower alkylene or C2 to C3 lower alkenylene, or O, particularly preferably methylene or O.

$R^2$ is optionally substituted aryl, preferably phenyl. Examples of a substituent on aryl preferably include same or different 1 to 3, preferably 1 to 2 substituents selected from the group consisting of halogen, hydroxy, amino, lower alkylamino, cyano, carboxy, formyl, oxo, lower alkyl, lower alkoxy, lower alkylthio, carbamoyl, and lower alkylcarbamoyl, and Substituent group S1 (optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting O, S, SO, SO$_2$, NR$^5$ (R$^5$ is selected independently from the same substituent group of $R^4$), —N═ and ═N—), lower alkoxy lower alkyl, amino lower alkyl optionally substituted with mono- or di-lower alkyl, halogenated lower alkyl, lower alkoxy, carbamoyl optionally substituted with mono- or di-lower alkyl, optionally substituted lower alkylsulfonylamino, halogenated lower alkoxy, hydroxy lower alkyl). The substituent is a group more preferably selected from halogen, hydroxy, amino, cyano, lower alkyl, and lower alkoxy, and Substituent group S1, particularly preferably selected from halogen (e.g. F) and/or Substituent group S. When one substituent is present on aryl, its position is preferably a 4-position. $R^2$ is more preferably phenyl, or phenyl substituted with at least halogen, particularly preferably 4-halogenophenyl (e.g. 4-F-phenyl) or 2,4-dihalogenophenyl (e.g. 2,4-F-phenyl).

$R^2$ is more preferably phenyl optionally substituted with 1 to 3 $R^5$ described later.

In all compounds of the present invention, a —X—$R^2$ part is preferably represented by the following formula.

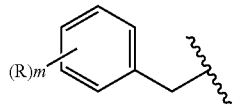

[Chemical formula 11]

R's are each independently a group selected from the group consisting of halogen and Substituent group S1.

Substituent group S1: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, SO$_2$, NR$^a$ (R$^a$ is hydrogen or lower alkyl), —N═ and ═N—), lower alkoxy lower alkyl, optionally substituted amino lower alkyl (substituent: mono- or di-lower alkyl, lower alkylcarbonyl, or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, and hydroxy lower alkyl.

And, m is an integer of 0 to 3, preferably 0, or 1 to 2. When m is 1, R is preferably halogen and, when m is 2, R is preferably two halogens, or halogen and other group.

R is preferably present at a 4-position and, optionally, other position (e.g. 2-position) on a benzene ring.

When m=2, R is more preferably same or different groups selected from the group consisting of halogen, lower alkyl, lower alkoxy, lower alkoxy lower alkyl, halogenated lower alkyl; halogenated lower alkoxy, lower alkylsulfonylamino, carbamoyl, and lower alkylcarbamoyl, particularly preferably two Fs.

$R^3$ may be a variety of substituents as far as they do not adversely affect on the pharmacological activity of Compound (I), and examples include hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino. Examples of a substituent of "optionally substituted" include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, and halogenated lower alkoxy, more preferably halogen, hydroxy, amino, lower alkylamino, lower alkyl, and lower alkoxy. $R^3$ is more preferably hydrogen, halogen, hydroxy, lower alkyl, lower alkenyl, lower alkoxy, lower alkenyloxy or optionally substituted amino, further preferably hydrogen or lower alkyl (e.g. methyl), particularly preferably hydrogen.

The present invention provides the following compounds (in each of the following formulas, each symbol is as defined above unless otherwise is indicated).

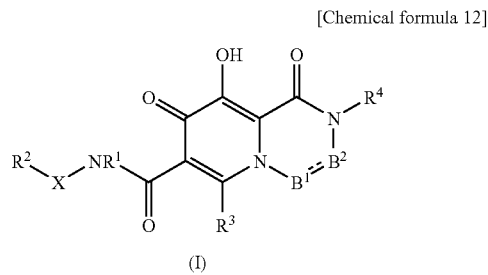

[Chemical formula 12]

(I)

$R^1$ is hydrogen or lower alkyl, preferably hydrogen.

X is a single bond, a heteroatom group selected from O, S, SO, SO$_2$ and NH, or lower alkylene or lower alkenylene which may be intervened by the heteroatom group; preferably a single bond, O, S, or lower alkylene (more preferably C1 to C3) which may be intervened by O or S.

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy group, or optionally substituted amino, more preferably hydrogen or optionally substituted lower alkyl.

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclic lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from the group consisting of O, S, SO, $SO_2$, $NR^a$ ($R^a$ is hydrogen or lower alkyl), —N= and =N—), more preferably hydrogen, optionally substituted lower alkyl, optionally substituted cycloalkyl, optionally substituted cycloalkyl lower alkyl, optionally substituted lower alkenyl, optionally substituted aryl, optionally substituted aryl lower alkyl, optionally substituted heterocyclic group, or optionally substituted heterocyclic lower alkyl.

A broken line indicates the presence or absence of a bond.

$B^1$ and $B^2$ are such that any one of them is $CR^{20}R^{21}$, and the other is $NR^{22}$ and, in this case, a broken line is not present.

When $B^2$ is $NR^{22}$, $R^4$ and $R^{22}$ may be connected together to form an optionally substituted heterocycle (e.g. G ring);

When $B^2$ is $CHR^{21}$, $R^4$ and $R^{21}$ may be connected together to form an optionally substituted heterocycle (e.g. H ring).

Alternatively, $B^1$ and $B^2$ are independently C, $CR^{23}$, or N. $B^1$ and $B^2$ parts may be connected together to form an optionally substituted heterocycle (e.g. C ring) and, in this case, when $B^1$ and $B^2$ are independently $CR^{23}$ or N, a broken line indicates the absence of a bond.

$R^{20}$, $R^{21}$, $R^{22}$ and $R^{23}$ are independently selected from hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclic lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from the group consisting of O, S, SO, $SO_2$, $NR^5$ ($R^5$ is selected independently from the same substituent group of $R^4$), —N= and =N—), hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryl oxycabronyl, optionally substituted heterocyclecarbonyl, optionally substituted heterocyclic lower alkylcarbonyl, optionally substituted heterocycleoxycarbonyl, optionally substituted aminocarbonyl, substituted thiourea, and substituted sulfonyl.

$R^2$, $R^{21}$, $R^{22}$ and $R^{22}$ are more preferably selected from hydrogen, optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocyclic lower alkyl, optionally substituted lower alkylcarbonyl, optionally substituted cycloalkylcarbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclecarbonyl, optionally substituted heterocyclic lower alkylcarobnyl, optionally substituted heterocycleoxycarbonyl, optionally substituted aminocarbonyl, substituted thiourea, and substituted sulfonyl.

The Compound (I) includes Compounds (I-10), (I-6), (I-9) and (I-12) shown below.

[Chemical formula 13]

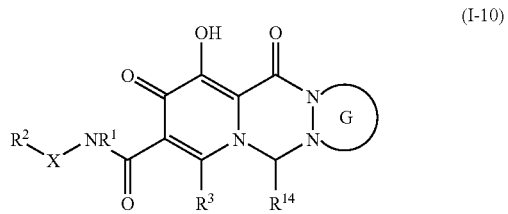

(I-10)

G ring is a 5- to 7-membered ring containing 2 to 3 of O, S and/or N atoms, and contains at least 2 N atoms. More preferably, the ring is selected from the aforementioned heterorings, and the following rings are exemplified.

[Chemical formula 14]

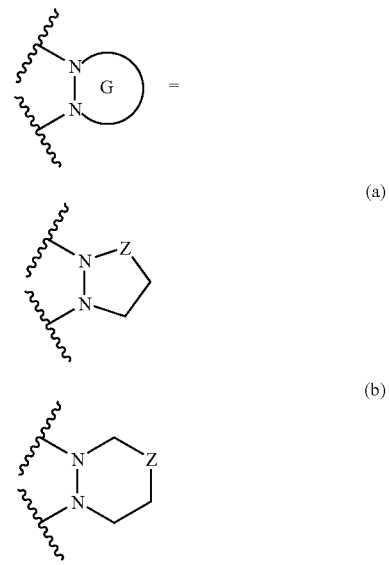

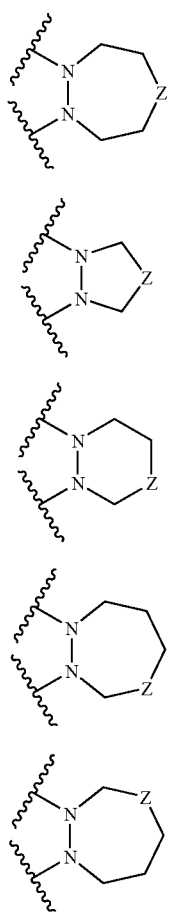

(c)

(d)

(e)

(f)

(g)

(Z is Ch$_2$, O, S, SO, SO$_2$, or Nr$^{19}$ Described Later)

As a substituent on the G ring, same or different one or more substituents selected from the Substituent group S2 are exemplified. Alternatively, a substituent part on the G ring may be connected with a neighboring atom to further form a fused ring or a spiro ring, preferably an optionally substituted carbocycle (preferably 5- to 6-membered ring) or an optionally substituted heterocycle (preferably 5- to 6-membered ring).

One of preferable aspects of a substituent on the G ring is lower alkyl (e.g. methyl, isopropyl), lower alkoxy lower alkyl (e.g. 2-methoxyethyl), or optionally substituted amino (example of substituent: lower alkyl (e.g. methyl), lower alkylcarbonyl (e.g. acetyl)).

R$^3$ is preferably hydrogen or optionally substituted lower alkyl, more preferably hydrogen.

As R$^{14}$, the same groups as those in the case of R$^{20}$, R$^{21}$, R$^{22}$ and R$^{23}$ are exemplified. R$^{14}$ is preferably hydrogen, optionally substituted lower alkyl (substituent: amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclic lower alkyl, optionally substituted lower alkylcarbonyl (substituent: lower alkoxy), optionally substituted benzoyl (substituent: lower alkoxy), substituted sulfonyl (substituent: lower alkyl, aryl, heterocyclic group), more preferably hydrogen or optionally substituted lower alkyl.

[Chemical formula 15]

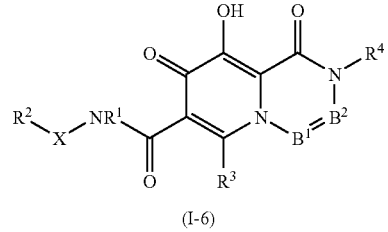

(I-6)

Preferably, B$^1$ is CR$^{20}$R$^{21}$, and B$^2$ is NR$^{22}$ (R$^{20}$, R$^{21}$ and R$^{22}$ are as defined above).

In addition, preferably, B$^1$ is NR$^{22}$, and B$^2$ is CR$^{20}$R$^{21}$ (R$^{20}$, R$^{21}$ and R$^{22}$ are as defined above).

R$^3$ is preferably hydrogen or optionally substituted lower alkyl, more preferably hydrogen.

R$^{20}$, R$^{21}$ and R$^{22}$ are preferably independently hydrogen, optionally substituted lower alkyl (example of substituent: amino, lower alkylamino, lower carbonylamino, lower alkoxy, aryloxy, cyano, halogen, acylamino (e.g. lower carbonylamino), lower alkynyl, hydroxy, lower alkoxycarbonyl, optionally substituted heterocyclecarbonyl (example of substituent: lower alkyl, lower alkoxy), lower alkenyl, optionally substituted carbamoyl (example of substituent: lower alkyl), lower alkylcarbonyloxy, lower alkyloxycarbonyl, lower alkylcarobnyl amino, oxo, lower alkynyl), cycloalkyl, cycloalkyl lower alkyl, optionally substituted aryl (example of substituent: lower alkyl, halogen, lower alkyloxy, nitro), optionally substituted aryl lower alkyl (example of substituent: lower alkyl, halogen, lower alkyloxy, nitro, oxo), optionally substituted heterocyclic group (example of substituent: lower alkyl, halogen, lower alkyloxy, nitro), optionally substituted heterocyclic lower alkyl (example substituent: lower alkyl, halogen, lower alkyloxy, nitro, oxo), optionally substituted lower alkylcarbonyl (substituent: lower alkoxy, halogen), cycloalkylcarbonyl, optionally substituted benzoyl (substituent: lower alkoxy, halogen), substituted sulfonyl (substituent: lower alkyl, aryl, heterocyclic group (preferably 5- to 6-membered aromatic heterocyclic group)).

More preferably, R$^{20}$ and R$^{21}$ are both hydrogen.

In Compound (I-6), more preferably, R$^1$ is hydrogen or lower alkyl, more preferably hydrogen; X is lower alkylene; R$^2$ is phenyl, or phenyl substituted with at least halogen, more preferably phenyl substituted with 1 to 2 halogens (e.g. F); R$^3$ is hydrogen; B$^1$ is CH$^2$ or NR$^{22}$; B$^2$ is NR$^{22}$ or CH$^2$, more preferably B$^1$ is NR$^{22}$; B$^2$ is CH$^2$.

R$^4$ is preferably optionally substituted lower alkyl (e.g. methyl, ethyl, n-propyl, i-propyl, n-butyl; example of substituent: hydroxy, amino, lower alkylamino, lower alkoxy, aryloxy, oxo, lower alkoxycarbonyl, optionally substituted heterocyclecarbonyl (example of substituent: lower alkyl, lower alkoxy)), specifically lower alkylamino lower alkyl (e.g. 2-dimethylaminoethyl, 2-diethylaminoethyl), lower alkoxy lower alkyl (e.g. 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl) or aryloxy lower alkyl (e.g. 2-phenoxyethyl, 3-phenoxypropyl); optionally substituted cycloalkyl (e.g. cyclopropyl); optionally substituted cycloalkyl lower alkyl (e.g. cyclopropylmethyl, 1-adamantylmethyl, 2-adamantylmethyl, dodecahedranemethyl, cudanemethyl); optionally substituted aryl (e.g. phenyl; example of substituent; lower alkyl, halogen, lower alkyloxy, nitro, or a substituent part may be lower alkylene which may be intervened by a heteroatom (e.g. O)); optionally substituted aryl lower alkyl (e.g. benzyl; example of substituent: lower alkyl, halogen, lower alkyloxy, nitro, or a substituent part may be lower alkylene which may be intervened by a heteroatom (e.g. O)); optionally substituted heterocyclic group (preferably 5- to 6-membered ring) (e.g. picolyl, pyridyl; example of substituent: lower alkyl, halogen, lower alkyloxy, nitro); or optionally substituted heterocyclic group (preferably 5- to 6-membered ring) lower alkyl (e.g. piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; the heterocycle may be fused with a benzene ring).

$R^{22}$ is preferably optionally substituted alkyl (e.g. methyl, ethyl, n-propyl, i-propyl, n-butyl, neopentyl; example of substituent: amino, lower alkylamino, lower alkoxy, aryloxy, cyano, halogen, (substituted) carbamoyl, acylamino, oxo), specifically lower alkylamino lower alkyl (e.g. 2-dimethylaminoethyl, 2-diethylaminoethyl), lower alkoxy lower alkyl (e.g. 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl), aryloxy lower alkyl (e.g. 2-phenoxyethyl, 3-phenoxypropyl), cyano lower alkyl (e.g. cyanomethyl), halogenated lower alkyl (e.g. fluoromethyl, 2,2,2-trifluoromethyl), or carboranemethyl, acylamino lower alkyl (e.g. 2-acetamideethyl); lower alkenyl (e.g. allyl, propargyl, crotyl); cycloalkyl lower alkyl (e.g. 3-cyclopropyl, cyclopropylmethyl, 1-adamantylmethyl, 2-adamantylmethyl, dodecahedranemethyl, cubanemethyl); optionally substituted aryl (e.g. phenyl; a substituent part may be lower alkylene which may be intervened by a heteroatom (e.g. O)); optionally substituted aryl lower alkyl (e.g. benzyl; a substituent part may be lower alkylene which may be intervened by a heteroatom (e.g. O)); optionally substituted heterocyclic group (e.g. picolyl pyridyl; example of substituent: lower alkyl); optionally substituted heterocyclic lower alkyl (e.g. piperonylmethyl, morpholinoethyl, furanmethyl, tetrahydrofuranmethyl, dioxanemethyl, tetrahydropyranmethyl, triazolemethyl, tetrazolemethyl, thiazolemethyl, oxazolemethyl, 1,2,4-oxadiazolemethyl, 1,3,4-oxadiazolemethyl, isoxazole methyl, imidazolemethyl, methylpyrrolemethyl, 18-crownethermethyl; example of substituent: lower alkyl); optionally substituted lower alkylcarbonyl (e.g. acetyl; example substituent: lower alkoxy (e.g. methoxy)); optionally substituted arylcarbonyl (e.g. benzoyl; example of substituent; lower alkoxy); substituted thiourea (e.g. urea, lower alkylurea (e.g. dimethylurea), dimethylthiourea); or substituted sulfonyl (e.g. alkylsulfonyl (e.g. methanesulfonyl), arylsulfonyl (e.g. benzenesulfonyl), heterocyclic sulfonyl (e.g. thiophenesulfonyl)).

[Chemical formula 16]

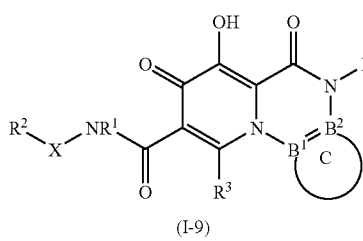

(I-9)

C ring indicates an optionally substituted carbocycle or an optionally substituted heterocycle. When the C ring is a heterocycle, $B^1$ and $B^2$ are independently C, CH or N. Provided that, when $B^1$ and $B^2$ are independently $CR^{23}$ or N, a broken line indicates the presence of a bond. When the C ring is a heterocycle, the same heterocycles as the A ring and the G ring are exemplified, and a substituent on the C ring is also exemplified similarly. That is, as a substituent on the C ring, same or different one or more substituents selected from Substituent group S2 are exemplified. Alternatively, a substituent part on the C ring may be taken together with a neighboring atom to further form a fused ring or a spiro ring, preferably an optionally substituted carbocycle (preferably 5- to 6-membered ring) or an optionally substituted heterocycle (preferably 5- to 6-membered ring).

When the C ring is a carbocycle, $B^1$ and $B^2$ are independently C or CH and, as the carbocycle, a 5- to 7-membered ring is exemplified.

A broken line indicates the presence or absence of a bond, preferably the absence of a bond.

The C ring includes the following rings, preferably (i) and (l).

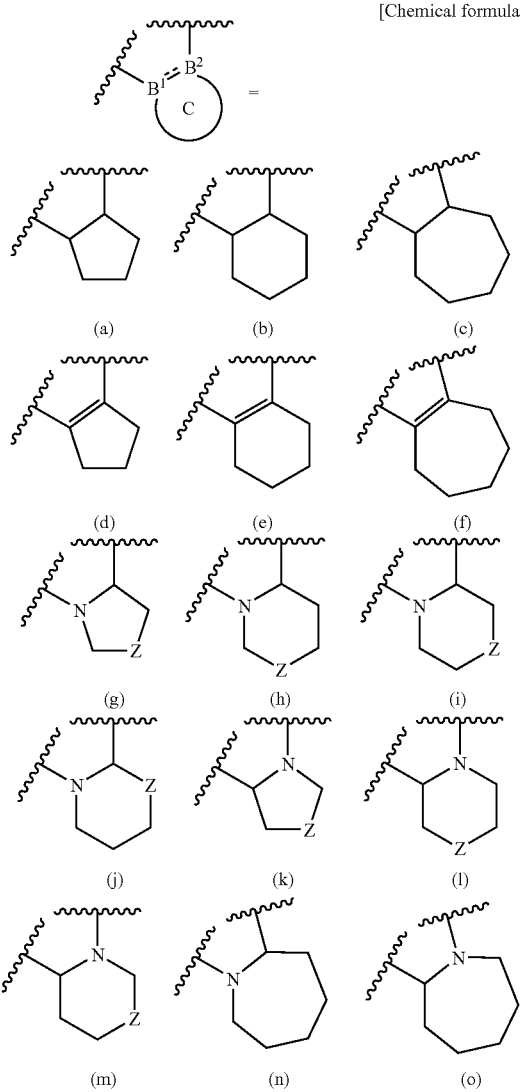

[Chemical formula 17]

(Z is $Ch_2$, O, S, SO, $SO_2$, or $Nr^{19}$ Described Later)

One of preferable aspects as a substituent on the C ring is lower alkyl (e.g. methyl, isopropyl), lower alkoxy lower alkyl (e.g. 2-methoxyethyl), and optionally substituted amino (example of substituent: lower alkyl (e.g. methyl), lower alkylcarbonyl (e.g. acetyl)).

$R^{19}$ is more preferably hydrogen, lower alkyl, or lower alkoxy lower alkyl.

$R^3$ is preferably hydrogen, or optionally substituted lower alkyl, more preferably hydrogen.

In Compound (I-9), as $R^4$, the same groups as those for $R^4$ of Compound (I-6) are preferably exemplified.

[Chemical formula 18]

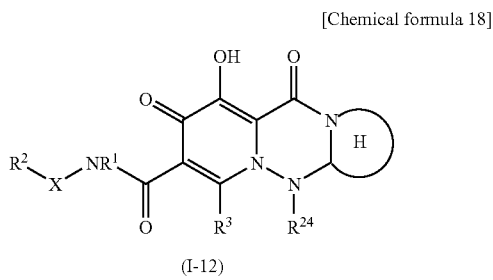

(I-12)

H ring means a heterocycle having the same meaning as that of the A ring, is preferably a 5- to 7-membered ring and, as a substituent on each ring, the same substituents as those in the case of the A ring are exemplified. That is, as a substituent on the H ring, same or different one or more substituents selected from the Substituent group S2 are exemplified. Alternatively, a substituent part on the H ring may be connected with a neighboring atom to further form a fused ring or a spiro ring, preferably an optionally substituted carbocycle (preferably 5- to 6-membered ring) or an optionally substituted heterocycle (preferably 5- to 6-membered ring).

$R^3$ is preferably hydrogen, or optionally substituted lower alkyl, more preferably hydrogen.

As $R^{24}$, the same groups as those in the case of $R^{20}$, $R^{21}$, $R^{22}$ and $R^{23}$ are exemplified. $R^{24}$ is preferably hydrogen, optionally substituted lower alkyl (substituent: amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclic lower alkyl, optionally substituted lower alkylcarbonyl (substituent: lower alkoxy, halogen), optionally substituted benzoyl (substituent: lower alkoxy, halogen), or substituted sulfonyl (substituent: lower alkyl, aryl, heterocyclic group (preferably 5- to 6-membered aromatic heterocyclic group)), more preferably hydrogen, or optionally substituted lower alkyl.

Compound (I) has at least the following characteristics as its chemical structure.

(1) The main structure, condensed heterocycle, is substituted with oxo (=O), hydroxy (OH) and oxo (=O).

(2) A substituted carbamoyl group (—$CONR^1XR^2$) is attached to the position neighboring to the oxo group on the heterocycle.

Particularly, by possession of such the structure, Compound (I) exhibits a remarkably potent integrase inhibitory activity and/or cell-growth inhibitory activity against virus including HIV. A preferable compound is also effective to a resistant strain. In contrast, other partial structures have a relatively large freedom degree, may have a variety of substituents, and may form a condensed ring, and the condensed ring may be further substituted.

The present invention provides a pharmaceutically acceptable salt or a solvate of Compound (I). All theoretically possible tautomer, geometrical isomer, optically active compound, and racemate thereof of the present compound are within the scope of the invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine, meglumine, diethanolamine, or ethylenediamine salts; aralkyl amine salts such as N, N-dibenzylethylenediamine or benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararates, malates, citrates salts, or ascorbates; sulfonates such as methanesulfonates, isethionates, benzenesulfonates, or p-toluenesulfonates; and acidic amino acid salts such as aspartates or glutamates are exemplified.

Solvates of a compound of the present invention include alcholates and hydrates.

A general process for producing the present compound will be exemplified below.

(Method of Preparing Raw Material)

[Chemical formula 41]

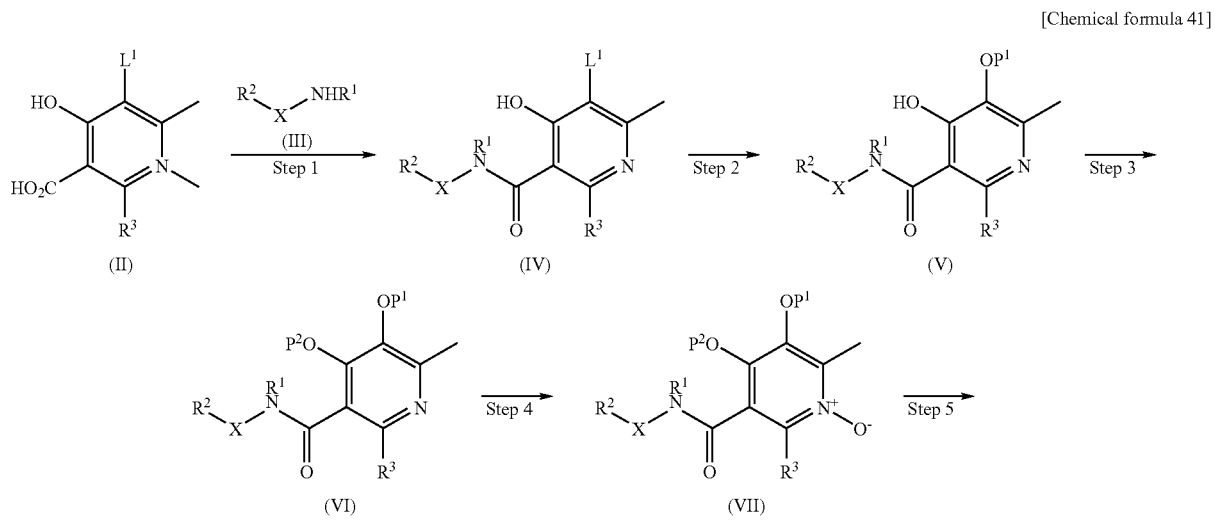

-continued

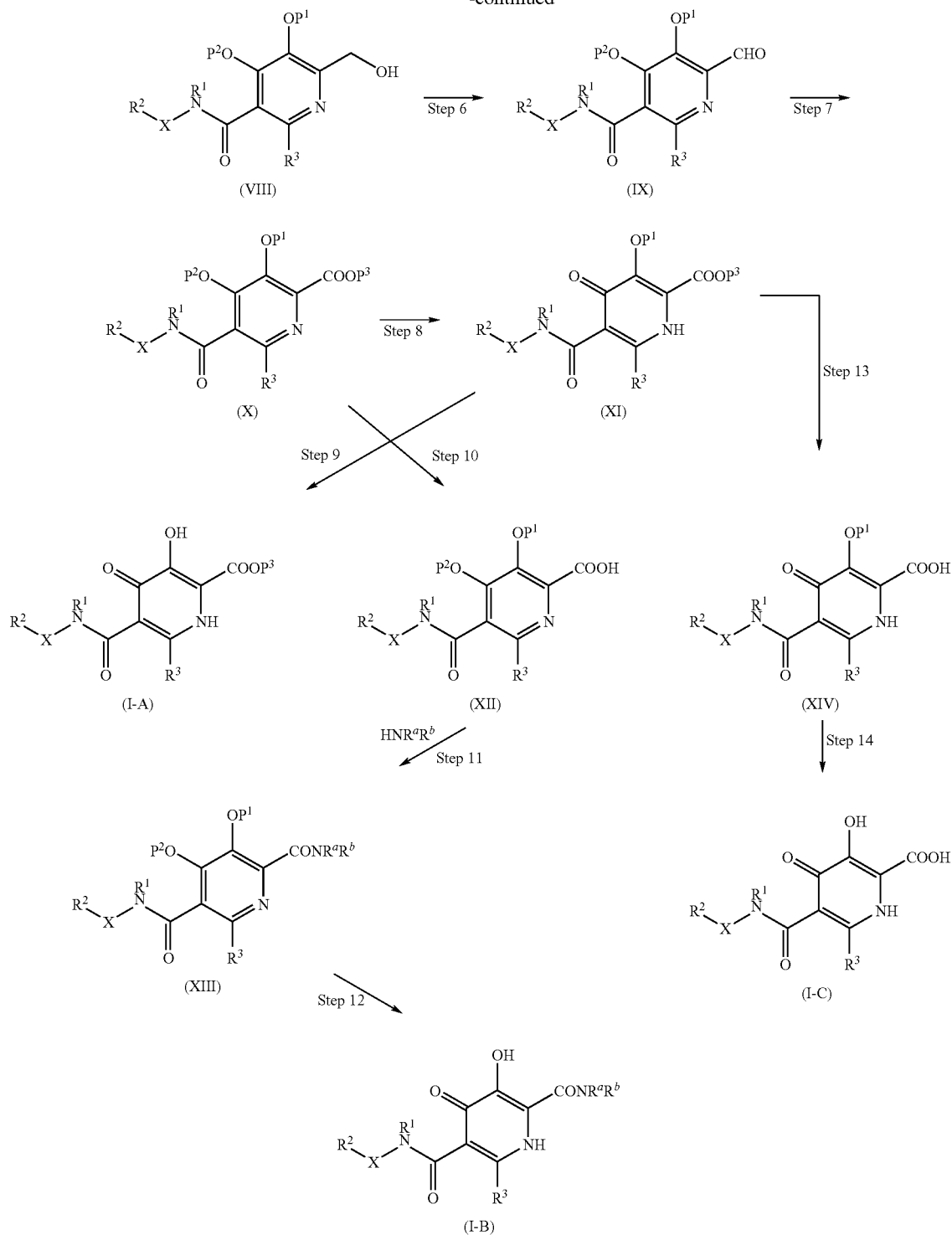

(wherein $L^1$ is a leaving group (e.g.; halogen); $P^1$ and $P^2$ are a hydroxy protecting group; $P^3$ is a carboxy protecting group (e.g.: lower alkyl); $R^a$ and $R^b$ are hydrogen or a substituent on an amino group)

Examples of a hydroxy protecting group ($P^1$, $P^2$) include acyl (e.g.: acetyl, pivaloyl, benzoyl), aralkyl (e.g.: benzyl), lower alkyl (e.g.: methyl), alkoxyalkyl (e.g.: methoxymethyl, methoxyethyl), lower alkylsulfonyl (e.g.: methanesulfonyl), arylsulfonyl (e.g.: benzenesulfonyl, toluenesulfonyl), alkoxycarbonyl (e.g.: methoxycarbonyl) and the like.

As a carboxy protecting group ($P^3$), lower alkyl (e.g.; methyl, ethyl), and aralkyl (e.g.: benzyl) are exemplified.

(First Step)

The present step is a reaction for condensing a compound (II) and a compound (III) to synthesize a compound (IV). The reaction may be performed according to the condition for a reaction of amidating carboxylic acid which is generally performed. A compound (II) may be reacted as it is, or may be reacted after converted into corresponding acid chloride or active ester. Preferably, the reaction is performed in a suitable solvent in the presence of a condensing agent.

As a condensing agent, dicyclohexylcarbodiimide, 1-ethyl-3-(3-dimethylaminopropyl)carbodiimide hydrochloride and the like may be used. If necessary, a reagent such as 1-hydroxybenzotriazole and N-hydroxysuccinimide, or a base such as triethylamine, N-methylmorpholine, and pyridine may be added.

A reaction temperature is 0 to 150° C., preferably room temperature to 70° C.

As a reaction solvent, an aprotic solvent can be broadly used, and tetrahydrofuran (THF), 1,4-dioxane, dimethylformamide (DMF), methylene chloride, chloroform and the like are preferable.

A reaction time is a few minutes to a few tens hours, preferably 9 to 17 hours.
(Second Step)

The present step is a reaction for introducing a protected hydroxy group ($OP^1$) into a compound (IV) to produce a compound (V). The reaction may be performed according to the condition for an alkoxylating reaction which is generally performed.

For example, a compound (V) in which $P^1$ is methyl can be synthesized by reacting a compound (IV) with metal alkoxide (e.g.: sodium methoxide).

A reaction temperature is 0 to 200° C., preferably 80 to 120° C.

As a reaction solvent, alcohol, dimethylformamide (DMF), and dimethyl sulfoxide (DMSO) are exemplified.

A reaction time is a few minutes to a few tens hours, preferably 5 to 10 hours.
(Third Step)

The present step is a reaction for protecting a hydroxy group of a compound (V) to produce a compound (VI). The reaction may be performed according to the condition for a reaction of protecting a hydroxy group which is generally performed. For example, by using diisopropyl azodicarboxylate or diethyl azodicarboxylate together with an alcohol and various phosphines, a compound (VI) in which $P^2$ is alkyl can be synthesized.

A reaction temperature is 0 to 100° C., preferably 0° C. to room temperature.

As a reaction solvent, THF, toluene, dichloromethane and the like are exemplified.

A reaction time is a few minutes to a few tens hours, preferably 1 to 3 hours.
(Fourth Step)

The present step is a reaction of oxidizing a nitrogen atom of a compound (VI) to produce a compound (VII). The reaction may be performed according to the condition for an oxidation reaction using an oxidizing agent which is generally performed.

A reaction temperature is 0 to 100° C., preferably under ice-cooling to room temperature.

As a reaction solvent, chloroform, methylene chloride, acetic acid and the like are exemplified.

Examples of an oxidizing agent include metachloroperbenzoic acid, hydrogen peroxide and the like.

A reaction time is a few minutes to a few tens hours, preferably 1 to 5 hours.
(Fifth Step)

The present step is a reaction for hydroxylating a methyl group of a compound (VII). Preferably, after acetoxylation by a reaction with acetic anhydride (reaction temperature: 0 to 150° C., preferably 120 to 140° C.), this may be hydrolyzed (e.g.: treatment with a base (e.g.: alkali metal hydroxide)).

A reaction time is a few minutes to a few tens hours, preferably 0.5 to 2 hours for acetoxylation, and 0.5 to 1 hour for hydrolysis.
(Sixth Step)

The present step is a reaction for oxidizing a hydroxy group of a compound (VIII) to synthesize a compound (IX).

A reaction temperature is 0 to 150° C., preferably room temperature to 70° C.

As a reaction solvent, chloroform and the like are exemplified.

As an oxidizing agent, dimethyl sulfoxide and the like are exemplified.

A reaction time is a few minutes to a few tens hours, preferably 0.1 to 1 hour.
(Seventh Step)

The present step is a reaction for oxidizing a formyl group of a compound (IX) to synthesize a compound (X).

A reaction temperature is 0 to 150° C., preferably under ice-cooling to room temperature.

As a reaction solvent, an alcohol and the like are exemplified.

As an oxidizing agent, potassium hydroxide and iodine are exemplified.

A reaction time is a few minutes to a few tens hours, preferably 0.5 to 3 hours.
(Eighth Step)

The present step is a reaction for deprotecting an $OP^2$ part of a compound (X) to synthesize a compound (XI). The reaction may be performed according to the condition for a reaction of deprotecting a hydroxy protecting group which is generally performed.

A reaction temperature is 0 to 150° C., preferably under ice-cooling to room temperature.

As a reaction solvent, acetonitrile, methylene chloride, THF and the like are exemplified.

A reaction time is a few minutes to a few tens hours, preferably 1 to 3 hours.
(Ninth Step)

The present step is a reaction for deprotecting an $OP^1$ part of a compound (XI) to synthesize a compound (I-A). The reaction may be treated preferably with a Lewis acid (e.g.: aluminum chloride).

A reaction temperature is 0 to 150° C., preferably 10 to 50° C.

As a reaction solvent, methylene chloride, THF and the like are exemplified.

A reaction time is a few minutes to a few tens hours, preferably 1 to 3 hours.
(Tenth Step)

The present step is a reaction for deprotecting an ester part ($COOP^3$) of a compound (X) to synthesize carboxylic acid (XII). Preferably, hydrolysis with an alkali (e.g.: NaOH) may be performed.

A reaction temperature is 0 to 150° C., preferably 10 to 50° C.

As a reaction solvent, methanol, water and the like are exemplified.

A reaction time is a few minutes to a few tens hours, preferably a few minutes to 2 hours.

Carboxylic acid (XII) can be converted into various derivatives (e.g.; amide).
(Eleventh Step)

The present step is a reaction for reacting a compound (XII) with various amines to synthesize a compound (XIII). The reaction may be performed according to the condition for a reaction of amidating carboxylic acid which is generally performed and, for example, the reaction may be performed as in the first step.

A reaction temperature is 0 to 150° C., preferably room temperature to 70° C.

As a reaction solvent, an aprotic solvent can be broadly used, and tetrahydrofuran (THF), 1,4-dioxane, dimethylformamide (DMF), methylene chloride, chloroform and the like are preferable.

A reaction time is a few minutes to a few tens hours, preferably a few minutes to 3 hours.

An amide part of the resulting compound (XIII) may be further chemically modified (e.g.: N-alkylation).

(Twelfth Step)

The present step is a reaction for deprotecting $OP^1$ and $OP^2$ parts of a compound (XIII) to synthesize a compound (I-B). The reaction may be performed according to the condition for a reaction of deprotecting a hydroxy protecting group which is generally performed.

For example, when pyridine hydrochloride is used, a reaction temperature is 0 to 200° C., preferably 150 to 180 degree.

A reaction time is a few minutes to a few tens hours, preferably 1 to 5 minutes.

(Thirteenth Step)

The present step is a reaction for deprotecting an ester part ($COOP^3$) of a compound (XI) to synthesize carboxylic acid (XIV). Preferably, hydrolysis with an alkali (e.g.: lithium hydroxide) may be performed.

A reaction temperature is 0 to 150° C., preferably 10 to 50° C.

As a reaction solvent, methanol, water and the like are exemplified.

A reaction time is a few minutes to a few tens hours, preferably a few minutes to 3 hours.

(Fourteenth Step)

The present step is a reaction for deprotecting an $OP^1$ part of a compound (XIV) to synthesize a compound (I-C). The reaction may be treated preferably with a Lewis acid (e.g.: boron tribromide).

A reaction temperature is 0 to 150° C., preferably under ice-cooling to room temperature.

As a reaction solvent, dichloromethane and the like are exemplified.

A reaction time is a few minutes to a few tens hours, preferably a few minutes to 5 hours.

The monocyclic carbamoylpyridone derivative obtained above is derived into a bicyclic compound by the following method.

(Process 6)

[Chemical formula 47]

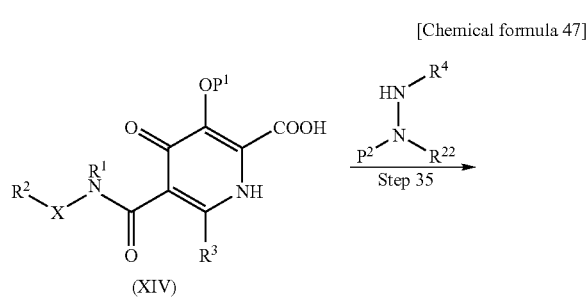

(XIV)

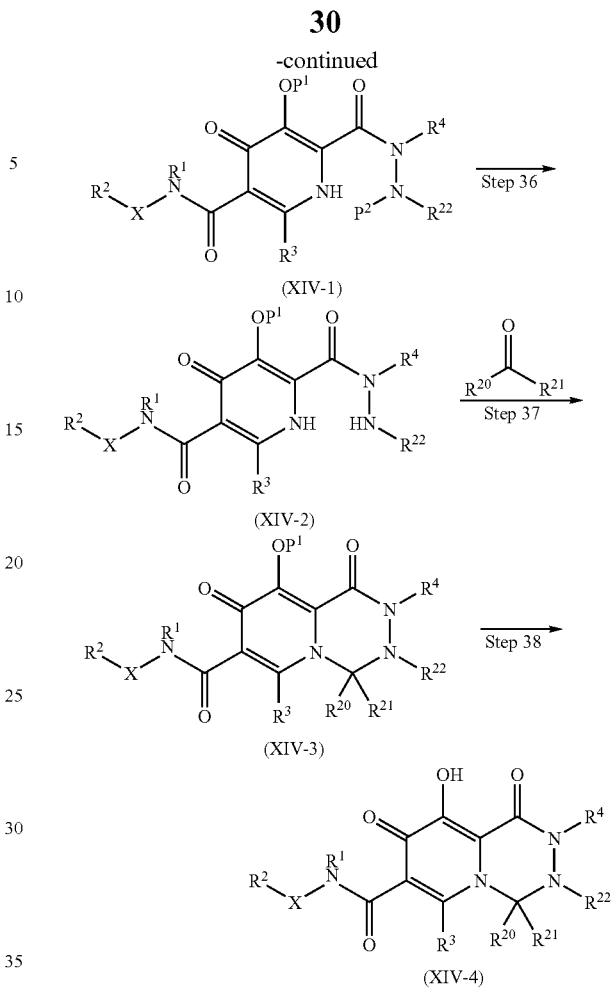

(wherein each symbol is as defined above)

(Thirty-Fifth Step)

A compound (XIV) is reacted with a protected hydrazine reagent according to a general amidation reaction to obtain a compound (XIV-1). The protected hydrazine reagent can be synthesized, for example, according to the method described in Pol. J. Chem. 2003. 77. 315-319. A compound (XIV) may be reacted as it is, or may be reacted after it is converted into corresponding acid chloride or active ester. Preferably, the reaction is performed in a suitable solvent in the presence of a condensing agent.

As condensing agent, dicyclohexylcarbodiimide, 1-ethyl-3-(3-dimethylaminopropyl)carbodiimide hydrochloride and the like can be used. If necessary, a reagent such as 1-hydroxybenzotriazole and N-hydroxysuccinimide and the like, and a base such as triethylamine, N-methylmorpholine, and pyridine may be added.

A reaction temperature is about 0 to 150° C., preferably room temperature to 70° C.

As a reaction solvent, an aprotic solvent can be broadly used, and tetrahydrofuran (THF), 1,4-dioxane, dimethylformamide (DMF), methylene chloride, chloroform and the like are preferable.

A reaction time is a few minutes to a few tens hours, preferably 10 minutes to 5 hours.

(Thirty-Sixth Step)

A $P^2$ part of a compound (XIV-1) is deprotected to obtain a compound (XIV-2).

A reaction temperature is usually 0 to 150° C., preferably room temperature to 60° C.

As a reaction solvent, ethyl acetate, 1,4-dioxane, and THF are exemplified.

A reaction time is usually a few minutes to a few tens hours, preferably a few minutes to 5 hours.

(Thirty-Seventh Step)

A compound (XIV-2) is reacted with a carbonyl compound according to a general animal forming reaction to obtain a compound (XIV-3).

A reaction temperature is usually about 0 to 100° C., preferably room temperature to 60° C.

As a reaction solvent, methylene chloride, THF, and toluene are exemplified.

A reaction time is usually a few minutes to a few tens hours, preferably a few minutes to 5 hours.

The present reaction is preferably performed in the presence of an acid catalyst (e.g. acetic acid, p-toluenesulfonic acid).

(Thirty-Eighth Step)

A P¹ part of a compound (XIV-3) is deprotected to obtain a compound (XIV-4).

A reaction temperature is usually about 0 to 180° C., preferably room temperature to 60° C.

As a reaction solvent, THF, 1,4-dioxane, and methylene chloride are exemplified.

A reaction time is usually a few minutes to a few hours, preferably a few minutes to 5 hours.

In the above reaction, by using a compound in which $R^4$ and $R^{22}$ taken together form a ring, as a protected hydrazine reagent, a tricyclic compound such as the compound (I-10) may be synthesized (G ring formation).

(Process 7)

[Chemical formula 48]

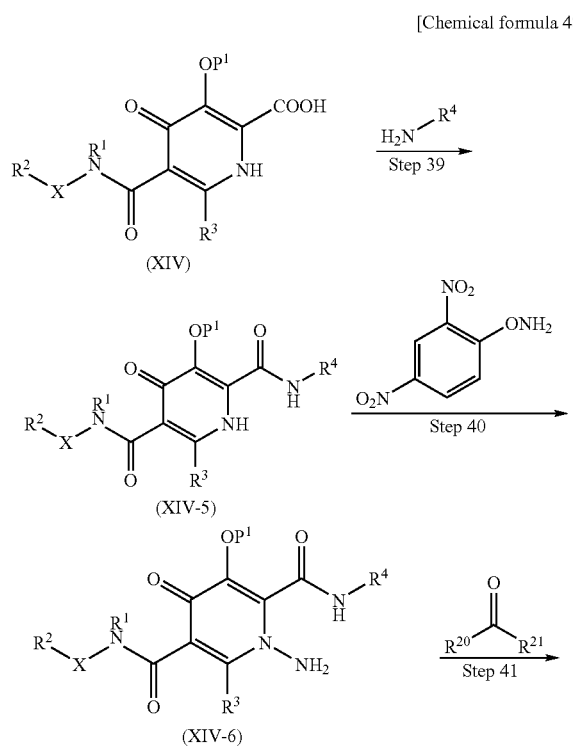

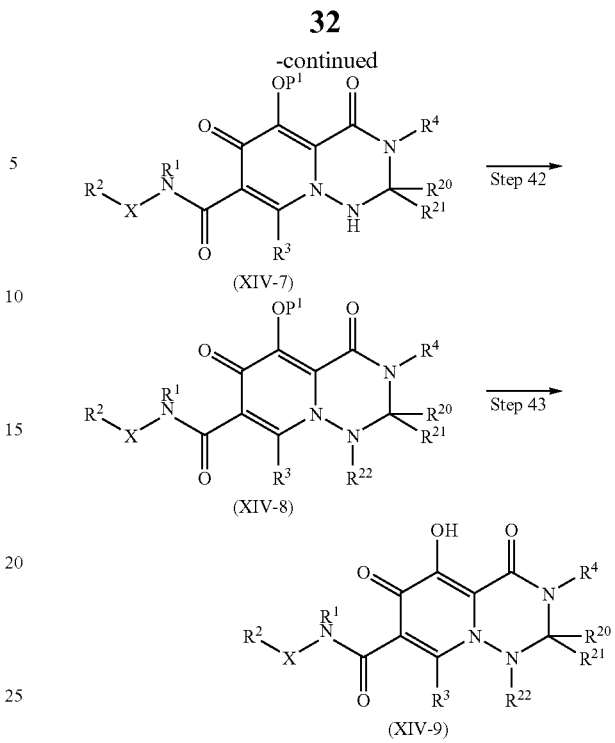

(wherein each symbol is as defined above)

(Thirty-Ninth Step)

A compound (XIV) is reacted with an amine reagent according to the thirty-fifth step to obtain a compound (XIV-5).

(Fortieth Step)

A compound (XIV-5) is reacted with an N-amination reagent to obtain a compound (XIV-6). Preparation of an N-amination reagent and an N-amination reaction are performed, for example, according to the method described in J. Med. Chem. 1984, 27.1103-1108.

(Forty-First Step)

A compound (XIV-6) is reacted with a carbonyl compound according to the thirty-seventh step to obtain a compound (XIV-7).

(Forty-Second Step)

An NH part of a compound (XIV-6) is variously modified to obtain a compound (XIV-8). As the modification method, general N-alkylation, alkylation using a halogenated compound, reductive amination using a carbonyl compound, acylation, and sulfonylation are exemplified.

(Forty-Third Step)

A P¹ part of a compound (XIV-8) is deprotected according to the thirty-eighth step to obtain a compound (XIV-9).

(Process 8)

[Chemical formula 49]

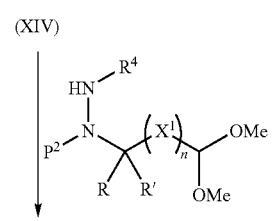

(Process 9)

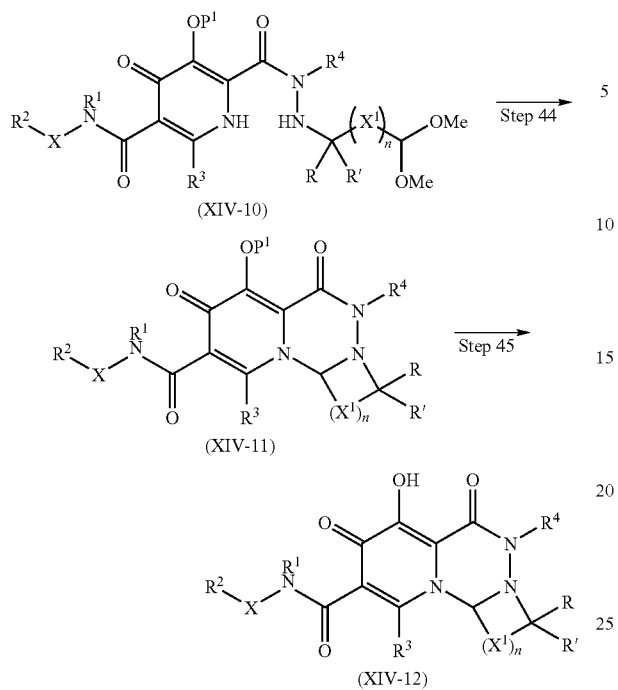

(XIV-10)

(XIV-11)

(XIV-12)

$X^1$ = C, O, S, SO, $SO_2$, N (wherein each symbol is defined above; n is an integer of 1 to 4; R and R' are an arbitrary substituent; respective $X^1$s are the same or different, and an $X^1$ (=C, N) may be substituted; n is preferably an integer of 1 to 4).

(Forty-Fourth Step)

A compound (XIV-10) is subjected to a general acetal deprotection reaction to obtain a compound (XIV-11). The present reaction is preferably performed under the acidic condition.

A reaction temperature is usually about 0 to 120° C., preferably room temperature to 60° C.

As a reaction solvent, THF, 1,4-dioxane, water, and methanol are exemplified.

A reaction time is usually a few minutes to a few tens hours, preferably a few minutes to 5 hours.

A compound (XIV-10) is obtained by reacting a compound (VIV) with a hydrazine reagent having a protected aldehyde-type substituent according to the thirty-fifth step.

(Forty-Fifth Step)

A $P^1$ part of a compound (XIV-11) is deprotected according to the thirty-eighth step to obtain a compound (XIV-12) (C ring formation).

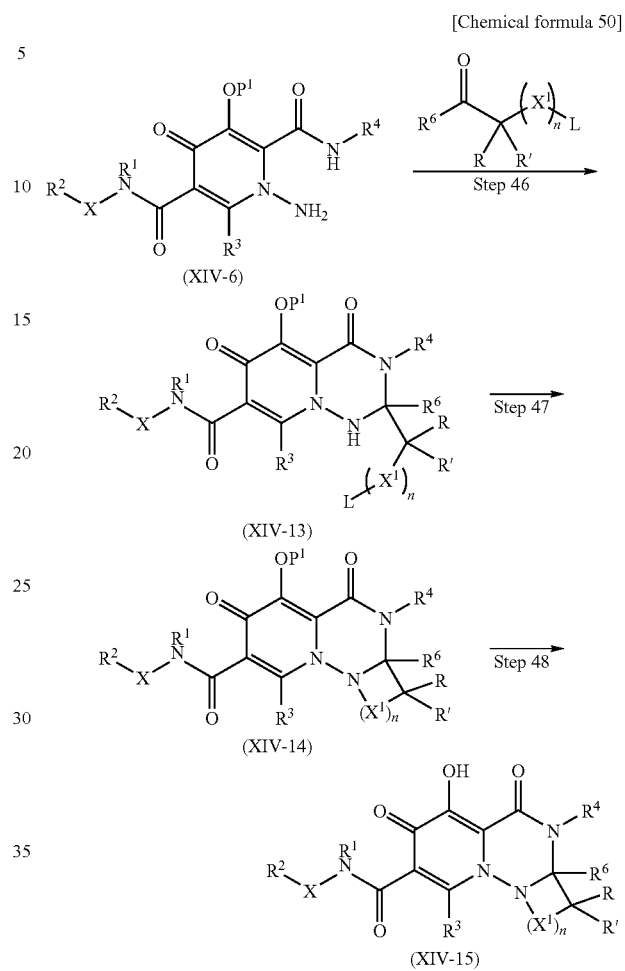

(XIV-6)

(XIV-13)

(XIV-14)

(XIV-15)

$X^1$ = C, O, S, SO, $SO_2$, N (wherein each symbol is as defined above; L is a leaving group; R and R' are an arbitrary substituent)

(Forty-Sixth Step)

A compound (XIV-6) is reacted with a carbonyl compound according to a general animal forming reaction to obtain a compound (XIV-13).

(Forty-Seventh Step)

A compound (XIV-13) is cyclized in a molecule to obtain a compound (XIV-14). A reaction is performed according to a general alkylation reaction or the similar condition.

(Forty-Eighth Step)

A $P^1$ part of a compound (XIV-14) is deprotected according to the thirty-eighth step to obtain a compound (XIV-15) (C ring formation).

(Process 11)

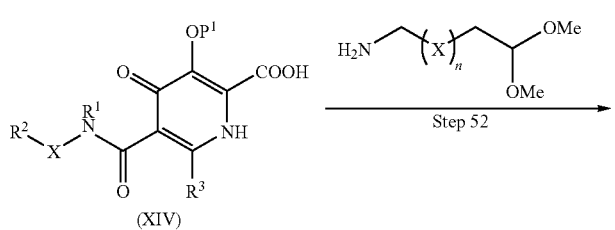

(XIV)

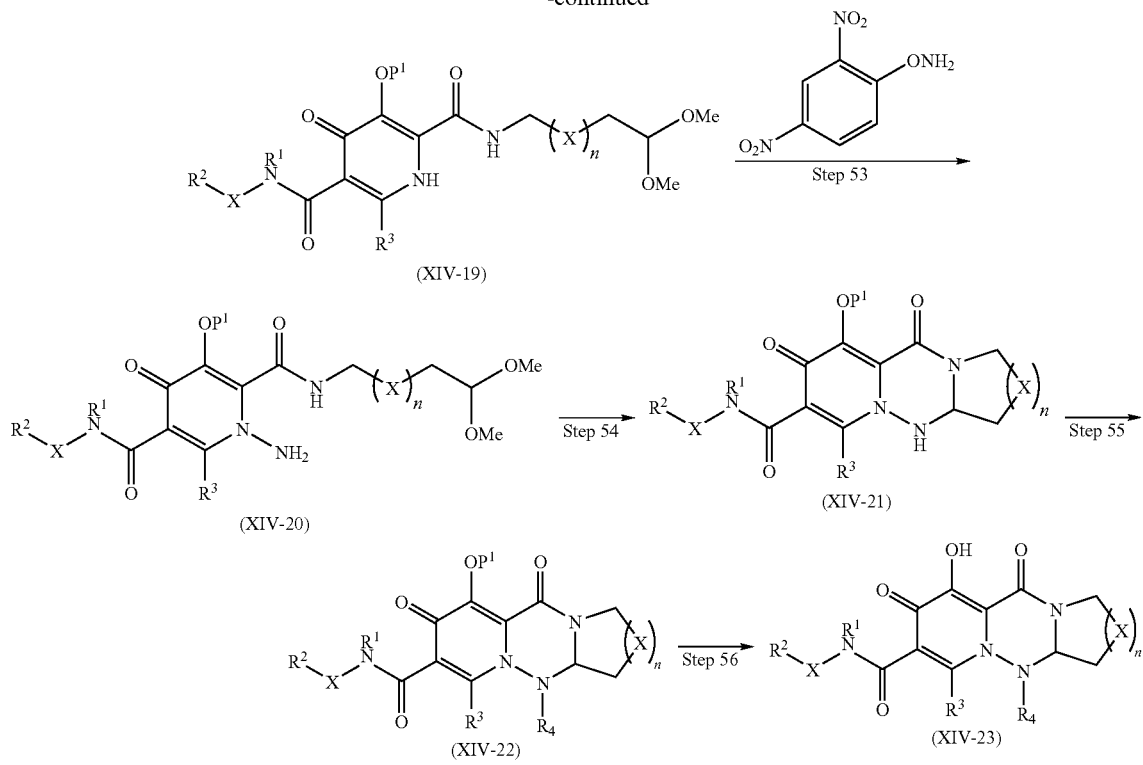

X = C, O, S, SO, SO₂

(wherein each symbol is as defined above)

(Fifty-Second Step)

A compound (XIV) is reacted with an amine reagent according to the thirty-fifth step to obtain a compound (XIV-19).

(Fifty-Third Step)

A compound (XIV-19) is reacted with an N-amination reagent to obtain a compound (XIV-20). Preparation of an N-amination reagent and an N-amination reaction are performed, for example, according to the method described in J. Med. Chem. 1984, 27, 1103-1108.

(Fifty-Fourth Step)

A compound (XIV-20) is subjected to a general acetal deprotection reaction according to the forty-fourth step to obtain a compound (XIV-21).

(Fifty-Fifth Step)

An NH part of a compound (XIV-21) is variously modified to obtain a compound (XIV-22). As the modification method, general N-alkylation, alkylation using a halogenated compound, reductive amination using a carbonyl compound, acylation, and sulfonation are exemplified.

(Fifty-Sixth Step)

A P¹ part of a compound (XIV-22) is deprotected according to the thirty-eighth step to obtain a compound (XIV-23).

In addition, the present compound obtained above may be further chemically modified to synthesize another compound. In addition, when there is a reactive functional group (e.g.: OH, COOH, NH₂) on a side chain part etc. in the above reaction, the group may be protected before the reaction and may be deprotected after the reaction, if desired.

The present compound is useful, for example, as a drug such as an anti-viral drug. The present compound has the remarkable inhibitory action on integrase of a virus. Therefore, the present compound can be expected to have the preventive or therapeutic effect for various diseases derived from a virus which produces at least integrase, and is grown at infection in an animal cell, and is useful as an integrase inhibiting agent for retrovirus (e.g. HIV-1, HIV-2, HTLV-1, SIV, FIV etc.), and is useful as an anti-HIV drug etc.

In addition, the present compound may be used in a combination therapy by combining an anti-HIV drug having the different action mechanism such as a reverse transcriptase inhibiter and/or a protease inhibiting agent. Particularly, currently, an integrase inhibitor is not marketed, and it is useful to use in a combination therapy by combining the present compound with a reverse transcriptase inhibiter and/or a protease inhibiter.

Further, the above use includes not only use as a medical mixture for anti-HIV, but also use as a joint use agent for increasing the anti-HIV activity of other anti-HIV drug such as cocktail therapy.

In addition, the present compound can be used in order to prevent infection with a retrovirus vector from spreading into a tissue other than an objective tissue, upon use of a retrovirus vector based on HIV or MLV in the field of gene therapy. Particularly, when a cell is infected with a vector in vitro, and the cell is returned into a body, if the present compound is administered in advance, unnecessary infection can be prevented in a body.

The present compound can be administered orally or parenterally. In the case of oral administration, the present compound can be also used as a conventional preparation, for example, as any dosage form of a solid agent such as tablets, powders, granules, capsules and the like; an aqueous agent; an oily suspension; or a liquid agent such as syrup and elixir. In the case of parenteral administration, the present compound can be used as an aqueous or oily suspension injectable, or a nasal drop. Upon preparation of it, conventional excipients, binders, lubricants, aqueous solvents, oily solvents, emulsifiers, suspending agents, preservatives, stabilizers and the like may be arbitrarily used. As an anti-HIV-drug, particularly, an oral agent is preferable. A preparation of the present invention is prepared by combining (e.g. mixing) a therapeutically effective amount of the present compound with a pharmaceutically acceptable carrier or diluent.

A dose of the present invention is different depending on an administration method, an age, a weight and condition of a patient, and a kind of a disease and, usually, in the case of oral administration, about 0.05 mg to 3000 mg, preferably about 0.1 mg to 1000 mg may be administered per adult a day, if necessary, by dividing the dose. In addition, in the case of parenteral administration, about 0.01 mg to 1000 mg, preferably about 0.05 mg to 500 mg is administered per adult a day.

Examples are shown below.

Example A-1

9-Hydroxy-2-(2-methoxy-ethyl)-1,8-dioxo-1,8-dihydro-2H-pyrid[1,2-a]pyrazine-7-carboxylic acid 4-fluoro-benzylamide Example B-1

9-Hydroxy-2-(2-methoxy-ethyl)-1,8-dioxo-1,3,4,8-tetrahydro-2H-pyrid[1,2-a]pyrazine-7-carboxylic acid 4-fluoro-benzylamide

[Chemical formula 52]

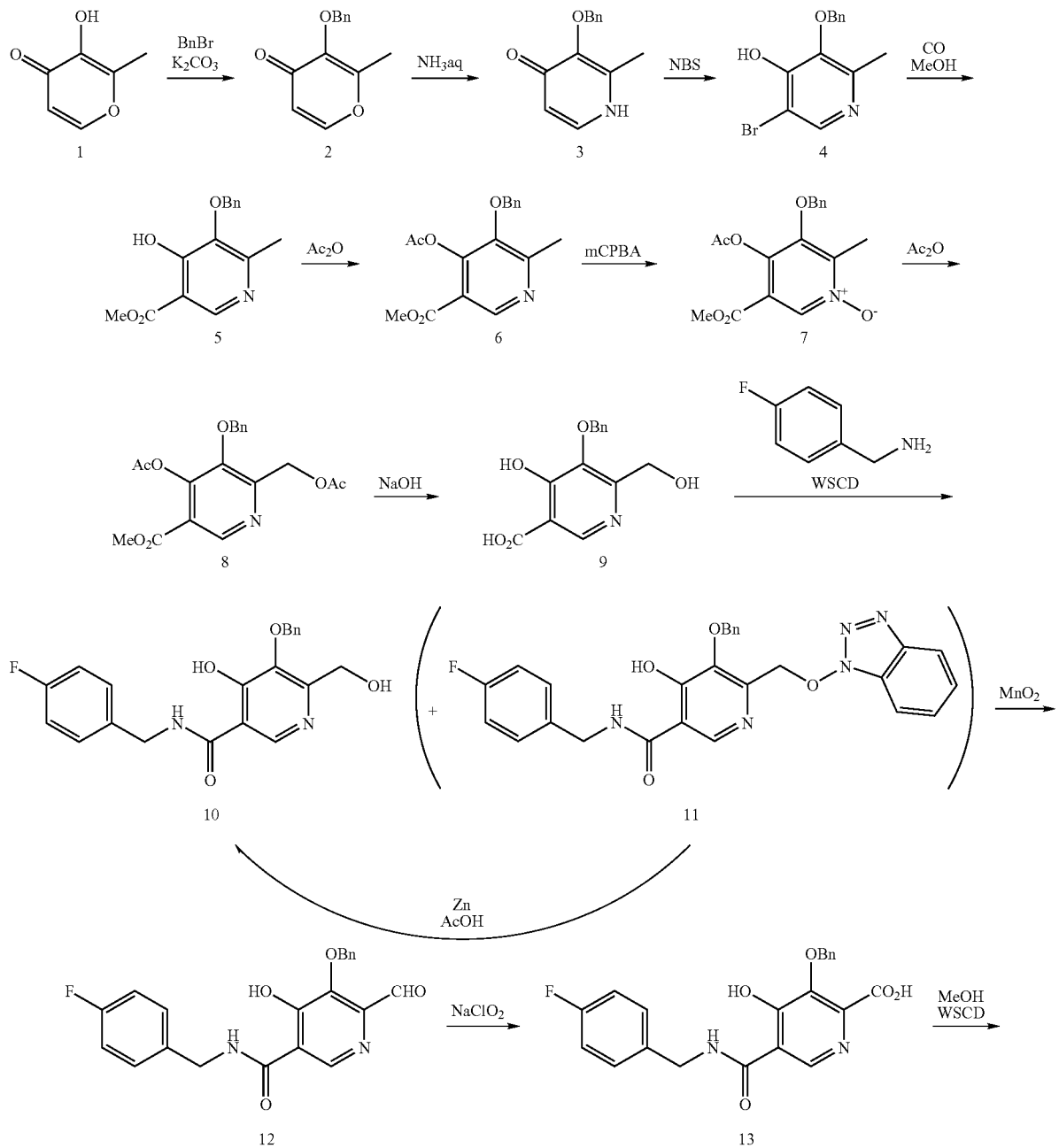

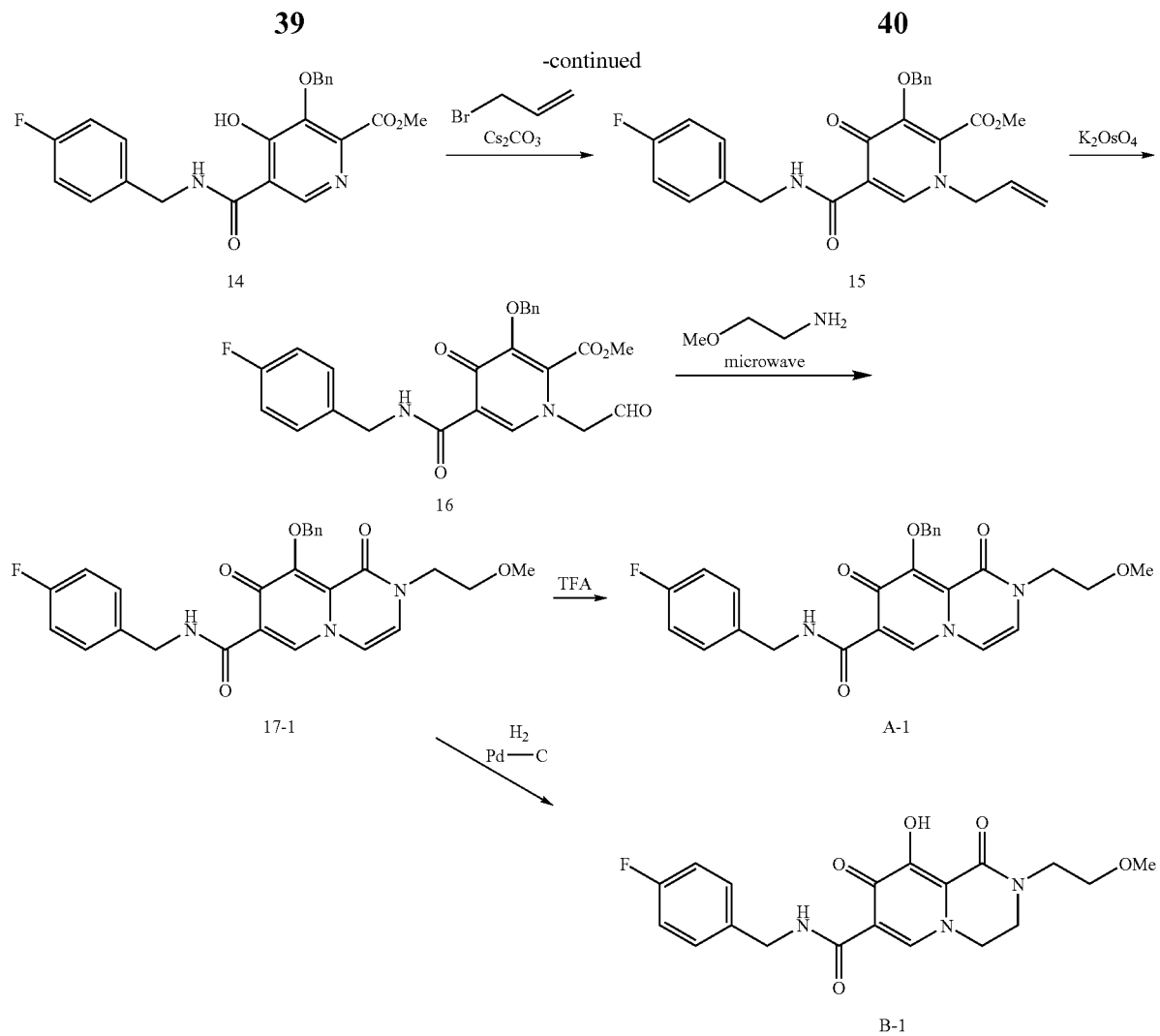

1) Maltol 1 (189 g, 1.5 mol) was dissolved in dimethylformamide (1890 ml), and benzyl bromide (184 ml, 1.5 mol) was added. After the solution was stirred at 80° C. for 15 minutes, potassium carbonate (228 g, 1.65 mol) was added, and the mixture was stirred for 1 hour. After the reaction solution was cooled to room temperature, an inorganic salt was filtered, and the filtrate was distilled off under reduced pressure. To the again precipitated inorganic salt was added tetrahydrofuran (1000 ml), this was filtered, and the filtrate was distilled off under reduced pressure to obtain the crude product (329 g, >100%) of 3-benzyloxy-2-methyl-pyran-4-one 2 as a brown oil.

NMR (CDCl$_3$) δ: 2.09 (3H, s), 5.15 (2H, s), 6.36 (1H, d, J=5.6 Hz), 7.29-7.41 (5H, m), 7.60 (1H, d, J=5.6 Hz).

2) The compound 2 (162.2 g, 750 mmol) was dissolved in ethanol (487 ml), and aqueous ammonia (28%, 974 ml) and a 6N aqueous sodium hydroxide solution (150 ml, 900 mmol) were added. After the reaction solution was stirred at 90° C. for 1 hour, this was cooled to under ice-cooling, and ammonium chloride (58 g, 1080 mmol) was added. To the reaction solution was added chloroform, this was extracted, and the organic layer was washed with an aqueous saturated sodium bicarbonate solution, and dried with anhydrous sodium sulfate. The solvent was distilled off under reduced pressure, isopropyl alcohol and diethyl ether were added to the residue, and precipitated crystals were filtered to obtain 3-benzyloxy-2-methyl-1H-pyridine-4-one 3 (69.1 g, 43%) as a pale yellow crystal.

NMR (DMSO-d$_6$) δ: 2.05 (3H, s), 5.04 (2H, s), 6.14 (1H, d, J=7.0 Hz), 7.31-7.42 (5H, m), 7.46 (1H, d, J=7.2 Hz), 11.29 (1H, brs).

3) The above compound 3 (129 g, 599 mmol) was suspended in acetonitrile (1300 ml), and N-bromosuccinic acid imide (117 g, 659 mmol) was added, followed by stirring at room temperature for 90 minutes. Precipitated crystals were filtered, and washed with acetonitrile and diethyl ether to obtain 3-benzyloxy-5-bromo-2-methyl-pyridine-4-ol 4 (154 g, 88%) as a colorless crystal.

NMR (DMSO-d$_6$) δ: 2.06 (3H, s), 5.04 (2H, s), 7.32-7.42 (5H, m), 8.03 (1H, d, J=5.5 Hz), 11.82 (1H, brs).

4) To a solution of the compound 4 (88 g, 300 mmol), palladium acetate (13.4 g, 60 mmol) and 1,3-bis(diphenylphosphino)propane (30.8 g, 516 mmol) in dimethylformamide (660 ml) were added methanol (264 ml) and triethylamine (210 ml, 1.5 mol) at room temperature. The interior of a reaction vessel was replaced with carbon monoxide, and the material was stirred at room temperature for 30 minutes, and stirred at 80 degree for 18 hours. A vessel to which ethyl acetate (1500 ml), an aqueous saturated ammonium chloride solution (1500 ml) and water (1500 ml) had been added was stirred under ice-cooling, and the reaction solution was added thereto. Precipitates were filtered, and washed with water (300 ml), ethyl acetate (300 ml) and diethyl ether (300 ml) to obtain 5-benzyloxy-4-hydroxy-6-methyl-nicotinic acid methyl ester 5 (44.9 g, 55%) as a colorless crystal.

NMR (DMSO-$d_6$) δ: 2.06 (3H, s), 3.72 (3H, s), 5.02 (2H, s), 7.33-7.42 (5H, m), 8.07 (1H, s).

5) After a solution of the compound 5 (19.1 g, 70 mmol) in acetic anhydride (134 ml) was stirred at 130° C. for 40 minutes, the solvent was distilled off under reduced pressure to obtain 4-acetoxy-5-benzyloxy-6-methyl-nicotinic acid methyl ester 6 (19.9 g, 90%) as a flesh colored crystal.

NMR (CDCl$_3$) δ: 2.29 (3H, s), 2.52 (3H, s), 3.89 (3H, s), 4.98 (2H, s), 7.36-7.41 (5H, m), 8.85 (1H, s).

6) To a solution of the compound 6 (46.2 g, 147 mmol) in chloroform (370 ml) was added metachloroperbenzoic acid (65%) (42.8 g, 161 mmol) in portions under ice-cooling, and this was stirred at room temperature for 90 minutes. To the reaction solution was added a 10% aqueous potassium carbonate solution, and this was stirred for 10 minutes, followed by extraction with chloroform. The organic layer was washed with successively with a 10% aqueous potassium carbonate solution, an aqueous saturated ammonium chloride solution, and an aqueous saturated sodium chloride solution, and dried with anhydrous sodium sulfate. The solvent was distilled off under reduced pressure, and the residue was washed with diisopropyl ether to obtain 4-acetoxy-5-benzyloxy-6-methyl-1-oxy-nicotinic acid methyl ester 7 (42.6 g, 87%) as a colorless crystal.

NMR (CDCl$_3$) δ: 2.30 (3H, s), 2.41 (3H, s), 3.90 (3H, s), 5.02 (2H, s), 7.37-7.39 (5H, m), 8.70 (1H, s).

7) To acetic anhydride (500 ml) which had been heated to stir at 130° C. was added the compound 7 (42.6 g, 129 mmol) over 2 minutes, and this was stirred for 20 minutes. The solvent was distilled off under reduced pressure to obtain 4-acetoxy-6-acetoxymethyl-5-benzyloxy-nicotinic acid methyl ester 8 (49.6 g, >100%) as a black oil.

NMR (CDCl$_3$) δ: 2.10 (3H, s), 2.28 (3H, s), 3.91 (3H, s), 5.07 (2H, s), 5.20 (2H, s), 7.35-7.41 (5H, m), 8.94 (1H, s).

8) To a solution of the compound 8 (46.8 g, 125 mmol) in methanol (140 ml) was added a 2N aqueous sodium hydroxide solution (376 ml) under ice-cooling, and this was stirred at 50° C. for 40 minutes. To the reaction solution were added diethyl ether and 2N hydrochloric acid under ice-cooling, and precipitated crystals were filtered. Resulting crystals were washed with water and diethyl ether to obtain 5-benzyloxy-4-hydroxy-6-hydroxymethyl-nicotinic acid 9 (23.3 g, 68%) as a colorless crystal.

NMR (DMSO-$d_6$) δ: 4.49 (2H, s), 5.19 (2H, s), 5.85 (1H, brs), 7.14-7.20 (2H, m), 7.33-7.43 (7H, m), 8.30 (1H, s), 10.73 (1H, t, J=5.8 Hz), 11.96 (1H, brs).

9) To a solution of the compound 9 (131 g, 475 mmol), 1-(3-dimethylaminopropyl)-3-ethylcarbodiimide hydrochloride (219 g, 1140 mmol) and 1-hydroxybenzotriazole (128 g, 950 mmol) in dimethylformamide (1300 ml) was added 4-fluorobenzylamine (109 ml, 950 mmol), and this was stirred at 80° C. for 1.5 hours. After the reaction solution was cooled to room temperature, hydrochloric acid was added, followed by extraction with ethyl acetate. The extract was washed with a 5% aqueous potassium carbonate solution, an aqueous saturated ammonium chloride solution, and an aqueous saturated sodium chloride solution, and dried with anhydrous sodium sulfate. The solvent was distilled off under reduced pressure to obtain a mixture (175 g) of 10 and 11. The resulting mixture was dissolved in acetic acid (1050 ml) and water (1050 ml), and zinc (31.1 g, 475 mmol) was added, followed by heating to reflux for 1 hour. After the reaction solution was cooled to room temperature, a 10% aqueous potassium carbonate solution was added, followed by extraction with ethyl acetate. The extract was washed with an aqueous saturated ammonium chloride solution, and an aqueous saturated sodium chloride solution, and dried with anhydrous sodium sulfate. After the solvent was distilled off under reduced pressure, this was washed with diethyl ether to obtain 5-benzyloxy-N-(4-fluoro-benzyl)-4-hydroxy-6-hydroxymethyl-nicotinic acid amide 10 (107 g, 59%) as a colorless crystal.

NMR (DMSO-$d_6$) δ: 4.45 (2H, d, J=4.3 Hz), 4.52 (2H, d, J=5.8 Hz), 5.09 (2H, s), 6.01 (1H, brs), 7.36-7.43 (5H, m), 8.31 (1H, s), 12.63 (1H, brs).

10) After manganese dioxide (49 g) was added to a suspension of the compound 10 (9.8 g, 25.6 mmol) in chloroform (490 ml), the mixture was stirred at room temperature for 1 hour. After the reaction solution was stirred at 60° C. for 20 minutes, Celite filtration was performed, and this was washed with chloroform heated at 50° C. The filtrate was distilled off under reduced pressure to obtain 5-benzyloxy-N-(4-fluoro-benzyl)-6-formyl-4-hydroxy-nicotinic acid amide 12 (8.2 g, 84%) as a pale yellow crystal.

NMR (DMSO-$d_6$) δ: 4.53 (2H, d, J=5.8 Hz), 5.38 (2H, s), 7.15-7.21 (2H, m), 7.35-7.46 (7H, m), 8.33 (1H, s), 9.90 (1H, s), 10.35 (1H, t, J=5.8 Hz), 12.49 (1H, brs).

11) To an aqueous solution (105 ml) of sodium chlorite (7.13 g, 78.8 mmol), and sulfamic acid (7.65 g, 78.8 mmol) was added a solution of the compound 12 (15.0 g, 39.4 mmol) in tetrahydrofuran (630 ml) under ice-cooling, and the mixture was stirred at room temperature for 1 hour. After water (2500 ml) was added to the reaction solution, precipitated crystals were filtered. Washing with diethyl ether afforded 3-benzyloxy-5-(4-fluoro-benzylcarbamoyl)-4-hydroxy-pyridine-2-carboxylic acid 13 (14.0 g, 90%) as a colorless crystal.

NMR (DMSO-$d_6$) δ: 4.52 (2H, d, J=5.8 Hz), 5.13 (2H, s), 7.14-7.19 (2H, m), 7.31-7.40 (5H, m), 7.47-7.49 (2H, m), 8.31 (1H, d, J=4.5 Hz), 10.44 (1H, t, J=5.9 Hz), 12.47 (1H, brs).

12) A solution of the compound 13 (198 mg, 0.500 mmol), 1-(3-dimethylaminopropyl)-3-ethylcarbodiimide hydrochloride (115 mg, 0.600 mmol) and 1-hydroxybenzotriazole (81 mg, 0.600 mmol) in dimethylformamide (3 ml) was stirred at room temperature for 1.5 hours. Then, methanol (3 ml) and triethylamine (153 ul, 1.10 mmol) were added, and the mixture was heated to reflux for 1.5 hours. The reaction solution was diluted with ethyl acetate, washed with an aqueous saturated sodium bicarbonate solution, a 10% aqueous citric acid solution, and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-hydroxy-pyridine-2-carboxylic acid methyl ester 14 (141 mg, 69%) as a colorless crystal.

NMR (DMSO-$d_6$) δ: 3.85 (3H, s), 4.52 (2H, d, J=6.0 Hz), 5.15 (2H, s), 7.13-7.21 (2H, m), 7.31-7.47 (7H, m), 8.33 (1H, s), 10.41 (1H, t, J=6.0 Hz), 12.59 (1H, brs).

13) After 3-bromopropene (2.15 ml, 24.8 mmol) was added to a solution of the compound 14 (6.79 g, 16.5 mmol), and cesium carbonate (8.09 g, 24.8 mmol) in dimethylformamide (54 ml), the mixture was stirred at room temperature for 4.5 hours. To the reaction solution was added an aqueous ammonium chloride solution, and this was extracted with ethyl acetate, washed with water and an aqueous saturated sodium chloride solution, and dried with anhydrous sodium sulfate. The solvent was distilled off under reduced pressure, and the residue was washed with diethyl ether to obtain 1-allyl-3- benzyloxy-5-(4-fluoro-benzylcarbamoyl)-4-oxo-1,4-dihydro-pyridine-2-carboxylic acid methyl ester 15 (6.15 g, 83%) as a colorless crystal.

NMR (CDCl$_3$) δ: 3.76 (3H, s), 4.54 (2H, d, J=6.0 Hz), 4.60 (2H, d, J=6.0 Hz), 5.20-5.37 (2H, m), 5.25 (2H, s), 5.80-5.93 (1H, m), 6.98-7.04 (2H, m), 7.31-7.35 (7H, m), 8.45 (1H, s), 10.41 (1H, m).

14) To a solution of the compound 15 (7.6 g, 16.9 mmol) in 1,4-dioxane (228 ml) was added an aqueous solution (38 ml) of potassium osmate dihydrate (372 mg, 1.01 mmol), and sodium metaperiodate (14.5 g, 67.6 mmol) was further added, followed by stirring at room temperature for 2 hours. The reaction solution was added to a vessel to which ethyl acetate (300 ml) and water (300 ml) had been added, while stirring. The organic layer was washed with water, a 5% aqueous sodium hydrogen sulfite solution and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-oxo-1-(2-oxo-ethyl)-1,4-dihydro-pyridine-2-carboxylic acid methyl ester 16 (5.39 g, 71%) as a colorless crystal.

NMR (CDCl$_3$) δ: 3.74 (3H, s), 4.60 (2H, d, J=5.9 Hz), 4.87 (2H, s), 5.27 (2H, s), 6.98-7.04 (2H, m), 7.30-7.40 (7H, m), 8.39 (1H, s), 9.58 (1H, s), 10.38 (1H, s).

15) To a solution of the compound 16 (400 mg, 0.884 mmol) in methylene chloride (12 ml) were added 2-methoxyethylamine (77 ul, 0.884 mmol) and acetic acid (18 ul), and the mixture was stirred at room temperature for 5 minutes. Thereafter, the reaction was performed at 140° C. for 30 minutes in a microwave reaction apparatus. The solvent was distilled off under reduced pressure, the residue was subjected to silica gel column chromatography, and fractions eluting with toluene-acetone were concentrated under reduced pressure to obtain 9-benzyloxy-2-(2-methoxy-ethyl)-1,8-dioxo-1,8-dihydro-2H-pyrid[1,2-a]pyrazine-7-carboxylic acid 4-fluoro-benzylamide 17-1 (226 mg, 54%) as a yellow solid.

NMR (CDCl$_3$) δ: 3.35 (3H, s), 3.65 (2H, t, J=5.1 Hz), 3.97 (2H, t, J=4.5 Hz), 4.63 (2H, d, J=5.7 Hz), 5.28 (2H, s), 6.56 (2H, m), 7.01 (2H, t, J=8.7 Hz), 7.38-7.30 (5H, m), 7.65 (2H, d, J=6.6 Hz), 10.63 (1H, s).

According to the similar method, the following compounds were synthesized.

Compound 17-2

9-Benzyloxy-2-(2-dimethylamino-ethyl)-1,8-dioxo-1,8-dihydro-2H-pyrid[1,2-a]pyrazine-7-carboxylic acid 4-fluoro-benzylamide NMR (CDCl$_3$) δ: 2.68 (6H, s), 3.33 (2H, t, J=6.6 Hz), 4.28 (2H, t, J=6.6 Hz), 4.62 (2H, d, J=6.0 Hz), 5.25 (2H, s), 6.85-6.92 (2H, m), 7.03 (2H, t, J=8.7 Hz), 7.31-7.40 (5H, m), 7.62 (2H, d, J=6.3 Hz), 8.65 (1H, s), 10.63 (1H, t, J=6.0 Hz).

Compound 17-3

9-Benzyloxy-2-(2-morpholin-4-yl-ethyl)-1,8-dioxo-1,8-dihydro-2H-pyrid[1,2-a]pyrazine-7-carboxylic acid 4-fluoro-benzylamide NMR (CDCl$_3$) δ: 2.59 (4H, s), 2.74 (2H, s), 3.73 (4H, s), 3.95 (2H, s), 4.62 (2H, d, J=6.0 Hz), 5.28 (1H, s), 6.53 (1H, d, J=6.0 Hz), 6.63 (1H, d, J=6.0 Hz), 7.01 (2H, t, J=8.7 Hz), 7.26-7.38 (5H, m), 7.64 (2H, d, J=6.9 Hz), 8.61 (1H, s), 10.61 (1H, t, J=5.4 Hz).

Compound 17-4

9-Benzyloxy-1,8-dioxo-2-(2-piperidin-1-yl-ethyl)-1,8-dihydro-2H-pyrid[1,2-a]pyrazine-7-carboxylic acid 4-fluoro-benzylamide NMR (CDCl$_3$) δ: 1.55-1.76 (6H, m), 2.71-2.87 (6H, m), 4.13 (2H, brs), 4.62 (2H, d, J=6 Hz), 5.28 (2H, s), 6.62 (1H, d, J=6.2 Hz), 6.77 (1H, m), 6.97-7.04 (2H, m), 7.30-7.39 (5H, m), 7.62-7.63 (2H, m), 8.59 (1H, s), 10.56-10.61 (1H, m).

Compound 17-5

9-Benzyloxy-2-(2-methyl-butyl)-1,8-dioxo-1,8-dihydro-2H-pyrid[1,2-a]pyrazine-7-carboxylic acid 4-fluoro-benzylamide NMR (CDCl$_3$) δ: 0.92-0.99 (6H, m), 1.17-1.26 (1H, m), 1.44-1.50 (1H, m), 1.88-1.92 (1H, m), 3.52-3.59 (1H, m), 3.68-3.75 (1H, m), 4.62 (2H, d, J=6 Hz), 5.29 (2H, s), 6.36 (1H, d, J=6 Hz), 6.59 (1H, d, J=6 Hz), 6.98-7.04 (2H, m), 7.29-7.37 (6H, m), 7.62-7.65 (2H, m), 8.57 (1H, s), 10.62 (1H, m).

Compound 17-6

9-Benzyloxy-2-(2-isopropoxy-ethyl)-1,8-dioxo-1,8-dihydro-2H-pyrid[1,2-a]pyrazine-7-carboxylic acid 4-fluoro-benzylamide NMR (CDCl$_3$) δ: 1.12 (6H, d, J=6 Hz), 3.51-3.59 (1H, m), 3.68 (2H, t, J=4.8 Hz), 3.96 (2H, t, J=4.8 Hz), 4.62 (2H, d, J=6 Hz), 5.28 (2H, s), 6.58-6.64 (2H, m), 6.98-7.04 (2H, m), 7.30-7.39 (5H, m), 7.64-7.66 (2H, m), 8.59 (1H, brs), 10.63 (1H, brs).

Compound 17-7

9-Benzyloxy-2-isopropyl-1,8-dioxo-1,8-dihydro-2H-pyrid[1,2-a]pyrazine-7-carboxylic acid 4-fluoro-benzylamide NMR (CDCl$_3$) δ: 1.31 (6H, d, J=6.9 Hz), 4.62 (2H, d, J=6.0 Hz), 5.08-5.17 (1H, m), 5.27 (2H, s), 6.39 (1H, d, J=6.3 Hz), 6.73 (1H, d, J=6.3 Hz), 6.98-7.04 (2H, m), 7.16-7.39 (5H, m), 7.66-7.68 (2H, m), 8.66 (1H, s), 10.67 (1H, t, J=5.5 Hz).

Compound 17-8

9-Benzyloxy-2-cyclohexyl-1,8-dioxo-1,8-dihydro-2H-pyrid[1,2-a]pyrazine-7-carboxylic Acid 4-fluoro-benzylamide NMR (CDCl$_3$) δ: 1.15-1.92 (10H, m), 4.62 (2H, d, J=6.1 Hz), 4.70-4.78 (1H, m), 5.27 (2H, s), 6.43 (1H, d, J=6.4 Hz), 6.69 (1H, d, J=6.3 Hz), 7.01-7.16 (2H, m), 7.18-7.37 (5H, m), 7.66-7.68 (2H, m), 8.63 (1H, s), 10.67 (1H, t, J=5.5 Hz).

Compound 17-9

9-Benzyloxy-2-(4-fluoro-benzyl)-1,8-dioxo-1,8-dihydro-2H-pyrid[1,2-a]pyrazine-7-carboxylic acid 4-fluoro-benzylamide NMR (CDCl$_3$) δ: 4.61 (2H, d, J=6.0 Hz), 4.92 (2H, s), 5.31 (2H, s), 6.28 (1H, d, J=6.1 Hz), 6.62 (1H, d, J=6.3 Hz), 6.97-7.09 (4H, m), 7.25-7.38 (7H, m), 7.62-7.66 (2H, m), 8.60 (1H, s), 10.59 (1H, t, J=6.0 Hz).

Compound 17-10

9-Benzyloxy-1,8-dioxo-2-[2-(propyl-m-toluoyl-amino)-ethyl]-1,8-dihydro-2H-pyrid[1,2-a]pyrazine-7-carboxylic acid 4-fluoro-benzylamide NMR (CDCl$_3$) δ: 1.09 (3H, t, J=6.6 Hz), 2.29 (3H, s), 3.28-3.32 (2H, m), 3.61-3.65 (2H, m), 3.94-3.98 (2H, m), 4.62 (2H, d, J=5.7 Hz), 5.31 (2H, s), 6.21 (1H, d, J=6.0 Hz), 6.49 (1H, d, J=6.0 Hz), 6.54 (3H, brs), 6.89-7.04 (2H, m), 7.08-7.39 (6H, m), 7.66 (2H, d, J=6.3 Hz), 8.54 (1H, s), 10.57-10.62 (1H, m).

Compound 17-11

9-Benzyloxy-1,8-dioxo-2-[3-(2-oxo-pyrrolodin-1-yl)-propyl]-1,8-dihydro-2H-pyrid[1,2-a]pyrazine-7-carboxylic acid 4-fluoro-benzylamide NMR (CDCl$_3$) δ: 1.96 (2H, t, J=6.6 Hz), 2.07 (2H, t, J=7.5 Hz), 2.42 (2H, t, J=7.8 Hz), 3.36 (2H, t, J=6.6 Hz), 3.43 (2H, t, J=6.9 Hz), 3.76 (2H, t, J=6.6 Hz), 4.62 (2H, d, J=6.0 Hz), 5.28 (2H, s), 6.62 (1H, d, J=6.3 Hz), 6.78 (1H, d, J=6.3 Hz), 6.98-7.04 (2H, m), 7.30-7.38 (5H, m), 7.63-7.65 (2H, m), 8.59 (1H, s), 10.59-10.63 (1H, m).

Compound 17-12

9-Benzyloxy-1,8-dioxo-2-(2-tetrahydrofuran-2-ylm-ethyl)-1,8-dihydro-2H-pyrid[1,2-a]pyrazine-7-carboxylic acid 4-fluoro-benzylamide NMR (CDCl$_3$) δ: 1.48-1.62 (1H, m), 1.87-1.98 (2H, m), 2.05-2.17 (1H, m), 3.47 (1H, dd, J=14.1, 8.1 Hz), 3.73-3.82 (1H, m), 3.84-3.92 (1H, m), 4.12-4.21 (1H, m), 4.21 (1H, dd, J=13.8, 2.4 Hz), 4.62 (2H, d, J=6.0 Hz), 5.28 (2H, s), 6.58 (1H, d, J=6.2 Hz), 6.67 (1H, d, J=6.2 Hz), 6.97-7.05 (2H, m), 7.28-7.39 (5H, m), 7.62-7.66 (2H, m), 8.58 (1H, m), 10.60-10.68 (1H, m).

Compound 17-13

9-Benzyloxy-1,8-dioxo-2-pyridin-4-ylmethyl-1,8-dihydro-2H-pyrid[1,2-a]pyrazine-7-carboxylic Acid 4-fluoro-benzylamide NMR (CDCl$_3$) δ: 4.63 (2H, d, J=6.0 Hz), 5.00 (2H, s), 5.31 (2H, s), 6.37 (1H, d, J=6.1 Hz), 6.68 (1H, d, J=6.1 Hz), 6.97-7.06 (2H, m), 7.28-7.38 (7H, m), 7.56-7.61 (2H, m), 8.61 (1H, s), 8.62-8.66 (2H, m), 10.50 (1H, t, J=6.0 Hz).

Compound 17-14

4-[9-Benzyloxy-7-(4-fluoro-benzylcarbamoyl)-1,8-dioxo-1,8-dihydro-2H-pyrid[1,2-a]pyrazin-2-yl]-piperidine-1-carboxylic acid Ethyl Ester NMR (CDCl$_3$) δ: 1.26 (3H, t, J=7.0 Hz), 1.62-1.69 (2H, m), 1.84-1.87 (2H, m), 2.88-2.96 (2H, m), 4.16 (2H, q, J=7.0 Hz), 4.35 (1H, brs), 4.62 (2H, d, J=5.9 Hz), 5.27 (2H, s), 6.37 (1H, d, J=6.3 Hz), 6.69 (1H, d, J=5.6 Hz), 6.98-7.04 (2H, m), 7.16-7.40 (5H, m), 7.64-7.67 (2H, m), 8.62 (1H, brs), 10.59 (1H, brs).

Compound 17-15

9-Benzyloxy-2-methyl-1,8-dioxo-1,8-dihydro-2H-pyrid[1,2-a]pyrazine-7-carboxylic acid 4-fluoro-benzylamide NMR (CDCl$_3$) δ: 3.40 (3H, s), 4.62 (2H, d, J=6.0 Hz), 5.27 (2H, s), 6.37 (1H, d, J=6.0 Hz), 6.64 (1H, d, J=6.0 Hz), 6.97-7.05 (2H, m), 7.28-7.40 (5H, m), 7.63-7.68 (2H, m), 8.60 (1H, brs), 10.61 (1H, brs).

Compound 17-16

2-(2-Acetylamino-ethyl)-9-benzyloxy-1,8-dioxo-1,8-dihydro-2H-pyrid[1,2-a]pyrazine-7-carboxylic acid 4-fluoro-benzylamide NMR (DMSO-d$_6$) δ: 1.76 (3H, s), 3.33 (2H, s), 3.79 (2H, s), 4.55 (2H, d, J=5.1 Hz), 5.05 (2H, s), 6.89 (1H, d, J=6.0 Hz), 7.17 (2H, t, J=8.4 Hz), 7.30-7.50 (5H, m), 7.61 (2H, d, J=5.1 Hz), 7.96 (1H, s), 8.93 (1H, s), 10.61 (1H, s).

Compound 17-17

9-Benzyloxy-2-(3-isopropoxy-propyl)-1,8-dioxo-1,8-dihydro-2H-pyrid[1,2-a]pyrazine-7-carboxylic acid 4-fluoro-benzylamide NMR (CDCl$_3$) δ: 1.15 (6H, d, J=6.1 Hz), 1.93-2.02 (2H, m), 3.45 (2H, t, J=5.7 Hz), 3.55 (1H, sep, J=6.1 Hz), 3.90 (2H, d, J=6.8 Hz), 4.62 (2H, d, J=6.0 Hz), 5.28 (2H, s), 6.49 (1H, d, J=6.3 Hz), 6.59 (1H, d, J=6.3 Hz), 6.97-7.05 (2H, m), 7.27-7.38 (5H, m), 7.62-7.65 (2H, m), 8.58 (1H, s), 10.58-10.65 (1H, m).

Compound 17-18

9-Benzyloxy-2-(4-dimethylamino-benzyl)-1,8-di-oxo-1,8-dihydro-2H-pyrid[1,2-a]pyrazine-7-carboxylic Acid 4-fluoro-benzylamide NMR (CDCl$_3$) δ: 2.98 (6H, s), 4.62 (2H, d, J=6.0 Hz), 4.88 (2H, s), 5.31 (2H, s), 6.35 (1H, d, J=6.2 Hz), 6.54 (1H, d, J=6.2 Hz), 6.77 (2H, brs), 6.87-7.05 (2H, m), 7.19-7.25 (2H, m), 7.29-7.41 (2H, m), 7.65-7.70 (2H, m), 8.54 (1H, s), 10.62 (1H, t, J=5.6 Hz).

Compound 17-19

9-Benzyloxy-1,8-dioxo-2-(4-sulfamoyl-1-benzyl)-1,8-dihydro-2H-pyrid[1,2-a]pyrazine-7-carboxylic acid 4-fluoro-benzylamide NMR (CDCl$_3$) δ: 4.62 (2H, s), 5.04 (2H, s), 5.28 (2H, s), 6.51 (1H, d, J=6.3 Hz), 6.87 (1H, d, J=6.3 Hz), 7.00-7.06 (2H, m), 7.20-7.40 (5H, m), 7.44-7.47 (2H, m), 7.59-7.62 (2H, m), 7.90-7.93 (2H, m), 8.63 (1H, s).

Compound 17-20

9-Benzyloxy-2-[3-(4-methyl-piperazin-1-yl)-propyl]-1,8-dioxo-1,8-dihydro-2H-pyrid[1,2-a]pyrazine-7-carboxylic Acid 4-fluoro-benzylamide NMR (CDCl$_3$) δ: 1.87-1.97 (2H, m), 2.34 (3H, s), 2.42 (2H, d, J=6.8 Hz), 2.54 (8H, brs), 3.85 (2H, d, J=6.9 Hz), 4.62 (2H, d, J=5.9 Hz), 5.28 (2H, s), 6.52 (1H, d, J=6.3 Hz), 6.60

(1H, d, J=6.3 Hz), 6.95-7.05 (2H, m), 7.28-7.38 (5H, m), 7.61-7.66 (2H, m), 8.59 (1H, s), 10.61 (1H, t, J=5.9 Hz).

Compound 17-21

9-Benzyloxy-2-(3-methoxy-propyl)-1,8-dioxo-1,8-dihydro-2H-pyrid[1,2-a]pyrazine-7-carboxylic acid 4-fluoro-benzylamide NMR (CDCl$_3$) δ: 1.99 (2H, quin, J=5.7 Hz), 3.34 (3H, s), 3.60 (2H, t, J=6.3 Hz), 3.95 (2H, t, J=6.3 Hz), 4.62 (2H, d, J=5.7 Hz), 5.28 (2H, s), 6.45 (1H, d, J=6.3 Hz), 6.61 (1H, d, J=6.3 Hz), 7.01 (2H, t, J=6.6 Hz), 7.28-7.38 (5H, m), 7.64 (2H, d, J=6.6 Hz), 8.59 (1H, s), 10.62 (1H, s).

Compound 17-22

9-Benzyloxy-1,8-dioxo-2-(2-propoxy-ethyl)-1,8-dihydro-2H-pyrid[1,2-a]pyrazine-7-carboxylic acid 4-fluoro-benzylamide NMR (CDCl$_3$) δ: 0.89 (3H, t, J=7.5 Hz), 1.55 (2H, m), 3.38 (2H, t, J=6.6 Hz), 3.68 (2H, t, J=4.8 Hz), 3.98 (2H, t, J=4.5 Hz), 4.62 (2H, d, J=5.7 Hz), 5.28 (2H, s), 6.57 (1H, d, J=5.7 Hz), 6.60 (1H, d, J=5.7 Hz), 7.01 (2H, t, J=8.7 Hz), 7.30-7.38 (5H, m), 7.65 (2H, d, J=6.9 Hz), 8.59 (1H, s), 10.63 (1H, s).

Compound 17-23

9-Benzyloxy-1,8-dioxo-2-(2-phenoxy-ethyl)-1,8-dihydro-2H-pyrid[1,2-a]pyrazine-7-carboxylic Acid 4-fluoro-benzylamide NMR (CDCl$_3$) δ: 4.17-4.20 (2H, m), 4.25-4.28 (2H, m), 4.62 (2H, d, J=5.6 Hz), 5.28 (2H, s), 6.60-6.66 (1H, m), 6.86 (2H, d, J=8.0 Hz), 6.95-7.04 (2H, m), 7.28-7.37 (8H, m), 7.64 (2H, d, J=7.0 Hz), 8.59 (1H, s), 10.60 (1H, brs).

Compound 17-24

9-Benzyloxy-1,8-dioxo-2-(2-pyridin-3-yl-ethyl)-1,8-dihydro-2H-pyrid[1,2-a]pyrazine-7-carboxylic Acid 4-fluoro-benzylamide NMR (CDCl$_3$) δ: 3.04 (2H, t, J=7.2 Hz), 4.00 (2H, t, J=7.2 Hz), 4.62 (2H, d, J=6.0 Hz), 5.29 (2H, s), 6.10 (1H, d, J=6.3 Hz), 6.52 (1H, d, J=6.3 Hz), 7.01 (2H, m), 7.24 (1H, m), 7.30-7.39 (5H, m), 7.53 (1H, m), 7.62-7.66 (2H, m), 8.46 (1H, m), 8.52 (1H, dd, J=1.5 Hz, 4.5 Hz), 8.56 (1H, s), 10.57 (1H, brt, J=6.0 Hz).

Compound 17-25

9-Benzyloxy-2-dimethylcarbamoylmethyl-1,8-dioxo-1,8-dihydro-2H-pyrid[1,2-a]pyrazine-7-carboxylic acid 4-fluoro-benzylamide NMR (CDCl$_3$) δ: 3.01 (3H, s), 3.13 (3H, s), 4.59 (2H, s), 4.63 (2H, d, J=6.0 Hz), 5.26 (2H, s), 6.42 (1H, d, J=6.0 Hz), 6.64 (1H, d, J=6.0 Hz), 7.01 (2H, m), 7.29-7.36 (5H, m), 7.64 (2H, m), 8.60 (1H, s), 10.59 (1H, brt, J=6.0 Hz).

Compound 17-26

9-Benzyloxy-2-(2-ethoxy-ethyl)-1,8-dioxo-1,8-dihydro-2H-pyrid[1,2-a]pyrazine-7-carboxylic acid 4-fluoro-benzylamide NMR (CDCl$_3$) δ: 1.18 (3H, t, J=7.0 Hz), 3.49 (2H, q, J=7.0 Hz), 3.66-3.71 (2H, m), 3.96-4.00 (2H, m), 4.63 (2H, d, J=6.0 Hz), 5.28 (2H, s), 6.57 (1H, d, J=5.9 Hz), 6.61 (1H, d, J=5.9 Hz), 6.98-7.06 (2H, m), 7.29-7.40 (5H, m), 7.63-7.67 (2H, m), 8.59 (1H, s), 10.60-10.68 (1H, m).

Compound 17-27

9-Benzyloxy-2-furan-2-ylmethyl-1,8-dioxo-1,8-dihydro-2H-pyrid[1,2-a]pyrazine-7-carboxylic Acid 4-fluoro-benzylamide NMR (DMSO-d$_6$) δ: 4.55 (2H, d, J=5.7 Hz), 4.99 (2H, s), 5.07 (2H, s), 6.44 (1H, dd, J=1.8 Hz, 3.0 Hz), 6.51 (1H, dd, J=0.9 Hz, 3.0 Hz), 6.99 (1H, d, J=6.3 Hz), 7.17 (2H, m), 7.31-7.41 (4H, m), 7.46 (1H, d, J=6.6 Hz), 7.58-7.62 (2H, m), 7.65 (1H, dd, J=0.9 Hz, 1.8 Hz), 8.89 (1H, s), 10.57 (1H, brt, J=5.7 Hz).

Compound 17-28

9-Benzyloxy-2-[2-(4-chloro-phenyl)-ethyl]-1,8-dioxo-1,8-dihydro-2H-pyrid[1,2-a]pyrazine-7-carboxylic acid 4-fluoro-benzylamide NMR (CDCl$_3$) δ: 3.00 (2H, t, J=7.2 Hz), 3.98 (2H, t, J=7.2 Hz), 4.62 (2H, d, J=5.4 Hz), 5.30 (2H, s), 6.06 (1H, d, J=6.3 Hz), 6.46 (1H, d, J=6.3 Hz), 7.01 (2H, m), 7.11 (2H, m), 7.17-7.40 (9H, m), 7.64 (2H, m), 8.53 (1H, s), 10.58 (1H, brt, J=5.4 Hz).

Compound 17-29

9-Benzyloxy-2-(1-benzyl-pyrrolidin-3-yl)-1,8-dioxo-1,8-dihydro-2H-pyrid[1,2-a]pyrazine-7-carboxylic Acid 4-fluoro-benzylamide NMR (CDCl$_3$) δ: 1.75 (1H, m), 2.21 (1H, m), 2.44-2.55 (2H, m), 2.87 (1H, brd, J=10.8 Hz), 3.15 (1H, brt, J=8.7 Hz), 3.56 (1H, d, J=9.9 Hz), 3.69 (1H, d, J=9.9 Hz), 4.62 (2H, d, J=5.7 Hz), 5.25 (2H, s), 6.66 (1H, d, J=6.3 Hz), 6.98 (1H, d, J=6.3 Hz), 7.00 (2H, m), 7.15-7.38 (10H, m), 7.62-7.66 (2H, m), 8.58 (1H, s), 10.63 (1H, brt, J=5.7 Hz).

Compound 17-30

9-Benzyloxy-1,8-dioxo-2-thiophen-2-ylmethyl-1,8-dihydro-2H-pyrid[1,2-a]pyrazine-7-carboxylic Acid 4-fluoro-benzylamide NMR (CDCl$_3$) δ: 4.63 (2H, d, J=5.2 Hz), 5.13 (2H, s), 5.32 (2H, s), 6.43-6.44 (1H, m), 6.58-6.60 (1H, m), 6.98-7.04 (3H, m), 7.13-7.14 (1H, m), 7.28-7.39 (6H, m), 7.65-7.67 (2H, m), 8.56 (1H, s), 10.58 (1H, brs).

Compound 17-31

9-Benzyloxy-2-(3-dimethylamino-2,2-dimethyl-propyl)-1,8-dioxo-1,8-dihydro-2H-pyrid[1,2-a]pyrazine-7-carboxylic acid 4-fluoro-benzylamide NMR (CDCl$_3$) δ: 0.99 (6H, brs), 1.62 (1H, brs), 2.22 (1H, brs), 2.33 (6H, brs), 3.83 (2H, brs), 4.62 (2H, d, J=6.0 Hz), 5.29 (2H, s), 6.56 (1H, d, J=6.3 Hz), 6.64 (1H, brs), 7.01 (2H, t, J=8.1 Hz), 7.27-7.36 (5H, m), 7.62 (2H, d, J=8.1 Hz), 8.57 (1H, s), 10.62 (1H, t, J=5.7 Hz).

Compound 17-32

9-Benzyloxy-2-(3-morpholin-4-yl-propyl)-1,8-dioxo-1,8-dihydro-2H-pyrid[1,2-a]pyrazine-7-carboxylic Acid 4-fluoro-benzylamide NMR (CDCl$_3$) δ: 1.92 (2H, tt, J=6.6 Hz, 6.9 Hz), 2.39 (2H, t, J=6.6 Hz), 2.43 (4H, brt, J=4.8 Hz), 3.70 (4H, brt, J=4.8 Hz), 3.86 (2H, t, J=6.9 Hz), 4.62 (2H, d, J=6.0 Hz), 5.28 (2H, s), 6.50 (1H, d, J=6.3 Hz), 6.61 (1H, d, J=6.3 Hz), 7.01 (2H, m), 7.29-7.38 (5H, m), 7.62-7.65 (2H, m), 8.60 (1H, s), 10.62 (1H, brt, J=6.0 Hz).

16) To the compound 17-1 (140 mg, 0.293 mmol) was added trifluoroacetic acid (1.4 ml) under ice-cooling, and the mixture was stirred at 0° C. for 5 minutes and, then, at room temperature for 1.5 hours. The solvent was distilled off under reduced pressure, and this was diluted with chloroform, and added to ice water. This was washed with an aqueous saturated sodium bicarbonate solution, a 10% aqueous citric acid solution and water, and dried with anhydrous sodium sulfate. The solvent was distilled off under reduced pressure, and the residue was recrystallized with methylene chloride-ethanol to obtain Example A-1 (89 mg, 79%) as a yellow crystal.

melting point: 223-224° C.

NMR (DMSO-d$_6$) δ: 3.25 (3H, s), 3.58 (2H, t, J=5.4 Hz), 3.92 (2H, t, J=5.1 Hz), 4.53 (2H, d, J=5.7 Hz), 6.87 (1H, d, 6.3 Hz), 7.14 (2H, t, J=9.0 Hz), 7.33-7.38 (2H, m), 7.47 (1H, d, J=6.0 Hz), 8.77 (1H, s), 10.56 (1H, t, J=6.0 Hz), 12.00 (1H, brs).

17) The compound 17-1 (157 mg, 0.329 mmol) was dissolved in dimethylformamide (18 ml) and methanol (1 ml), 10% palladium-carbon powder (31 mg) was added, and the mixture was stirred at room temperature for 20 hours under the hydrogen atmosphere. The reaction solution was filtered with Celite, and the filtrate was concentrated under reduced pressure. The residue was dissolved in chloroform, this was filtered with Celite again, and the filtrate was concentrated under reduced pressure. The residue was recrystallized with methylene chloride-methanol to obtain Example B-1 (66 mg, 52%) as a brown crystal.

melting point: 197-199° C.

NMR (DMSO-d$_6$) δ: 3.27 (3H, s), 3.55 (2H, t, J=5.1 Hz), 3.68 (2H, t, J=5.1 Hz), 3.79 (2H, s), 4.36 (2H, s), 4.51 (2H, d, J=5.7 Hz), 7.15 (2H, t, J=8.7 Hz), 7.32-7.37 (2H, m), 8.38 (1H, s), 10.46 (1H, t, J=5.4 Hz), 12.41 (1H, s).

According to the same manner as that of Example A-1, the following Example compounds A-2 to A-29, and A-31 to A-32 were synthesized.

Example A-2

2-(2-Dimethylamino-ethyl)-9-hydroxy-1,8-dioxo-1,8-dihydro-2H-pyrid[1,2-a]pyrazine-7-carboxylic acid 4-fluoro-benzylamide melting point: 224-225° C.

NMR (DMSO-d$_6$) δ: 2.24 (6H, s), 2.59 (2H, t, J=6.0 Hz), 3.87 (2H, t, J=6.0 Hz), 4.55 (2H, d, J=6.0 Hz), 6.94 (1H, d, J=6.3 Hz), 7.17 (2H, t, J=6.9 Hz), 7.35-7.40 (2H, m), 7.50 (1H, d, J=6.3 Hz), 8.80 (1H, s), 10.59 (1H, t, J=6.0 Hz), 12.05 (1H, s).

Example A-3

9-Hydroxy-2-(2-morpholin-4-yl-ethyl)-1,8-dioxo-1,8-dihydro-2H-pyrid[1,2-a]pyrazine-7-carboxylic acid 4-fluoro-benzylamide melting point: 212-215° C.

NMR (DMSO-d$_6$) δ: 2.51 (4H, s), 2.38 (3H, s), 3.55 (4H, s), 3.90 (2H, s), 4.55 (2H, d, J=6.0 Hz), 6.95 (1H, d, J=6.3 Hz), 7.17 (2H, t, J=8.7 Hz), 7.35-7.40 (2H, m), 7.50 (1H, d, J=6.3 Hz), 10.58 (1H, t, J=6.3 Hz), 12.10 (1H, s).

Example A-4

9-Hydroxy-1,8-dioxo-2-(2-piperidin-1-yl-ethyl)-1,8-dihydro-2H-pyrid[1,2-a]pyrazine-7-carboxylic acid 4-fluoro-benzylamide melting point: 217-218° C.
Elementary analysis for $C_{23}H_{25}FN_4O_4$
Cal'd (%): C, 62.72; H, 5.72; F, 4.31; N, 12.72.
Found (%): C, 58.98; H, 5.46; F, 6.16; N, 11.66.
NMR (DMSO-d$_6$) δ: 1.41-1.51 (6H, m), 2.49-2.73 (6H, m), 3.91 (2H, m), 4.54 (2H, d, J=6 Hz), 6.93 (1H, d, J=6 Hz), 7.13-7.19 (2H, m), 7.35-7.39 (2H, m), 7.50 (1H, d, J=6 Hz), 8.80 (1H, s), 10.57 (1H, t, J=5.7 Hz), 12.14 (1H, brs).

Example A-5

9-Hydroxy-2-(2-methyl-butyl)-1,8-dioxo-1,8-dihydro-2H-pyrid[1,2-a]pyrazine-7-carboxylic acid 4-fluoro-benzylamide melting point: 242-243° C.
Elementary analysis for $C_{21}H_{22}FN_3O_4$
Cal'd (%): C, 63.15; H, 5.55; F, 4.76; N, 10.52.
Found (%): C, 63.14; H, 5.57; F, 4.63; N, 10.54.
NMR (DMSO-d$_6$) δ: 0.86-0.94 (6H, m), 1.08-1.20 (1H, m), 1.33-1.55 (1H, m), 1.81-1.90 (1H, m), 3.51-3.58 (1H, m), 3.65-3.71 (1H, m), 4.54 (2H, d, J=6 Hz), 6.92 (1H, d, J=6.3 Hz), 7.13-7.20 (2H, m), 7.34-7.39 (2H, m), 7.50 (1H, d, J=6.3 Hz), 8.79 (1H, s), 10.60 (1H, t, J=5.7 Hz), 12.13 (1H, brs).

Example A-6

9-Hydroxy-2-(2-isopropoxy-ethyl)-1,8-dioxo-1,8-dihydro-2H-pyrid[1,2-a]pyrazine-7-carboxylic acid 4-fluoro-benzylamide melting point: 209-210° C.
Elementary analysis for $C_{21}H_{22}FN_3O_5$
Cal'd (%): C, 60.72; H, 5.34; F, 4.57; N, 10.12.
Found (%): C, 60.78; H, 5.29; F, 4.34; N, 10.11.
NMR (DMSO-d$_6$) δ: 1.06 (6H, d, J=6.3 Hz), 3.54-3.64 (3H, m), 3.90 (2H, t, J=5.4 Hz), 6.89 (1H, d, J=6.3 Hz), 7.13-7.19 (2H, m), 7.35-7.39 (2H, m), 7.47 (1H, d, J=6.3 Hz), 8.77 (1H, s), 10.58 (1H, t, J=5.7 Hz), 12.04 (1H, brs).

Example A-7

9-Hydroxy-2-isopropyl-1,8-dioxo-1,8-dihydro-2H-pyrid[1,2-a]pyrazine-7-carboxylic acid 4-fluoro-benzylamide melting point: 282-283° C.
NMR (DMSO-d$_6$) δ: 1.29 (6H, d, J=6.9 Hz), 4.54 (2H, d, J=5.9 Hz), 4.83-4.92 (1H, m), 7.04 (1H, d, J=6.4 Hz), 7.13-

7.19 (2H, m), 7.35-7.40 (2H, m), 7.56 (1H, d, J=6.4 Hz), 8.80 (1H, s), 10.61 (1H, t, J=5.8 Hz), 12.26 (1H, brs).

Example A-8

2-Cyclohexyl-9-hydroxy-1,8-dioxo-1,8-dihydro-2H-pyrid[1,2-a]pyrazine-7-carboxylic acid 4-fluoro-benzylamide melting point: >300° C.

NMR (DMSO-$d_6$) δ: 1.15-1.84 (10H, m), 4.43-4.49 (1H, m), 4.53 (2H, d, J=5.8 Hz), 7.05 (1H, d, J=6.4 Hz), 7.13-7.19 (2H, m), 7.34-7.39 (2H, m), 7.53 (1H, d, J=6.4 Hz), 8.79 (1H, s), 10.61 (1H, t, J=5.8 Hz), 12.23 (1H, brs).

Example A-9

9-Hydroxy-1,8-dioxo-2-[2-(propyl-m-toluoyl-amino)-ethyl]-1,8-dihydro-2H-pyrid[1,2-a]pyrazine-7-carboxylic acid 4-fluoro-benzylamide melting point: 190-192° C.

NMR (CDCl$_3$) δ: 1.10-1.16 (3H, m), 2.29 (3H, s), 3.29-3.38 (2H, m), 3.63-3.69 (2H, m), 3.94-3.99 (2H, m), 4.62 (2H, d, J=6.0 Hz), 6.13-6.19 (1H, m), 6.52-6.61 (4H, m), 6.96-7.40 (2H, m), 6.96-7.04 (2H, m), 7.04-7.17 (1H, m), 7.29-7.36 (2H, m), 8.47 (1H, s), 10.56 (1H, brs), 11.89 (1H, brs).

Example A-10

9-Hydroxy-1,8-dioxo-2-[3-(2-oxo-pyrrolidin-1-yl)-propyl]-1,8-dihydro-2H-pyrid[1,2-a]pyrazine-7-carboxylic acid 4-fluoro-benzylamide melting point: 262-264° C.

NMR (CDCl$_3$) δ: 1.93-2.04 (2H, m), 2.04-2.15 (2H, m), 2.39-2.46 (2H, m), 3.35-3.46 (4H, m), 3.75-3.81 (2H, m), 4.62 (2H, d, J=5.7 Hz), 6.69 (1H, d, J=6.3 Hz), 6.78 (1H, d, J=6.3 Hz), 6.95-7.04 (2H, m), 7.29-7.37 (2H, m), 8.53 (1H, s), 10.58 (1H, brs), 11.89 (1H, brs).

Example A-11

9-Hydroxy-1,8-dioxo-2-(2-tetrahydrofuran-2-ylmethyl)-1,8-dihydro-2H-pyrid[1,2-a]pyrazine-7-carboxylic acid 4-fluoro-benzylamide melting point: 248-249° C.

NMR (CDCl$_3$) δ: 1.52-1.66 (1H, m), 1.90-2.00 (2H, m), 2.06-2.18 (1H, m), 3.52-3.61 (1H, m), 3.71-3.83 (1H, m), 3.85-3.94 (1H, m), 4.12-4.24 (1H, m), 4.63 (2H, d, J=6.0 Hz), 6.59 (1H, d, J=6.5 Hz), 6.66 (1H, d, J=6.5 Hz), 6.96-7.04 (2H, m), 7.29-7.37 (2H, m), 8.52 (1H, s), 10.61 (1H, brs), 11.97 (1H, brs).

Example A-12

9-Hydroxy-1,8-dioxo-2-pyridin-4-ylmethyl-1,8-dihydro-2H-pyrid[1,2-a]pyrazine-7-carboxylic Acid 4-fluoro-benzylamide melting point: 265-268° C.

NMR (DMSO-$d_6$) δ: 4.55 (2H, d, J=5.4 Hz), 5.02 (2H, s), 7.02 (1H, d, J=6.5 Hz), 7.13-7.22 (2H, m), 7.34-7.42 (4H, m), 7.56 (1H, d, J=6.51 Hz), 8.54-8.57 (2H, m), 8.83 (1H, s), 10.54-10.56 (1H, m), 11.78 (1H, s).

Example A-13

4-[7-(4-Fluoro-benzylcarbamoyl)-9-hydroxy-1,8-dioxo-1,8-dihydro-pyrid[1,2-a]pyrazin-2-yl]-piperidine-1-carboxylic acid ethyl ester melting point: 288-289° C.

NMR (CDCl$_3$) δ: 1.29 (3H, t, J=7.0 Hz), 1.64-1.75 (2H, m), 1.86-1.92 (2H, m), 2.89-2.97 (2H, m), 4.16 (2H, q, J=7.0 Hz), 4.30-4.50 (2H, m), 4.62 (2H, d, J=5.8 Hz), 4.80-4.88 (1H, m), 6.33 (1H, d, J=6.6 Hz), 6.76 (1H, d, J=6.6 Hz), 6.97-7.03 (2H, m), 7.31-7.35 (2H, m), 8.56 (1H, s), 10.57 (1H, brs), 11.98 (1H, brs).

Example A-14

9-Hydroxy-2-methyl-1,8-dioxo-1,8-dihydro-2H-pyrid[1,2-a]pyrazine-7-carboxylic acid 4-fluoro-benzylamide melting point: 276-279° C.

NMR (CDCl$_3$) δ: 3.43 (3H, s), 4.63 (2H, d, J=5.7 Hz), 6.33 (1H, d, J=6.2 Hz), 6.71 (1H, d, J=6.2 Hz), 6.86-7.05 (2H, m), 7.30-7.37 (2H, m), 8.53 (1H, s), 10.59 (1H, brs), 11.95 (1H, brs).

Example A-15

2-(2-Acetylamino-ethyl)-9-hydroxy-1,8-dioxo-1,8-dihydro-2H-pyrid[1,2-a]pyrazine-7-carboxylic acid 4-fluoro-benzylamide melting point: >300° C.

NMR (DMSO-$d_6$) δ: 1.76 (3H, s), 3.37 (2H, t, J=5.7 Hz), 3.79 (2H, t, J=5.7 Hz), 4.54 (2H, d, J=5.7 Hz), 6.85 (1H, d, J=6.3 Hz), 7.16 (2H, m), 7.37 (2H, m), 7.48 (1H, d, J=6.3 Hz), 7.95 (1H, brt, J=5.7 Hz), 8.82 (1H, s), 10.58 (1H, brt, J=5.7 Hz), 12.07 (1H, s).

Example A-16

9-Hydroxy-2-(3-isopropoxy-propyl)-1,8-dioxo-1,8-dihydro-2H-pyrid[1,2-a]pyrazine-7-carboxylic acid 4-fluoro-benzylamide melting point: 180-181° C.

NMR (CDCl$_3$) δ: 1.14 (6H, d, J=6.1 Hz), 1.94-2.04 (2H, m), 3.48 (2H, t, J=5.7 Hz), 3.55 (1H, sep, J=6.1 Hz), 3.92 (2H, t, J=6.6 Hz), 4.63 (2H, d, J=6.0 Hz), 6.42 (1H, d, J=6.2 Hz), 6.67 (1H, d, J=6.2 Hz), 6.96-7.04 (2H, m), 7.30-7.37 (2H, m), 8.52 (1H, s), 10.61 (1H, brs), 12.05 (1H, brs).

Example A-17

2-(4-Dimethylamino-benzyl)-9-hydroxy-1,8-dioxo-1,8-dihydro-2H-pyrid[1,2-a]pyrazine-7-carboxylic acid 4-fluoro-benzylamide melting point: 245-247° C.

NMR (CDCl$_3$) δ: 2.98 (6H, s), 4.62 (2H, d, J=5.7 Hz), 4.87 (2H, s), 6.32 (1H, d, J=6.2 Hz), 6.63 (1H, d, J=6.2 Hz), 6.79

(2H, brs), 6.96-7.23 (2H, m), 7.21-7.25 (2H, m), 7.30-7.36 (2H, m), 8.49 (1H, s), 10.61 (1H, t, J=5.7 Hz), 12.08 (1H, brs).

Example A-18

9-Hydroxy-2-(3-methoxy-propyl)-1,8-dioxo-1,8-dihydro-2H-pyrid[1,2-a]pyrazine-7-carboxylic acid 4-fluoro-benzylamide melting point: 197-199° C.
NMR (CDCl$_3$) δ: 1.96-2.04 (2H, m), 3.34 (3H, s), 3.45 (2H, t, J=5.4 Hz), 3.90 (2H, t, J=6.9 Hz), 4.62 (2H, d, J=5.7 Hz), 5.11 (2H, s), 6.38 (1H, d, J=6.0 Hz), 6.70 (1H, d, J=6.0 Hz), 6.97-7.03 (2H, m), 7.31-7.35 (2H, m), 8.55 (1H, s), 10.61 (1H, brs), 12.03 (1H, brs).

Example A-19

9-Hydroxy-1,8-dioxo-2-(2-propoxy-ethyl)-1,8-dihydro-2H-pyrid[1,2-a]pyrazine-7-carboxylic acid 4-fluoro-benzylamide melting point: 215-217° C.
NMR (CDCl$_3$) δ: 0.90 (3H, t, J=7.5 Hz), 1.58 (2H, m), 3.41 (2H, t, J=6.6 Hz), 3.69 (2H, t, J=4.7 Hz), 3.97 (2H, t, J=4.6 Hz), 4.63 (2H, d, J=5.8 Hz), 6.53 (1H, d, J=6.3 Hz), 6.67 (1H, d, J=6.3 Hz), 6.97-7.03 (2H, m), 7.31-7.36 (2H, m), 8.54 (1H, s), 10.62 (1H, brs), 11.97 (1H, brs).

Example A-20

9-Hydroxy-1,8-dioxo-2-(2-phenoxy-ethyl)-1,8-dihydro-2H-pyrid[1,2-a]pyrazine-7-carboxylic acid 4-fluoro-benzylamide melting point: 237-239° C.
NMR (CDCl$_3$) δ: 4.18-4.21 (2H, m), 4.26-4.29 (2H, m), 4.62 (2H, d, J=5.8 Hz), 6.57 (1H, d, J=6.3 Hz), 6.71 (1H, d, J=6.3 Hz), 6.86 (2H, d, J=8.1 Hz), 6.97-7.02 (3H, m), 7.29-7.35 (4H, m), 8.56 (1H, s), 10.58 (1H, t, J=5.7 Hz), 11.84 (1H, brs).

Example A-21

9-Hydroxy-1,8-dioxo-2-(2-pyridin-3-yl-ethyl)-1,8-dihydro-2H-pyrid[1,2-a]pyrazine-7-carboxylic acid 4-fluoro-benzylamide melting point: 256-257° C.
NMR (CDCl$_3$) δ: 3.00 (2H, t, J=7.5 Hz), 4.02 (2H, t, J=7.5 Hz), 4.54 (2H, d, J=6.0 Hz), 6.89 (1H, d, J=6.3 Hz), 7.16 (2H, m), 7.30-7.39 (3H, m), 7.48 (1H, d, J=6.3 Hz), 7.70 (1H, m), 8.44 (1H, dd, J=1.8 Hz, 5.1 Hz), 8.48 (1H, m), 8.78 (1H, s), 10.56 (1H, t, J=6.0 Hz), 11.98 (1H, s).

Example A-22

2-Dimethylcarbamoylmethyl-9-hydroxy-1,8-dioxo-1,8-dihydro-2H-pyrid[1,2-a]pyrazine-7-carboxylic acid 4-fluoro-benzylamide melting point: >300° C.
NMR (DMSO-d$_6$) δ: 2.87 (3H, s), 3.03 (3H, s), 4.55 (2H, d, J=6.0 Hz), 4.71 (2H, s), 6.80 (1H, d, J=6.3 Hz), 7.16 (2H, m), 7.38 (2H, m), 7.48 (1H, d, J=6.3 Hz), 8.82 (1H, s), 10.54 (1H, brt, J=6.0 Hz), 11.83 (1H, s).

Example A-23

2-(2-Ethoxy-ethyl)-9-hydroxy-1,8-dioxo-1,8-dihydro-2H-pyrid[1,2-a]pyrazine-7-carboxylic acid 4-fluoro-benzylamide melting point: 212-214° C.
NMR (CDCl$_3$) δ: 1.19 (3H, t, J=7.0 Hz), 3.51 (2H, q, J=7.0 Hz), 3.67-3.72 (2H, m), 3.95-4.01 (2H, m), 4.63 (2H, d, J=5.7 Hz), 6.54 (1H, d, J=6.0 Hz), 6.65 (1H, d, J=6.0 Hz), 6.96-7.02 (2H, m), 7.29-7.36 (2H, m), 8.52 (1H, s), 10.62 (1H, brs), 11.97 (1H, brs).

Example A-24

2-Furan-2-ylmethyl-9-hydroxy-1,8-dioxo-1,8-dihydro-2H-pyrid[1,2-a]pyrazine-7-carboxylic acid 4-fluoro-benzylamide melting point: 234-237° C.
NMR (DMSO-d$_6$) δ: 4.54 (2H, d, J=6.0 Hz), 4.98 (2H, s), 6.45 (1H, dd, J=2.1 Hz, 3.3 Hz), 6.53 (1H, dd, J=0.6 Hz, 3.3 Hz), 6.93 (1H, d, J=6.3 Hz), 7.16 (2H, m), 7.36 (2H, m), 7.47 (1H, d, J=6.3 Hz), 7.65 (1H, dd, J=0.6 Hz, 2.1 Hz), 8.74 (1H, s), 10.56 (1H, brt, J=6.0 Hz), 11.85 (1H, s).

Example A-25

2-[2-(4-Chloro-phenyl)-ethyl]-9-hydroxy-1,8-dioxo-1,8-dihydro-2H-pyrid[1,2-a]pyrazine-7-carboxylic acid 4-fluoro-benzylamide melting point: 288-291° C.
NMR (DMSO-d$_6$) δ: 2.96 (2H, t, J=7.5 Hz), 2.98 (2H, t, J=7.5 Hz), 4.54 (2H, d, J=6.0 Hz), 6.87 (1H, d, J=6.3 Hz), 7.16 (2H, m), 7.30 (2H, m), 7.34-7.39 (4H, m), 7.47 (1H, d, J=6.3 Hz), 8.78 (1H, s), 10.57 (1H, brt, J=6.0 Hz), 12.01 (1H, s).

Example A-26

2-(1-Benzyl-pyrrolidin-3-yl)-9-hydroxy-1,8-dioxo-1,8-dihydro-2H-pyrid[1,2-a]pyrazine-7-carboxylic acid 4-fluoro-benzylamide melting point: 218-219° C.
NMR (CDCl$_3$) δ: 1.82 (1H, m), 2.24 (1H, q, J=8.4 Hz), 2.36 (1H, m), 2.56 (1H, m), 2.83 (1H, m), 3.00 (1H, m), 3.63 (2H, s), 4.54 (2H, d, J=6.0 Hz), 5.19 (1H, m), 7.11 (1H, d, J=6.3 Hz), 7.16 (2H, m), 7.23-7.39 (7H, m), 7.56 (1H, d, J=6.3 Hz), 8.78 (1H, s), 10.58 (1H, t, J=6.0 Hz), 12.14 (1H, s).

Example A-27

9-Hydroxy-1,8-dioxo-2-thiophen-2-ylmethyl-1,8-dihydro-2H-pyrid[1,2-a]pyrazine-7-carboxylic acid 4-fluoro-benzylamide melting point: 233-236° C.
NMR (CDCl$_3$) δ: 4.61 (2H, d, J=6.0 Hz), 5.11 (2H, s), 6.37 (1H, d, J=6.3 Hz), 6.72 (1H, d, J=6.3 Hz), 6.96-7.04 (3H, m), 7.15 (1H, d, J=3.3 Hz), 7.32-7.36 (3H, m), 8.56 (1H, s), 10.56 (1H, brs), 11.87 (1H, brs).

Example A-28

2-(3-Dimethylamino-2,2-dimethyl-propyl)-9-hydroxy-1,8-dioxo-1,8-dihydro-2H-pyrid [1,2-a]pyrazine-7-carboxylic acid 4-fluoro-benzylamide melting point: 208-210° C.

NMR (DMSO-$d_6$) δ: 0.91 (6H, s), 2.17 (2H, s), 2.25 (6H, s), 3.70 (2H, s), 4.54 (2H, d, J=5.7 Hz), 6.84 (1H, d, J=6.0 Hz), 7.14-7.19 (2H, m), 7.35-7.39 (2H, m), 7.46 (1H, d, J=6.0 Hz), 8.81 (1H, s), 10.60 (1H, t, J=6.3 Hz), 12.18 (1H, brs).

Example A-29

9-Hydroxy-2-(3-morpholin-4-yl-propyl)-1,8-dioxo-1,8-dihydro-2H-pyrid[1,2-a]pyrazine-7-carboxylic acid 4-fluoro-benzylamide melting point: 197-198° C.

NMR (CDCl$_3$) δ: 1.81 (2H, tt, J=6.3 Hz, 6.9 Hz), 2.31 (4H, brs), 2.33 (2H, t, J=6.3 Hz), 3.49 (4H, brt, J=4.5 Hz), 3.80 (2H, t, J=6.9 Hz), 4.54 (2H, d, J=6.0 Hz), 6.95 (1H, d, J=6.3 Hz), 7.16 (2H, m), 7.34 (2H, m), 7.50 (1H, d, J=6.3 Hz), 8.80 (1H, s), 10.59 (1H, t, J=6.0 Hz), 12.16 (1H, s).

Example A-30

2-(4-Fluorobenzyl)-9-hydroxy-1,8-dioxo-1,8-dihydro-2H-pyrid[1,2-a]pyrazine-7-carboxylic acid 4-fluoro-benzylamide

[Chemical formula 53]

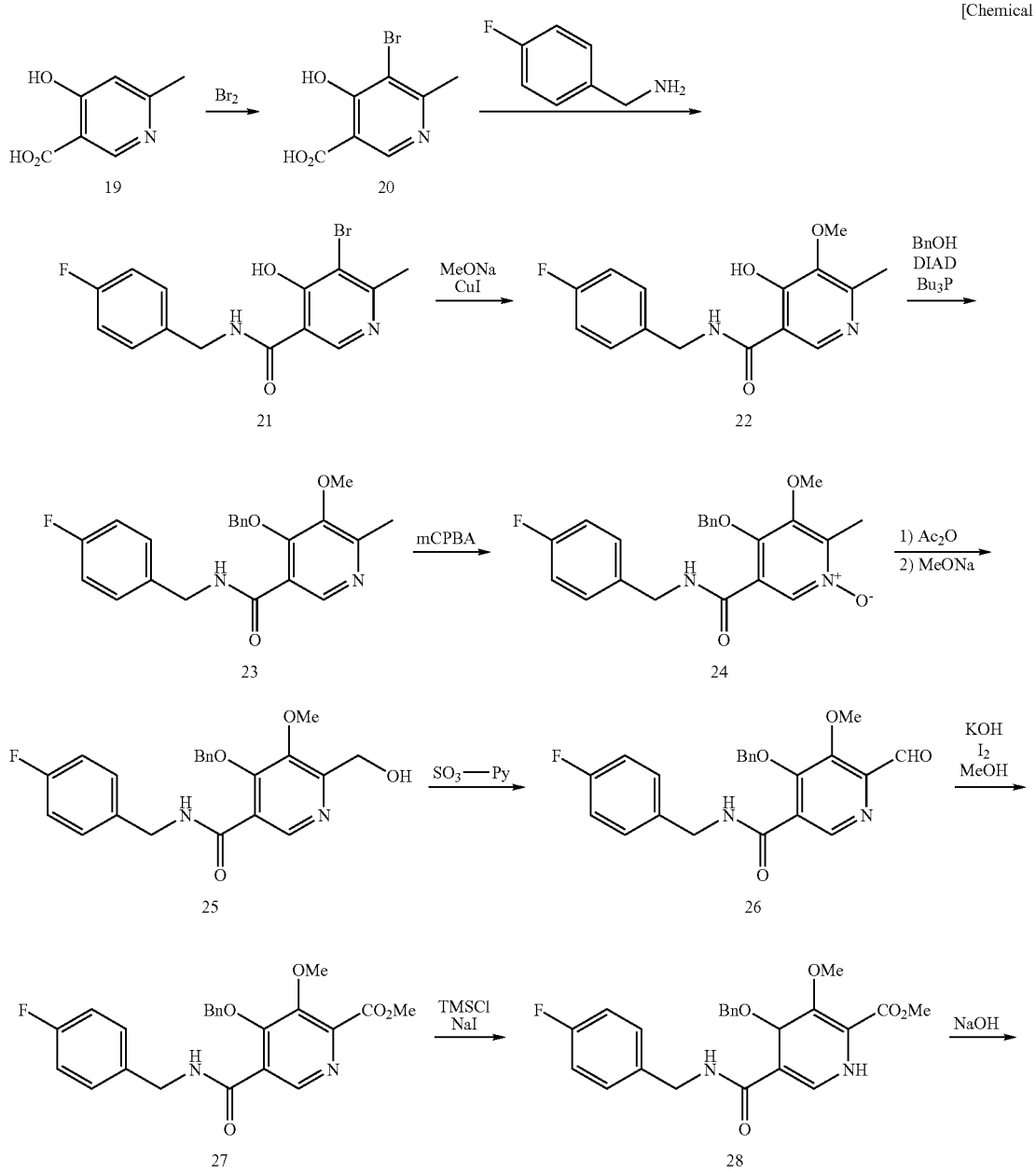

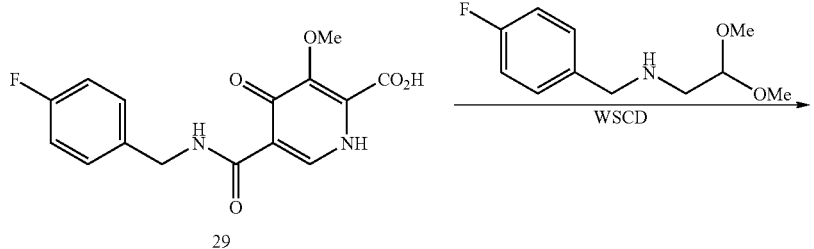

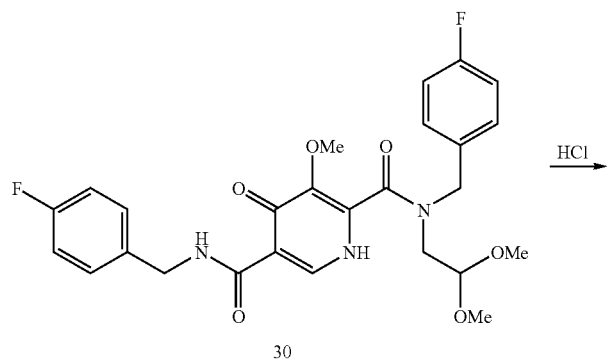

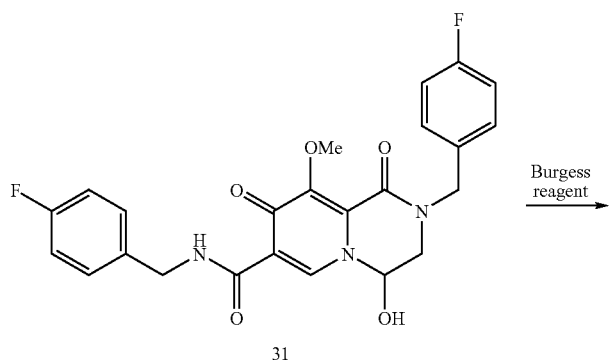

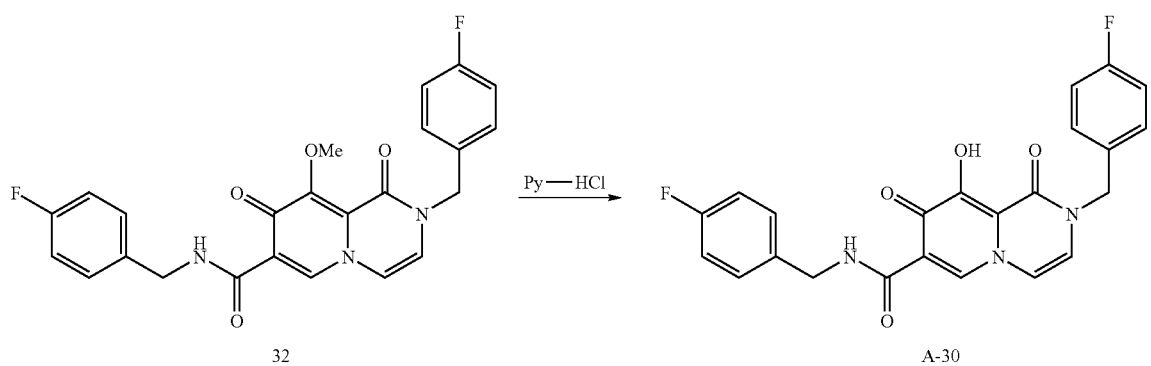

1) 4-Hydroxy-6-methylnicotinic acid 19 (95.6 g, 0.625 mol) was dissolved in acetic acid (950 ml) and water (190 ml), and bromine (39 ml, 0.750 mol) was added over 15 minutes. After the solution was stirred at 60° C. for 5 hours, the solvent was distilled off under reduced pressure, methanol (200 ml) was added and, crystals were collected by filtration. The solution was distilled off under reduced pressure, methanol was added again to the residue, and crystals were collected by filtration. A total of 142.2 g (98%) of 5-bromo-4-hydroxy-6-methylnicotinic acid 20 was obtained as a colorless crystal.

NMR (DMSO-$d_6$) δ: 2.53 (3H, s), 8.56 (1H, s), 13.45 (1H, brs), 14.80 (1H, brs).

2) The compound 20 (138 g, 0.596 mol), 1-ethyl-3-(3-dimethylaminopropyl)carbodiimide hydrochloride (148 g, 0.775 mol), and 1-hydroxybenzotriazole (100 g, 0.656 mol) were dissolved in dimethylformamide (970 ml), and 4-fluorobenzylamine (79 ml, 0.715 mol) was added. After the reaction solution was stirred at room temperature for 9 hours, water (2000 ml) was added, and crystals were collected by filtration, followed by washing with ether. 5-Bromo-N-(4-fluorobenzyl)-4-hydroxy-6-methylnicotinamide 21 (156 g, 77%) was obtained as a colorless crystal.

NMR (DMSO-$d_6$) δ: 2.47 (3H, s), 4.50 (2H, d, J=5.9 Hz), 7.12-7.20 (m, 2H), 7.32-7.39 (m, 2H), 8.38 (1H, s), 10.50 (1H, t, J=5.9 Hz), 12.72 (1H, brs).

3) The compound 21 (75.2 g, 222 mmol) and copper (I) iodide (21.1 g, 111 mmol) were dissolved in dimethylformamide (750 ml), a 28% sodium methoxide-methanol solution (216 ml, 888 mmol) was added, and the mixture was stirred at 105° C. for 100 minutes. After cooling, ice-water (800 ml) was added, and unnecessary matters were filtered. To the solution was added 2 M hydrochloric acid (443 ml), and crystals were collected by filtration. N-(4-fluorobenzyl)-4-hydroxy-5-methoxy-6-methylnicotinamide 22 (56.0 g, 87%) was obtained as a colorless crystal.

NMR (DMSO-$d_6$) δ: 2.26 (3H, s), 3.74 (3H, s), 4.49 (2H, d, J=6.0 Hz), 7.10-7.19 (2H, m), 7.30-7.38 (2H, m), 8.24 (1H, s), 10.68 (1H, t, J=6.0 Hz), 12.21 (1H, brs).

4) To a solution of the compound 22 (100 g, 344 mmol), benzyl alcohol (46 ml, 447 mmol), and tributylphosphine (128 ml, 516 mmol) in tetrahydrofuran (1000 ml) was added a 40% diisopropyl azodicarboxylate-toluene solution (280 ml, 516 mmol) under ice-cooling over 30 minutes. After stirred for 30 minutes under ice-cooling, a temperature was raised to room temperature, followed by stirring for 2 hours. The solvent was distilled off under reduced pressure, to the residue were added toluene (100 ml) and hexane (2000 ml), and precipitated crystals were filtered. The solvent was distilled off under reduced pressure, to the residue were added diethyl ether (200 ml) and hexane (2000 ml), and precipitated crystals were filtered. The solvent was distilled off under reduced pressure, and the residue was purified by silica gel column chromatography (hexane/ethyl acetate). 4-Benzyloxy-N-(4-fluorobenzyl)-5-methoxy-6-methylnicotinamide 23 (68.5 g, 52%) was obtained as a colorless crystal.

NMR (CDCl$_3$) δ: 2.58 (3H, s), 3.86 (3H, s), 4.40 (2H, d, J=5.7 Hz), 5.21 (2H, s), 6.91-7.00 (2H, m), 7.08-7.14 (2H, m), 7.19-7.27 (2H, m), 7.32-7.40 (3H, m), 7.87 (1H, brs), 8.97 (1H, s).

5) To a solution of the compound 23 (67.5 g, 177 mmol) in chloroform (350 ml) was added a solution of metachloroperbenzoic acid (65%) (49.5 g, 186 mmol) in chloroform (350 ml) over 30 minutes under ice-cooling. After stirred for 45 minutes under ice-cooling, a temperature was raised to room temperature, followed by stirring for 75 minutes. To the reaction solution was added an aqueous saturated sodium bicarbonate solution, followed by extraction with chloroform. The organic layer was washed with an aqueous saturated sodium bicarbonate solution, and dried with anhydrous sodium sulfate. The solvent was distilled off under reduced pressure, to the residue was added diethyl ether (200 ml), and precipitated crystals (47.8 g) were collected by filtration. The solvent was distilled off under reduced pressure, and the residue was purified by silica gel column chromatography (toluene/acetone) to obtain 2.65 g of crystals. A total of 50.5 g (72%) of 4-benzyloxy-N-(4-fluorobenzyl)-5-methoxy-6-methyl-1-oxynicotinamide 24 was obtained as a colorless crystal.

NMR (CDCl$_3$) δ: 2.55 (3H, s), 3.90 (3H, s), 4.40 (2H, d, J=5.7 Hz), 5.16 (2H, s), 6.93-6.70 (2H, s), 6.90-7.19 (5H, m), 7.30-7.38 (2H, m), 7.94 (1H, brs), 8.81 (1H, s).

6) The compound 24 (49.4 g, 125 mmol) was dissolved in acetic anhydride (350 ml), and this was stirred at 80° C. for 30 minutes. The solvent was distilled off under reduced pressure, this was dissolved in methanol (500 ml), and a 28% sodium methoxide-methanol solution (7.5 ml, 31.3 mmol) was added under ice-cooling, followed by stirring at room temperature for 1 hour. To the reaction solution was added Amberlite (registered trade mark) IR-120B until the solution became neutral, and a solid matter was filtered. The solvent was distilled off under reduced pressure, and the residue was purified by silica gel column chromatography (hexane/ethyl acetate). 4-Benzyloxy-N-(4-fluorobenzyl)-6-hydroxymethyl-5-methoxynicotinamide 25 (25.4 g, 51%) was obtained as a colorless crystal.

NMR (CDCl$_3$) δ: 3.42 (1H, brs), 3.89 (3H, s), 4.41 (2H, d, J=5.7 Hz), 4.83 (2H, s), 5.23 (2H, s), 6.92-6.99 (2H, m), 7.09-7.14 (2H, m), 7.19-7.23 (2H, m), 7.28-7.37 (3H, m), 7.85 (1H, brs), 9.03 (1H, s).

7) To a solution of the compound 25 (25.0 g, 63.1 mmol), dimethyl sulfoxide (44.8 ml, 631 mmol), and triethylamine (44.3 ml, 378 mmol) in chloroform (250 ml) was added a sulfur trioxide pyridine complex (50.2 g, 315 mmol) under ice-cooling, and the mixture was stirred at room temperature for 20 minutes. To the reaction solution was added water, chroloform was distilled off under reduced pressure, and the residue was extracted with ethyl acetate. The extract was washed with water, and dried with anhydrous sodium sulfate. The solvent was distilled off under reduced pressure, to the residue was added diethyl ether, and crystals (17.7 g) were collected by filtration. The solvent was distilled off under reduced pressure, and the residue was purified by silica gel column chromatography to obtain 3.16 g of crystals. A total of 20.9 g (84%) of 4-benzyloxy-N-(4-fluorobenzyl)-6-formyl-5-methoxynicotinamide 26 was obtained as a colorless crystal.

NMR (CDCl$_3$) δ: 4.02 (3H, s), 4.41 (2H, d, J=5.7 Hz), 5.30 (2H, s), 6.93-6.70 (2H, m), 7.09-7.15 (2H, m), 7.20-7.27 (2H, m), 7.31-7.40 (3H, m), 7.83 (1H, brs), 9.20 (1H, s), 10.26 (1H, s).

8) To a solution of the compound 26 (300 mg, 0.761 mmol) in methanol (1 ml) was added a solution of potassium hydroxide (111 mg, 1.99 mmol) in methanol (1 ml) under ice-cooling, and a solution of iodine (251 mg, 1.00 mmol) in methanol (4 ml) was further added, followed by stirring at the same temperature for 1 hour. To the reaction solution were added a 5% aqueous sodium hydrogen sulfite solution and water, and precipitated crystals were collected by filtration. Methyl 4-benzyloxy-5-(4-fluorobenzylcarbamoyl)-3-methoxypyridine-2-carboxylate 27 (275 mg, 85%) was obtained as a colorless crystal.

NMR (CDCl$_3$) δ: 3.99 (3H, s), 4.02 (3H, s), 7.40 (2H, d, J=5.7 Hz), 5.26 (2H, s), 6.92-6.99 (2H, m), 7.10-7.15 (2H, m), 7.19-7.23 (2H, m), 7.25-7.39 (3H, m), 7.81 (1H, brs), 9.09 (1H, s).

9) To a suspension of sodium iodide (5.51 g, 36.8 mmol) in acetonitrile (50 ml) was added chlorotrimethylsilane (4.66 ml, 36.8 mmol), and the mixture was stirred at room temperature for 10 minutes. After to this solution was added the compound 27 (2.60 g, 6.13 mmol) under ice-cooling, this was stirred at the same temperature for 20 minutes. To the reaction solution was added a 5% sodium hydrogen sulfite solution, followed by extraction with ethyl acetate. The extract was washed with an aqueous saturated sodium bicarbonate solution and an aqueous saturated sodium chlorite solution, and dried with anhydrous sodium sulfate. The solvent was distilled off under reduced pressure, and the resulting solid matter was recrystallized to obtain (acetone-diisopropyl ether) and methyl 5-(4-fluorobenzylcarbamoyl)-3-methoxy-4-oxo-1,4-dihydropyridine-2-carboxylate 28 (1.73 g, 84%) as a colorless crystal.

NMR (CDCl$_3$) δ: 4.04 (6H, s), 4.60 (2H, d, J=6.0 Hz), 6.96-7.03 (2H, m), 7.29-7.35 (2H, m), 8.63 (1H, s), 9.68 (1H, brs), 10.34 (1H, brs).

10) The compound 28 (900 mg, 2.12 mmol) was dissolved in methanol (8 ml), and a 2N aqueous sodium hydroxide solution (4 ml) was added. The solution was stirred at room temperature for 2 hours, 2 M hydrochloric acid (3 ml) was added, and crystals were collected by filtration. 4-Benzyloxy-5-(4-fluoro-benzylcarbamoyl)-3-methoxy-pyridine-2-carboxylic acid 29 (474 mg, 54%) was obtained as a colorless crystal.

NMR (CDCl$_3$) δ: 4.05 (3H, s), 4.40 (2H, d, J=5.6 Hz), 5.36 (2H, s), 6.94-7.01 (2H, m), 7.08-7.12 (2H, m), 7.21-7.24 (2H, m), 7.29-7.41 (3H, m), 7.87 (1H, brs), 9.03 (1H, s).

11) From the compound 29 (641 mg, 2 mmol), a crude compound 30 (932 mg) was obtained according to the method of the step 21. To this dioxane (6 ml) solution was added 2N hydrochloric acid (3 ml) at room temperature, thereafter, this was warmed to 70° C. for 30 minutes, and cooled to room temperature, and sodium hydrogen carbonate was added. Precipitated crystals were washed with water, and dried to obtain a compound 31 (513 mg, 61%).

1H-NMR (DMSO-d$_6$) δ: 3.58 (1H, brs), 3.82 (3H, s), 3.83 (1H, brs), 4.51 (2H, d, J=6.0 Hz), 4.60 (1H, brs), 4.70 (1H, brs), 5.84 (1H, brs), 7.10-7.20 (4H, m), 7.30-7.42 (4H, m), 7.68 (1H, brs), 8.57 (1H, s), 10.41 (1H, brs).

12) To a solution of the compound 31 (513 mg, 1.1 mmol) in acetonitrile (5 ml) was added a Burgess reagent (520 mg, 2.2 mmol), and this was warmed at 70° C. for 1.5 hours. After cooled to room temperature, water was added to stop the reaction, and this was extracted with chloroform, washed with water, and dried with magnesium sulfate. The solvent was distilled off under reduced pressure, the residue was subjected to silica gel column chromatography, and fractions eluted with chloroform-methanol were concentrated under reduced pressure to obtain a compound 32 (95 mg, 19%).

1H-NMR (CDCl$_3$) δ: 4.08 (3H, s), 4.60 (2H, d, J=5.8 Hz), 4.95 (2H, s), 6.38 (1H, d, J=6.1 Hz), 6.62 (1H, d, J=6.1 Hz), 6.95-7.10 (4H, m), 7.27-7.40 (4H, m), 8.57 (1H, s), 10.54 (1H, brs).

13) To the compound 32 (95 mg, 0.2 mmol) was added pyridine hydrochloride (2 g), and this was warmed at 180° C. for 5 minutes. After cooled to room temperature, water was added, and precipitated crystals were washed with water, and dried to obtain Example A-30 (86 mg, 93%).

melting point: 290-293° C.

Elementary analysis for $C_{23}H_{17}F_2N_3O_4$

Cal'd (%): C, 63.16; H, 3.92; F, 8.69; N, 9.61.

Found (%): C, 62.97; H, 3.87; F, 8.36; N, 9.65.

1H-NMR (DMSO-d$_6$) δ: 4.54 (2H, d, J=5.6 Hz), 4.95 (2H, s), 7.02 (1H, d, J=5.6 Hz), 7.10-7.22 (4H, m), 7.30-7.57 (5H, m), 8.78 (1H, s), 10.57 (1H, t, J=5.9 Hz), 11.9 (1H, brs).

Example A-31

2-[3-(3-Chloro-5-trifluoromethyl-pyridin-2-ylamino)-propyl]-9-hydroxy-1,8-dioxo-1,8-dihydro-2H-pyrid[1,2-a]pyrazine-7-carboxylic acid 4-fluoro-benzylamide melting point: 281-283° C.

NMR (DMSO-d$_6$) δ: 1.97-2.00 (2H, m), 3.43-3.51 (2H, m), 3.83 (2H, t, J=6.8 Hz), 4.54 (2H, d, J=5.6 Hz), 6.97 (1H, d, J=6.0 Hz), 7.14-7.18 (2H, m), 7.30 (1H, t, J=5.2 Hz), 7.35-7.39 (2H, m), 7.50 (1H, d, J=6.0 Hz), 7.93 (1H, s), 8.27 (1H, s), 8.78 (1H, s), 10.58 (1H, t, J=5.6 Hz), 12.05 (1H, s).

Example A-32

2-(2-Benzyloxy-ethyl)-9-hydroxy-1,8-dioxo-1,8-dihydro-2H-pyrid[1,2-a]pyrazine-7-carboxylic acid 4-fluoro-benzylamide melting pint: 191° C.

NMR (DMSO-d$_6$) δ: 3.76 (2H, t, J=5.0 Hz), 3.98 (2H, t, J=5.2 Hz), 4.52 (2H, s), 4.63 (2H, d, J=5.8 Hz), 6.49 (1H, d, J=6.4 Hz), 6.63 (1H, d, J=6.3 Hz), 6.98-7.03 (2H, m), 7.25-7.36 (7H, m), 8.53 (1H, s), 10.60-10.64 (1H, m), 11.92 (1H, brs).

Example A-33

9-Hydroxy-2-(2-hydroxy-ethyl)-1,8-dioxo-1,8-dihydro-2H-pyrid[1,2-a]pyrazine-7-carboxylic acid 4-fluoro-benzylamide melting point: 287° C.

NMR (DMSO-d$_6$) δ: 3.63-3.68 (2H, m), 3.81-3.84 (2H, m), 4.54 (2H, d, J=5.8 Hz), 4.95 (1H, t, J=5.5 Hz), 6.90 (1H, d, J=5.9 Hz), 7.14-7.20 (2H, m), 7.35-7.38 (2H, m), 7.48 (1H, d, J=5.8 Hz), 8.81 (1H, s), 10.60 (1H, t, J=5.9 Hz), 12.12 (1H, brs).

According to the same manner as that of Example B-1, the following Examples compounds B-2 to B-28 were synthesized.

Example B-2

2-(2-Dimethylamino-ethyl)-9-hydroxy-1,8-dioxo-1,3,4,8-tetrahydro-2H-pyrid[1,2-a]pyrazine-7-carboxylic acid 4-fluoro-benzylamide melting point: 218-220° C.

NMR (DMSO-d$_6$) δ: 2.19 (6H, s), 3.60 (2H, t, J=6.3 Hz), 3.79 (2H, s), 4.37 (2H, s), 4.52 (2H, d, J=4.5 Hz), 7.15 (2H, t, J=9.0 Hz), 7.32-7.37 (2H, m), 8.40 (1H, s), 10.45 (1H, t, J=6.3 Hz), 12.40 (1H, s).

Example B-3

9-Hydroxy-2-(2-morpholin-4-yl-ethyl)-1,8-dioxo-1,3,4,8-tetrahydro-2H-pyrid[1,2-a]pyrazine-7-carboxylic Acid 4-fluoro-benzylamide melting point: 205-207° C.

NMR (DMSO-d$_6$) δ: 2.43 (2H, s), 2.50 (4H, s), 3.54 (4H, s), 3.63 (2H, s), 3.81 (2H, s), 4.40 (2H, s), 4.52 (2H, d, J=6.0 Hz), 7.16 (2H, t, J=9.0 Hz), 7.33-7.37 (2H, m), 8.43 (1H, s), 10.45 (1H, t, J=5.7 Hz), 12.48 (1H, s).

Example B-4

9-Hydroxy-1,8-dioxo-2-(2-piperidin-1-yl-ethyl)-1,3,4,8-tetrahydro-2H-pyrid[1,2-a]pyrazine-7-carboxylic acid 4-fluoro-benzylamide melting point: 232-235° C.

Elementary analysis for $C_{23}H_{27}FN_4O_4$

Cal'd (%): C, 62.43; H, 6.15; F, 4.29; N, 12.66.

Found (%): C, 61.78; H, 5.76; F, 4.04; N, 12.50.

NMR (DMSO-d$_6$) δ: 1.37-1.46 (6H, m), 2.38-2.50 (6H, m), 3.61 (2H, t, J=6.6 Hz), 3.79 (2H, m), 4.37 (2H, m), 4.52

(2H, d, J=6 Hz), 7.12-7.18 (2H, m), 7.32-7.37 (2H, m), 8.41 (1H, s), 10.44 (1H, t, J=6 Hz), 12.50 (1H, brs).

Example B-5

9-Hydroxy-2-(2-methyl-butyl)-1,8-dioxo-1,8-dihydro-1,3,4,8-tetrahydro-2H-pyrid[1,2-a]pyrazine-7-carboxylic Acid 4-fluoro-benzylamide melting point: 278-280° C.
Elementary analysis for $C_{21}H_{24}FN_3O_4$
Cal'd (%): C, 62.83; H, 6.03; F, 4.73; N, 10.47.
Found (%): C, 62.45; H, 6.00; F, 4.50; N, 10.43.
NMR (DMSO-$d_6$) δ: 0.86-0.93 (6H, m), 1.08-1.18 (1H, m), 1.37-1.44 (1H, m), 1.78-1.84 (1H, m), 3.30-3.38 (2H, m), 3.73-3.77 (2H, m), 4.37-4.44 (2H, m), 4.52 (2H, d, J=6 Hz), 7.12-7.18 (2H, m), 7.32-7.37 (2H, m), 8.41 (1H, s), 10.46 (1H, t, J=6 Hz), 12.54 (1H, brs).

Example B-6

9-Hydroxy-2-(2-isopropoxy-ethyl)-1,8-dioxo-1,3,4,8-tetrahydro-2H-pyrid[1,2-a]pyrazine-7-carboxylic Acid 4-fluoro-benzylamide melting point: 210-212° C.
Elementary analysis for $C_{21}H_{24}FN_3O_5$
Cal'd (%): C, 60.42; H, 5.80; F, 4.55; N, 10.07.
Found (%): C, 59.77; H, 5.66; F, 4.42; N, 10.01.
NMR (DMSO-$d_6$) δ: 1.08 (6H, d, J=6 Hz), 3.54-3.66 (5H, m), 3.79-3.83 (2H, m), 4.35-4.39 (2H, m), 4.52 (2H, d, J=6 Hz), 7.12-7.18 (2H, m), 7.32-7.37 (2H, m), 8.40 (1H, s), 10.44 (1H, t, J=6 Hz), 12.42 (1H, brs).

Example B-7

9-Hydroxy-2-isopropyl-1,8-dioxo-1,3,4,8-tetrahydro-2H-pyrid[1,2-a]pyrazine-7-carboxylic acid 4-fluoro-benzylamide melting point: 286-287° C.
NMR (DMSO-$d_6$) δ: 1.17 (6H, d, J=6.9 Hz), 3.64-3.70 (2H, m), 4.36-4.38 (2H, m), 4.52 (2H, d, J=6.0 Hz), 4.70-4.79 (1H, m), 7.13-7.19 (2H, m), 7.33-7.37 (2H, m), 8.43 (1H, s), 10.47 (1H, t, J=6.0 Hz), 12.60 (1H, brs).

Example B-8

2-Cyclohexyl-9-hydroxy-1,8-dioxo-1,3,4,8-tetrahydro-2H-pyrid[1,2-a]pyrazine-7-carboxylic acid 4-fluoro-benzylamide melting point: >300° C.
NMR (DMSO-$d_6$) δ: 1.03-1.81 (10H, m), 3.69-3.72 (2H, m), 4.29-4.36 (3H, m), 4.52 (2H, d, J=6.1 Hz), 7.13-7.19 (2H, m), 7.33-7.37 (2H, m), 8.43 (1H, s), 10.47 (1H, t, J=5.8 Hz), 12.59 (1H, brs).

Example B-9

2-(4-Fluoro-benzyl)-9-hydroxy-1,8-dioxo-1,3,4,8-tetrahydro-2H-pyrid[1,2-a]pyrazine-7-carboxylic acid 4-fluoro-benzylamide melting point: 271-272° C.
NMR (DMSO-$d_6$) δ: 3.71-3.75 (2H, m), 4.37-4.41 (2H, m), 4.52 (2H, d, J=6.0 Hz), 4.71 (2H, s), 7.13-7.23 (4H, m), 7.33-7.45 (4H, m), 8.41 (1H, s), 10.44 (1H, t, J=5.9 Hz), 12.36 (1H, brs).

Example B-10

9-Hydroxy-1,8-dioxo-2-[2-(propyl-m-toluoyl-amino)-ethyl]-1,3,4,8-tetrahydro-2H-pyrid[1,2-a]pyrazine-7-carboxylic Acid 4-fluoro-benzylamide melting point: 185-188° C.
NMR (CDCl$_3$) δ: 1.12-1.18 (3H, m), 2.26 (3H, s), 3.30-4.40 (10H, m), 4.60 (2H, d, J=5.4 Hz), 6.57 (2H, brs), 6.97-7.02 (2H, m), 7.04-7.16 (1H, m), 7.26-7.34 (3H, m), 8.23 (1H, s), 10.43 (1H, brs), 12.29 (1H, brs).

Example B-11

9-Hydroxy-1,8-dioxo-2-[3-(2-oxo-pyrrolidin-1-yl)-propyl]-1,3,4,8-tetrahydro-2H-pyrid[1,2-a]pyrazine-7-carboxylic Acid 4-fluoro-benzylamide melting point: 207-209° C.
NMR (CDCl$_3$) δ: 1.92-1.96 (2H, m), 2.05-2.10 (2H, m), 2.40 (2H, t, J=8.1 Hz), 3.35 (2H, t, J=6.6 Hz), 3.43 (2H, t, J=6.9 Hz), 3.55 (2H, t, J=6.6 Hz), 3.82-3.86 (2H, m), 4.26-4.30 (2H, m), 4.60 (2H, d, J=6.0 Hz), 6.96-7.02 (2H, m), 7.30-7.35 (2H, m), 8.32 (1H, s), 10.43-10.47 (1H, m), 12.26 (1H, brs).

Example B-12

9-Hydroxy-1,8-dioxo-2-(2-tetrahydrofuran-2-ylm-ethyl)-1,3,4,8-tetrahydro-2H-pyrid[1,2-a]pyrazine-7-carboxylic Acid 4-fluoro-benzylamide melting point: 250-251° C.
NMR (CDCl$_3$) δ: 1.50-1.59 (2H, m), 1.89-1.98 (2H, m), 2.03-2.14 (1H, m), 3.25 (1H, dd, J=8.4 Hz, 13.8 Hz), 4.25-3.73 (7H, m), 4.59 (2H, d, J=5.1 Hz), 7.00 (2H, d, J=8.4 Hz), 7.32 (2H, dd, J=5.4 Hz, 8.4 Hz), 8.31 (1H, s), 10.47 (1H, t, 5.1 Hz), 12.29 (1H, brs).

Example B-13

4-[7-(4-Fluoro-benzylcarbamoyl)-9-hydroxy-1,8-dioxo-1,3,4,8-tetrahydro-pyrid[1,2-a]pyrazine-2-yl]-piperidine-1-carboxylic acid ethyl ester melting point: 258-260° C.
NMR (CDCl$_3$) δ: 1.28 (3H, t, J=7.2 Hz), 1.54-1.92 (4H, m), 4.14-4.43 (6H, m), 4.60 (2H, d, J=5.4 Hz), 6.97-7.05 (2H, m), 7.29-7.34 (2H, m), 8.32 (1H, s), 10.43 (1H, t, J=5.4 Hz), 12.27 (1H, brs).

Example B-14

2-(2-Acetylamino-ethyl)-9-hydroxy-1,8-dioxo-1,3,4,8-tetrahydro-2H-pyrid[1,2-a]pyrazine-7-carboxylic acid 4-fluoro-benzylamide melting point: 249-251° C.
NMR (CDCl$_3$) δ: 1.93 (3H, s), 3.48-3.52 (2H, m), 3.67-3.71 (2H, m), 3.82-3.86 (2H, m), 4.28-4.32 (2H, m), 4.59 (2H, s), 6.99-7.04 (2H, m), 7.30-7.33 (2H, m), 8.30 (1H, s).

Example B-15

9-Hydroxy-2-(3-isopropoxy-propyl)-1,8-dioxo-1,3,4,8-tetrahydro-2H-pyrid[1,2-a]pyrazine-7-carboxylic acid 4-fluoro-benzylamide melting point: 239-241° C.
NMR (CDCl$_3$) δ: 1.10 (6H, d, J=6.0 Hz), 1.88-1.96 (2H, m), 3.48-3.57 (3H, m), 3.69 (2H, t, J=6.6 Hz), 3.77-3.81 (2H, m), 4.21-4.24 (2H, m), 4.60 (2H, d, J=5.7 Hz), 6.96-7.02 (2H, m), 7.30-7.35 (2H, m), 8.30 (1H, s), 10.45-10.49 (1H, m), 12.42 (1H, brs).

Example B-16

2-(4-Dimethylamino-benzyl)-9-hydroxy-1,8-dioxo-1,3,4,8-tetrahydro-2H-pyrid[1,2-a]pyrazine-7-carboxylic acid 4-fluoro-benzylamide melting point: 260-262° C.
NMR (CDCl$_3$) δ: 2.97 (6H, s), 3.59-3.63 (2H, m), 4.09-4.13 (2H, m), 4.59 (2H, d, J=5.7 Hz), 4.67 (2H, s), 6.70-6.78 (2H, m), 6.96-7.02 (2H, m), 7.19 (2H, d, J=8.7 Hz), 7.29-7.34 (2H, m), 8.27 (1H, s), 10.46 (1H, t, J=5.7 Hz), 12.45 (1H, brs).

Example B-17

9-Hydroxy-1,8-dioxo-2-(4-sulfamoyl-1-benzyl)-1,3,4,8-tetrahydro-2H-pyrid[1,2-a]pyrazine-7-carboxylic acid 4-fluoro-benzylamide melting point: 266-270° C.
NMR (DMSO-d$_6$) δ: 3.75-3.81 (2H, m), 4.41-4.45 (2H, m), 4.52 (2H, d, J=6.0 Hz), 4.80 (2H, s), 7.13-7.19 (2H, m), 7.33-7.37 (4H, m), 7.56 (2H, d, J=8.1 Hz), 7.81 (2H, d, J=8.1 Hz), 8.44 (1H, s), 10.44 (1H, t, J=6.0 Hz), 12.28 (1H, brs).

Example B-18

9-Hydroxy-2-(3-methoxy-propyl)-1,8-dioxo-1,3,4,8-tetrahydro-2H-pyrid[1,2-a]pyrazine-7-carboxylic Acid 4-fluoro-benzylamide melting point: 238-240° C.
NMR (CDCl$_3$) δ: 1.93 (2H, quin, J=5.7 Hz), 3.31 (3H, s), 3.47 (2H, t, J=5.7 Hz), 3.68 (2H, t, J=6.9 Hz), 3.75-3.79 (2H, m), 4.21-4.24 (2H, m), 4.60 (2H, d, J=5.7 Hz), 6.97-7.02 (2H, m), 7.30-7.35 (2H, m), 8.31 (1H, s), 10.46 (1H, t, J=7.8 Hz), 12.38 (1H, brs).

Example B-19

9-Hydroxy-1,8-dioxo-2-(2-propoxy-ethyl)-1,3,4,8-tetrahydro-2H-pyrid[1,2-a]pyrazine-7-carboxylic acid 4-fluoro-benzylamide melting point: 196-197° C.
NMR (CDCl$_3$) δ: 0.91 (3H, t, J=7.5 Hz), 1.52-1.63 (2H, m), 3.41 (2H, t, J=7.5 Hz), 3.67 (2H, t, J=4.2 Hz), 3.76 (2H, t, J=4.2 Hz), 3.88-3.92 (2H, m), 4.19-4.23 (2H, m), 4.60 (2H, d, J=6.0 Hz), 6.97-7.03 (2H, m), 7.30-7.35 (2H, m), 8.32 (1H, s), 10.47 (1H, t, J=5.7 Hz), 12.29 (1H, brs).

Example B-20

9-Hydroxy-1,8-dioxo-2-(2-phenoxy-ethyl)-1,3,4,8-tetrahydro-2H-pyrid[1,2-a]pyrazine-7-carboxylic acid 4-fluoro-benzylamide melting point: 200-201° C.
NMR (CDCl$_3$) δ: 3.96-4.02 (4H, m), 4.20-4.28 (4H, m), 4.60 (2H, d, J=6.0 Hz), 6.86-6.89 (2H, m), 6.96-7.02 (3H, m), 7.28-7.34 (4H, m), 8.31 (1H, s), 10.43 (1H, brs), 12.15 (1H, brs).

Example B-21

2-Dimethylcarbamoylmethyl-9-hydroxy-1,8-dioxo-1,3,4,8-tetrahydro-2H-pyrid[1,2-a]pyrazine-7-carboxylic acid 4-fluoro-benzylamide melting point: 245° C.
NMR (CDCl$_3$) δ: 3.00 (3H, s), 3.08 (3H, s), 3.83-3.87 (2H, m), 4.37-4.41 (2H, m), 4.42 (2H, s), 4.60 (2H, s), 6.98-7.04 (2H, m), 7.30-7.34 (2H, m), 8.33 (1H, s).

Example B-22

2-(2-Ethoxy-ethyl)-9-hydroxy-1,8-dioxo-1,3,4,8-tetrahydro-2H-pyrid[1,2-a]pyrazine-7-carboxylic Acid 4-fluoro-benzylamide melting point: 201-202° C.
NMR (CDCl$_3$) δ: 1.19 (3H, t, J=7.2 Hz), 3.51 (2H, q, J=7.2 Hz), 3.67 (2H, t, J=5.4 Hz), 3.76 (2H, t, J=5.4 Hz), 3.88-3.92 (2H, m), 4.20-4.23 (2H, m), 4.60 (2H, d, J=5.7 Hz), 6.96-7.02 (2H, m), 7.30-7.34 (2H, m), 8.31 (1H, s), 10.46 (1H, brs), 12.28 (1H, brs).

Example B-23

9-Hydroxy-1,8-dioxo-2-phenethyl-1,3,4,8-tetrahydro-2H-pyrid[1,2-a]pyrazine-7-carboxylic Acid 4-fluoro-benzylamide melting point: 241° C.
NMR (CDCl$_3$) δ: 3.00 (2H, t, J=6.3 Hz), 3.41 (2H, brs), 3.82 (2H, t, J=6.6 Hz), 3.97 (2H, brs), 4.59 (2H, d, J=5.1 Hz), 6.96-7.02 (2H, m), 7.22-7.36 (7H, m), 8.24 (1H, brs), 10.45 (1H, brs), 12.31 (1H, brs).

Example B-24

2-(3-Dimethylamino-2,2-dimethyl-propyl)-9-hydroxy-1,8-dioxo-1,3,4,8-tetrahydro-2H-pyrid[1,2-a]pyrazine-7-carboxylic acid 4-fluoro-benzylamide melting point: 212-214° C.
NMR (CDCl$_3$) δ: 1.03 (6H, s), 2.25 (2H, brs), 2.37 (6H, s), 3.55 (2H, s), 3.86-3.90 (2H, m), 4.20-4.24 (2H, m), 4.60 (2H, d, J=6.0 Hz), 6.96-7.02 (2H, m), 7.29-7.34 (2H, m), 8.30 (1H, s), 10.46 (1H, t, J=4.5 Hz), 12.43 (1H, brs).

Example B-25

9-Hydroxy-2-(3-morpholin-4-yl-propyl)-1,8-dioxo-1,3,4,8-tetrahydro-2H-pyrid[1,2-a]pyrazine-7-carboxylic acid 4-fluoro-benzylamide melting point: 181-185° C.
NMR (CDCl$_3$) δ: 2.08 (2H, brs), 2.73 (6H, brs), 3.67 (2H, t, J=6.6 Hz), 3.80-3.84 (6H, m), 4.22-4.26 (2H, m), 4.61 (2H, d, J=6.0 Hz), 6.98-7.04 (2H, m), 7.33-7.38 (2H, m), 8.28 (1H, s), 10.41 (1H, t, J=6.0 Hz), 12.19 (1H, brs).

Example B-26

Diethyl {2-[7-(4-fluorobenzylcarbamoyl)-9-hydroxy-1,8-dioxo-1,3,4,8-tetrahydropyrid[1,2-a]pyrazin-2-yl]ethyl}phosphonate NMR (DMSO-d$_6$) δ: 1.24 (6H, d, J=7.0 Hz), 2.1-2.23 (2H, m), 3.64-3.72 (2H, m), 3.79-3.82 (2H, m), 3.99-4.06 (4H, m), 4.37-4.41 (2H, m), 7.52 (2H, d, J=5.7 Hz), 7.12-7.18 (2H, m), 7.33-7.38 (2H, m), 8.42 (1H, s), 10.43 (1H, t, J=5.7 Hz), 12.34 (1H, s).

Example B-27

2-(3-Tert-butylamino-propyl)-9-hydroxy-1,8-dioxo-1,3,4,8-tetrahydro-2H-pyrid[1,2-a]pyrazine-7-carboxylic acid 4-fluoro-benzylamide melting point: 216° C.
NMR (DMSO-d$_6$) δ: 1.40 (9H, s), 2.18 (2H, s), 2.92 (2H, s), 3.40 (2H, s), 3.90 (2H, s), 4.39 (2H, s), 4.59 (2H, s), 7.01 (2H, t, J=11.6 Hz), 7.31 (2H, m), 8.34 (1H, s), 10.48 (1H, s).

Example B-28

9-Hydroxy-2-(2-hydroxy-ethyl)-1,8-dioxo-1,3,4,8-tetrahydro-2H-pyrid[1,2-a]pyrazine-7-carboxylic acid 4-fluoro-benzylamide melting point: 213° C.
NMR (DMSO-d$_6$) δ: 3.57-3.63 (4H, m), 3.80-3.84 (2H, m), 4.36-4.41 (2H, m), 4.52 (2H, d, J=5.8 Hz), 4.89 (1H, t, J=5.5 Hz), 7.13-7.20 (2H, m), 7.32-7.38 (2H, m), 8.42 (1H, s), 10.46 (1H, t, J=5.8 Hz), 12.52 (1H, brs).

Example K-1

2-(4-Fluorobenzyl)-9-hydroxy-4-methyl-1,8-dioxo-1,3,4,8-tetrahydro-2H-pyrid[1,2-d][1,2,4]triazine-7-carboxylic acid 4-fluorobenzylamide

[Chemical formula 64]

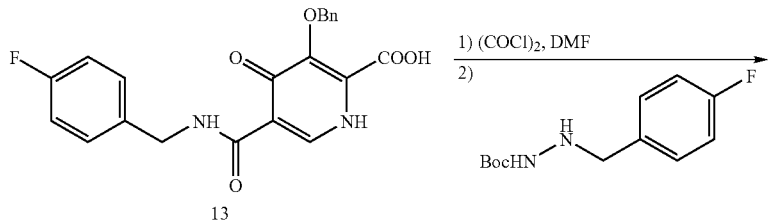

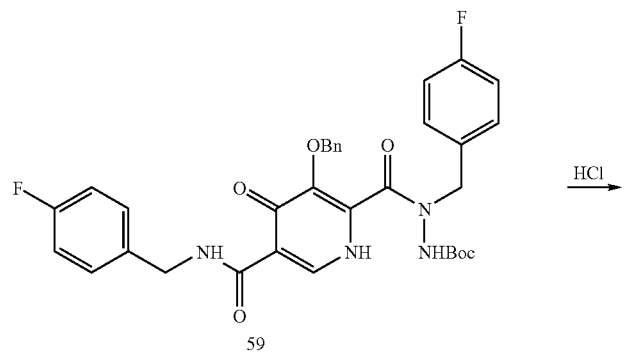

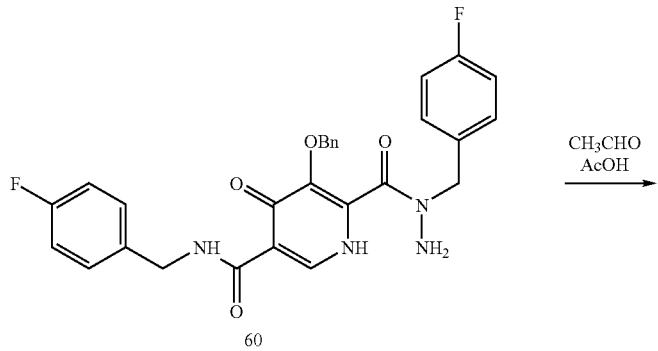

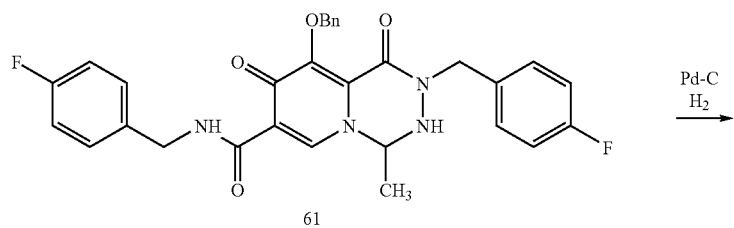

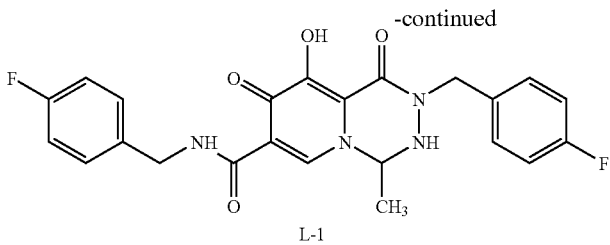
L-1

1) To a solution of a compound 13 (3.00 g, 7.57 mmol) in dichloromethane (30 ml) were added oxalyl chloride (0.79 ml, 9.08 mmol) and dimethylformamide (catalytic amount) at room temperature, and the mixture was stirred for 1.5 hours as it was. A solution of N'-(4-fluoro-benzyl)-hydrazinecarboxylic acid tert-butyl ester (2.00 g, 8.33 mmol) and triethylamine (1.16 ml, 8.33 mmol) in dichloromethane (30 ml) was added at 0° C., and a temperature was raised to room temperature, followed by stirring for 1.5 hours. An aqueous ammonium chloride solution was added, this was extracted with chloroform, and the organic layer was washed with water. This was dried with anhydrous sodium sulfate, and the solvent was distilled off under reduced pressure. The residue was purified by silica gel column chromatography (eluent: n-hexane-ethyl acetate) to obtain a compound 59 (133 mg) at a yield of 85%.

NMR (CDCl$_3$) δ: 4.20 (1H, brs), 4.61 (2H, d, J=6.0 Hz), 5.00 (2H, brs), 5.60 (1H, brs), 6.82 (1H, s), 6.91 (2H, t, J=8.4 Hz), 7.01 (2H, t, J=8.7 Hz), 7.10 (2H, dd, J=5.4 Hz, 8.7 Hz), 7.22-7.36 (7H, m), 8.52 (1H, d, J=6.6 Hz), 10.24 (1H, s), 10.47 (1H, t, J=5.7 Hz).

2) N'-(4-fluoro-benzyl)-hydrazinecarboxylic acid tert-butyl ester was synthesized by the method described in the literature (J. Med. Chem. 1996, 39, 3203-3216). To the compound 59 (597 mg, 0.996 mmol) was added 4N hydrochloric acid (ethyl acetate solution) at 0° C., and a temperature was raised to room temperature, followed by stirring for 1 hour. An aqueous sodium bicarbonate solution was added to neutralize it, followed by extraction with ethyl acetate. The organic layer was washed with water, dried with anhydrous sodium sulfate, and the solvent was distilled off to obtain a compound 60 (500 mg) at a yield of 100%.

NMR (CDCl$_3$) δ: 4.53 (4H, s), 5.20 (2H, s), 6.81-7.35 (13H, m), 8.48 (1H, s), 10.60 (1H, s), 11.80 (1H, s).

3) To a solution of a compound 61 (180 mg, 0.347 mmol) in dichloromethane (1.8 ml) were added acetaldehyde (26 μl, 0.417 mmol) and acetic acid (40 μl, 0.694 mmol) at 0° C., and a temperature was raised to room temperature, followed by stirring for 4 hours. The reaction solution was concentrated under reduced pressure, and the residue was purified by silica gel column chromatography (eluent: chloroform-methanol) to obtain a compound 61 (165 mg) at a yield of 87%.

NMR (CDCl$_3$) δ: 0.83 (3H, s), 3.46 (1H, s), 4.31 (1H, s), 4.58 (2H, d, J=5.4 Hz), 4.89 (1H, s), 5.11 (2H, s), 6.07 (1H, s), 6.96-7.67 (13H, m), 8.00 (1H, s), 10.22 (1H, s).

4) According to the method of synthesizing Example B-1, Example compound K-1 was obtained.

melting point: 247-249° C.

NMR (CDCl$_3$) δ: 1.24 (3H, m), 4.54 (3H, m), 4.80 (2H, m), 6.22 (1H, s), 7.06 (4H, m), 7.37 (4H, m), 8.03 (1H, s), 10.09 (1H, s), 11.57 (1H, s).

According to the same manner as that of Example K-1, the following Example compounds K-2 to K-6 were synthesized.

Example K-2

2-(4-Fluorobenzyl)-9-hydroxy-1,8-dioxo-1,3,4,8-tetrahydro-2H-pyrid[1,2-d][1,2,4]triazine-7-carboxylic acid 4-fluorobenzylamide melting point: >300° C.
NMR (DMSO-d$_6$) δ: 4.50 (2H, d, J=5.7 Hz), 4.68 (2H, s), 5.16 (2H, d, J=7.2 Hz), 6.83 (1H, t, J=7.8 Hz), 7.14 (4H, m), 7.36 (4H, m), 8.38 (1H, s), 10.39 (1H, t, J=5.7 Hz), 11.20 (1H, s).

Example K-3

2-(4-Fluorobenzyl)-9-hydroxy-4-isobutyl-1,8-dioxo-1,3,4,8-tetrahydro-2H-pyrid[1,2-d][1,2,4]triazine-7-carboxylic acid 4-fluorobenzylamide melting point: 206° C.
NMR (DMSO-d$_6$) δ: 0.64 (3H, d, J=6.0 Hz), 0.80 (3H, d, J=6.0 Hz), 1.23 (2H, s), 1.55 (1H, t, J=9.3 Hz), 4.50 (3H, m), 4.89 (1H, d, 14.1 Hz), 5.50 (1H, s), 7.06 (1H, s), 7.33-7.44 (4H, m), 8.43 (1H, s), 10.40 (1H, t, J=5.7 Hz), 11.44 (1H, s).

Example K-4

2-(4-Fluorobenzyl)-9-hydroxy-4-isopropyl-1,8-dioxo-1,3,4,8-tetrahydro-2H-pyrid[1,2-d][1,2,4]triazine-7-carboxylic acid 4-fluorobenzylamide melting point: 207° C.
NMR (DMSO-d$_6$) δ: 0.64 (3H, d, J=6.6 Hz), 0.69 (3H, d, J=6.6 Hz), 1.89 (1H, m), 4.51 (2H, d, J=6.3 Hz), 4.60 (1H, d, J=14.4 Hz), 4.79 (1H, d, J=14.4 Hz), 5.10 (1H, d, J=8.1 Hz), 7.01 (1H, s), 7.13-7.22 (4H, m), 7.33-7.44 (4H, m), 8.40 (1H, s), 10.42 (1H, t, J=6.0 Hz), 11.44 (1H, s).

Example K-5

4-Cyclopropyl-2-(4-fluorobenzyl)-9-hydroxy-1,8-dioxo-1,3,4,8-tetrahydro-2H-pyrid[1,2-d][1,2,4]triazine-7-carboxylic acid 4-fluorobenzylamide melting point: 235° C.
NMR (DMSO-d$_6$) δ: 0.30-0.57 (4H, m), 1.09 (1H, m), 4.51 (2H, d, J=6.0 Hz), 4.60 (1H, d, J=14.4 Hz), 4.78 (1H, s), 4.83 (1H, d, J=14.4 Hz), 7.10-7.22 (4H, m), 7.33-7.46 (4H, m), 8.52 (1H, s), 10.38 (1H, t, J=6.0 Hz), 11.39 (1H, s).

Example K-6

4-Tert-butyl-2-(4-fluorobenzyl)-9-hydroxy-1,8-dioxo-1,3,4,8-tetrahydro-2H-pyrid[1,2-d][1,2,4]triazine-7-carboxylic acid 4-fluorobenzylamide melting point: 270° C.
NMR (DMSO-d$_6$) δ: 0.91 (9H, s), 4.45 (1H, d, J=14.4 Hz), 4.52 (2H, d, J=6.0 Hz), 5.03 (1H, d, J=14.4 Hz), 5.27 (1H, d, J=3.3 Hz), 7.05 (1H, d, J=3.3 Hz), 7.13-7.24 (4H, m), 7.33-7.46 (4H, m), 8.41 (1H, s), 10.40 (1H, t, J=5.7 Hz), 11.51 (1H, s).

The present invention further includes the following compounds.

[Chemical formula 77]

(I-9)
Z = C, Ra = H

| No | (R) m | $R^b$ | $R^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)COCH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)COCH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)COCH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)COCH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)COCH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)COCH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F-Ph) |
| 32 | 4-F | —CH(CH$_3$)$_2$ | —CH$_2$(4-F-Ph) |
| 33 | 4-F | —CH$_2$CH$_2$OCH$_3$ | —CH$_2$(4-F-Ph) |
| 34 | 4-F | —N(CH$_3$)COCH$_3$ | —CH$_2$(4-F-Ph) |
| 35 | 4-F | —N(CH$_3$)$_2$ | —CH$_2$(4-F-Ph) |
| 36 | 2,4-F | —CH$_3$ | —CH$_2$(4-F-Ph) |
| 37 | 2,4-F | —CH(CH$_3$)$_2$ | —CH$_2$(4-F-Ph) |
| 38 | 2,4-F | —CH$_2$CH$_2$OCH$_3$ | —CH$_2$(4-F-Ph) |
| 39 | 2,4-F | —N(CH$_3$)COCH$_3$ | —CH$_2$(4-F-Ph) |
| 40 | 2,4-F | —N(CH$_3$)$_2$ | —CH$_2$(4-F-Ph) |
| 41 | 2-F, 3-Cl | —CH$_3$ | —CH$_2$(4-F-Ph) |
| 42 | 2-F, 3-Cl | —CH(CH$_3$)$_2$ | —CH$_2$(4-F-Ph) |
| 43 | 2-F, 3-Cl | —CH$_2$CH$_2$OCH$_3$ | —CH$_2$(4-F-Ph) |
| 44 | 2-F, 3-Cl | —N(CH$_3$)COCH$_3$ | —CH$_2$(4-F-Ph) |
| 45 | 2-F, 3-Cl | —N(CH$_3$)$_2$ | —CH$_2$(4-F-Ph) |
| 46 | 4-F | H | CH$_3$ |
| 47 | 2,4-F | H | CH$_3$ |
| 48 | 2-F, 3-Cl | H | CH$_3$ |
| 49 | 4-F | H | CH$_2$CH$_2$OCH$_3$ |
| 50 | 2,4-F | H | CH$_2$CH$_2$OCH$_3$ |
| 51 | 2-F, 3-Cl | H | CH$_2$CH$_2$OCH$_3$ |
| 52 | 4-F | H | —CH$_2$(4-F-Ph) |

[Chemical formula 78]

(I-9)
Z = C, Rb = H

| No | (R) m | $R^b$ | $R^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)COCH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)COCH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)COCH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)COCH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |

-continued

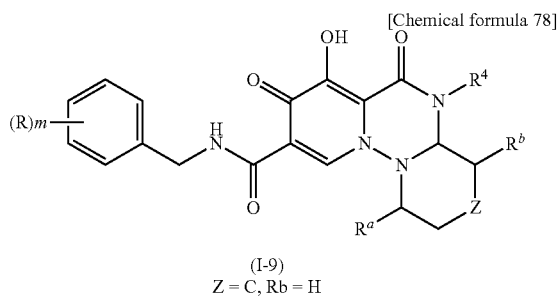

(I-9)
Z = C, Rb = H

| No | (R) m | R$^b$ | R$^4$ |
|---|---|---|---|
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)COCH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)COCH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F-Ph) |
| 32 | 4-F | —CH(CH$_3$)$_2$ | —CH$_2$(4-F-Ph) |
| 33 | 4-F | —CH$_2$CH$_2$OCH$_3$ | —CH$_2$(4-F-Ph) |
| 34 | 4-F | —N(CH$_3$)COCH$_3$ | —CH$_2$(4-F-Ph) |
| 35 | 4-F | —N(CH$_3$)$_2$ | —CH$_2$(4-F-Ph) |
| 36 | 2,4-F | —CH$_3$ | —CH$_2$(4-F-Ph) |
| 37 | 2,4-F | —CH(CH$_3$)$_2$ | —CH$_2$(4-F-Ph) |
| 38 | 2,4-F | —CH$_2$CH$_2$OCH$_3$ | —CH$_2$(4-F-Ph) |
| 39 | 2,4-F | —N(CH$_3$)COCH$_3$ | —CH$_2$(4-F-Ph) |
| 40 | 2,4-F | —N(CH$_3$)$_2$ | —CH$_2$(4-F-Ph) |
| 41 | 2-F, 3-Cl | —CH$_3$ | —CH$_2$(4-F-Ph) |
| 42 | 2-F, 3-Cl | —CH(CH$_3$)$_2$ | —CH$_2$(4-F-Ph) |
| 43 | 2-F, 3-Cl | —CH$_2$CH$_2$OCH$_3$ | —CH$_2$(4-F-Ph) |
| 44 | 2-F, 3-Cl | —N(CH$_3$)COCH$_3$ | —CH$_2$(4-F-Ph) |
| 45 | 2-F, 3-Cl | —N(CH$_3$)$_2$ | —CH$_2$(4-F-Ph) |

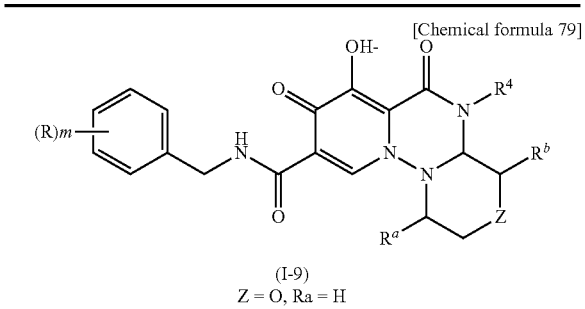

(I-9)
Z = O, Ra = H

| No | (R) m | R$^b$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)COCH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |

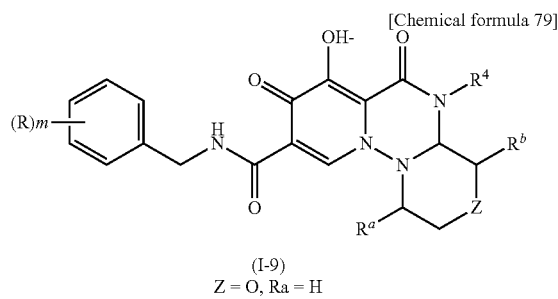

(I-9)
Z = O, Ra = H

| No | (R) m | R$^b$ | R$^4$ |
|---|---|---|---|
| 8 | 2,4-F | —CH$_2$CH$_2$OCH$_3$ | CH$_3$ |
| 9 | 2,4-F | —N(CH$_3$)COCH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)COCH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)COCH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)COCH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)COCH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F-Ph) |
| 32 | 4-F | —CH(CH$_3$)$_2$ | —CH$_2$(4-F-Ph) |
| 33 | 4-F | —CH$_2$CH$_2$OCH$_3$ | —CH$_2$(4-F-Ph) |
| 34 | 4-F | —N(CH$_3$)COCH$_3$ | —CH$_2$(4-F-Ph) |
| 35 | 4-F | —N(CH$_3$)$_2$ | —CH$_2$(4-F-Ph) |
| 36 | 2,4-F | —CH$_3$ | —CH$_2$(4-F-Ph) |
| 37 | 2,4-F | —CH(CH$_3$)$_2$ | —CH$_2$(4-F-Ph) |
| 38 | 2,4-F | —CH$_2$CH$_2$OCH$_3$ | —CH$_2$(4-F-Ph) |
| 39 | 2,4-F | —N(CH$_3$)COCH$_3$ | —CH$_2$(4-F-Ph) |
| 40 | 2,4-F | —N(CH$_3$)$_2$ | —CH$_2$(4-F-Ph) |
| 41 | 2-F, 3-Cl | —CH$_3$ | —CH$_2$(4-F-Ph) |
| 42 | 2-F, 3-Cl | —CH(CH$_3$)$_2$ | —CH$_2$(4-F-Ph) |
| 43 | 2-F, 3-Cl | —CH$_2$CH$_2$OCH$_3$ | —CH$_2$(4-F-Ph) |
| 44 | 2-F, 3-Cl | —N(CH$_3$)COCH$_3$ | —CH$_2$(4-F-Ph) |
| 45 | 2-F, 3-Cl | —N(CH$_3$)$_2$ | —CH$_2$(4-F-Ph) |
| 46 | 4-F | H | CH$_3$ |
| 47 | 2,4-F | H | CH$_3$ |
| 48 | 2-F, 3-Cl | H | CH$_3$ |
| 49 | 4-F | H | CH$_2$CH$_2$OCH$_3$ |
| 50 | 2,4-F | H | CH$_2$CH$_2$OCH$_3$ |
| 51 | 2-F, 3-Cl | H | CH$_2$CH$_2$OCH$_3$ |
| 52 | 4-F | H | —CH$_2$(4-F-Ph) |

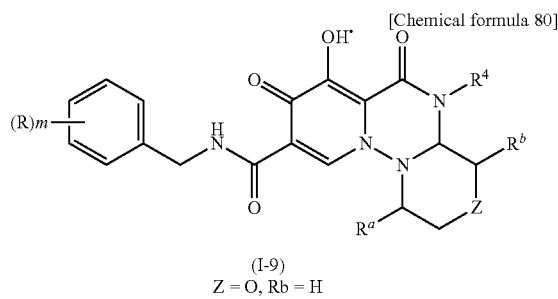

(I-9)
Z = O, Rb = H

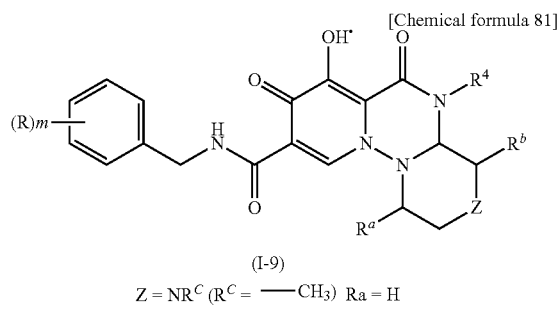

(I-9)
Z = NR^C (R^C = —CH_3)  Ra = H

| No | (R)m | $R^b$ | $R^4$ |
|---|---|---|---|
| 1 | 4-F | —CH_3 | CH_3 |
| 2 | 4-F | —CH(CH_3)_2 | CH_3 |
| 3 | 4-F | —CH_2CH_2OCH_3 | CH_3 |
| 4 | 4-F | —N(CH_3)COCH_3 | CH_3 |
| 5 | 4-F | —N(CH_3)_2 | CH_3 |
| 6 | 2,4-F | —CH_3 | CH_3 |
| 7 | 2,4-F | —CH(CH_3)_2 | CH_3 |
| 8 | 2,4-F | —CH_2CH_2OCH_3 | CH_3 |
| 9 | 2,4-F | —N(CH_3)COCH_3 | CH_3 |
| 10 | 2,4-F | —N(CH_3)_2 | CH_3 |
| 11 | 2-F, 3-Cl | —CH_3 | CH_3 |
| 12 | 2-F, 3-Cl | —CH(CH_3)_2 | CH_3 |
| 13 | 2-F, 3-Cl | —CH_2CH_2OCH_3 | CH_3 |
| 14 | 2-F, 3-Cl | —N(CH_3)COCH_3 | CH_3 |
| 15 | 2-F, 3-Cl | —N(CH_3)_2 | CH_3 |
| 16 | 4-F | —CH_3 | CH_2CH_2OCH_3 |
| 17 | 4-F | —CH(CH_3)_2 | CH_2CH_2OCH_3 |
| 18 | 4-F | —CH_2CH_2OCH_3 | CH_2CH_2OCH_3 |
| 19 | 4-F | —N(CH_3)COCH_3 | CH_2CH_2OCH_3 |
| 20 | 4-F | —N(CH_3)_2 | CH_2CH_2OCH_3 |
| 21 | 2,4-F | —CH_3 | CH_2CH_2OCH_3 |
| 22 | 2,4-F | —CH(CH_3)_2 | CH_2CH_2OCH_3 |
| 23 | 2,4-F | —CH_2CH_2OCH_3 | CH_2CH_2OCH_3 |
| 24 | 2,4-F | —N(CH_3)COCH_3 | CH_2CH_2OCH_3 |
| 25 | 2,4-F | —N(CH_3)_2 | CH_2CH_2OCH_3 |
| 26 | 2-F, 3-Cl | —CH_3 | CH_2CH_2OCH_3 |
| 27 | 2-F, 3-Cl | —CH(CH_3)_2 | CH_2CH_2OCH_3 |
| 28 | 2-F, 3-Cl | —CH_2CH_2OCH_3 | CH_2CH_2OCH_3 |
| 29 | 2-F, 3-Cl | —N(CH_3)COCH_3 | CH_2CH_2OCH_3 |
| 30 | 2-F, 3-Cl | —N(CH_3)_2 | CH_2CH_2OCH_3 |
| 31 | 4-F | —CH_3 | —CH_2(4-F-Ph) |
| 32 | 4-F | —CH(CH_3)_2 | —CH_2(4-F-Ph) |
| 33 | 4-F | —CH_2CH_2OCH_3 | —CH_2(4-F-Ph) |
| 34 | 4-F | —N(CH_3)COCH_3 | —CH_2(4-F-Ph) |
| 35 | 4-F | —N(CH_3)_2 | —CH_2(4-F-Ph) |
| 36 | 2,4-F | —CH_3 | —CH_2(4-F-Ph) |
| 37 | 2,4-F | —CH(CH_3)_2 | —CH_2(4-F-Ph) |
| 38 | 2,4-F | —CH_2CH_2OCH_3 | —CH_2(4-F-Ph) |
| 39 | 2,4-F | —N(CH_3)COCH_3 | —CH_2(4-F-Ph) |
| 40 | 2,4-F | —N(CH_3)_2 | —CH_2(4-F-Ph) |
| 41 | 2-F, 3-Cl | —CH_3 | —CH_2(4-F-Ph) |
| 42 | 2-F, 3-Cl | —CH(CH_3)_2 | —CH_2(4-F-Ph) |
| 43 | 2-F, 3-Cl | —CH_2CH_2OCH_3 | —CH_2(4-F-Ph) |
| 44 | 2-F, 3-Cl | —N(CH_3)COCH_3 | —CH_2(4-F-Ph) |
| 45 | 2-F, 3-Cl | —N(CH_3)_2 | —CH_2(4-F-Ph) |

| No | (R)m | $R^b$ | $R^4$ |
|---|---|---|---|
| 1 | 4-F | —CH_3 | CH_3 |
| 2 | 4-F | —CH(CH_3)_2 | CH_3 |
| 3 | 4-F | —CH_2CH_2OCH_3 | CH_3 |
| 4 | 4-F | —N(CH_3)COCH_3 | CH_3 |
| 5 | 4-F | —N(CH_3)_2 | CH_3 |
| 6 | 2,4-F | —CH_3 | CH_3 |
| 7 | 2,4-F | —CH(CH_3)_2 | CH_3 |
| 8 | 2,4-F | —CH_2CH_2OCH_3 | CH_3 |
| 9 | 2,4-F | —N(CH_3)COCH_3 | CH_3 |
| 10 | 2,4-F | —N(CH_3)_2 | CH_3 |
| 11 | 2-F, 3-Cl | —CH_3 | CH_3 |
| 12 | 2-F, 3-Cl | —CH(CH_3)_2 | CH_3 |
| 13 | 2-F, 3-Cl | —CH_2CH_2OCH_3 | CH_3 |
| 14 | 2-F, 3-Cl | —N(CH_3)COCH_3 | CH_3 |
| 15 | 2-F, 3-Cl | —N(CH_3)_2 | CH_3 |
| 16 | 4-F | —CH_3 | CH_2CH_2OCH_3 |
| 17 | 4-F | —CH(CH_3)_2 | CH_2CH_2OCH_3 |
| 18 | 4-F | —CH_2CH_2OCH_3 | CH_2CH_2OCH_3 |
| 19 | 4-F | —N(CH_3)COCH_3 | CH_2CH_2OCH_3 |
| 20 | 4-F | —N(CH_3)_2 | CH_2CH_2OCH_3 |
| 21 | 2,4-F | —CH_3 | CH_2CH_2OCH_3 |
| 22 | 2,4-F | —CH(CH_3)_2 | CH_2CH_2OCH_3 |
| 23 | 2,4-F | —CH_2CH_2OCH_3 | CH_2CH_2OCH_3 |
| 24 | 2,4-F | —N(CH_3)COCH_3 | CH_2CH_2OCH_3 |
| 25 | 2,4-F | —N(CH_3)_2 | CH_2CH_2OCH_3 |
| 26 | 2-F, 3-Cl | —CH_3 | CH_2CH_2OCH_3 |
| 27 | 2-F, 3-Cl | —CH(CH_3)_2 | CH_2CH_2OCH_3 |
| 28 | 2-F, 3-Cl | —CH_2CH_2OCH_3 | CH_2CH_2OCH_3 |
| 29 | 2-F, 3-Cl | —N(CH_3)COCH_3 | CH_2CH_2OCH_3 |
| 30 | 2-F, 3-Cl | —N(CH_3)_2 | CH_2CH_2OCH_3 |
| 31 | 4-F | —CH_3 | —CH_2(4-F-Ph) |
| 32 | 4-F | —CH(CH_3)_2 | —CH_2(4-F-Ph) |
| 33 | 4-F | —CH_2CH_2OCH_3 | —CH_2(4-F-Ph) |
| 34 | 4-F | —N(CH_3)COCH_3 | —CH_2(4-F-Ph) |
| 35 | 4-F | —N(CH_3)_2 | —CH_2(4-F-Ph) |
| 36 | 2,4-F | —CH_3 | —CH_2(4-F-Ph) |
| 37 | 2,4-F | —CH(CH_3)_2 | —CH_2(4-F-Ph) |
| 38 | 2,4-F | —CH_2CH_2OCH_3 | —CH_2(4-F-Ph) |
| 39 | 2,4-F | —N(CH_3)COCH_3 | —CH_2(4-F-Ph) |
| 40 | 2,4-F | —N(CH_3)_2 | —CH_2(4-F-Ph) |
| 41 | 2-F, 3-Cl | —CH_3 | —CH_2(4-F-Ph) |
| 42 | 2-F, 3-Cl | —CH(CH_3)_2 | —CH_2(4-F-Ph) |
| 43 | 2-F, 3-Cl | —CH_2CH_2OCH_3 | —CH_2(4-F-Ph) |
| 44 | 2-F, 3-Cl | —N(CH_3)COCH_3 | —CH_2(4-F-Ph) |
| 45 | 2-F, 3-Cl | —N(CH_3)_2 | —CH_2(4-F-Ph) |
| 46 | 4-F | H | CH_3 |
| 47 | 2,4-F | H | CH_3 |

-continued

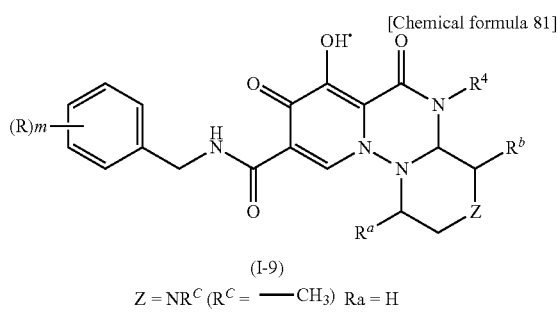

(I-9)

Z = NR$^C$ (R$^C$ = —CH$_3$) Ra = H

| No | (R) m | R$^b$ | R$^4$ |
|----|-------|-------|-------|
| 48 | 2-F, 3-Cl | H | CH$_3$ |
| 49 | 4-F | H | CH$_2$CH$_2$OCH$_3$ |
| 50 | 2,4-F | H | CH$_2$CH$_2$OCH$_3$ |
| 51 | 2-F, 3-Cl | H | CH$_2$CH$_2$OCH$_3$ |
| 52 | 4-F | H | —CH$_2$(4-F-Ph) |

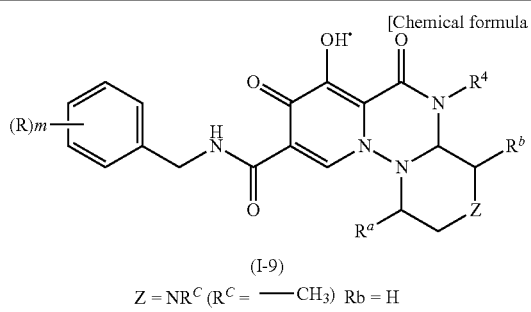

(I-9)

Z = NR$^C$ (R$^C$ = —CH$_3$) Rb = H

| No | (R) m | R$^b$ | R$^4$ |
|----|-------|-------|-------|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)COCH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)COCH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)COCH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)COCH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)COCH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |

-continued

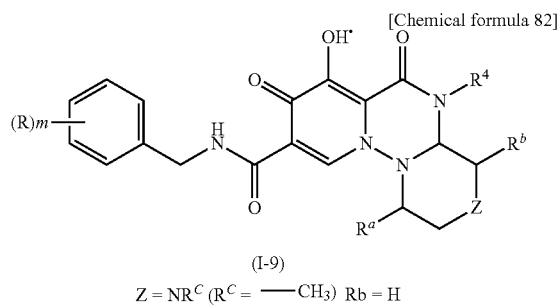

(I-9)

Z = NR$^C$ (R$^C$ = —CH$_3$) Rb = H

| No | (R) m | R$^b$ | R$^4$ |
|----|-------|-------|-------|
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)COCH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F-Ph) |
| 32 | 4-F | —CH(CH$_3$)$_2$ | —CH$_2$(4-F-Ph) |
| 33 | 4-F | —CH$_2$CH$_2$OCH$_3$ | —CH$_2$(4-F-Ph) |
| 34 | 4-F | —N(CH$_3$)COCH$_3$ | —CH$_2$(4-F-Ph) |
| 35 | 4-F | —N(CH$_3$)$_2$ | —CH$_2$(4-F-Ph) |
| 36 | 2,4-F | —CH$_3$ | —CH$_2$(4-F-Ph) |
| 37 | 2,4-F | —CH(CH$_3$)$_2$ | —CH$_2$(4-F-Ph) |
| 38 | 2,4-F | —CH$_2$CH$_2$OCH$_3$ | —CH$_2$(4-F-Ph) |
| 39 | 2,4-F | —N(CH$_3$)COCH$_3$ | —CH$_2$(4-F-Ph) |
| 40 | 2,4-F | —N(CH$_3$)$_2$ | —CH$_2$(4-F-Ph) |
| 41 | 2-F, 3-Cl | —CH$_3$ | —CH$_2$(4-F-Ph) |
| 42 | 2-F, 3-Cl | —CH(CH$_3$)$_2$ | —CH$_2$(4-F-Ph) |
| 43 | 2-F, 3-Cl | —CH$_2$CH$_2$OCH$_3$ | —CH$_2$(4-F-Ph) |
| 44 | 2-F, 3-Cl | —N(CH$_3$)COCH$_3$ | —CH$_2$(4-F-Ph) |
| 45 | 2-F, 3-Cl | —N(CH$_3$)$_2$ | —CH$_2$(4-F-Ph) |

[Chemical formula 83]

(I-9)

Z = NR$^C$ (R$^C$ = —CH(CH$_3$)$_2$) Ra = H

| No | (R) m | R$^b$ | R$^4$ |
|----|-------|-------|-------|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)COCH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)COCH$_3$ | CH$_3$ |
| 10 | 2,4-F | —N(CH$_3$)$_2$ | CH$_3$ |
| 11 | 2-F, 3-Cl | —CH$_3$ | CH$_3$ |

-continued

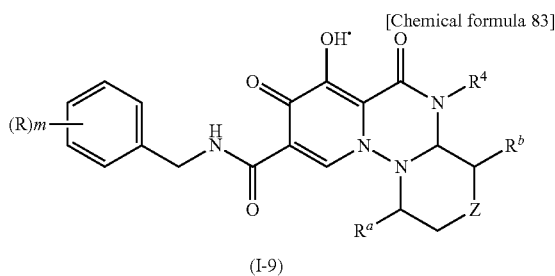

(I-9)
Z = NR$^C$ (R$^C$ = —CH(CH$_3$)$_2$)  Ra = H

| No | (R) m | R$^b$ | R$^4$ |
|----|-------|-------|-------|
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)COCH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)COCH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)COCH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)COCH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F-Ph) |
| 32 | 4-F | —CH(CH$_3$)$_2$ | —CH$_2$(4-F-Ph) |
| 33 | 4-F | —CH$_2$CH$_2$OCH$_3$ | —CH$_2$(4-F-Ph) |
| 34 | 4-F | —N(CH$_3$)COCH$_3$ | —CH$_2$(4-F-Ph) |
| 35 | 4-F | —N(CH$_3$)$_2$ | —CH$_2$(4-F-Ph) |
| 36 | 2,4-F | —CH$_3$ | —CH$_2$(4-F-Ph) |
| 37 | 2,4-F | —CH(CH$_3$)$_2$ | —CH$_2$(4-F-Ph) |
| 38 | 2,4-F | —CH$_2$CH$_2$OCH$_3$ | —CH$_2$(4-F-Ph) |
| 39 | 2,4-F | —N(CH$_3$)COCH$_3$ | —CH$_2$(4-F-Ph) |
| 40 | 2,4-F | —N(CH$_3$)$_2$ | —CH$_2$(4-F-Ph) |
| 41 | 2-F, 3-Cl | —CH$_3$ | —CH$_2$(4-F-Ph) |
| 42 | 2-F, 3-Cl | —CH(CH$_3$)$_2$ | —CH$_2$(4-F-Ph) |
| 43 | 2-F, 3-Cl | —CH$_2$CH$_2$OCH$_3$ | —CH$_2$(4-F-Ph) |
| 44 | 2-F, 3-Cl | —N(CH$_3$)COCH$_3$ | —CH$_2$(4-F-Ph) |
| 45 | 2-F, 3-Cl | —N(CH$_3$)$_2$ | —CH$_2$(4-F-Ph) |
| 46 | 4-F | H | CH$_3$ |
| 47 | 2,4-F | H | CH$_3$ |
| 48 | 2-F, 3-Cl | H | CH$_3$ |
| 49 | 4-F | H | CH$_2$CH$_2$OCH$_3$ |
| 50 | 2,4-F | H | CH$_2$CH$_2$OCH$_3$ |
| 51 | 2-F, 3-Cl | H | CH$_2$CH$_2$OCH$_3$ |
| 52 | 4-F | H | —CH$_2$(4-F-Ph) |

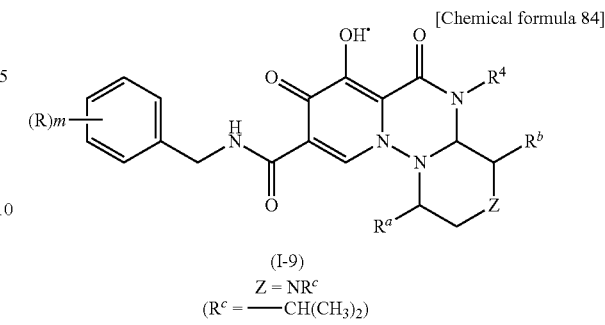

(I-9)
Z = NR$^c$
(R$^c$ = —CH(CH$_3$)$_2$)
Rb = H

| No | (R) m | R$^a$ | R$^4$ |
|----|-------|-------|-------|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |

-continued

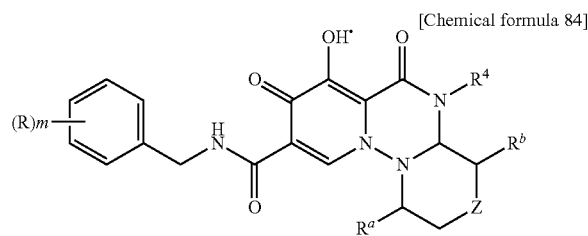

(I-9)
Z = NR$^c$
(R$^c$ = —CH(CH$_3$)$_2$)
R$^b$ = H

| No | (R) m | R$^a$ | R$^4$ |
|---|---|---|---|
| 45 | 2-F, 3-Cl | —N(CH$_3$)$_2$ | —CH$_2$(4-F—Ph) |

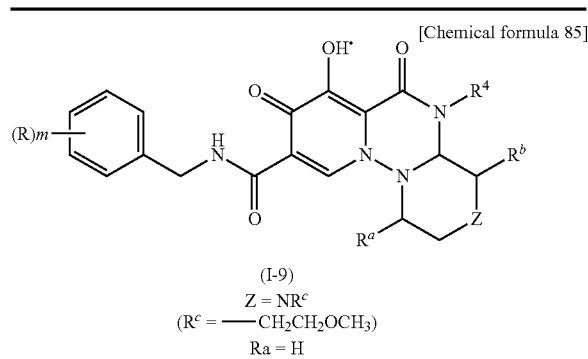

(I-9)
Z = NR$^c$
(R$^c$ = —CH$_2$CH$_2$OCH$_3$)
R$^a$ = H

| No | (R) m | R$^b$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |

-continued

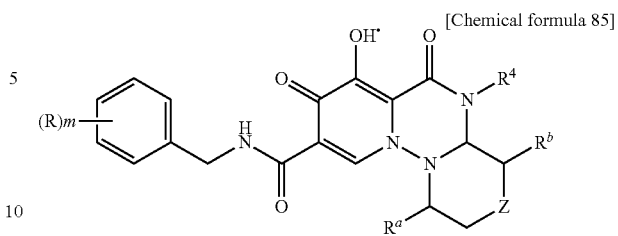

(I-9)
Z = NR$^c$
(R$^c$ = —CH$_2$CH$_2$OCH$_3$)
R$^a$ = H

| No | (R) m | R$^b$ | R$^4$ |
|---|---|---|---|
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |
| 46 | 4-F | H | CH$_3$ |
| 47 | 2,4-F | H | CH$_3$ |
| 48 | 2-F, 3-Cl | H | CH$_3$ |
| 49 | 4-F | H | CH$_2$CH$_2$OCH$_3$ |
| 50 | 2,4-F | H | CH$_2$CH$_2$OCH$_3$ |
| 51 | 2-F, 3-Cl | H | CH$_2$CH$_2$OCH$_3$ |
| 52 | 4-F | H | —CH$_2$(4-F—Ph) |

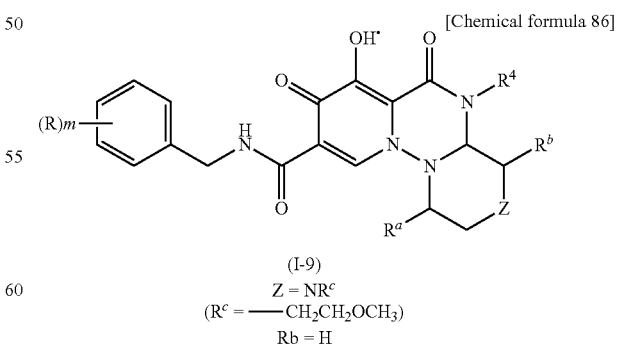

(I-9)
Z = NR$^c$
(R$^c$ = —CH$_2$CH$_2$OCH$_3$)
R$^b$ = H

| No | (R) m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |

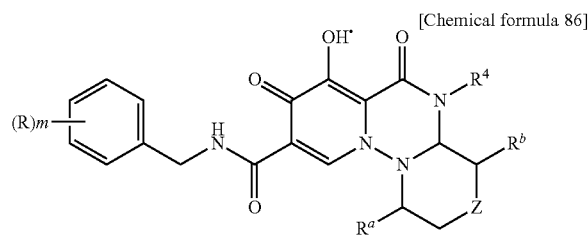

(I-9)
Z = NR$^c$
(R$^c$ = —CH$_2$CH$_2$OCH$_3$)
Rb = H

| No | (R) m | R$^a$ | R$^4$ |
|---|---|---|---|
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

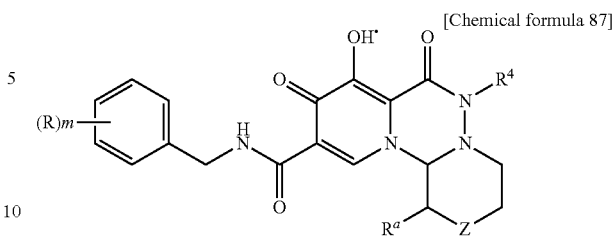

(I-9)
Z = C

| No | (R) m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

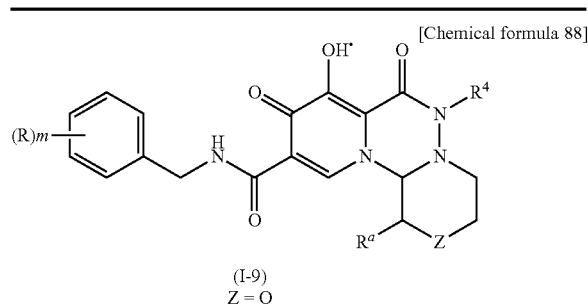

(I-9)
Z = O

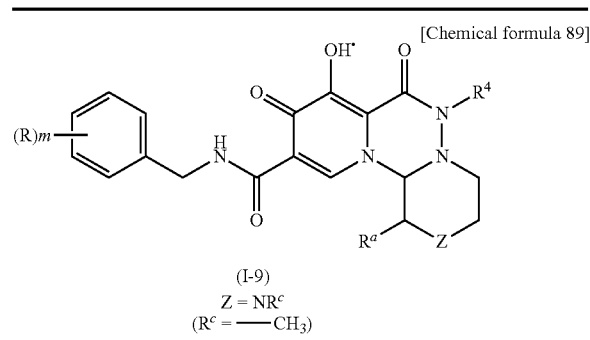

(I-9)
Z = NR$^c$
(R$^c$ = —CH$_3$)

| No | (R)m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

| No | (R)m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

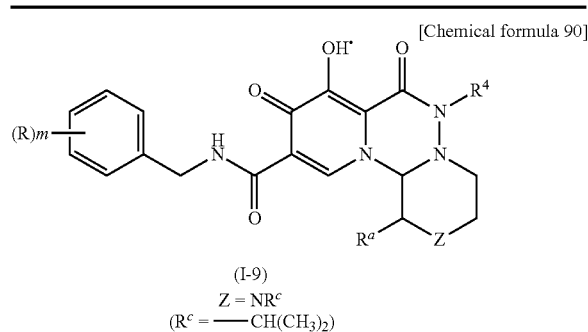

(I-9)
Z = NR$^c$
(R$^c$ = —CH(CH$_3$)$_2$)

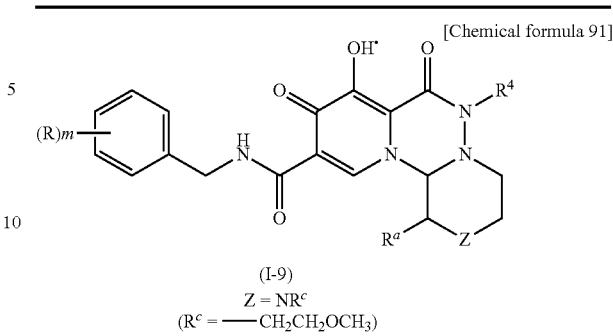

(I-9)
Z = NR$^c$
(R$^c$ = —CH$_2$CH$_2$OCH$_3$)

| No | (R) m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

| No | (R) m | R$^a$ | R$^4$ |
|---|---|---|---|
| 1 | 4-F | —CH$_3$ | CH$_3$ |
| 2 | 4-F | —CH(CH$_3$)$_2$ | CH$_3$ |
| 3 | 4-F | —CH$_2$CH$_2$OCH$_3$ | CH$_3$ |
| 4 | 4-F | —N(CH$_3$)CO CH$_3$ | CH$_3$ |
| 5 | 4-F | —N(CH$_3$)$_2$ | CH$_3$ |
| 6 | 2,4-F | —CH$_3$ | CH$_3$ |
| 7 | 2,4-F | —CH(CH$_3$)$_2$ | CH$_3$ |
| 8 | 2,4-F | —CH$_2$CH$_2$OCH$_3$ | CH$_3$ |
| 9 | 2,4-F | —N(CH$_3$)CO CH$_3$ | CH$_3$ |
| 10 | 2,4-F | —N(CH$_3$)$_2$ | CH$_3$ |
| 11 | 2-F, 3-Cl | —CH$_3$ | CH$_3$ |
| 12 | 2-F, 3-Cl | —CH(CH$_3$)$_2$ | CH$_3$ |
| 13 | 2-F, 3-Cl | —CH$_2$CH$_2$OCH$_3$ | CH$_3$ |
| 14 | 2-F, 3-Cl | —N(CH$_3$)CO CH$_3$ | CH$_3$ |
| 15 | 2-F, 3-Cl | —N(CH$_3$)$_2$ | CH$_3$ |
| 16 | 4-F | —CH$_3$ | CH$_2$CH$_2$OCH$_3$ |
| 17 | 4-F | —CH(CH$_3$)$_2$ | CH$_2$CH$_2$OCH$_3$ |
| 18 | 4-F | —CH$_2$CH$_2$OCH$_3$ | CH$_2$CH$_2$OCH$_3$ |
| 19 | 4-F | —N(CH$_3$)CO CH$_3$ | CH$_2$CH$_2$OCH$_3$ |
| 20 | 4-F | —N(CH$_3$)$_2$ | CH$_2$CH$_2$OCH$_3$ |
| 21 | 2,4-F | —CH$_3$ | CH$_2$CH$_2$OCH$_3$ |
| 22 | 2,4-F | —CH(CH$_3$)$_2$ | CH$_2$CH$_2$OCH$_3$ |
| 23 | 2,4-F | —CH$_2$CH$_2$OCH$_3$ | CH$_2$CH$_2$OCH$_3$ |
| 24 | 2,4-F | —N(CH$_3$)CO CH$_3$ | CH$_2$CH$_2$OCH$_3$ |
| 25 | 2,4-F | —N(CH$_3$)$_2$ | CH$_2$CH$_2$OCH$_3$ |
| 26 | 2-F, 3-Cl | —CH$_3$ | CH$_2$CH$_2$OCH$_3$ |
| 27 | 2-F, 3-Cl | —CH(CH$_3$)$_2$ | CH$_2$CH$_2$OCH$_3$ |
| 28 | 2-F, 3-Cl | —CH$_2$CH$_2$OCH$_3$ | CH$_2$CH$_2$OCH$_3$ |
| 29 | 2-F, 3-Cl | —N(CH$_3$)CO CH$_3$ | CH$_2$CH$_2$OCH$_3$ |
| 30 | 2-F, 3-Cl | —N(CH$_3$)$_2$ | CH$_2$CH$_2$OCH$_3$ |
| 31 | 4-F | —CH$_3$ | —CH$_2$(4-F—Ph) |
| 32 | 4-F | —CH(CH$_3$)$_2$ | —CH$_2$(4-F—Ph) |
| 33 | 4-F | —CH$_2$CH$_2$OCH$_3$ | —CH$_2$(4-F—Ph) |
| 34 | 4-F | —N(CH$_3$)CO CH$_3$ | —CH$_2$(4-F—Ph) |
| 35 | 4-F | —N(CH$_3$)$_2$ | —CH$_2$(4-F—Ph) |
| 36 | 2,4-F | —CH$_3$ | —CH$_2$(4-F—Ph) |
| 37 | 2,4-F | —CH(CH$_3$)$_2$ | —CH$_2$(4-F—Ph) |
| 38 | 2,4-F | —CH$_2$CH$_2$OCH$_3$ | —CH$_2$(4-F—Ph) |
| 39 | 2,4-F | —N(CH$_3$)CO CH$_3$ | —CH$_2$(4-F—Ph) |
| 40 | 2,4-F | —N(CH$_3$)$_2$ | —CH$_2$(4-F—Ph) |
| 41 | 2-F, 3-Cl | —CH$_3$ | —CH$_2$(4-F—Ph) |
| 42 | 2-F, 3-Cl | —CH(CH$_3$)$_2$ | —CH$_2$(4-F—Ph) |
| 43 | 2-F, 3-Cl | —CH$_2$CH$_2$OCH$_3$ | —CH$_2$(4-F—Ph) |
| 44 | 2-F, 3-Cl | —N(CH$_3$)CO CH$_3$ | —CH$_2$(4-F—Ph) |
| 45 | 2-F, 3-Cl | —N(CH$_3$)$_2$ | —CH$_2$(4-F—Ph) |

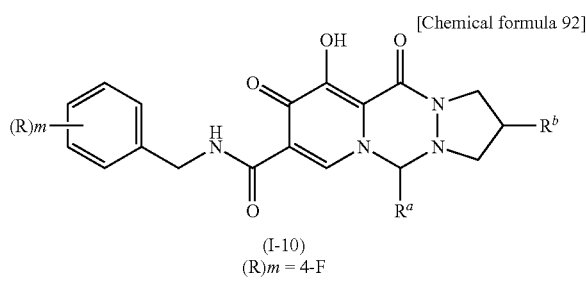

(I-10)
(R)m = 4-F

| No | $R^a$ | $R^b$ |
|----|-------|-------|
| 1 | H | H |
| 2 | —CH₃ | H |
| 3 | —CH(CH₃)₂ | H |
| 4 | —CH₂CH₂OCH₃ | H |
| 5 | H | —CH₃ |
| 6 | —CH₃ | —CH₃ |
| 7 | —CH(CH₃)₂ | —CH₃ |
| 8 | —CH₂CH₂OCH₃ | —CH₃ |
| 9 | H | —CH(CH₃)₂ |
| 10 | —CH₃ | —CH(CH₃)₂ |
| 11 | —CH(CH₃)₂ | —CH(CH₃)₂ |
| 12 | —CH₂CH₂OCH₃ | —CH(CH₃)₂ |
| 13 | H | —CH₂CH₂OCH₃ |
| 14 | —CH₃ | —CH₂CH₂OCH₃ |
| 15 | —CH(CH₃)₂ | —CH₂CH₂OCH₃ |
| 16 | —CH₂CH₂OCH₃ | —CH₂CH₂OCH₃ |
| 17 | H | —N(CH₃)₂ |
| 18 | —CH₃ | —N(CH₃)₂ |
| 19 | —CH(CH₃)₂ | —N(CH₃)₂ |
| 20 | —CH₂CH₂OCH₃ | —N(CH₃)₂ |
| 21 | H | —N(CH₃)CO CH₃ |
| 22 | —CH₃ | —N(CH₃)CO CH₃ |
| 23 | —CH(CH₃)₂ | —N(CH₃)CO CH₃ |
| 24 | —CH₂CH₂OCH₃ | —N(CH₃)CO CH₃ |

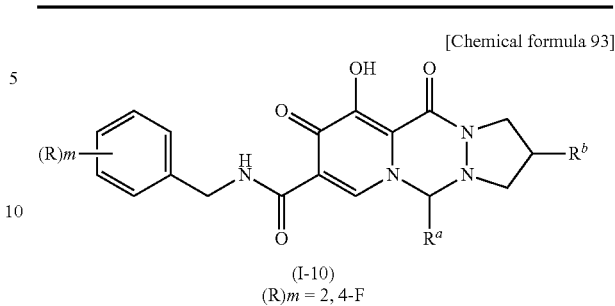

(I-10)
(R)m = 2, 4-F

| No | $R^a$ | $R^b$ |
|----|-------|-------|
| 1 | H | H |
| 2 | —CH₃ | H |
| 3 | —CH(CH₃)₂ | H |
| 4 | —CH₂CH₂OCH₃ | H |
| 5 | H | —CH₃ |
| 6 | —CH₃ | —CH₃ |
| 7 | —CH(CH₃)₂ | —CH₃ |
| 8 | —CH₂CH₂OCH₃ | —CH₃ |
| 9 | H | —CH(CH₃)₂ |
| 10 | —CH₃ | —CH(CH₃)₂ |
| 11 | —CH(CH₃)₂ | —CH(CH₃)₂ |
| 12 | —CH₂CH₂OCH₃ | —CH(CH₃)₂ |
| 13 | H | —CH₂CH₂OCH₃ |
| 14 | —CH₃ | —CH₂CH₂OCH₃ |
| 15 | —CH(CH₃)₂ | —CH₂CH₂OCH₃ |
| 16 | —CH₂CH₂OCH₃ | —CH₂CH₂OCH₃ |
| 17 | H | —N(CH₃)₂ |
| 18 | —CH₃ | —N(CH₃)₂ |
| 19 | —CH(CH₃)₂ | —N(CH₃)₂ |
| 20 | —CH₂CH₂OCH₃ | —N(CH₃)₂ |
| 21 | H | —N(CH₃)CO CH₃ |
| 22 | —CH₃ | —N(CH₃)CO CH₃ |
| 23 | —CH(CH₃)₂ | —N(CH₃)CO CH₃ |
| 24 | —CH₂CH₂OCH₃ | —N(CH₃)CO CH₃ |

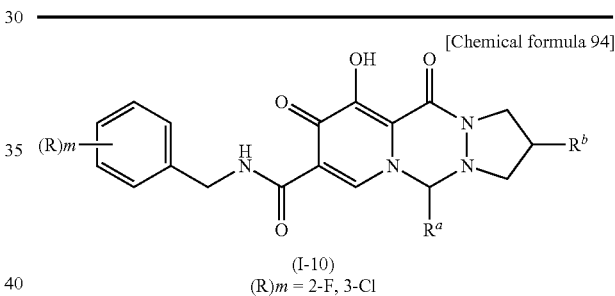

(I-10)
(R)m = 2-F, 3-Cl

| No | $R^a$ | $R^b$ |
|----|-------|-------|
| 1 | H | H |
| 2 | —CH₃ | H |
| 3 | —CH(CH₃)₂ | H |
| 4 | —CH₂CH₂OCH₃ | H |
| 5 | H | —CH₃ |
| 6 | —CH₃ | —CH₃ |
| 7 | —CH(CH₃)₂ | —CH₃ |
| 8 | —CH₂CH₂OCH₃ | —CH₃ |
| 9 | H | —CH(CH₃)₂ |
| 10 | —CH₃ | —CH(CH₃)₂ |
| 11 | —CH(CH₃)₂ | —CH(CH₃)₂ |
| 12 | —CH₂CH₂OCH₃ | —CH(CH₃)₂ |
| 13 | H | —CH₂CH₂OCH₃ |
| 14 | —CH₃ | —CH₂CH₂OCH₃ |
| 15 | —CH(CH₃)₂ | —CH₂CH₂OCH₃ |
| 16 | —CH₂CH₂OCH₃ | —CH₂CH₂OCH₃ |
| 17 | H | —N(CH₃)₂ |
| 18 | —CH₃ | —N(CH₃)₂ |
| 19 | —CH(CH₃)₂ | —N(CH₃)₂ |
| 20 | —CH₂CH₂OCH₃ | —N(CH₃)₂ |
| 21 | H | —N(CH₃)CO CH₃ |
| 22 | —CH₃ | —N(CH₃)CO CH₃ |
| 23 | —CH(CH₃)₂ | —N(CH₃)CO CH₃ |
| 24 | —CH₂CH₂OCH₃ | —N(CH₃)CO CH₃ |

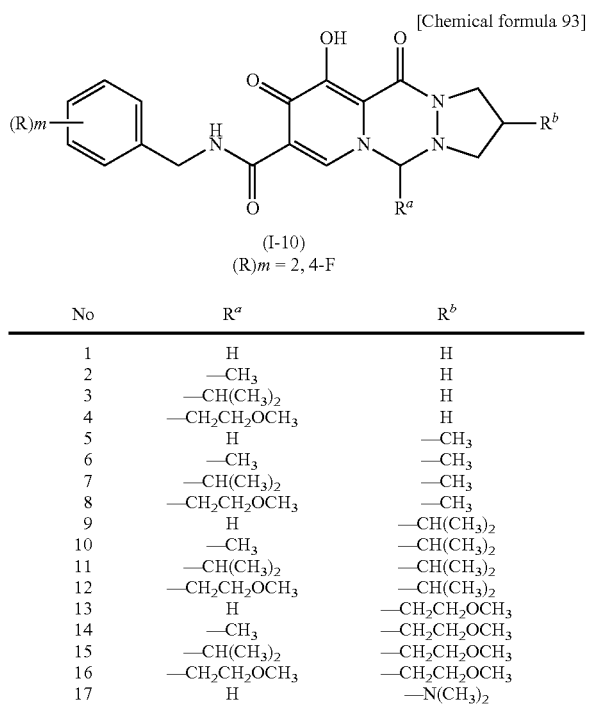

(I-10)
(R)m = 2, 4-F

| No | $R^a$ | $R^b$ |
|----|-------|-------|
| 1 | H | H |
| 2 | —CH₃ | H |
| 3 | —CH(CH₃)₂ | H |
| 4 | —CH₂CH₂OCH₃ | H |
| 5 | H | —CH₃ |
| 6 | —CH₃ | —CH₃ |
| 7 | —CH(CH₃)₂ | —CH₃ |
| 8 | —CH₂CH₂OCH₃ | —CH₃ |
| 9 | H | —CH(CH₃)₂ |
| 10 | —CH₃ | —CH(CH₃)₂ |
| 11 | —CH(CH₃)₂ | —CH(CH₃)₂ |
| 12 | —CH₂CH₂OCH₃ | —CH(CH₃)₂ |
| 13 | H | —CH₂CH₂OCH₃ |
| 14 | —CH₃ | —CH₂CH₂OCH₃ |
| 15 | —CH(CH₃)₂ | —CH₂CH₂OCH₃ |
| 16 | —CH₂CH₂OCH₃ | —CH₂CH₂OCH₃ |
| 17 | H | —N(CH₃)₂ |

[Chemical formula 95]

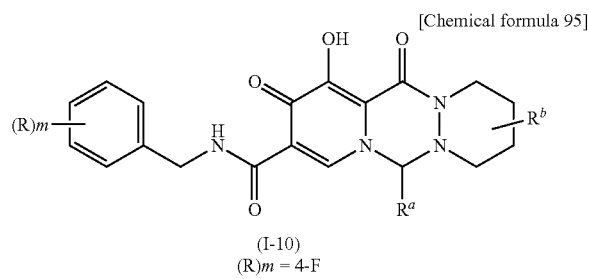

(I-10)
(R)m = 4-F

| No | $R^a$ | $R^b$ |
|---|---|---|
| 1 | H | H |
| 2 | —CH$_3$ | H |
| 3 | —CH(CH$_3$)$_2$ | H |
| 4 | —CH$_2$CH$_2$OCH$_3$ | H |
| 5 | H | —CH$_3$ |
| 6 | —CH$_3$ | —CH$_3$ |
| 7 | —CH(CH$_3$)$_2$ | —CH$_3$ |
| 8 | —CH$_2$CH$_2$OCH$_3$ | —CH$_3$ |
| 9 | H | —CH(CH$_3$)$_2$ |
| 10 | —CH$_3$ | —CH(CH$_3$)$_2$ |
| 11 | —CH(CH$_3$)$_2$ | —CH(CH$_3$)$_2$ |
| 12 | —CH$_2$CH$_2$OCH$_3$ | —CH(CH$_3$)$_2$ |
| 13 | H | —CH$_2$CH$_2$OCH$_3$ |
| 14 | —CH$_3$ | —CH$_2$CH$_2$OCH$_3$ |
| 15 | —CH(CH$_3$)$_2$ | —CH$_2$CH$_2$OCH$_3$ |
| 16 | —CH$_2$CH$_2$OCH$_3$ | —CH$_2$CH$_2$OCH$_3$ |
| 17 | H | —N(CH$_3$)$_2$ |
| 18 | —CH$_3$ | —N(CH$_3$)$_2$ |
| 19 | —CH(CH$_3$)$_2$ | —N(CH$_3$)$_2$ |
| 20 | —CH$_2$CH$_2$OCH$_3$ | —N(CH$_3$)$_2$ |
| 21 | H | —N(CH$_3$)CO CH$_3$ |
| 22 | —CH$_3$ | —N(CH$_3$)CO CH$_3$ |
| 23 | —CH(CH$_3$)$_2$ | —N(CH$_3$)CO CH$_3$ |
| 24 | —CH$_2$CH$_2$OCH$_3$ | —N(CH$_3$)CO CH$_3$ |

[Chemical formula 96]

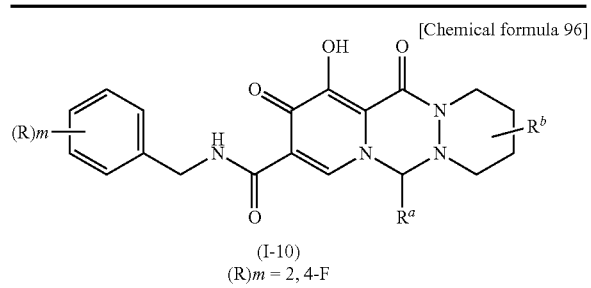

(I-10)
(R)m = 2, 4-F

| No | $R^a$ | $R^b$ |
|---|---|---|
| 1 | H | H |
| 2 | —CH$_3$ | H |
| 3 | —CH(CH$_3$)$_2$ | H |
| 4 | —CH$_2$CH$_2$OCH$_3$ | H |
| 5 | H | —CH$_3$ |
| 6 | —CH$_3$ | —CH$_3$ |
| 7 | —CH(CH$_3$)$_2$ | —CH$_3$ |
| 8 | —CH$_2$CH$_2$OCH$_3$ | —CH$_3$ |
| 9 | H | —CH(CH$_3$)$_2$ |
| 10 | —CH$_3$ | —CH(CH$_3$)$_2$ |
| 11 | —CH(CH$_3$)$_2$ | —CH(CH$_3$)$_2$ |
| 12 | —CH$_2$CH$_2$OCH$_3$ | —CH(CH$_3$)$_2$ |
| 13 | H | —CH$_2$CH$_2$OCH$_3$ |
| 14 | —CH$_3$ | —CH$_2$CH$_2$OCH$_3$ |
| 15 | —CH(CH$_3$)$_2$ | —CH$_2$CH$_2$OCH$_3$ |
| 16 | —CH$_2$CH$_2$OCH$_3$ | —CH$_2$CH$_2$OCH$_3$ |
| 17 | H | —N(CH$_3$)$_2$ |

-continued

[Chemical formula 96]

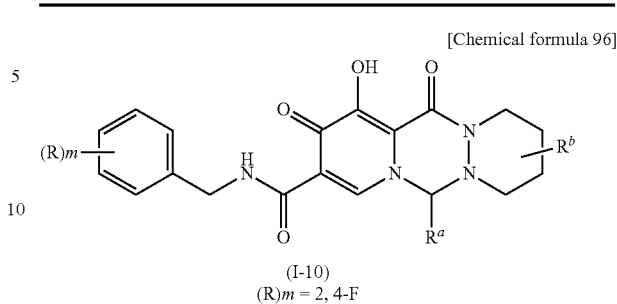

(I-10)
(R)m = 2, 4-F

| No | $R^a$ | $R^b$ |
|---|---|---|
| 18 | —CH$_3$ | —N(CH$_3$)$_2$ |
| 19 | —CH(CH$_3$)$_2$ | —N(CH$_3$)$_2$ |
| 20 | —CH$_2$CH$_2$OCH$_3$ | —N(CH$_3$)$_2$ |
| 21 | H | —N(CH$_3$)CO CH$_3$ |
| 22 | —CH$_3$ | —N(CH$_3$)CO CH$_3$ |
| 23 | —CH(CH$_3$)$_2$ | —N(CH$_3$)CO CH$_3$ |
| 24 | —CH$_2$CH$_2$OCH$_3$ | —N(CH$_3$)CO CH$_3$ |

[Chemical formula 97]

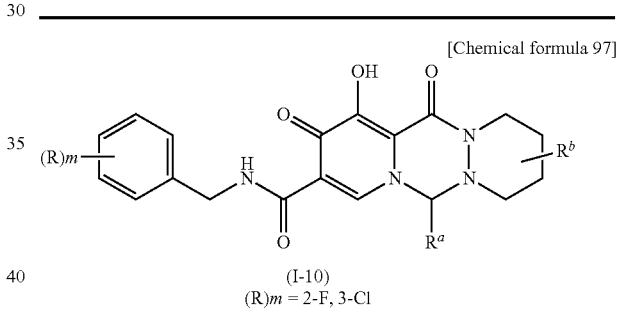

(I-10)
(R)m = 2-F, 3-Cl

| No | $R^a$ | $R^b$ |
|---|---|---|
| 1 | H | H |
| 2 | —CH$_3$ | H |
| 3 | —CH(CH$_3$)$_2$ | H |
| 4 | —CH$_2$CH$_2$OCH$_3$ | H |
| 5 | H | —CH$_3$ |
| 6 | —CH$_3$ | —CH$_3$ |
| 7 | —CH(CH$_3$)$_2$ | —CH$_3$ |
| 8 | —CH$_2$CH$_2$OCH$_3$ | —CH$_3$ |
| 9 | H | —CH(CH$_3$)$_2$ |
| 10 | —CH$_3$ | —CH(CH$_3$)$_2$ |
| 11 | —CH(CH$_3$)$_2$ | —CH(CH$_3$)$_2$ |
| 12 | —CH$_2$CH$_2$OCH$_3$ | —CH(CH$_3$)$_2$ |
| 13 | H | —CH$_2$CH$_2$OCH$_3$ |
| 14 | —CH$_3$ | —CH$_2$CH$_2$OCH$_3$ |
| 15 | —CH(CH$_3$)$_2$ | —CH$_2$CH$_2$OCH$_3$ |
| 16 | —CH$_2$CH$_2$OCH$_3$ | —CH$_2$CH$_2$OCH$_3$ |
| 17 | H | —N(CH$_3$)$_2$ |
| 18 | —CH$_3$ | —N(CH$_3$)$_2$ |
| 19 | —CH(CH$_3$)$_2$ | —N(CH$_3$)$_2$ |
| 20 | —CH$_2$CH$_2$OCH$_3$ | —N(CH$_3$)$_2$ |

-continued

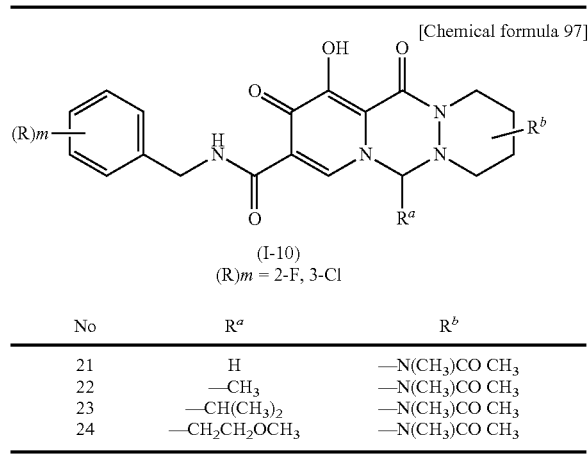

(I-10)
(R)m = 2-F, 3-Cl

| No | $R^a$ | $R^b$ |
|---|---|---|
| 21 | H | —N(CH$_3$)CO CH$_3$ |
| 22 | —CH$_3$ | —N(CH$_3$)CO CH$_3$ |
| 23 | —CH(CH$_3$)$_2$ | —N(CH$_3$)CO CH$_3$ |
| 24 | —CH$_2$CH$_2$OCH$_3$ | —N(CH$_3$)CO CH$_3$ |

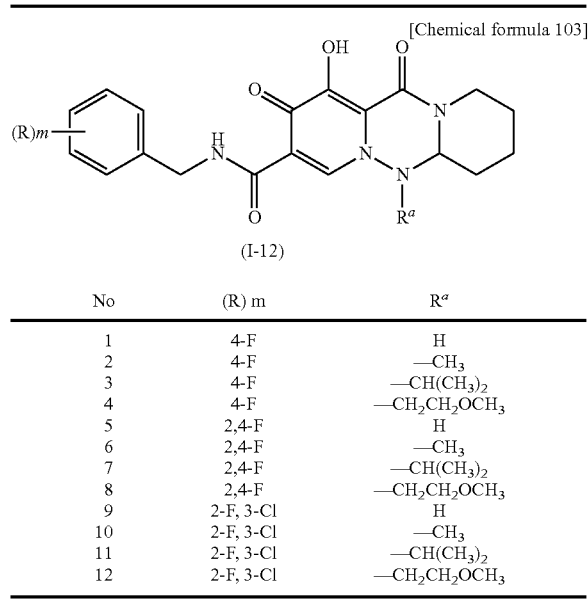

(I-12)

| No | (R) m | $R^a$ |
|---|---|---|
| 1 | 4-F | H |
| 2 | 4-F | —CH$_3$ |
| 3 | 4-F | —CH(CH$_3$)$_2$ |
| 4 | 4-F | —CH$_2$CH$_2$OCH$_3$ |
| 5 | 2,4-F | H |
| 6 | 2,4-F | —CH$_3$ |
| 7 | 2,4-F | —CH(CH$_3$)$_2$ |
| 8 | 2,4-F | —CH$_2$CH$_2$OCH$_3$ |
| 9 | 2-F, 3-Cl | H |
| 10 | 2-F, 3-Cl | —CH$_3$ |
| 11 | 2-F, 3-Cl | —CH(CH$_3$)$_2$ |
| 12 | 2-F, 3-Cl | —CH$_2$CH$_2$OCH$_3$ |

Further, the following compounds were synthesized.

One aspect of Compound (I-10)

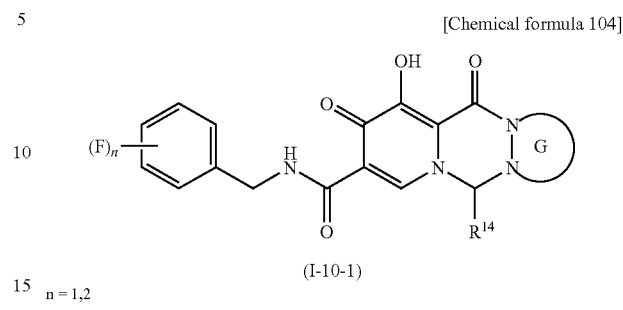

(I-10-1)
n = 1, 2

One aspect of Compound (I-6)

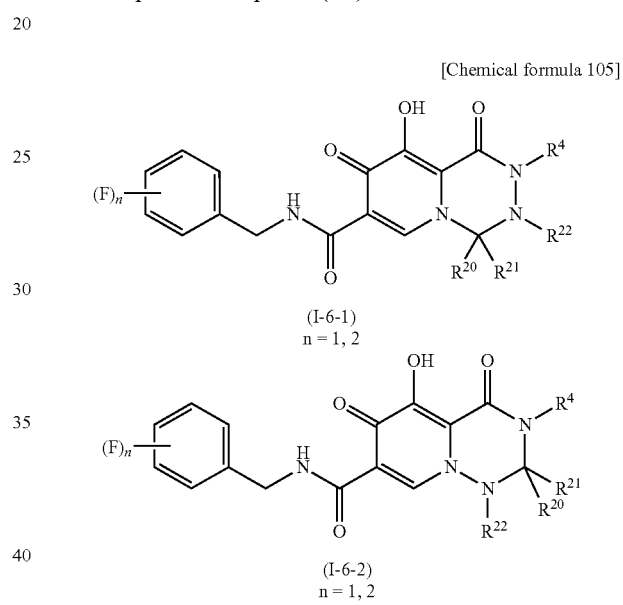

(I-6-1)
n = 1, 2

(I-6-2)
n = 1, 2

Specific compounds are as follows. "Ex No." indicates Example No.

| Ex No. | |
|---|---|
| | [Chemical formula 106] |
| K-08 | 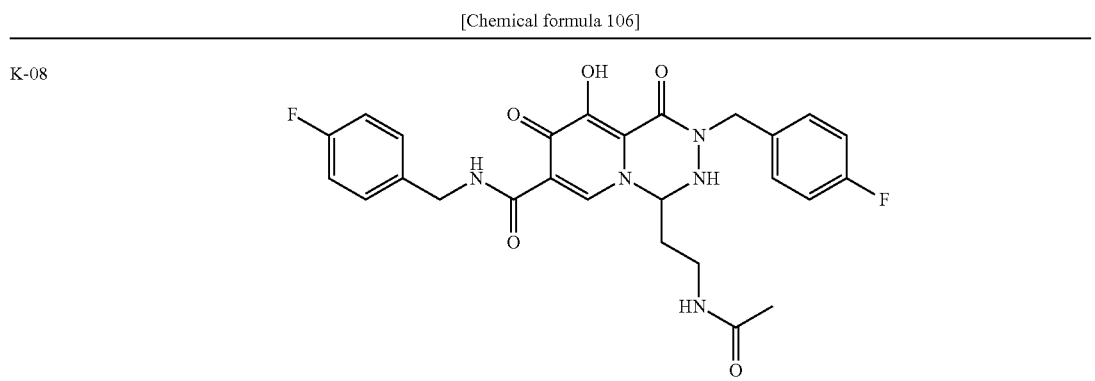 |

| Ex No. | |
|---|---|
| K-07 | 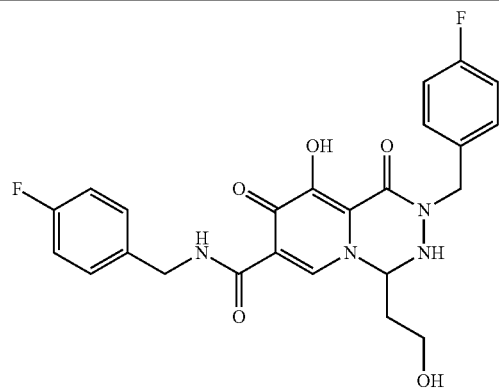 |
| K-31 | 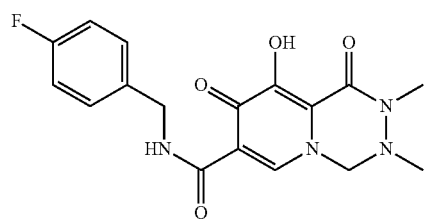 |
| K-32 | 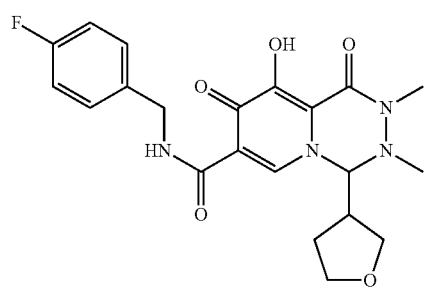 |
| K-33 | 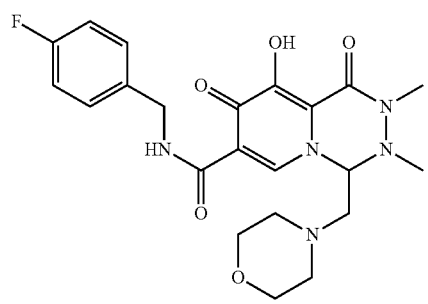 |
[Chemical formula 107]
| | |
|---|---|
| K-34 | 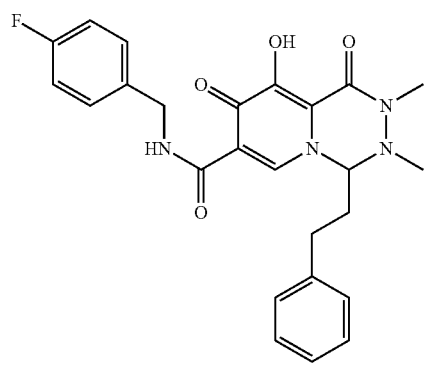 |

| Ex No. | |
|---|---|
| K-35 | 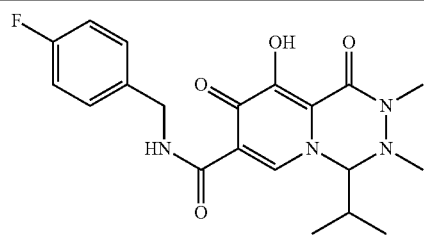 |
| K-09 | 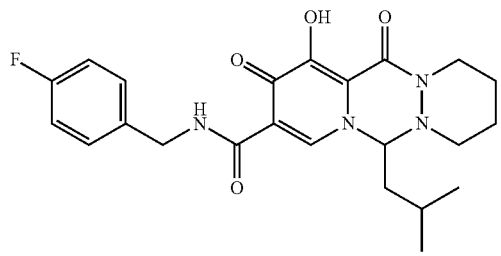 |
| K-10 | 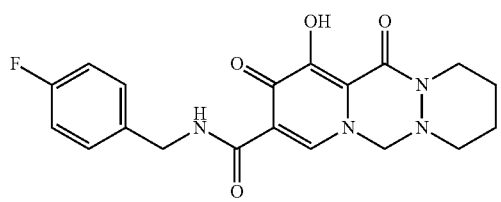 |
| K-11 | 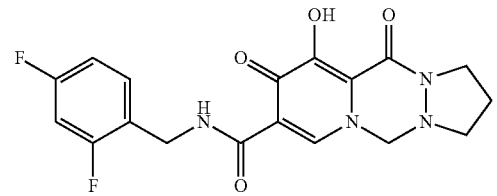 |
[Chemical formula 108]
| | |
|---|---|
| K-36 | 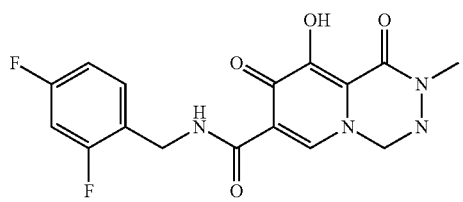 |
| K-12 | 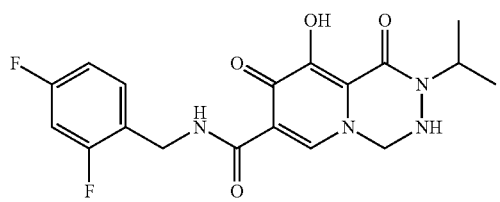 |
| K-13 | 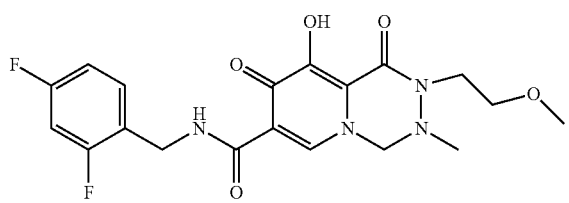 |

| Ex No. | |
|---|---|
| K-14 | 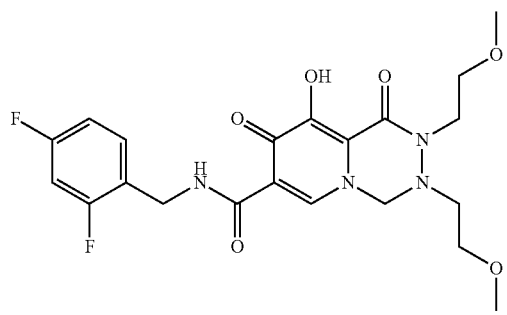 |
| K-15 | 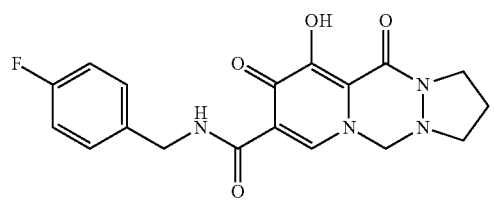 |
| K-37 | 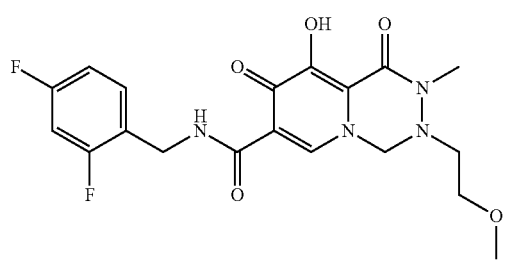 |
[Chemical formula 109]
| | |
|---|---|
| K-16 | 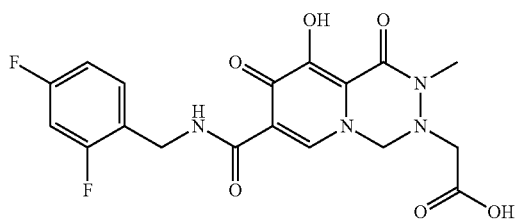 |
| K-17 | 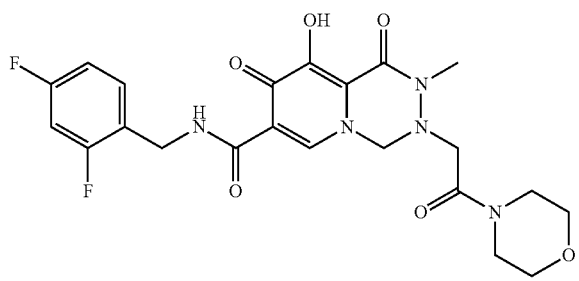 |
| K-19 | 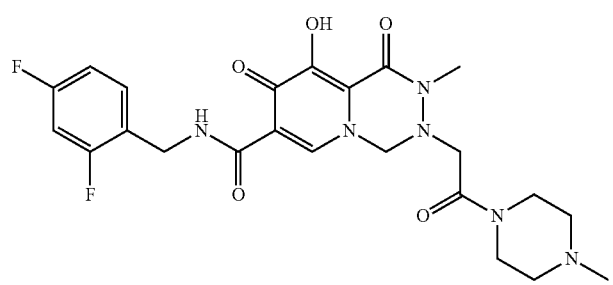 |

| Ex No. | |
|---|---|
| K-18 | 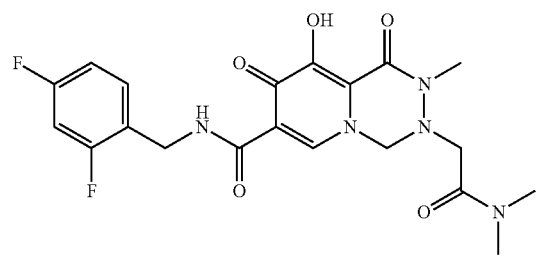 |
| K-20 | 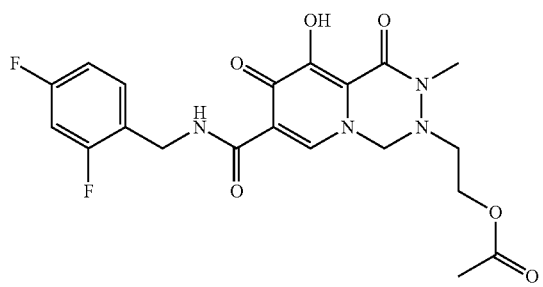 |
| K-21 | 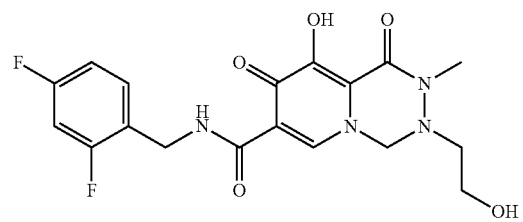 |
[Chemical formula 110]
| | |
|---|---|
| K-22 | 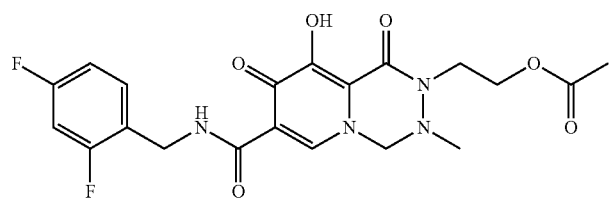 |
| K-23 | 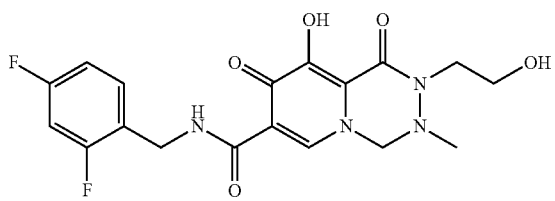 |
| K-24 | 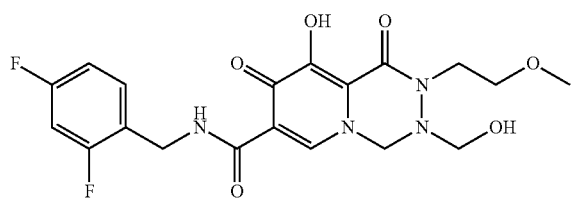 |

| Ex No. | |
|---|---|
| K-25 | 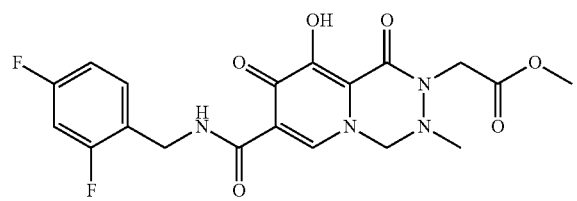 |
| K-38 | 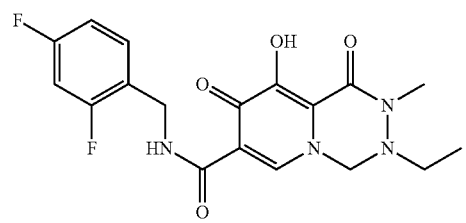 |
| K-26 | 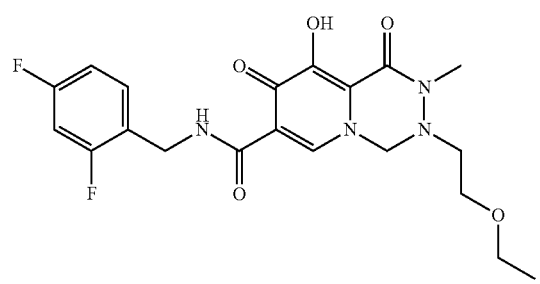 |
[Chemical formula 111]
| Ex No. | |
|---|---|
| K-27 | 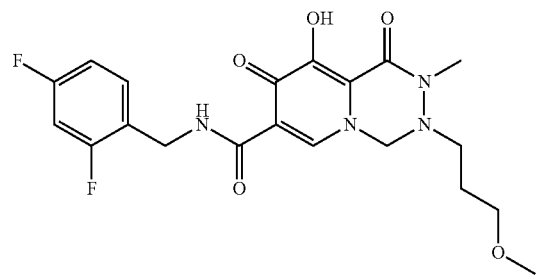 |
| K-28 | 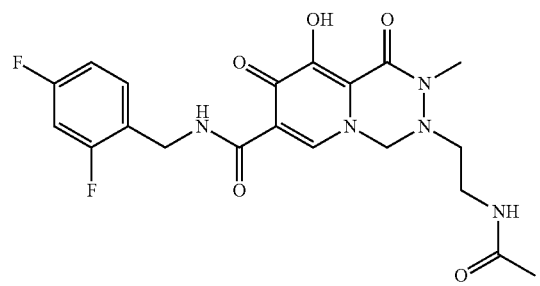 |
| K-39 | 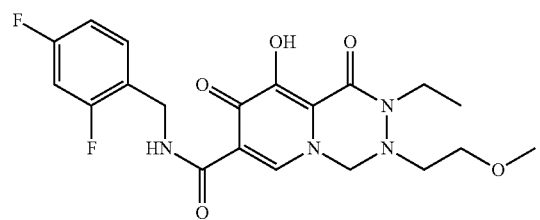 |

| Ex No. | |
|---|---|
| K-29 | 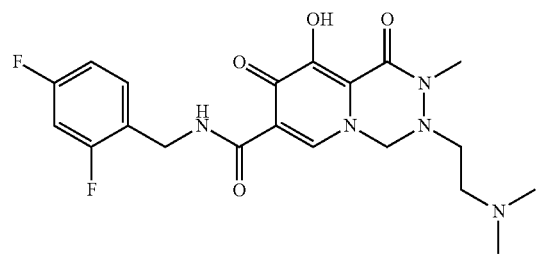 |
| K-30 | 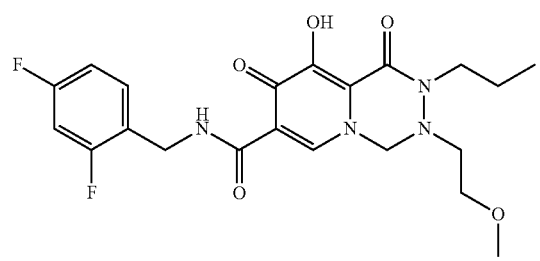 |
| K-40 | 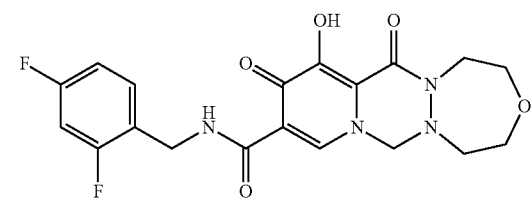 |
[Chemical formula 112]
| | |
|---|---|
| K-41 | 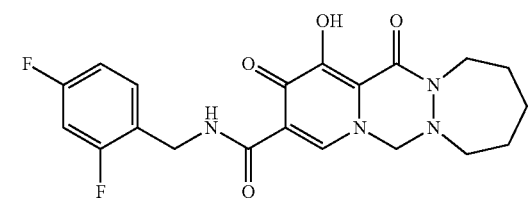 |
| N-01 | 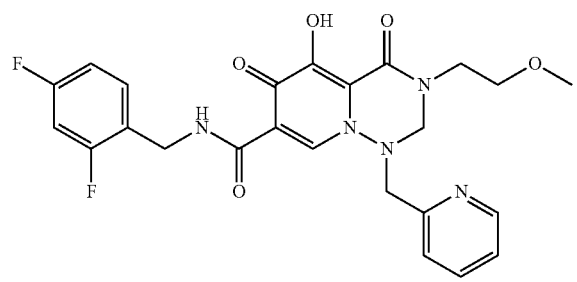 |
| O-02 | 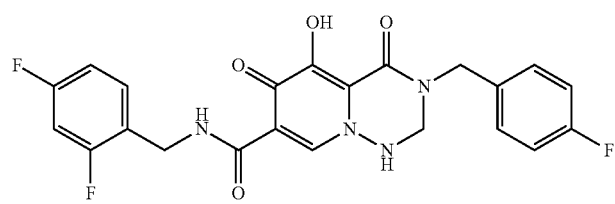 |

| Ex No. | |
|---|---|
| N-02 | 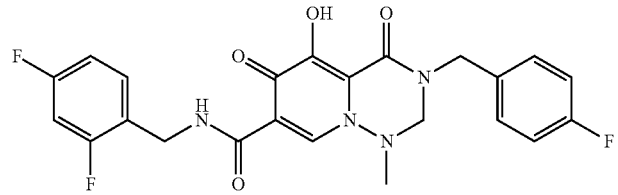 |
| Q-15 | 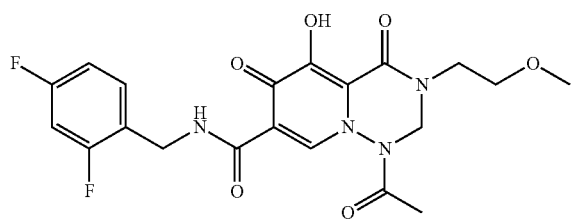 |
| Q-02 | 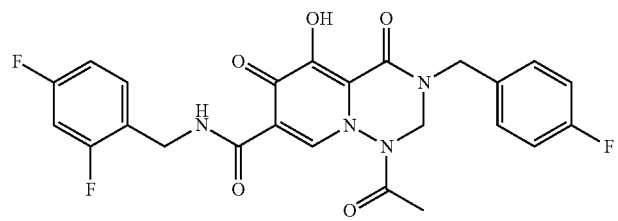 |
[Chemical formula 113]
| | |
|---|---|
| Q-03 | 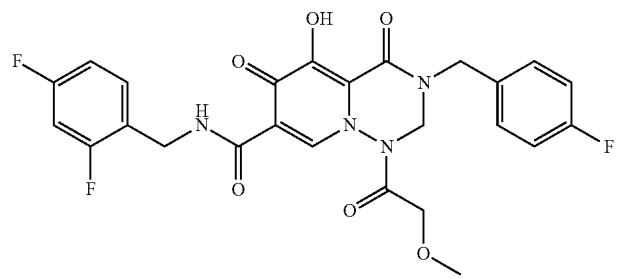 |
| O-03 | 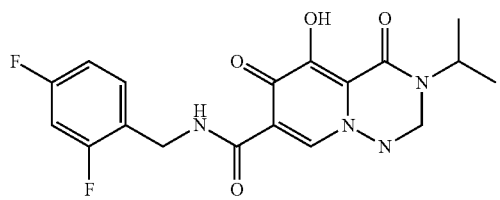 |
| N-03 | 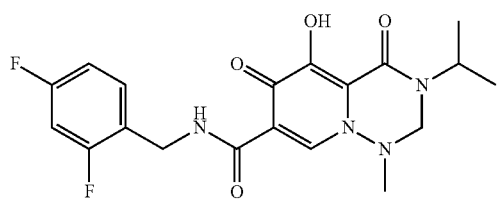 |

| Ex No. | |
|---|---|
| Q-14 | 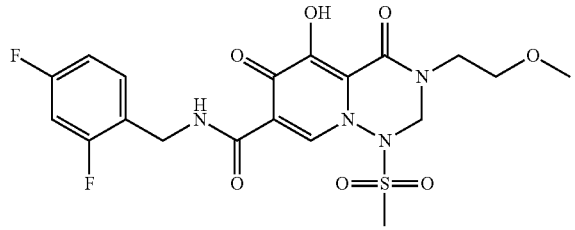 |
| N-57 | 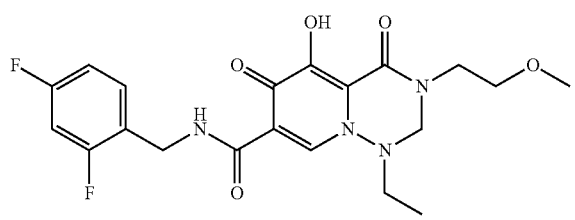 |
| N-56 | 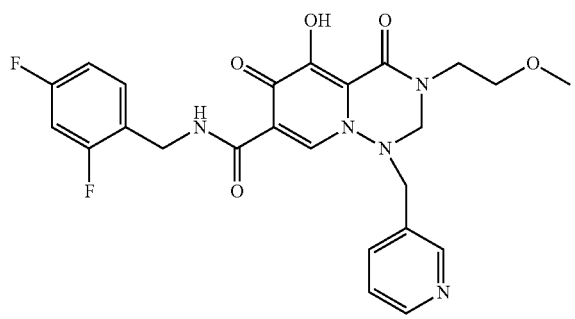 |
[Chemical formula 114]
| | |
|---|---|
| Q-13 | 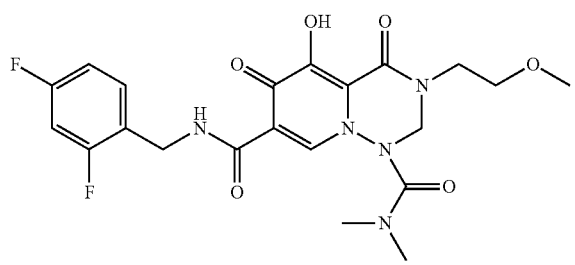 |
| N-55 | 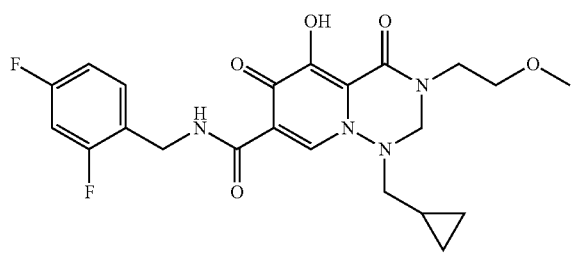 |

| Ex No. | |
|---|---|
| N-24 | 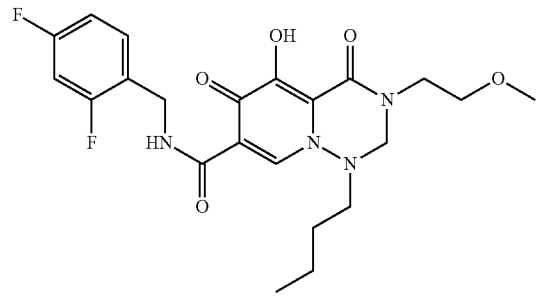 |
| N-25 | 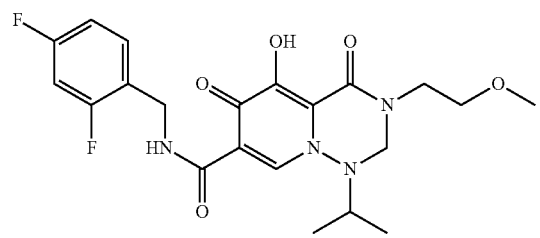 |
| Q-04 | 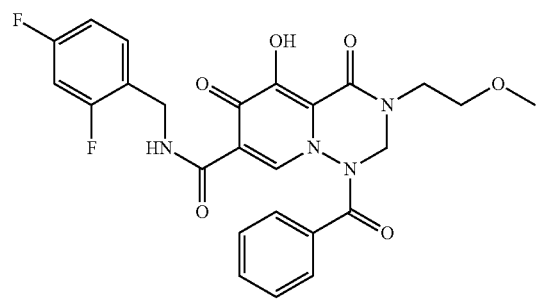 |
| Q-01 | 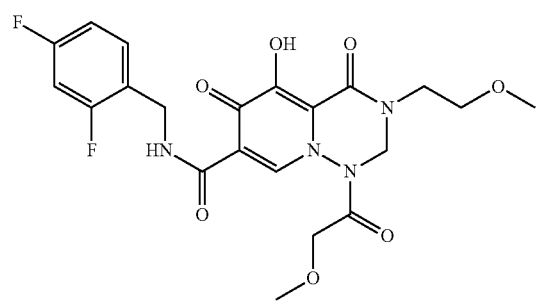 |
[Chemical formula 115]
| | |
|---|---|
| Q-05 | 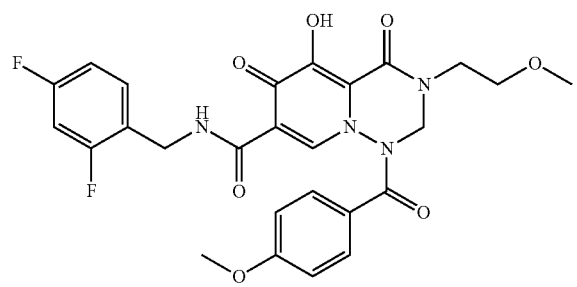 |

| Ex No. | |
|---|---|
| O-04 | 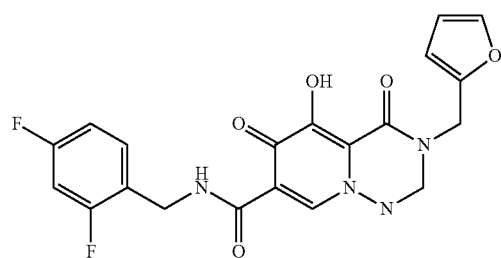 |
| N-54 | 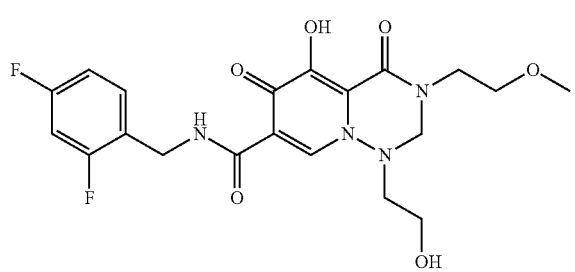 |
| N-53 | 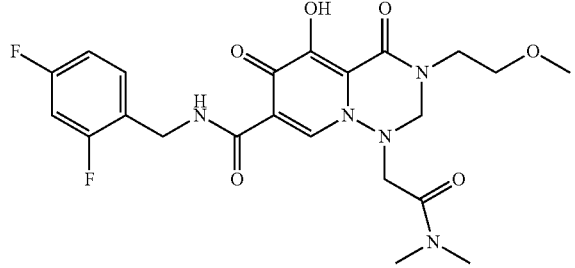 |
| N-52 | 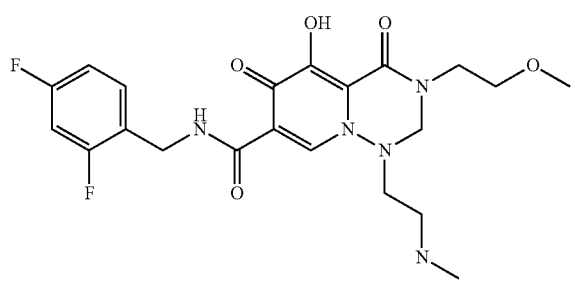 |
| N-51 | 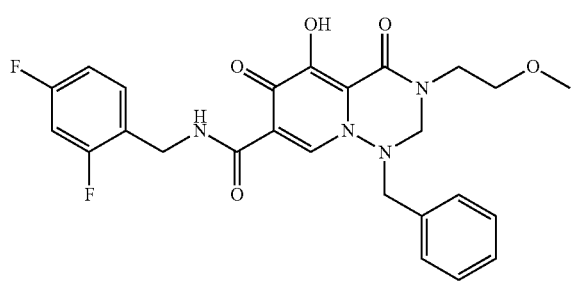 |

-continued
| Ex No. |
|---|
| [Chemical formula 116] |
N-50
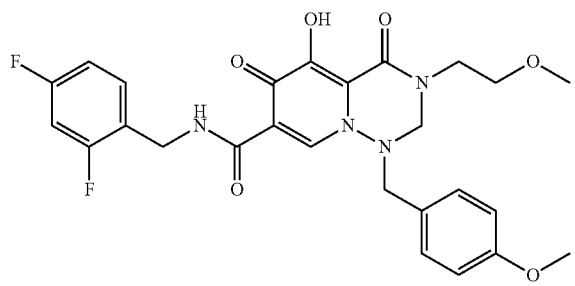
N-49
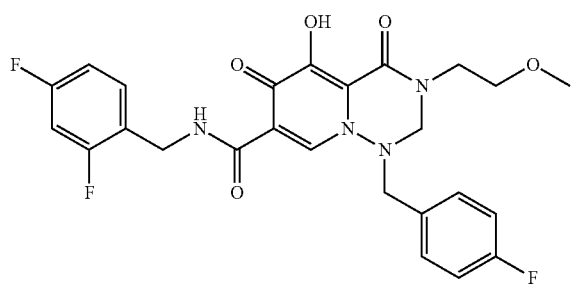
Q-06
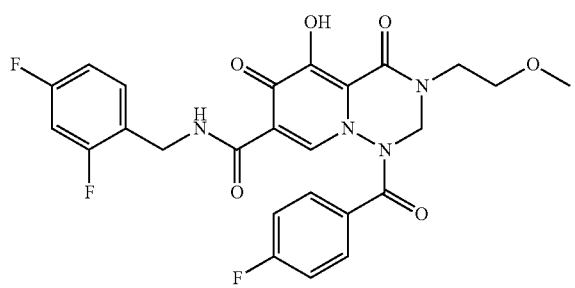
Q-07
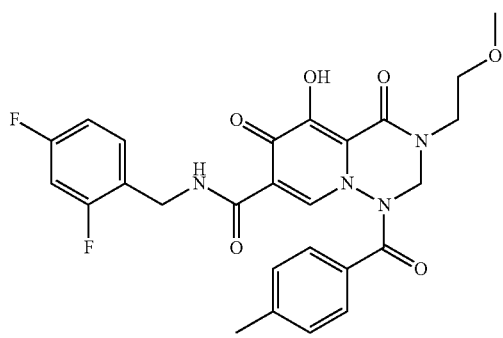
O-05
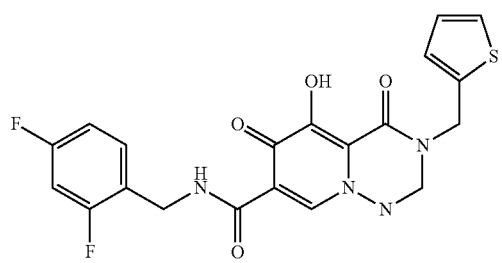

| Ex No. | |
|---|---|
| N-04 | 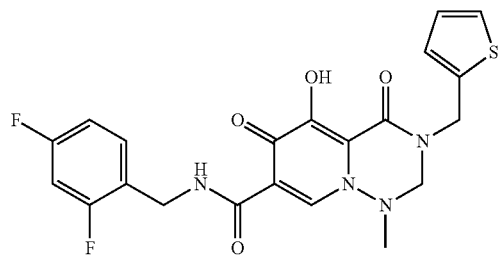 |
[Chemical formula 117]
| | |
|---|---|
| N-05 | 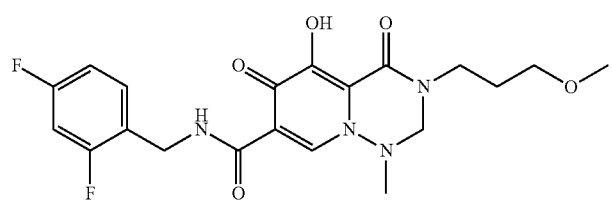 |
| N-07 | 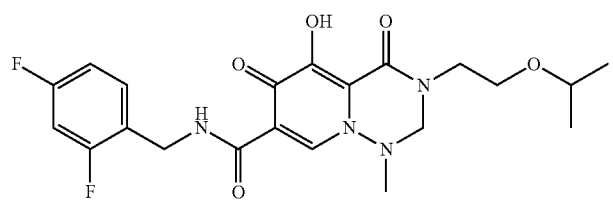 |
| N-08 | 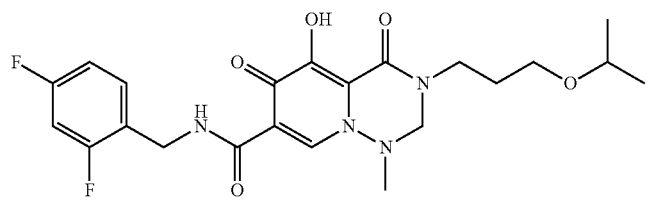 |
| N-06 | 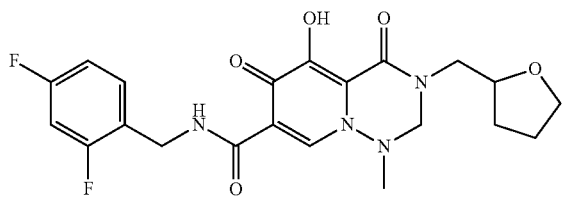 |
| Q-08 | 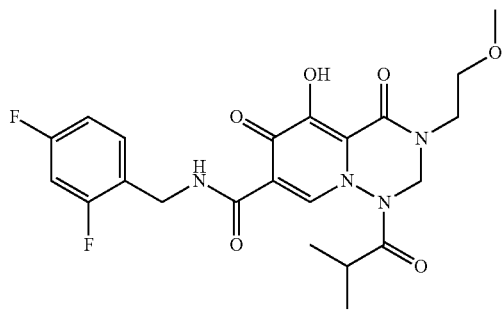 |

| Ex No. | |
|---|---|
| Q-09 | 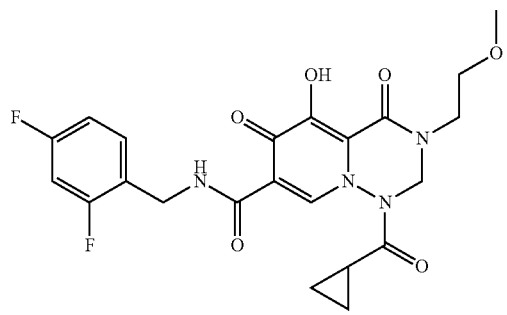 |
[Chemical formula 118]
| | |
|---|---|
| N-09 | 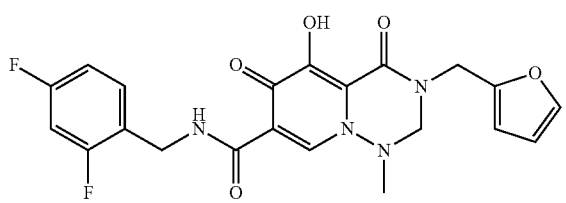 |
| N-10 | 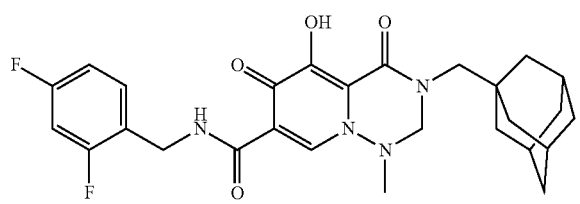 |
| N-11 | 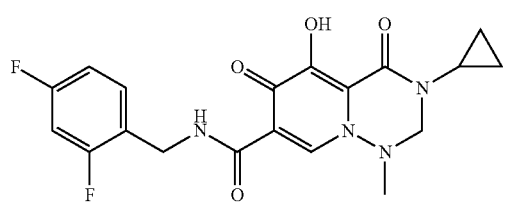 |
| N-12 | 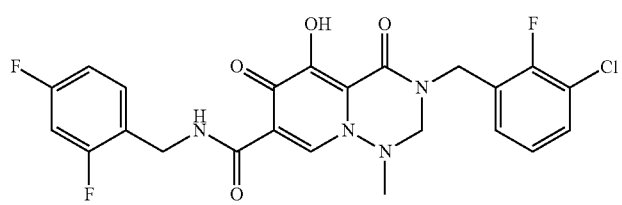 |
| N-13 | 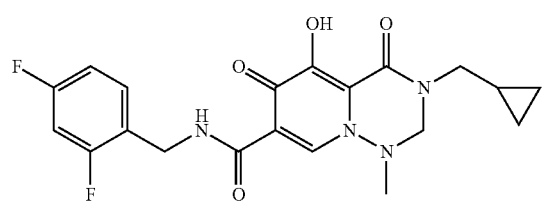 |

| Ex No. | |
|---|---|
| N-26 | 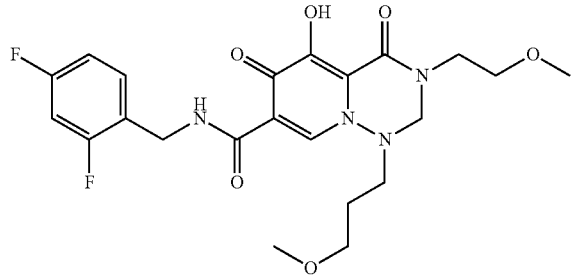 |
[Chemical formula 119]
| | |
|---|---|
| N-14 | 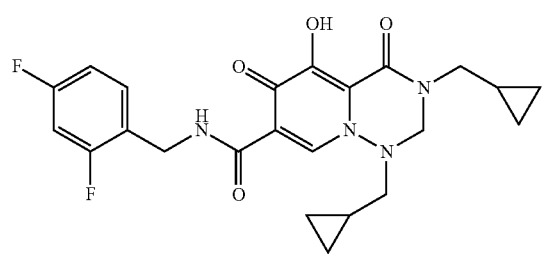 |
| N-15 | 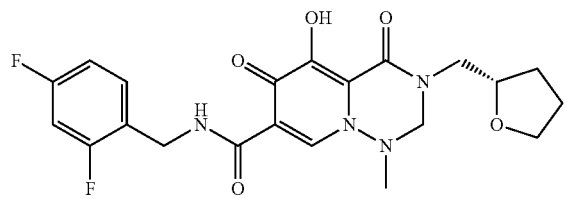 |
| N-27 | 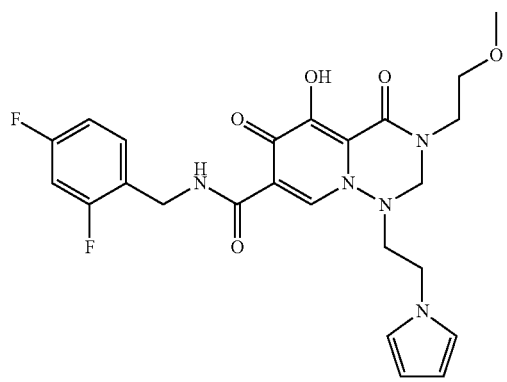 |
| N-28 | 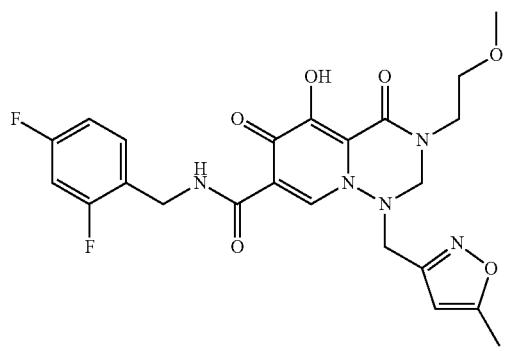 |

-continued
| Ex No. | |
|---|---|
| N-16 | 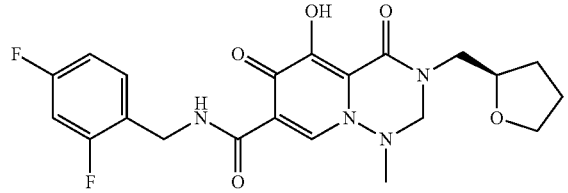 |
| | [Chemical formula 120] |
| N-17 | 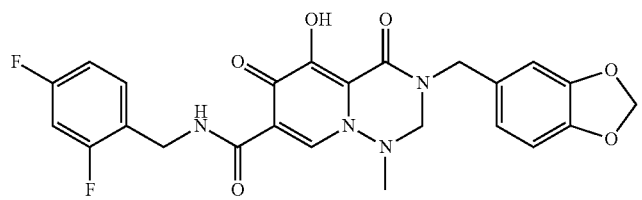 |
| N-48 | 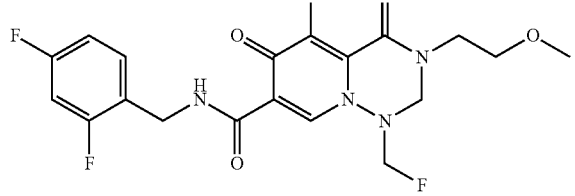 |
| N-47 | 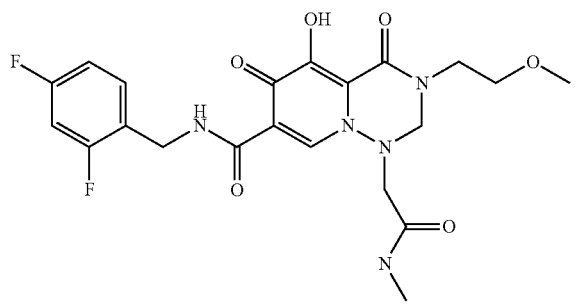 |
| N-46 | 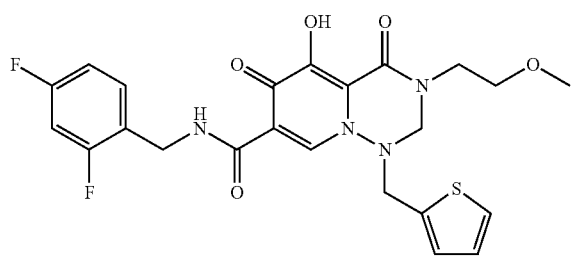 |

| Ex No. | |
|---|---|
| N-29 | 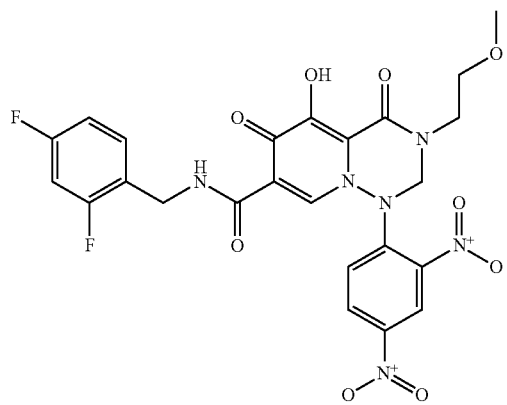 |
| O-07 | 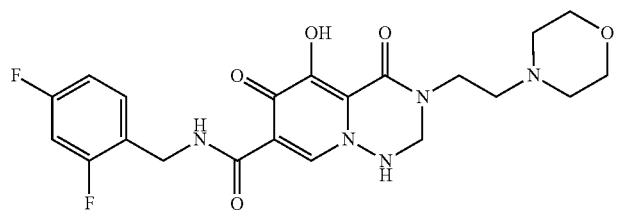 |
[Chemical formula 121]
| | |
|---|---|
| O-06 | 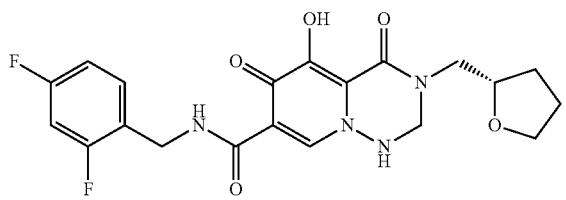 |
| O-08 | 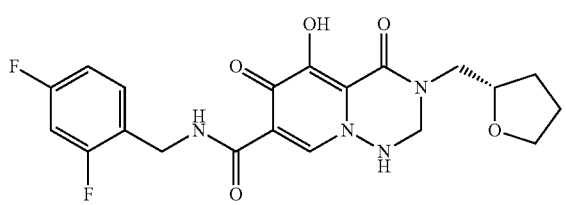 |
| O-09 | 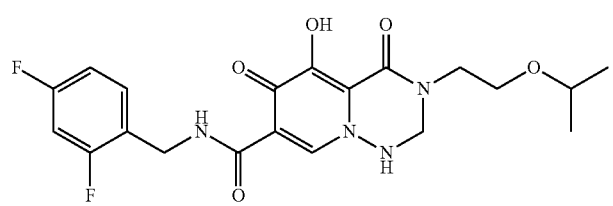 |
| O-10 | 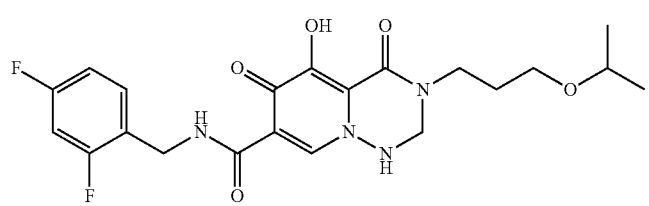 |

| Ex No. | |
|---|---|
| N-30 | 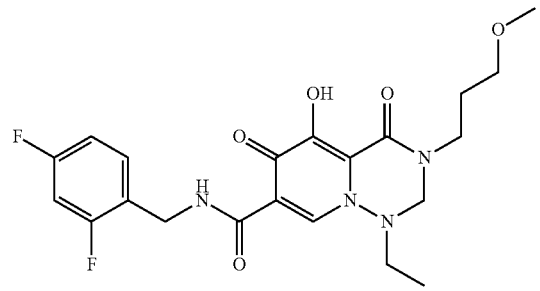 |
| N-45 | 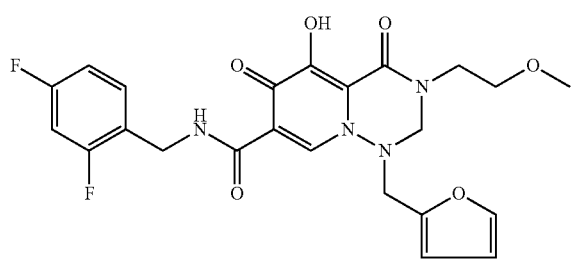 |
[Chemical formula 122]
| | |
|---|---|
| N-44 | 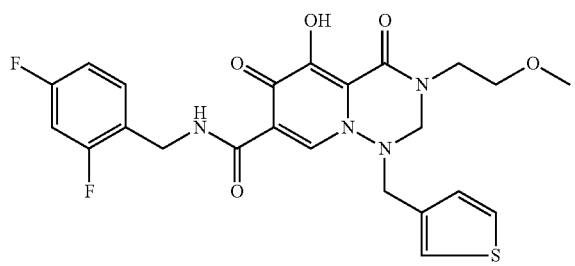 |
| N-43 | 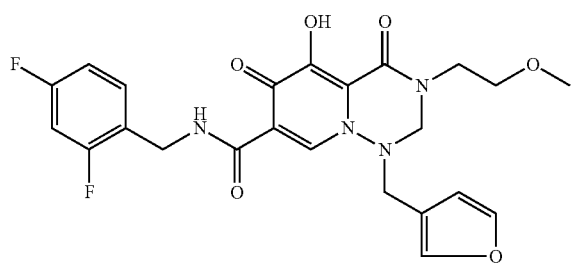 |
| O-11 | 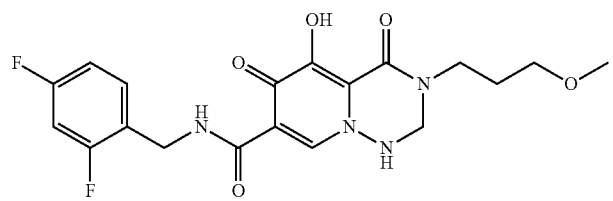 |
| O-13 | 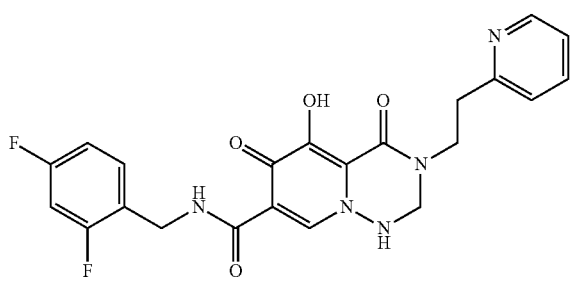 |

| Ex No. | |
|---|---|
| N-31 | 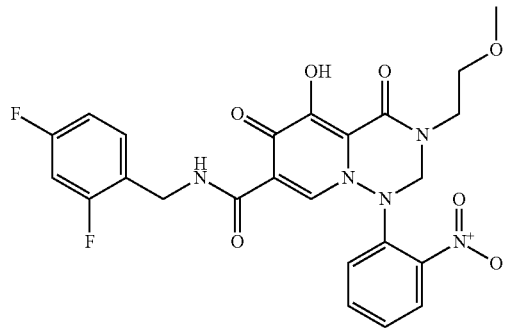 |
| | [Chemical formula 123] |
| N-32 | 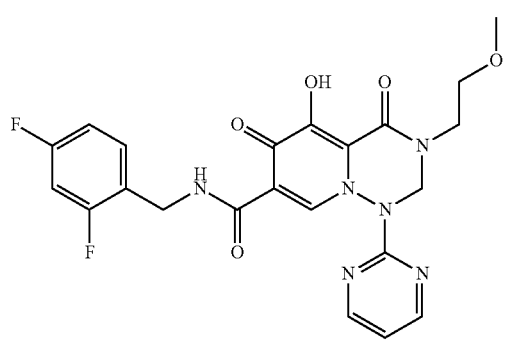 |
| Q-10 | 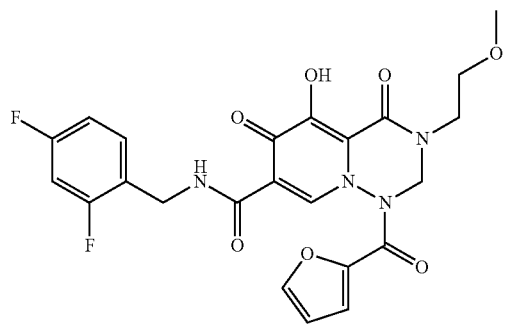 |
| Q-11 | 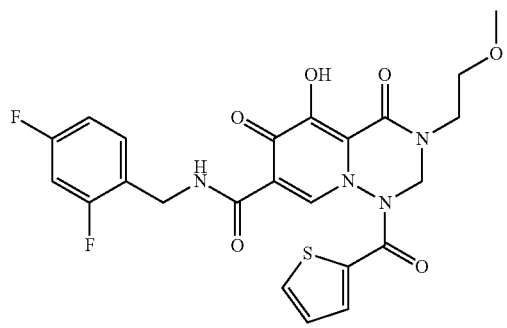 |

| Ex No. | |
|---|---|
| N-33 | 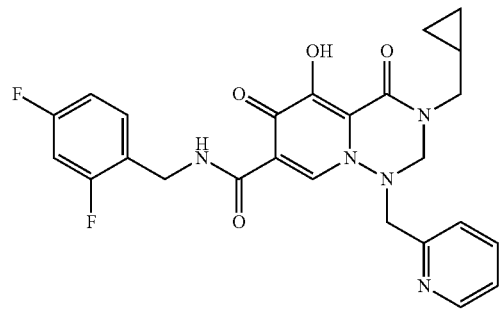 |
| [Chemical formula 124] | |
| N-42 | 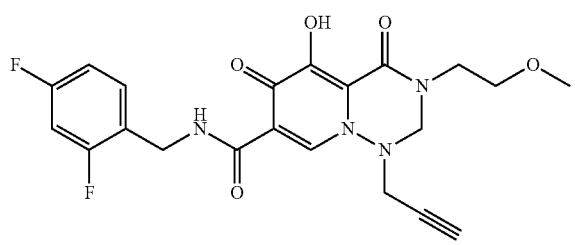 |
| O-01 | 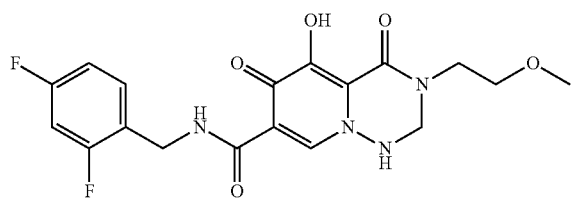 |
| Q-12 | 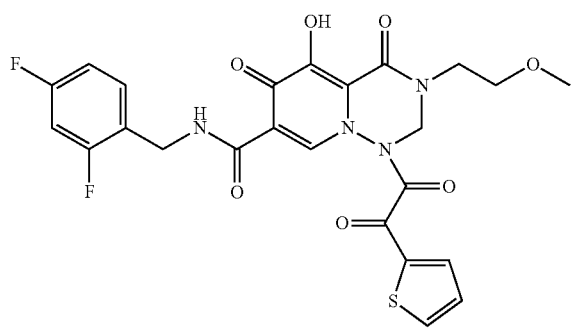 |
| N-18 | 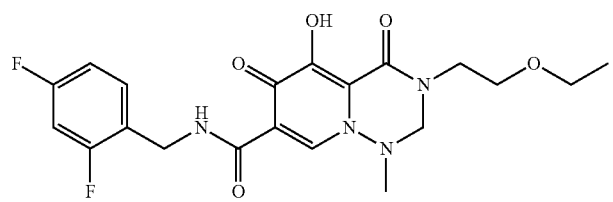 |
| N-19 | 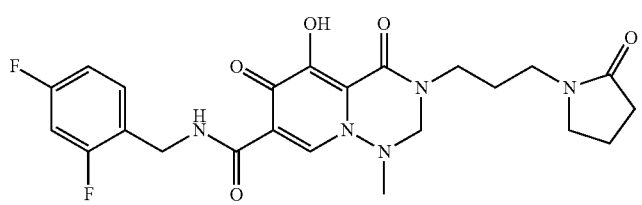 |

| Ex No. | |
|---|---|
| N-20 | 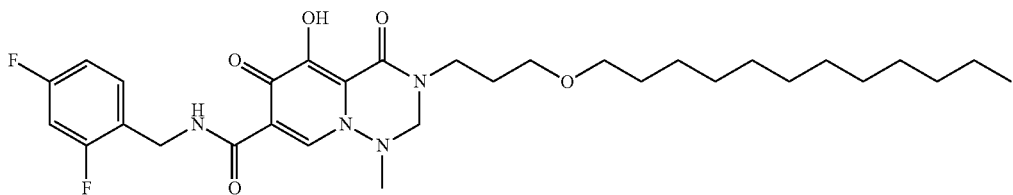 |
| | [Chemical formula 125] |
| N-41 | 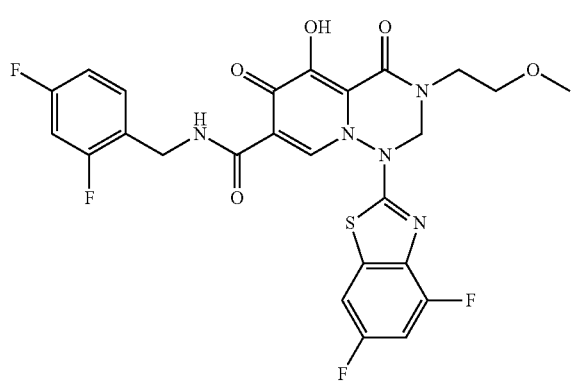 |
| N-34 | 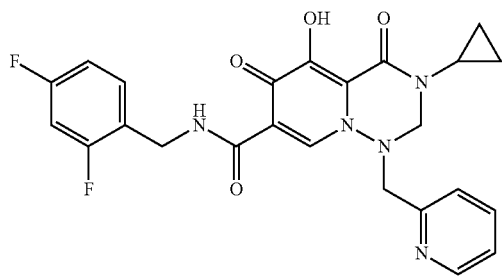 |
| N-35 | 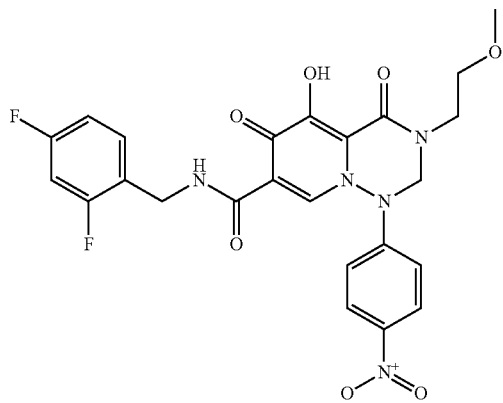 |

135 -continued
| Ex No. | |
|---|---|
| N-36 | 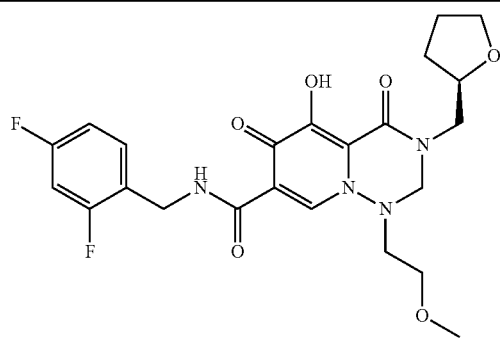 |
| | [Chemical formula 126] |
| N-37 | 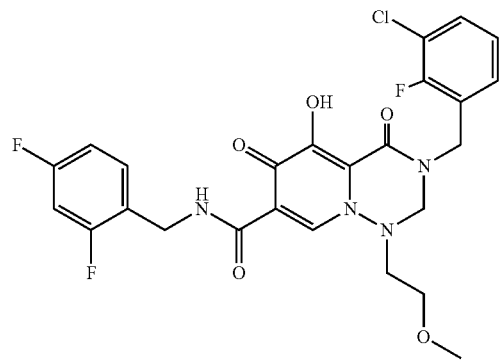 |
| N-21 | 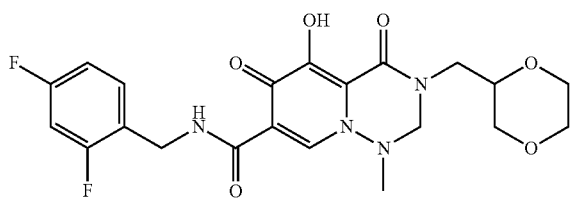 |
| O-12 | 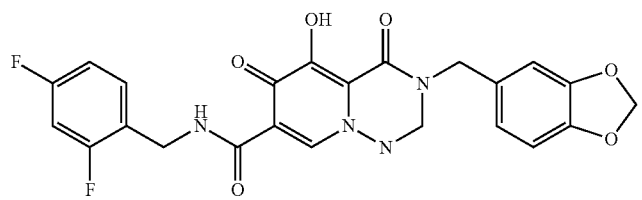 |
| N-22 | 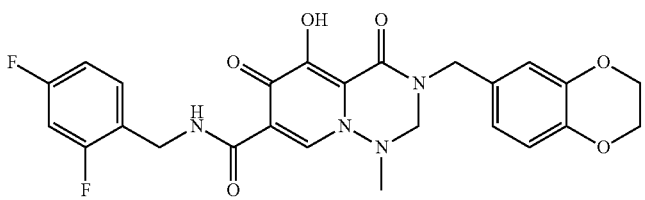 |
| N-23 | 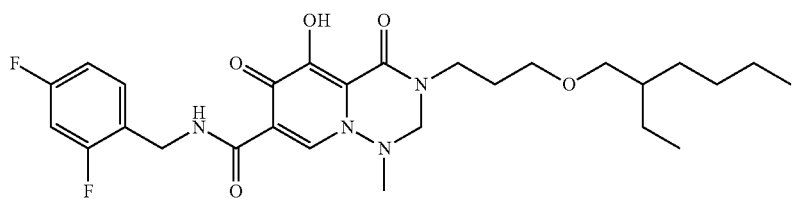 |

| Ex No. |
|---|
| [Chemical formula 127] |
N-38
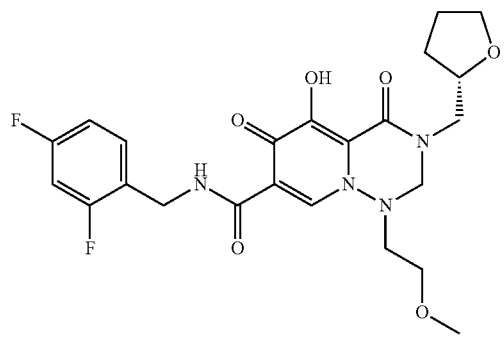
N-39
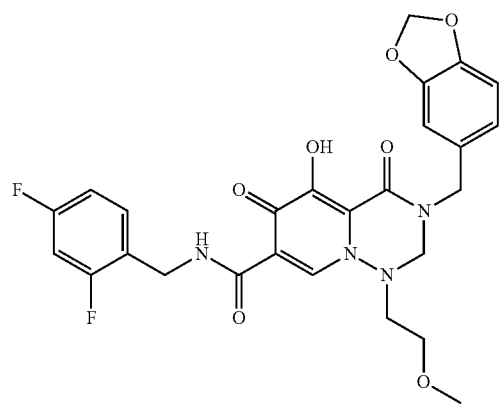
N-40
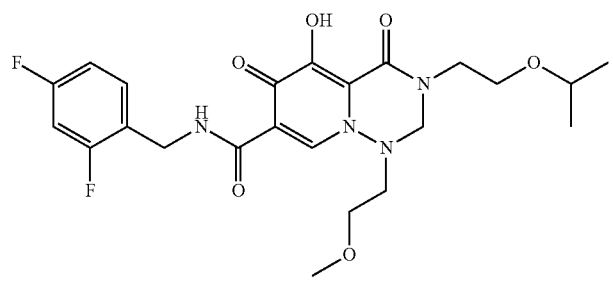
P-1
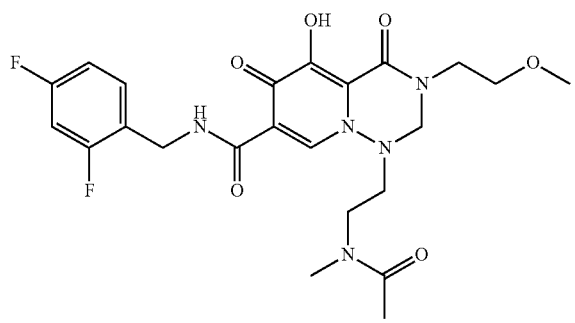

| Ex No. | |
|---|---|
| N-59 | 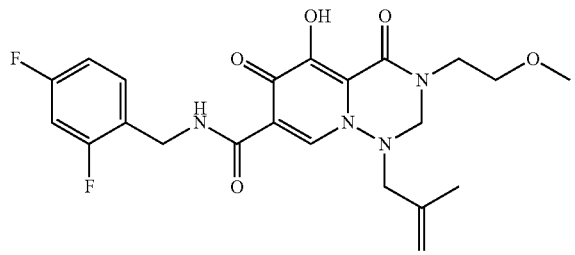 |
| | [Chemical formula 128] |
| N-60 | 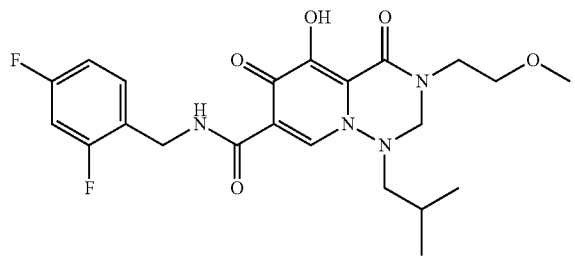 |
| N-58 | 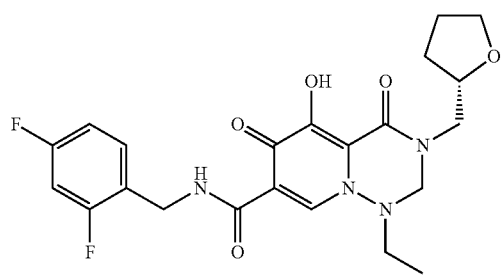 |

Physical properties of the above compounds are shown below. Example compounds K-7 to K41 were synthesized according to the same manner as that of Example K-1.

Example K-7

2-(4-Fluoro-benzyl)-9-hydroxy-4-(2-hydroxy-ethyl)-1,8-dioxo-1,3,4,8-tetrahydro-2H-pyrid[1,2-d][1,2,4]triazine-7-carboxylic acid-4-fluoro-benzylamide NMR (DMSO-$d_6$) δ: 1.68 (1H, dd, J=6.6 Hz, 12.3 Hz), 3.15 (2H, m), 4.51 (2H, d, J=6.3 Hz), 4.55 (1H, d, J=14.7 Hz), 4.64 (1H, s), 4.83 (1H, d, J=14.7 Hz), 5.47 (1H, m), 7.01 (1H, d, 2.7 Hz), 7.13-7.43 (8H, m), 8.34 (1H, s), 10.39 (1H, t, J=6.0 Hz).

Example K-8

4-(2-Acetylamino-ethyl)-2-(4-fluoro-benzyl)-9-hydroxy-1,8-dioxo-1,3,4,8-tetrahydro-2H-pyrid[1,2-d][1,2,4]triazine-7-carboxylic acid-4-fluoro-benzylamide NMR (DMSO-$d_6$) δ: 1.69 (2H, m), 1.78 (3H, s), 2.87 (1H, m), 4.52 (1H, s), 4.72 (1H, s), 5.42 (1H, s), 7.02 (1H, s), 7.16-7.43 (8H, m), 7.82 (1H, s), 8.48 (1H, s), 10.40 (1H, s), 11.57 (1H, s).

Example K-9

5-Hydroxy-9-isobutyl-6,10-dioxo-1,2,3,4,6,10-hexahydro-4-a,8a,9a-triaza-anthracene-7-carboxylic Acid 4-fluoro-benzylamide NMR (DMSO-$d_6$) δ: 0.92 (6H, t, J=6.0 Hz), 1.46-1.86 (7H, m), 2.75-3.08 (3H, m), 4.41 (1H, m), 4.52 (2H, m), 5.56 (1H, m), 7.16 (2H, t, J=9.0 Hz), 7.35 (2H, dd, J=6.0 Hz, 8.7 Hz), 8.39 (1H, s), 10.44 (1H, t, J=6.0 Hz), 11.88 (1H, s).

Example K-10

5-Hydroxy-6,10-dioxo-1,2,3,4,6,10-hexahydro-4-a,8a,9a-triaza-anthracene-7-carboxylic Acid 4-fluoro-benzylamide NMR (DMSO-$d_6$) δ: 1.56 (2H, m), 1.79 (2H, m), 2.94 (2H, t, J=4.5 Hz), 3.70 (2H, m), 4.52 (2H, d, J=6.0 Hz), 5.38 (1H, s), 7.16 (2H, t, J=6.0 Hz), 7.34 (2H, dd, J=5.4 Hz, 8.7 Hz), 8.40 (1H, s), 10.40 (1H, t, J=6.0 Hz), 11.73 (1H, s).

Example K-11

8-Hydroxy-7,9-dioxo-2,3,7,9-tetrahydro-1H-3a,4a,9a-triaza-cyclopenta[b]naphthalene-6-carboxylic acid 2,4-difluoro-benzylamide NMR (DMSO-d$_6$) δ: 2.19 (2H, t, J=6.6 Hz), 3.19 (2H, t, J=6.0 Hz), 7.06 (1H, m), 7.25 (1H, m), 7.41 (1H, m), 8.49 (1H, s), 10.37 (1H, t, J=5.7 Hz), 11.63 (1H, s).

Example K-12

9-Hydroxy-2-isopropyl-1,8-dioxo-1,3,4,8-tetrahydro-2H-pyrid[1,2-d][1,2,4]triazine-7-carboxylic Acid 2,4-difluoro-benzylamide NMR (DMSO-d$_6$) δ: 1.05 (6H, t, J=5.4 Hz), 4.20-4.43 (3H, m), 5.01 (1H, d, J=12.6 Hz), 5.38 (1H, d, J=13.2 Hz), 6.01 (1H, s), 6.89 (1H, m), 7.07 (1H, m), 7.23 (1H, m), 8.14 (1H, s), 10.30 (1H, s).

Example K-13

9-Hydroxy-2-(2-methoxy-ethyl)-3-methyl-1,8-dioxo-1,3,4,8-tetrahydro-2H-pyrid[1,2-d][1,2,4]triazine-7-carboxylic acid 2,4-difluoro-benzylamide NMR (DMSO-d$_6$) δ: 2.61 (3H, s), 3.33 (3H, s), 3.54 (3H, m), 3.98 (1H, s), 4.55 (1H, s), 5.19 (1H, m), 5.38 (1H, s), 7.08 (1H, m), 7.24 (1H, m), 7.42 (1H, m), 8.41 (1H, s), 10.39 (1H, t, J=6.0 Hz), 11.10 (1H, s).

Example K-14

9-Hydroxy-2,3-bis-(2-methoxy-ethyl)-1,8-dioxo-1,3,4,8-tetrahydro-2H-pyrid[1,2-d][1,2,4]triazine-7-carboxylic acid 2,4-difluoro-benzylamide NMR (DMSO-d$_6$) δ: 3.21 (3H, s), 3.26 (3H, s), 3.43 (7H, m), 4.07 (1H, m), 4.55 (1H, s), 5.15 (1H, d, J=12.6 Hz), 5.46 (1H, d, J=13.2 Hz), 7.07 (1H, m), 7.24 (1H, m), 7.42 (1H, m), 8.39 (1H, s), 10.39 (1H, t, J=5.4 Hz), 10.97 (1H, s).

Example K-15

8-Hydroxy-7,9-dioxo-2,3,7,9-tetrahydro-1H-3a,4a,9a-triaza-cyclopenta[b]naphthalene-6-carboxylic acid 4-fluoro-benzylamide NMR (DMSO-d$_6$) δ: 2.19 (2H, quint, J=7.5 Hz), 3.19 (2H, t, J=6.6 Hz), 3.76 (2H, t, J=6.9 Hz), 4.52 (2H, d, J=6.0 Hz), 5.17 (2H, s), 7.15 (1H, t, J=9.0 Hz), 7.35 (2H, dd, J=5.7 Hz, 8.7 Hz), 8.47 (1H, s), 10.35 (1H, t, J=5.7 Hz), 11.61 (1H, s).

Example K-16

[7-(2,4-Difluoro-benzylcarbamoyl)-9-hydroxy-2-methyl-1,8-dioxo-1,8-dihydro-2H-pyrid[1,2-d][1,2,4]triazin-3-yl]-acetic Acid NMR (DMSO-d$_6$) δ: 3.18 (3H, s), 3.70 (2H, s), 4.54 (2H, d, J=6.0 Hz), 5.42 (2H, s), 7.06 (1H, m), 7.23 (1H, m), 7.40 (1H, m), 8.43 (1H, s), 10.36 (1H, t, J=5.7 Hz), 11.10 (1H, s).

Example K-17

9-Hydroxy-2-methyl-3-(2-morpholin-4-yl-2-oxo-ethyl)-1,8-dioxo-1,3,4,8-tetrahydro-2H-pyrid[1,2-d][1,2,4]triazine-7-carboxylic acid 2,4-difluoro-benzylamide NMR (DMSO-d$_6$) δ: 3.16 (3H, s), 3.55 (4H, s), 3.84 (2H, s), 4.54 (2H, d, J=4.5 Hz), 5.39 (2H, s), 7.07 (1H, m), 7.29 (1H, m), 7.41 (1H, m), 8.35 (1H, s), 10.41 (1H, t, J=4.5 Hz), 11.19 (1H, s).

Example K-18

3-Dimethylcarbamoylmethyl-9-hydroxy-2-methyl-1,8-dioxo-1,3,4,8-tetrahydro-2H-pyrid[1,2-d][1,2,4]triazine-7-carboxylic acid 2,4-difluoro-benzylamide NMR (DMSO-d$_6$) δ: 2.81 (3H, s), 2.90 (3H, s), 3.16 (3H, s), 3.81 (2H, s), 4.54 (2H, d, J=5.7 Hz), 5.41 (2H, s), 7.07 (1H, m), 7.25 (1H, m), 7.40 (1H, m), 8.37 (1H, s), 10.39 (1H, t, J=6.3 Hz), 11.10 (1H, s).

Example K-19

9-Hydroxy-2-methyl-3-[2-(4-methyl-piperazin-1-yl)-2-oxo-ethyl]-1,8-dioxo-1,3,4,8-tetrahydro-2H-pyrid[1,2-d][1,2,4]triazine-7-carboxylic acid 2,4-difluoro-benzylamide NMR (DMSO-d$_6$) δ: 2.16 (3H, s), 2.25 (2H, m), 3.15 (3H, s), 3.40 (2H, s), 3.81 (1H, s), 4.54 (2H, d, J=6.0 Hz), 5.38 (2H, s), 7.07 (1H, m), 7.28 (1H, m), 7.41 (1H, m), 8.32 (1H, s), 10.43 (1H, t, J=6.0 Hz), 11.08 (1H, s).

Example K-20

Acetic Acid

2-[7-(2,4-difluoro-benzylcarbamoyl)-9-hydroxy-2-methyl-1,8-dioxo-1,8-dihydro-2H-pyrid[1,2-d][1,2,4]triazin-3-yl]-ethyl Ester NMR (DMSO-d$_6$) δ: 3.11 (2H, t, J=6.3 Hz), 3.14 (3H, s), 3.34 (2H, t, J=6.3 Hz), 4.07 (1H, s), 4.15 (1H, s), 4.56 (2H, d, J=6.0 Hz), 5.42 (2H, s), 7.06 (1H, m), 7.25 (1H, m), 7.41 (1H, m), 8.42 (1H, s), 10.40 (1H, t, J=6.0 Hz), 11.04 (1H, s).

Example K-21

9-Hydroxy-3-(2-hydroxyethyl-ethyl)-2-methyl-1,8-dioxo-1,3,4,8-tetrahydro-22H-pyrid[1,2-d][1,2,4]triazine-7-carboxylic acid 2,4-difluoro-benzylamide NMR (DMSO-d$_6$) δ: 2.90 (2H, s), 3.17 (3H, s), 3.53 (2H, d, J=4.2 Hz), 4.54 (2H, d, J=5.7 Hz), 4.81 (1H, t, J=4.8 Hz), 5.37 (1H, br s), 5.42 (1H, br s), 7.06 (1H, m), 7.24 (1H, m), 7.42 (1H, m), 8.40 (1H, s), 10.39 (1H, t, J=5.7 Hz), 11.10 (1H, s).

Example K-22

Acetic Acid

2-[7-(2,4-difluoro-benzylcarbamoyl)-9-hydroxy-3-methyl-1,8-dioxo-1,3,4,8-tetrahydro-pyrid[1,2-d][1,2,4]triazin-2-yl]-ethyl Ester NMR (DMSO-d$_6$) δ: 2.00 (3H, s), 2.61 (3H, s), 3.47 (1H, m), 4.22 (3H, m), 4.55 (2H, br s), 5.22 (1H, br s), 5.37 (1H, br s), 7.06 (1H, m), 7.24 (1H, m), 7.40 (1H, m), 8.40 (1H, s), 10.38 (1H, t, J=6.3 Hz), 11.00 (1H, s).

Example K-23

9-Hydroxy-2-(2-hydroxy-ethyl)-3-methyl-1,8-dioxo-1,3,4,8-tetrahydro-2H-pyrid[1,2-d][1,2,4]triazine-7-carboxylic acid 2,4-difluoro-benzylamide NMR (DMSO-$d_6$) δ: 2.61 (3H, s), 3.20 (1H, br s), 3.62 (2H, br s), 3.89 (1H, br s), 4.55 (2H, d, J=5.4 Hz), 4.83 (1H, t, J=5.7 Hz), 5.27 (1H, br s), 5.34 (1H, br s), 7.06 (1H, m), 7.23 (1H, m), 7.42 (1H, m), 8.39 (1H, s), 10.41 (1H, t, J=6.0 Hz), 11.22 (1H, s).

Example K-24

9-Hydroxy-3-hydroxymethyl-2-(2-methoxy-ethyl)-1,8-dioxo-1,3,4,8-tetrahydro-2H-pyrid[1,2-d][1,2,4]triazine-7-carboxylic acid 2,4-difluoro-benzylamide NMR (DMSO-$d_6$) δ: 3.26 (3H, s), 3.55 (2H, m), 4.15 (1H, br s), 4.51 (2H, m), 4.53 (1H, d, J=6.0 Hz), 5.21 (1H, br s), 5.57 (1H, br s), 6.11 (1H, t, J=7.2 Hz), 7.05 (1H, m), 7.23 (1H, m), 7.42 (1H, m), 8.35 (1H, s), 10.41 (1H, t, J=6.0 Hz), 11.12 (1H, s).

Example K-25

[7-(2,4-Difluoro-benzylcarbamoyl)-9-hydroxy-3-methyl-1,8-dioxo-1,3,4,8-tetrahydro-pyrid[1,2-d][1,2,4]triazin-2-yl]-acetic Acid Methyl Ester NMR (DMSO-$d_6$) δ: 2.63 (3H, s), 4.28 (1H, br s), 4.56 (1H, br s), 4.56 (1H, d, J=5.7 Hz), 5.34 (1H, br s), 5.35 (1H, br s), 7.07 (1H, m), 7.25 (1H, m), 7.42 (1H, m), 8.41 (1H, s), 10.34 (1H, t, J=5.7 Hz), 10.60 (1H, s).

Example K-26

3-(2-Ethoxy-ethyl)-9-hydroxy-2-methyl-1,8-dioxo-1,3,4,8-tetradhydro-2H-pyrid[1,2-d][1,2,4]triazine-7-carboxylic acid 2,4-difluoro-benzylamide NMR (DMSO-$d_6$) δ: 1.09 (3H, t, J=6.6 Hz), 3.03 (2H, br s), 3.37 (2H, q, J=6.6 Hz), 3.47 (2H, s), 4.54 (1H, d, J=6.0 Hz), 5.36 (1H, br s), 5.38 (1H, br s), 7.07 (1H, m), 7.25 (1H, m), 7.41 (1H, m), 8.38 (1H, s), 10.39 (1H, t, J=6.0 Hz), 11.09 (1H, br s).

Example K-27

9-Hydroxy-3-(3-methoxy-propyl)-2-methyl-1,8-dioxo-1,3,4,8-tetradhydro-2H-pyrid[1,2-d][1,2,4]triazine-7-carboxylic acid 2,4-difluoro-benzylamide NMR (DMSO-$d_6$) δ: 1.72 (2H, br s), 2.86 (2H, br s), 3.16 (3H, s), 3.21 (2H, br s), 4.55 (1H, d, J=5.7 Hz), 5.37 (1H, br s), 5.43 (1H, br s), 7.06 (1H, m), 7.25 (1H, m), 7.41 (1H, m), 8.50 (1H, s), 10.37 (1H, t, J=5.7 Hz), 11.10 (1H, br s).

Example K-28

3-(2-Acetylamino-ethyl)-9-hydroxy-2-methyl-1,8-dioxo-1,3,4,8-tetradhydro-2H-pyrid[1,2-d][1,2,4]triazine-7-carboxylic acid 2,4-difluoro-benzylamide NMR (DMSO-$d_6$) δ: 1.80 (3H, s), 2.86 (2H, t, J=6.6 Hz), 3.15 (3H, s), 3.21 (2H, t, J=6.6 Hz), 4.54 (2H, d, J=4.8 Hz), 5.36 (2H, br s), 7.06 (1H, m), 7.24 (1H, m), 7.42 (1H, m), 7.93 (1H, t, J=5.1 Hz), 8.42 (1H, s), 10.42 (1H, t, J=4.8 Hz), 11.18 (1H, br s).

Example K-29

3-(2-Dimethylamino-ethyl)-9-hydroxy-2-methyl-1,8-dioxo-1,3,4,8-tetrahydro-2H-pyrid[1,2-d][1,2,4]triazine-7-carboxylic acid 2,4-difluoro-benzylamide NMR (DMSO-$d_6$) δ: 2.10 (6H, s), 2.38 (2H, s), 2.85 (2H, s), 3.16 (3H, s), 4.54 (2H, d, J=5.7 Hz), 5.31 (1H, br s), 5.45 (1H, br s), 7.07 (1H, m), 7.25 (1H, m), 7.40 (1H, m), 8.35 (1H, s), 10.46 (1H, t, J=5.7 Hz), 11.03 (1H, br s).

Example K-30

9-Hydroxy-3-(2-ethoxy-ethyl)-1,8-dioxo-2-propyl-1,3,4,8-tetrahydro-2H-pyrid[1,2-d][1,2,4]triazine-7-carboxylic acid 2,4-difluoro-benzylamide NMR (DMSO-$d_6$) δ: 0.89 (3H, t, J=7.2 Hz), 1.64 (2H, m), 3.00 (2H, t, J=5.14 Hz), 3.07 (1H, m), 3.20 (3H, s), 3.20 (1H, m), 3.42 (2H, m), 4.54 (2H, s), 5.22 (1H, d, 12.6 Hz), 5.48 (1H, d, 12.6 Hz), 7.09 (1H, m), 7.24 (1H, m), 7.40 (1H, m), 8.39 (1H, s), 10.39 (1H, t, J=5.7 Hz), 11.13 (1H, br s).

Example K-31

9-Hydroxy-2,3-dimethyl-1,8-dioxo-1,3,4,8-tetrahydro-2H-pyrid[1,2-d][1,2,4]triazine-7-carboxylic Acid 4-fluoro-benzylamide NMR (CDCl$_3$) δ: 2.72 (3H, s), 3.26 (3H, s), 4.61 (2H, d, J=2.7 Hz), 6.97-7.03 (2H, m), 7.26-7.35 (2H, m), 8.32 (1H, s), 10.40 (1H, brs).

Example K-32

9-Hydroxy-2,3-dimethyl-1,8-dioxo-4-(tetrahydro-furan-3-yl)-1,3,4,8-tetrahydro-2H-pyrid[1,2-d][1,2,4]triazine-7-carboxylic acid 4-fluoro-benzylamide (diastereomer mixture ca. 1:1)

1H-NMR (DMSO-$d_6$) δ: 1.60-1.70 (1H, m), 3.15 (3H, d, J=7.1 Hz), 3.14-3.83 (m), 4.49-4.53 (2H, m) 5.40-5.50 (1H, m), 7.12-7.18 (2H, m), 7.33-7.38 (2H, m), 8.43 and 8.53 (1H, s), 10.30-10.40 (1H, brt), 11.30 (1H, brs).

Example K-33

9-Hydroxy-2,3-dimethyl-4-morpholin-4-ylmethyl-1,8-dioxo-1,3,4,8-tetrahydro-2H-pyrid[1,2-d][1,2,4]triazine-7-carboxylic acid 4-fluoro-benzylamide 1H-NMR (DMSO-$d_6$) δ: 2.79 (3H, s), 3.27 (3H, s), 4.03-3.66 (m), 4.58 (2H, d, J=5.71 Hz), 6.09 (1H, s), 7.26-7.16 (2H, m), 7.45-7.36 (2H, m), 8.57 (1H, s), 10.34 (1H, t, J=6.04 Hz), 11.44 (1H, br s).

Example K-34

9-Hydroxy-2,3-dimethyl-1,8-dioxo-4-phenethyl-1,3,4,8-tetrahydro-2H-pyrid[1,2-d][1,2,4]triazine-7-carboxylic acid 4-fluoro-benzylamide 1H-NMR (DMSO-$d_6$) δ: 2.72 (3H, s), 3.15-3.52 (m), 4.53 (2H, d, J=2.7 Hz), 7.11-7.18 (2H, m), 7.32-7.37 (2H, m), 8.31 (1H, s), 8.51 (1H, brs), 10.29 (1H, brs)

Example K-35

9-Hydroxy-4-isopropyl-2,3-dimethyl-1,8-dioxo-1,3,4,8-tetrahydro-2H-pyrid[1,2-d][1,2,4]triazine-7-carboxylic acid 4-fluoro-benzylamide 1H-NMR (DMSO-$d_6$) δ: 0.70 and 1.02 (each 3H, d, J=6.2 Hz), 2.63 (3H, s), 3.16 (3H, s), 3.25-3.52 (1H, m), 4.51 (2H, m), 5.18 (1H, d, J=8.4 Hz), 7.12-7.18 (2H, m), 7.33-7.38 (2H, m), 8.46 (1H, s), 10.30-10.40 (1H, m), 11.27 (1H, brs).

Example K-36

9-Hydroxy-2-methyl-1,8-dioxo-1,3,4,8-tetrahydro-2H-pyrid[1,2-d][1,2,4]triazine-7-carboxylic Acid 2,4-difluoro-benzylamide 1H-NMR (DMSO-$d_6$) δ: 3.18 (3H, s), 4.50-4.70 (3H, m), 5.47 (1H, brs), 6.13 (1H, t, J=7.0 Hz), 7.03-7.09 (1H, m), 7.19-7.27 (1H, m), 7.36-7.44 (1H, m), 8.36 (1H, s), 10.41 (1H, t, J=5.9 Hz), 11.26 (1H, brs).

Example K-37

9-Hydroxy-3-(2-methoxy-ethyl)-2-methyl-1,8-dioxo-1,3,4,8-tetrahydro-2H-pyrid[1,2-d][1,2,4]triazine-7-carboxylic acid 2,4-difluoro-benzylamide 1H-NMR (DMSO-$d_6$) δ: 2.98-3.14 (2H, m), 3.27 (3H, s), 3.33 (3H, s), 3.46-3.62 (2H, m), 4.64 (2H, d, J=5.9 Hz), 5.20-5.27 (2H, m), 6.75-6.90 (2H, m), 7.26-7.41 (1H, m), 8.26 (1H, s) 10.30-10.40 (1H, brt)

Example K-38

3-Ethyl-9-hydroxy-2-methyl-1,8-dioxo-1,3,4,8-tetrahydro-2H-pyrid[1,2-d][1,2,4]triazine-7-carboxylic acid 2,4-difluoro-benzylamide NMR (CDCl$_3$) δ: 1.21 (3H, t, J=7.0 Hz), 2.85-3.08 (2H, m), 3.31 (3H, s), 4.64 (2H, d, J=5.9 Hz), 4.83-5.37 (2H, m), 6.75-6.87 (2H, m), 7.32-7.43 (1H, m), 8.34 (1H, brs), 10.30-10.45 (1H, m), 11.13-11.31 (1H, m)

Example K-39

2-Ethyl-9-hydroxy-3-(2-methoxy-ethyl)-1,8-dioxo-1,3,4,8-tetrahydro-2H-pyrid[1,2-d][1,2,4]triazine-7-carboxylic acid 2,4-difluoro-benzylamide 1H-NMR (CDCl$_3$) δ: 1.35 (1H, t, J=7.13 Hz), 3.28-2.90 (1H, m), 3.37 (3H, s), 3.53 (3H, s), 3.75-3.58 (1H, m), 4.28-4.08 (1H, m), 4.69 (2H, d, J=5.88 Hz), 5.48-5.05 (2H, m), 6.90-6.80 (2H, m), 7.47-7.36 (1H, m), 8.31 (1H, s), 0.50-10.41 (1H, m).

Example K-40

1-Hydroxy-2,11-dioxo-2,6,7,9,10,11-hexahydro-8-oxa-4-a,5a,10a-triaza-cyclohepta[b]naphthalene-3-carboxylic acid 2,4-difluoro-benzylamide 1H-NMR (CDCl$_3$) δ: 3.41 (2H, br s), 3.82 (2H, br s), 4.12 (2H, br s), 4.55 (2H, br s), 4.64 (2H, d, J=6.0 Hz), 4.95 (1H, br s), 5.32 (1H, br s), 6.75-6.83 (2H, m), 7.31-7.41 (1H, m), 10.39 (1H, t, J=6.0 Hz), 11.31 (1H, br s).

Example K-41

1-Hydroxy-2,11-dioxo-2,7,8,9,10,11-hexahydro-6H-4-a,5a, 10a-triazacyclohepta[b]naphthalene-3-carboxylic acid 2,4-difluoro-benzylamide 1H-NMR (CDCl$_3$) δ: 1.68 (1H, br s), 1.91 (4H, br s), 2.92 (1H, br s), 3.00 (1H, br s), 3.21 (1H, br s), 4.39 (1H, br s), 4.63 (2H, d, J=6.0 Hz), 4.82 (1H, br s), 5.22 (1H, br s), 6.79-6.82 (2H, m), 7.27-7.40 (1H, m), 8.30 (1H, s), 10.40 (1H, t, J=6.0 Hz), 11.39 (1H, br s).

Example N-1

5-Hydroxy-3-(2-methoxy-ethyl)-4,6-dioxo-1-(pyridin-2-ylmethyl)-2,3,4,6-tetrahydro-1H-pyrid[2,1-f][1,2,4]triazine-7-carboxylic acid 2,4-difluoro-benzylamide O-1) 5-Hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide

[Chemical formula 129]

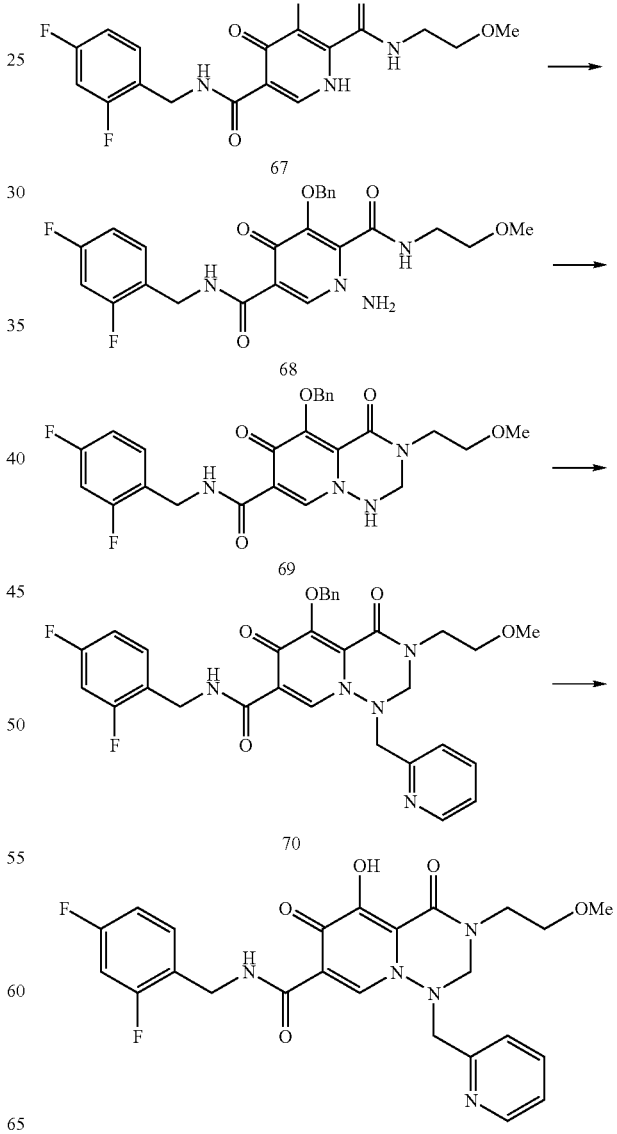

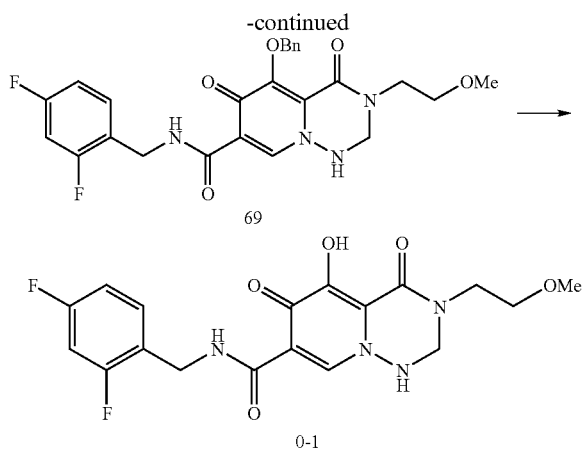

1) Using Compound 67 synthesized according to the method of synthesizing Compound 65, Compound 68 was synthesized by the following procedure.

To a solution of the Compound 67 (23.3 g, 49.4 mmol) in DMF (230 ml) was added potassium carbonate (13.7 g, 98.8 mmol), and the mixture was stirred at room temperature for 90 minutes. Then, O-(2,4-dinitrophenyl)-hydroxylamine (10.8 g, 54.4 mmol) was added, and the mixture was stirred at room temperature for 2 hours. To the reaction solution was added water, this was extracted ethyl acetate, and dried with sodium sulfate. The solvent was distilled off, and the resulting crystal was washed with diethyl ether to obtain 21.7 g (yield 90%) of 1-amino-3-benzyloxy-5-[3-(2,4-difluoro-phenyl)-propyl]-4-oxo-1,4-dihydro-pyridine-2-carboxylic acid (2-methoxy-ethyl)-amide 68.

NMR (CDCl$_3$) δ: 3.25 (3H, s), 3.42 (2H, t, J=4.9 Hz), 3.48 (2H, t, J=4.9 Hz), 4.60 (2H, d, J=4.8 Hz), 4.60 (2H, br s), 5.27 (3H, s), 6.74-6.84 (2H, m), 7.34-7.43 (6H, m), 7.77 (1H, br s), 9.37 (1H, br s), 10.38 (1H, t, J=4.8 Hz).

2) To a solution of the Compound 68 (10 g, 20.6 mmol) in toluene (300 ml) were added peraformaldehyde (790 mg, 26.3 mmol) and acetic acid (3.16 g, 52.6 mmol), and the mixture was heated and stirred at 80° C. for 40 minutes. After cooling, the solvent was distilled off. Further, the not-purified residue was dissolved in DMF (500 ml), and cesium carbonate (25.7 g, 78.9 mmol) was added under ice-cooling, followed by stirring for 30 minutes. To the reaction solution was added water, and this was extracted with ethyl acetate, washed with water, and dried with sodium sulfate. The solvent was distilled off, and the resulting crystal was washed with diethyl ether to obtain 9.85 g (yield 96%) of 5-benzyloxy-7-[3-(2,4-difluoro-phenyl)-propyl]-3-(2-methoxy-ethyl)-2,3-dihydro-1H-pyrid[2,1-f][1,2,4]triazine-4,6-dione 69.

NMR (CDCl$_3$) δ: 3.34 (3H, s), 3.55 (2H, t, J=4.7 Hz), 3.62 (2H, t, J=4.7 Hz), 4.51 (2H, d, J=7.9 Hz), 4.62 (2H, d, J=5.9 Hz), 5.29 (2H, s), 5.88 (1H, br s), 6.76-6.86 (2H, m), 7.29-7.42 (4H, m), 7.54-7.58 (2H, m), 8.51 (1H, s) 10.41 (1H, t, J=5.9 Hz).

3) According to the method of synthesizing Compound 15, 5-benzyloxy-7-[3-(2,4-difluoro-phenyl)-propyl]-3-(2-methoxy-ethyl)-1-pyridin-2-ylmethyl-2,3-dihydro-1H-pyrid[2,1-f][1,2,4]triazine-4,6-dione 70 (76.3 mg, 89%) was obtained from Compound 69 (72.2 g).

NMR (CDCl$_3$) δ: 3.28 (3H, s), 3.66 (2H, s), 3.80 (2H, br s), 3.30 (2H, br s), 4.61 (2H, d, J=6.0 Hz), 4.69 (2H, br s), 5.35 (1H, br s), 6.76-6.86 (2H, m), 7.29-7.39 (7H, m), 7.59-7.62 (2H, m), 7.74 (1H, d, J=1.9 Hz, 7.7 Hz), 8.32 (1H, s), 8.62 (1H, d, J=4.2 Hz), 10.38 (1H, t, J=6.0 Hz).

4) According to the method of synthesizing Example A-1, Example N-1 (44.3 mg, 69%) was obtained from Compound 70 (76.3 mg).

1H-NMR (CDCl$_3$) δ: 3.32 (3H, s), 3.64 (2H, t, J=4.8 Hz), 3.79 (2H, br s), 4.41 (2H, br s), 4.59 (2H, d, J=5.9 Hz), 4.88 (2H, br s), 6.75-6.84 (2H, m), 7.28-7.42 (2H, m), 7.84 (1H, dd, J=7.6 Hz, 7.6 Hz), 8.21 (1H, s), 8.63 (1H, d, J=4.4 Hz), 10.28 (1H, t, J=5.9 Hz), 11.67 (1H, br s).

5) According to the method of synthesizing Example A-1, Example O-1 (54.3 mg, 66%) was obtained form Compound 69 (100 g).

1H-NMR (CDCl$_3$) δ: 3.37 (3H, s), 3.59 (2H, t, J=4.5 Hz), 3.70 (2H, t, J=4.5 Hz), 4.62 (2H, d, J=6.0 Hz), 4.72 (2H, d, J=8.2 Hz), 5.91 (1H, t, J=8.2 Hz), 6.76-6.84 (2H, m), 7.32-7.40 (1H, m), 8.43 (1H, s), 10.29 (1H, t, J=6.0 Hz).

According to the same manner as that of Example N-1, the following Example Compounds N-2 to N-57 were synthesized.

Example N-2

3-(4-Fluoro-benzyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 2.71 (3H, s), 4.53 (2H, d, J=5.7 Hz), 4.68 (2H, s), 4.80 (2H, br s), 7.02-7.48 (7H, m), 8.24 (1H, s), 10.34 (1H, t, J=5.7 Hz), 11.58 (1H, br s).

Example N-3

5-Hydroxy-3-isopropyl-1-methyl-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 1.19 (6H, d, J=6.9 Hz), 2.83 (3H, s), 4.53 (2H, d, J=5.7 Hz), 4.66 (1H, m), 4.79 (2H, s), 7.07 (1H, m), 7.27 (1H, m), 7.40 (1H, m), 8.28 (1H, s), 10.37 (1H, t, J=5.7 Hz), 11.94 (1H, br s).

Example N-4

5-Hydroxy-1-methyl-4,6-dioxo-3-thiophen-2-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 2.67 (3H, s), 4.53 (2H, d, J=5.7 Hz), 4.87 (4H, br s), 7.00-7.50 (5H, m), 7.52 (1H, d, J=1.5 Hz), 8.27 (1H, s), 10.28 (1H, t, J=5.7 Hz), 11.40 (1H, br s).

Example N-5

5-Hydroxy-3-(3-methoxy-propyl)-1-methyl-4,6-dioxo-2,3,4,6-tetrahydro-1H-pyrid[2,1-f][1, 2,4]triazine-7-carboxylic acid 2,4-difluoro-benzylamide NMR (DMSO-d$_6$) δ: 1.82 (2H, quint, J=6.6 Hz), 2.86 (3H, s), 3.24 (3H, s), 3.40 (2H, t, J=6.0 Hz), 3.52 (2H, t, J=7.5 Hz), 4.53 (2H, d, J=6.0 Hz), 4.80 (2H, br s), 7.06 (1H, m), 7.23 (1H, m), 7.36 (1H, m), 8.26 (1H, s), 10.35 (1H, t, J=5.4 Hz), 11.79 (1H, br s).

Example N-6

5-Hydroxy-1-methyl-4,6-dioxo-3-(tetrahydro-furan-2-ylmethyl)-2,3,4,6-tetrahydro-1H-pyrid[2,1-f][1,2,4]triazine-7-carboxylic acid 2,4-difluoro-benzylamide NMR (DMSO-$d_6$) δ: 1.54-1.97 (4H, m), 2.88 (3H, s), 3.49 (1H, dd, J=7.8 Hz, 14.4 Hz), 3.68 (2H, m), 3.79 (1H, dd, J=8.1 Hz, 15.0 Hz), 4.07 (1H, m), 4.53 (2H, d, J=6.0 Hz), 4.84 (2H, br s), 7.06 (1H, m), 7.26 (1H, m), 7.36 (1H, m), 8.26 (1H, s), 10.35 (1H, t, J=6.0 Hz), 11.69 (1H, br s).

Example N-7

5-Hydroxy-3-(2-isopropoxy-ethyl)-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.06 (6H, d, J=6.0 Hz), 2.88 (3H, s), 3.37 (1H, m), 3.60 (4H, m), 4.53 (2H, d, J=6.0 Hz), 4.82 (2H, br s), 7.06 (1H, m), 7.23 (1H, m), 7.41 (1H, m), 8.28 (1H, s), 10.33 (1H, t, J=5.7 Hz), 11.74 (1H, br s).

Example N-8

5-Hydroxy-3-(3-isopropoxy-propyl)-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.07 (6H, d, J=6.0 Hz), 1.81 (2H, m), 2.87 (3H, s), 3.38 (1H, m), 3.43 (2H, t, J=6.0 Hz), 3.53 (2H, t, J=6.3 Hz), 4.53 (2H, d, J=6.0 Hz), 4.81 (2H, br s), 7.06 (1H, m), 7.23 (1H, m), 7.39 (1H, m), 8.27 (1H, s), 10.35 (1H, t, J=6.0 Hz), 11.84 (1H, br s).

Example N-9

3-Furan-2-ylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.70 (3H, s), 4.53 (2H, d, J=6.0 Hz), 4.74 (1H, s), 4.83 (2H, br s), 6.45 (1H, d, J=3.0 Hz), 6.50 (1H, d, J=2.4 Hz), 7.06 (1H, m), 7.21 (1H, m), 7.44 (1H, m), 7.61 (s, 1H), 8.28 (1H, s), 10.29 (1H, t, J=6.0 Hz), 11.50 (1H, br s).

Example N-10

3-Adamantan-1-ylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.52 (8H, m), 1.94 (3H, br s), 2.88 (3H, s), 3.28 (2H, br s), 4.53 (2H, d, J=6.0 Hz), 4.84 (2H, br s), 7.06 (1H, m), 7.24 (1H, m), 7.38 (1H, m), 8.24 (1H, s), 10.38 (1H, t, J=6.0 Hz), 11.71 (1H, br s).

Example N-11

3-Cyclopropyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.81 (4H, m), 2.80 (1H, m), 2.81 (3H, s), 4.53 (2H, d, J=5.7 Hz), 4.72 (2H, br s), 7.05 (1H, m), 7.23 (1H, m), 7.39 (1H, m), 8.26 (1H, s), 10.34 (1H, t, J=6.0 Hz), 11.87 (1H, br s).

Example N-12

3-(3-Chloro-2-fluoro-benzyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.81 (3H, s), 4.53 (2H, d, J=6.0 Hz), 4.80 (2H, s), 4.88 (2H, br s), 7.03-7.59 (6H, m), 8.31 (1H, s), 10.28 (1H, t, J=65.7 Hz), 11.46 (1H, br s).

Example N-13

3-Cyclopropylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.33 (2H, d, J=4.8 Hz), 0.51 (2H, d, J=6.6 Hz), 1.12 (1H, m), 2.89 (3H, s), 3.36 (2H, d, J=7.2 Hz), 4.53 (2H, d, J=5.4 Hz), 4.88 (2H, br s), 7.09 (1H, m), 7.23 (1H, m), 7.41 (1H, m), 8.28 (1H, s), 10.34 (1H, t, J=5.7 Hz), 11.76 (1H, br s).

Example N-14

1,3-Bis-cyclropropylmethyl-5-hydroxy-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.31-1.09 (6H, m), 3.33 (4H, br s), 4.54 (2H, d, J=5.4 Hz), 4.97 (2H, br s), 7.08 (1H, m), 7.22 (1H, m), 7.39 (1H, m), 8.31 (1H, s), 10.34 (1H, t, J=5.1 Hz), 11.80 (1H, br s).

Example N-15

5-Hydroxy-1-methyl-4,6-dioxo-3-[(S)-1-(tetrahydro-furan-2-yl)methyl]-2,3,4,6-tetrahydro-1H-pyrid[2,1-f][1,2,4]triazine-7-carboxylic acid 2,4-difluoro-benzylamide NMR (DMSO-$d_6$) δ: 1.56-1.90 (4H, m), 3.44-4.07 (5H, m), 4.53 (2H, d, J=6.0 Hz), 4.82 (2H, br s), 7.09 (1H, m), 7.28 (1H, m), 7.41 (1H, m), 8.23 (1H, s), 10.39 (1H, t, J=6.0 Hz), 11.71 (1H, br s).

Example N-16

5-Hydroxy-1-methyl-4,6-dioxo-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide NMR (DMSO-$d_6$) δ: 1.54-1.97 (4H, m), 2.88 (3H, s), 3.49 (1H, dd, J=7.8 Hz, 14.4 Hz), 3.68 (2H, m), 3.79 (1H, dd, J=8.1 Hz, 15.0 Hz), 4.07 (1H, m), 4.53 (2H, d, J=6.0 Hz), 4.84 (2H,

Example N-17

3-Benzo[1,3]dioxol-5-ylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.71 (3H, s), 4.54 (2H, d, J=5.7 Hz), 4.60 (2H, s), 4.77 (2H, br s), 6.00 (2H, s), 6.90 (2H, s), 6.98 (1H, s), 7.05 (1H, m), 7.28 (1H, m), 7.40 (1H, m), 8.22 (1H, s), 10.37 (1H, t, J=5.7 Hz), 11.65 (1H, br s).

Example N-18

3-(2-Ethoxy-ethyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.10 (3H, t, J=6.9 Hz), 2.88 (3H, s), 3.46 (2H, q, J=6.6 Hz), 3.60 (2H, d, J=4.8 Hz), 3.66 (2H, br s), 4.53 (2H, d, J=5.7 Hz), 4.83 (2H, br s), 7.05 (1H, m), 7.24 (1H, m), 7.41 (1H, m), 8.31 (1H, s), 10.31 (1H, t, J=5.7 Hz), 11.72 (1H, br s).

Example N-19

5-Hydroxy-1-methyl-4,6-dioxo-3-[3-(2-oxo-pyrrolidin-1-yl)-propyl]-2,3,4,6-tetrahydro-1H-pyrid[2,1-f][1,2,4]triazine-7-carboxylic acid 2,4-difluoro-benzylamide NMR (DMSO-$d_6$) δ: 1.79 (2H, m), 1.93 (2H, m), 2.22 (2H, t, J=8.1 Hz), 2.90 (3H, s), 3.23 (2H, t, J=6.6 Hz), 3.42 (4H, m), 4.54 (2H, d, J=6.0 Hz), 4.84 (2H, br s), 7.06 (1H, m), 7.21 (1H, m), 7.41 (1H, m), 8.32 (1H, s), 10.32 (1H, t, J=5.7 Hz), 11.76 (1H, br s).

Example N-20

3-(3-Dodecyloxy-propyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.85 (3H, t, J=6.3 Hz), 1.22 (20H, br s), 1.44 (2H, m), 1.82 (2H, m), 2.88 (3H, s), 3.39 (2H, t, J=6.0 Hz), 3.54 (2H, t, J=5.7 Hz), 4.53 (2H, d, J=6.0 Hz), 4.82 (2H, br s), 7.07 (1H, m), 7.25 (1H, m), 7.41 (1H, m), 8.31 (1H, s), 10.32 (1H, t, J=6.0 Hz), 11.85 (1H, br s).

Example N-21

3-[1,4]Dioxan-2-ylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.89 (3H, s), 3.25-3.81 (9H, m), 4.54 (2H, d, J=5.7 Hz), 4.84 (2H, br s), 7.06 (1H, m), 7.27 (1H, m), 7.42 (1H, m), 8.31 (1H, s), 10.31 (1H, t, J=6.0 Hz), 11.64 (1H, br s).

Example N-22

3-(2,3-Dihydro-benzo[1,4]dioxin-6-ylmethyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.72 (3H, s), 4.23 (4H, s), 4.54 (2H, m), 4.55 (2H, s), 4.78 (2H, br s), 6.78-7.41 (6H, m), 8.25 (1H, s), 10.35 (1H, s), 11.66 (1H, br s).

Example N-23

3-[3-(2-ethyl-hexyloxy)-propyl]-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.82-1.40 (17H, m), 1.82 (2H, m), 2.88 (3H, s), 3.24 (2H, d, 5.7 Hz), 3.41 (2H, t, J=6.0 Hz), 3.54 (2H, t, J=7.2 Hz), 4.53 (2H, d, J=5.7 Hz), 4.82 (2H, br s), 7.06 (1H, m), 7.25 (1H, m), 7.41 (1H, m), 8.31 (1H, s), 10.32 (1H, t, J=5.7 Hz), 11.85 (1H, br s).

Example N-24

1-butyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 0.99 (3H, t, J=7.39 Hz), 1.79-1.34 (4H, m), 3.14-3.00 (2H, m), 3.41 (3H, s), 3.83-3.62 (4H, m), 4.69 (2.2H, d, J=6.21 Hz), 4.95-4.71 (1H, m), 6.92-6.79 (1H, m), 7.49-7.37 (1H, m), 8.51 (1H, s), 10.47 (1H, brt, J=6.21 Hz), 11.82-11.53 (1H, brs)

Example N-25

5-Hydroxy-1-isopropyl-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 1.19-1.01 (6H, brm), 3.38 (3H, s), 3.48 (1H, s), 3.68-3.61 (2H, m), 3.76-3.70 (2H, m), 4.67 (2H, d, J=6.88 Hz), 4.91-4.83 (2H, m), 6.90-6.77 (2H, m), 7.46-7.35 (1H, m), 8.44 (1.4H, s), 10.40 (1H, brt, J=6.88 Hz), 11.58 (1H, brs)

Example N-26

5-Hydroxy-3-(2-methoxy-ethyl)-1-(3-methoxy-propyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 1.79 (2H, br s), 3.19 (1H, br s), 3.35 (3H, s), 3.38 (3H, s), 3.47 (2H, t, J=5.77 Hz), 3.65 (2H, t, J=4.53 Hz), 3.74 (2H, br s), 4.66 (2H, d, J=5.77 Hz), 4.94-4.70 (2H, m), 6.91-6.76 (2H, m), 7.45-7.34 (1H, m), 8.46 (1H, s), 10.39 (1H, br s), 11.77-11.46 (1H, m)

Example N-27

5-Hydroxy-3-(2-methoxy-ethyl)-4,6-dioxo-1-(3-pyrrol-1-yl-propyl)-2,3,4,6-tetrahydro-1H-pyrid[2,1-f][1,2,4]triazine-7-carboxylic acid 2,4-difluoro-benzylamide 1H-NMR (CDCl$_3$) δ: 1.97 (2H, br s), 2.96 (2H, t, J=7.22 Hz), 3.32 (3H, s), 3.73-3.57 (4H, m), 4.06 (2H, br s), 4.67 (2H, d, J=4.20 Hz), 5.03-4.60 (2H, m), 6.19 (2H, t, J=2.0 Hz), 6.65 (2H, t, J=2.0 Hz), 6.91-6.79 (2H, m), 7.47-7.34 (1H, m), 8.46 (1H, s), 10.43-10.31 (1H, m), 11.68-11.47 (1H, m)

Example N-28

5-Hydroxy-3-(2-methoxy-ethyl)-1-(5-methyl-isoxazol-3-ylmethyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 2.50 (3H, s) 3.38 (3H, s), 3.87-3.60 (6H, m), 4.27 (1H, br s), 4.66 (2H, d, J=6.04 Hz), 4.77 (1H, br s), 6.13 (1H, s), 6.92-6.75 (2H, m), 7.49-7.32 (2H, m), 8.45 (1H, s), 10.37 (1H, br s), 11.69 (1H, br s)

Example N-29

1-(2,4-Dinitrophenyl)-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (DMSO-d$_6$) δ: 3.22 (2H, br s), 3.36 (3H, s), 3.60 (2H, br s), 4.55 (2H, d, J=9.40 Hz), 5.41 (2H, br s), 7.12-7.03 (1H, m), 7.26 (1H, d, J=9.74 Hz), 7.31-7.21 (1H, m), 7.49-7.36 (1H, m), 8.47-8.38 (1H, m), 8.49 (1H, s), 9.01 (1H, d, J=9.74 Hz), 10.23-10.20 (1H, m), 11.56 (1H, br s)

Example N-30

1-Ethyl-5-hydroxy-3-(3-methoxy-propyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 1.19 (3H, t, J=7.60 Hz), 1.99-1.91 (2H, m), 3.13 (2H, q, J=15.19, 7.60 Hz), 3.35 (3H, s), 3.49 (2H, t, J=5.62 Hz), 3.66 (2H, t, J=7.22 Hz), 4.67 (2H, d, J=7.72 Hz), 8.49 (1H, s), 10.41 (1H, br s), 11.73 (1H, br s)

Example N-31

5-Hydroxy-3-(2-methoxy-ethyl)-1-(2-nitro-phenyl)-4,6-dioxo-2,3,4,6-tetrahydro-1H-pyrid[2,1-f][1,2,4]triazine-7-carboxylic acid 2,4-difluoro-benzylamide 1H-NMR (CDCl$_3$) δ: 2.94 (3H, s), 3.39-3.32 (2H, m), 3.66 (2H, br s), 4.62 (2H, d, J=6.21 Hz), 6.87-6.77 (3H, m), 7.41-7.31 (1H, m), 7.48 (1H, dt, J=10.63, 3.99 Hz), 7.60 (1H, td, J=7.76, 1.62 Hz), 8.09 (1H, dd, J=8.14, 1.59 Hz), 8.42 (1H, s), 10.26 (1H, t, J=6.21 Hz)

Example N-32

5-Hydroxy-3-(2-methoxy-ethyl)-4,6-dioxo-1-pyrimidin-2-yl-2,3,4,6-tetrahydro-1H-pyrid[2,1-f][1,2,4]triazine-7-carboxylic acid 2,4-difluoro-benzylamide 1H-NMR (CDCl$_3$) δ: 3.39 (3H, s), 3.72-3.41 (3H, m), 4.14-4.01 (2H, m), 4.71 (2H, d, J=5.37 Hz), 5.25 (1H, d, J=13.60 Hz), 6.15 (1H, d, J=13.60 Hz), 6.92-6.81 (2H, m), 7.13 (1H, t, J=4.11 Hz), 7.50-7.40 (1H, m), 8.57 (2H, d, J=4.11 Hz), 8.60 (1H, s) 10.51-10.37 (1H, m), 11.49 (1H, br s)

Example N-33

3-Cyclopropylmethyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl$_3$) δ: 0.42-0.33 (2H, m), 0.70-0.60 (2H, m), 1.22-1.02 (1H, m), 3.54 (2H, d, J=7.05 Hz), 4.41 (2H, br s), 4.65 (2H, d, J=6.29 Hz), 4.93 (2H, br s), 6.90-6.79 (2H, m), 7.46-7.33 (3H, m), 7.84 (1H, td, J=7.76, 1.79 Hz), 8.34 (1H, s), 8.66 (1H, d, J=4.87 Hz), 10.36 (1H, t, J=6.29 Hz), 11.83 (1H, br s)

Example N-34

3-Cyclopropyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.07-0.94 (4H, m), 2.90-2.80 (1H, m), 4.24 (2H, s), 4.64 (2H, d, J=6.21 Hz), 4.74 (2H, br s), 6.91-6.77 (2H, m), 7.46-7.32 (3H, m), 7.80 (1H, td, J=7.68, 1.73 Hz), 8.38 (1H, s), 8.64 (1H, d, J=5.87 Hz), 10.36 (1H, t, J=5.71 Hz), 12.06-11.70 (1H, m)

Example N-35

5-Hydroxy-3-(2-methoxy-ethyl)-1-(4-nitro-phenyl)-4,6-dioxo-2,3,4,6-tetrahydro-1H-pyrid[2,1-f][1,2,4]triazine-7-carboxylic acid 2,4-difluoro-benzylamide 1H-NMR (DMSO-d$_6$) δ: 3.07 (3H, s), 3.37-3.30 (2H, m), 3.56 (2H, br s), 4.58 (1H, d, J=5.87 Hz), 5.84-5.41 (2H, m), 7.15-7.07 (1H, m), 7.18 (2H, d, J=10.24 Hz), 7.36-7.24 (1H, m), 7.52-7.42 (1H, m), 8.24 (2H, d, J=9.40 Hz), 8.35 (1H, s), 10.37-10.21 (1H, m), 11.63-11.34 (1H, m)

Example N-36

5-Hydroxy-1-(2-methoxy-ethyl)-4,6-dioxo-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 2.14-1.92 (4H, m), 3.35-3.15 (1H, m), 3.37 (3H, s), 3.63-3.48 (2H, m), 3.95-3.73 (2H, m), 4.19-3.98 (2H, m), 4.67 (1H, d, J=5.54 Hz), 4.84 (1H, br s), 4.98 (1H, br s), 6.91-6.77 (1H, m), 7.47-7.32 (1H, m), 8.54 (1H, s), 10.46-10.36 (1H, m), 11.91-11.45 (1H, m)

Example N-37

3-(3-Chloro-2-fluoro-benzyl)-5-hydroxy-1-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.24-3.01 (2H, m), 3.34 (3H, s), 3.55-3.49 (2H, m), 4.66 (2H, d, J=7.22 Hz), 4.81 (2H, br s), 4.85 (2H, br s), 6.89-6.77 (3H, m), 7.20-7.13 (1H, m), 7.49-7.32 (2H, m), 8.51 (1H, s), 10.44-10.28 (1H, m)

Example N-38

5-Hydroxy-1-(2-methoxy-ethyl)-4,6-dioxo-3-[(S)-1 (tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 2.14-1.92 (4H, m), 3.35-3.15 (1H, m), 3.37 (3H, s), 3.63-3.48 (2H, m), 3.95-3.73 (2H, m), 4.19-3.98 (2H, m), 4.67 (1H, d, J=5.54 Hz), 4.84 (1H, br s), 4.98 (1H, br s), 6.91-6.77 (1H, m), 7.47-7.32 (1H, m), 8.54 (1H, s), 10.46-10.36 (1H, m), 11.91-11.45 (1H, m)

Example N-39

3-Benzo[1,3]dioxol-5-ylmethyl-5-hydroxy-1-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.06 (2H, br s), 3.33 (3H, s), 3.46 (4H, t, J=5.00 Hz), 4.72-4.62 (2H, m), 6.01 (2H, s), 6.89-6.78 (2H, m), 7.45-7.32 (1H, m), 8.49 (1H, s), 10.39-10.36 (1H, m), 11.93-11.50 (1H, m)

Example N-40

5-Hydroxy-3-(2-isopropoxy-ethyl)-1-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.17 (6H, d, J=6.21 Hz), 3.38 (3H, s), 3.82-3.50 (5H, m), 4.67 (2H, d, J=5.87 Hz), 4.89 (2H, br s), 6.88-6.78 (2H, m), 7.44-7.34 (1H, m), 8.53 (1H, s), 10.41 (1H, t, J=5.87 Hz)

Example N-41

1-(4,6-Difluoro-benzothiazoyl-2-yl)-5-hydroxy-3-(2-methoxy-ethyl)-4,6-dioxo-2,3,4,6-tetra hydro-1H-pyrid[2,1-f][1,2,4]triazine-7-carboxylic acid 2,4-difluoro-benzylamide 1H-NMR (CDCl3) δ: 3.34 (3H, s), 3.54 (3H, br s), 4.03 (1H, br s), 4.66 (2H, d J=5.7 Hz), 5.30 (1H, br s), 5.92 (1H, s), 6.78-6.88 (2H, m), 6.96-7.03 (1H, m), 7.19-7.23 (1H, m), 7.35-7.43 (1H, m), 8.64 (1H, s), 10.17 (1H, t, J=5.7 Hz), 11.52 (1H, s).

Example N-42

5-Hydroxy-3-(2-methoxy-ethyl)-4,6-dioxo-1-prop-2-ynyl-2,3,4,6-tetrahydro-1H-pyrid[2,1-f][1,2,4]triazine-7-carboxylic acid 2,4-difluoro-benzylamide 1H-NMR (CDCl3) δ: 2.49 (1H, t, J=2.5 Hz), 3.38 (3H, s), 3.69 (2H, t, J=4.5 Hz), 3.77 (2H, t, J=4.5 Hz), 3.96 (2H, d, J=2.5 Hz), 4.68 (2H, d, J=5.9 Hz), 4.88 (2H, s), 6.80-6.90 (2H, m), 7.37-7.45 (1H, m), 8.53 (1H, s), 10.32 (1H, t, J=5.9 Hz), 11.62 (1H, br s).

Example N-43

1-Furan-3-ylmethyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.35 (3H, s), 3.63 (2H, d, J=3.9 Hz), 3.70 (2H, br s), 4.06 (2H, br s), 4.62 (2H, d, J=6.0 Hz), 4.74 (2H, br s), 6.45 (1H, s), 6.76-6.85 (2H, m), 7.31-7.39 (1H, m), 7.48 (1H, t, J=1.8 Hz), 10.31 (1H, t, J=6.0 Hz), 11.60 (1H, br s).

Example N-44

5-Hydroxy-3-(2-methoxy-ethyl)-4,6-dioxo-1-thiophen-3-ylmethyl-2,3,4,6-tetrahydro-1H-pyrid[2,1-f][1,2,4]triazine-7-carboxylic acid 2,4-difluoro-benzylamide 1H-NMR (CDCl3) δ: 3.34 (3H, s), 3.62 (2H, t, J=3.9 Hz), 3.69 (2H, br s), 4.20 (2H, br s), 4.61 (2H, d, J=6.2 Hz), 4.78 (2H, br s), 6.76-6.85 (2H, m), 7.09 (1H, dd, J=1.3 Hz, 5.0 Hz), 7.14 (1H, dd, J=2.9 Hz, 5.0 Hz), 8.22 (1H, s), 10.28 (1H, J=6.2 Hz), 11.60 (1H, br s).

Example N-45

1-Furan-2-ylmethyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.36 (3H, s), 3.64 (2H, t, J=4.8 Hz), 3.74 (2H, br s), 4.20 (2H, s), 4.61 (2H, d, J=6.0 Hz), 4.76 (2H, br s), 6.27 (1H, d, J=3.2 Hz), 6.34 (1H, dd, J=1.9 Hz, 3.2 Hz), 6.76-6.84 (2H, m), 7.30-7.38 (1H, m), 7.45 (1H, dd, J=0.8 Hz, 1.9 Hz), 8.20 (1H, s), 10.29 (1H, t, J=6.0 Hz).

Example N-46

5-Hydroxy-3-(2-methoxy-ethyl)-4,6-dioxo-1-thiophen-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 3.49 (3H, s), 3.67 (2H, t, J=4.5 Hz), 3.76 (2H, br s), 4.43 (2H, br s), 4.67 (2H, d, J=5.5 Hz), 4.78 (2H, br s), 6.80-6.90 (2H, m), 6.96-7.04 (2H, m), 7.36-7.44 (1H, m), 7.44 (1H, dd, J=1.5 Hz, 5.1 Hz), 8.41 (1H, br s), 10.37 (1H, br s).

Example N-47

5-Hydroxy-3-(2-methoxy-ethyl)-1-methylcarbamoylmethyl-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 2.89 (3H, d, J=4.5 Hz), 3.35 (3H, s), 3.63 (2H, t, J=4.8 Hz), 3.72 (2H, br s), 4.61 (2H, d, J=5.7 Hz), 4.87 (2H, br s), 6.72 (1H, br s), 6.76-6.85 (2H, m), 7.31-7.39 (1H, m), 8.49 (1H, s), 10.23 (1H, t, J=5.7 Hz), 11.63 (1H, br s).

Example N-48

1-Fluoromethyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.44 (3H, s), 3.72 (4H, br s), 4.61 (2H, d, J=5.4 Hz), 4.80 (2H, s), 4.90 (2H, s), 4.77-4.87 (2H, m), 7.36-7.44 (1H, m), 8.52 (1H, s), 10.10 (1H, s), 11.65 (1H, br s).

Example N-49

1-(4-Fluoro-benzyl)-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.32 (3H, s), 3.61 (2H, br s), 3.68 (2H, br s), 4.15 (2H, s), 4.60 (2H, d, J=5.7 Hz), 4.81 (2H, br s), 6.75-6.85 (2H, m), 7.07 (2H, t, J=5.6 Hz), 7.23-7.36 (3H, m), 8.27 (1H, s), 10.24 (1H, t, J=5.7 Hz), 11.60 (1H, br s).

Example N-50

5-Hydroxy-1-(4-methoxy-benzyl)-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.32 (3H, s), 3.59 (2H, t, J=4.5 Hz), 3.68 (2H, br s), 3.80 (3H, s), 4.61 (2H, d, J=5.7 Hz), 4.65 (2H, br s), 6.75-6.85 (2H, m), 6.89 (2H, d, J=8.6 Hz), 7.17 (2H, d, J=8.6 Hz), 7.29-7.37 (1H, m), 8.28 (1H, s), 10.30 (1H, t, J=5.7 Hz), 11.61 (1H, br s).

Example N-51

1-Benzyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.31 (3H, s), 3.60 (2H, t, J=4.2 Hz), 3.68 (2H, br s), 4.17 (2H, s), 4.60 (2H, d, J=5.7 Hz), 4.68 (2H, br s), 6.75-6.85 (2H, m), 7.25-7.39 (6H, m), 8.27 (1H, s), 10.28 (1H, t, J=5.7 Hz), 11.61 (1H, br s).

Example N-52

5-Hydroxy-1,3-bis-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.34 (3H, s), 3.35 (3H, s), 3.54 (2H, t, J=4.5 Hz), 3.61 (2H, t, J=4.5 Hz), 3.72 (2H, br s), 4.64 (2H, d, J=5.9 Hz), 4.84 (2H, br s), 6.75-6.84 (2H, m), 7.32-7.40 (1H, m), 8.51 (1H, s), 10.38 (1H, br s), 11.62 (1H, br s).

Example N-53

1-Dimethylcarbamoylmethyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.04 (3H, s), 3.05 (3H, s), 3.35 (3H, s), 3.65 (2H, t, J=4.6 Hz), 3.77 (2H, br s), 3.96 (2H, br s), 4.68 (2H, d, J=5.9 Hz), 5.02 (2H, s), 6.80-6.89 (2H, m), 7.37-7.45 (1H, m), 8.56 (1H, s), 10.39 (1H, br s), 11.60 (1H, br s).

Example N-54

5-Hydroxy-1-(2-hydroxy-ethyl)-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.25 (2H, br s), 3.37 (3H, s), 3.66 (2H, t, J=4.2 Hz), 3.73 (2H, br s), 3.82 (2H, t, J=4.2 Hz), 4.63 (2H, d, J=5.7 Hz), 4.90 (2H, s), 6.76-6.85 (2H, m), 7.33-7.41 (1H, m), 8.63 (1H, br s), 10.45 (1H, br s), 11.6 (1H, br s).

Example N-55

1-Cyclopropylmethyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 0.00 (2H, br s), 0.60 (2H, m), 0.94 (1H, m), 2.93 (2H, br s), 3.38 (3H, s), 3.65 (2H, t, J=4.5 Hz), 3.74 (2H, t, J=4.5 Hz), 4.67 (2H, d, J=5.9 Hz), 4.83 (2H, br s), 6.79-6.88 (2H, m), 7.36-7.44 (1H, m), 8.56 (1H, s), 10.42 (1H, J=5.9 Hz), 11.61 (1H, br s).

Example N-56

5-Hydroxy-3-(2-methoxy-ethyl)-4,6-dioxo-1-pyridin-3-ylmethyl-2,3,4,6-tetrahydro-1H-pyrid[2,1-f][1,2,4]triazine-7-carboxylic acid 2,4-difluoro-benzylamide 1H-NMR (CDCl3) δ: 3.37 (3H, s), 3.68 (2H, br s), 3.75 (2H, br s), 4.38 (2H, br s), 4.63 (2H, d, J=5.9 Hz), 4.88 (2H, br s), 6.79-6.88 (2H, m), 7.32-7.41 (1H, m), 7.56-7.61 (1H, m), 7.94-7.97 (1H, m), 8.34 (1H, s), 8.74 (1H, br s), 10.26 (1H, t, J=5.9 Hz).

Example N-57

1-Ethyl-5-hydroxy-3-(2-methoxy-ethyl)-4,6-idoxo-2,3,4,6-tetrahydro-1H-pyrid[2,1-f][1,2,4]triazine-7-carboxylic acid 2,4-difluoro-benzylamide 1H-NMR (CDCl3) δ: 1.17 (3H, t, 7.13), 3.11 (2H, q, J=7.1 Hz), 3.36 (3H, s), 3.63 (2H, t, J=4.5 Hz), 3.71 (2H, br s), 4.64 (2H, d, J=5.9 Hz), 4.78 (2H, br s), 6.76-6.85 (2H, m), 7.33-7.41 (1H, m), 8.45 (1H, s), 10.38 (1H, t, J=5.9 Hz), 11.59 (1H, br s).

According to the same manner as that of Example O-1, the following Example Compounds O-2 to O-13 were synthesized.

Example O-2

3-(4-Fluoro-benzyl)-5-hydroxy-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 4.52 (2H, d, J=5.4 Hz), 4.64 (4H, br s), 7.02-7.44 (7H, m), 7.64 (1H, t, J=5.4 Hz), 7.98 (1H, s), 10.52 (1H, s).

Example O-3

5-Hydroxy-3-isopropyl-4,6-dioxo-2,3,4,6-tetrahydro-1H-pyrid[2,1-f][1,2,4]triazine-7-carboxylic Acid 2,4-difluoro-benzylamide NMR (DMSO-d$_6$) δ: 1.19 (6H, d, J=6.9 Hz), 4.62 (1H, m), 4.68 (2H, d, J=8.1 Hz), 7.06 (1H, m), 7.26 (1H, m), 7.40 (1H, m), 7.53 (1H, t, J=7.2 Hz), 8.12 (1H, s), 10.41 (1H, t, J=5.7 Hz), 11.94 (1H, br s).

Example O-4

3-Furan-2-ylmethyl-2-ylmethyl-5-hydroxy-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 4.52 (2H, d, J=5.7 Hz), 4.68 (4H, s), 6.44 (2H, m), 7.06 (1H, m), 7.27 (2H, m), 7.40 (2H, m), 7.64 (2H, s), 8.06 (1H, s), 10.43 (1H, t, J=5.7 Hz), 11.56 (1H, br s).

Example O-5

5-Hydroxy-4,6-dioxo-3-thiophen-2-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 4.53 (1H, d, J=3.8 Hz), 4.76 (2H, d, J=7.8 Hz), 4.85 (2H, s), 7.00-7.40 (5H, m), 7.50 (1H, d, J=3.6 Hz), 7.65 (1H, t, J=7.8 Hz), 8.15 (1H, s), 10.32 (1H, t, J=5.7 Hz), 11.58 (1H, br s).

Example O-6

5-Hydroxy-4,6-dioxo-3-[(S)-1-(tetrahydro-furan-2-yl)methyl]-2,3,4,6-tetrahydro-1H-pyrid[2,1-f][1,2,4]triazine-7-carboxylic acid 2,4-difluoro-benzylamide NMR (DMSO-$d_6$) δ: 1.52-1.94 (4H, m), 3.46 (1H, dd, J=7.5 Hz, 14.1 Hz), 3.66 (2H, m), 3.79 (1H, dd, J=6.9 Hz, 14.4 Hz), 4.04 (1H, m), 4.54 (2H, d, J=5.7 Hz), 6.75 (2H, d, J=16.0 Hz), 7.07 (1H, m), 7.25 (1H, m), 7.39 (1H, m), 7.61 (1H, t, J=8.1 Hz), 8.15 (1H, s), 10.37 (1H, t, J=5.7 Hz), 11.72 (1H, br s).

Example O-7

5-Hydroxy-3-(2-morpholin-4-yl-ethyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.43 (2H, br s), 3.55 (4H, br s), 3.60 (2H, t, J=5.7 Hz), 4.54 (2H, d, J=6.0 Hz), 4.78 (2H, d, J=8.1 Hz), 7.07 (1H, m), 7.24 (1H, m), 7.40 (1H, m), 7.55 (1H, t, J=8.1 Hz), 8.18 (1H, s), 10.35 (1H, t, J=6.2 Hz), 11.79 (1H, br s).

Example O-8

5-Hydroxy-4,6-dioxo-3-[(R)-1-(tetrahydro-furan-2-yl)methyl-2,3,4,6-tetrahydro-1H-pyrid[2,1-f][1,2,4]triazine-7-carboxylic acid 2,4-difluoro-benzylamide NMR (DMSO-$d_6$) δ: 1.52-1.94 (4H, m), 3.46 (1H, dd, J=7.5 Hz, 14.1 Hz), 3.66 (2H, m), 3.79 (1H, dd, J=6.9 Hz, 14.4 Hz), 4.04 (1H, m), 4.54 (2H, d, J=5.7 Hz), 6.75 (2H, d, J=16.0 Hz), 7.07 (1H, m), 7.25 (1H, m), 7.39 (1H, m), 7.61 (1H, t, J=8.1 Hz), 8.15 (1H, s), 10.37 (1H, t, J=5.7 Hz), 11.72 (1H, br s).

Example O-9

5-Hydroxy-3-(2-isopropoxy-ethyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.08 (2H, d, J=6.0 Hz), 3.56 (2H, t, J=5.7 Hz), 3.58 (1H, m), 3.60 (2H, t, J=5.7 Hz), 4.54 (2H, d, J=6.0 Hz), 4.75 (2H, d, J=8.1 Hz), 7.06 (1H, m), 7.28 (1H, m), 7.38 (1H, m), 7.55 (1H, t, J=8.4 Hz), 8.17 (1H, s), 10.36 (1H, t, J=5.7 Hz), 11.73 (1H, br s).

Example O-10

5-Hydroxy-3-(3-isopropoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.06 (6H, d, J=6.3 Hz), 1.78 (2H, m); 3.43 (2H, t, J=6.3 Hz), 3.53 (3H, m), 4.53 (2H, d, J=6.3 Hz), 4.72 (2H, d, J=13.5 Hz), 7.09 (1H, m), 7.24 (1H, m), 7.38 (1H, m), 7.57 (1H, t, J=8.1 Hz), 8.17 (1H, s), 10.36 (1H, t, J=6.3 Hz), 11.87 (1H, br s).

Example O-11

5-Hydroxy-3-(3-methoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.59 (1H, m), 3.01 (3H, s), 3.15 (2H, t, J=8.1 Hz), 3.28 (2H, t, J=8.1 Hz), 4.31 (2H, d, J=5.7 Hz), 4.50 (2H, d, J=8.1 Hz), 6.85 (1H, m), 7.03 (1H, m), 7.19 (1H, m), 7.36 (1H, t, J=8.1 Hz), 7.95 (1H, s), 10.14 (1H, t, J=6.0 Hz), 11.63 (1H, br s).

Example O-12

3-Benzo[1,3]dioxol-5-ylmethyl-5-hydroxy-4,6-dioxy-2,3,4,6-tetrahydro-1H-pyrid[2,1-f][1, 2,4]triazine-7-carboxylic acid 2,4-difluoro-benzylamide NMR (DMSO-$d_6$) δ: 4.52 (6H, br s), 5.98 (2H, s), 6.84-7.77 (7H, m), 10.73 (1H, br s).

Example O-13

5-Hydroxy-4,6-dioxo-3-(2-pyridin-2-yl-ethyl)-2,3,4,6-tetrahydro-1H-pyrid[2,1-f][1,2,4]triazine-7-carboxylic acid 2,4-difluoro-benzylamide 1H-NMR (DMSO-$d_6$) δ: 2.62-2.50 (2H, m), 3.10 (1H, t, J=7.30 Hz), 3.87 (1H, t, J=7.39 Hz), 4.49 (1H, d, J=6.88 Hz), 4.57 (3H, d, J=5.88 Hz), 4.75 (2H, d, J=7.89 Hz), 6.59-6.57 (1H, m), 7.12-7.09 (2H, m), 7.33-7.23 (1H, m), 7.48-7.36 (1H, m), 7.58 (1H, t, J=7.89 Hz) 7.76 (1H, td, J=7.64, 1.85 Hz), 8.18 (1H, s), 8.54 (1H, d, J=3.86 Hz), 10.42 (1H, t, J=5.71 Hz), 11.71 (1H, br s)

Example P-1

1-[2-(Acetyl-methyl-amino)-ethyl]-5-hydroxy-3-(2-methoxy-ethyl)-4,6-dioxo-2,3,4,6-tetra hydro-1H-pyrid[2,1-f][1,2,4]triazine-7-carboxylic acid 2,4-difluoro-benzylamide

[Chemical formula 130]

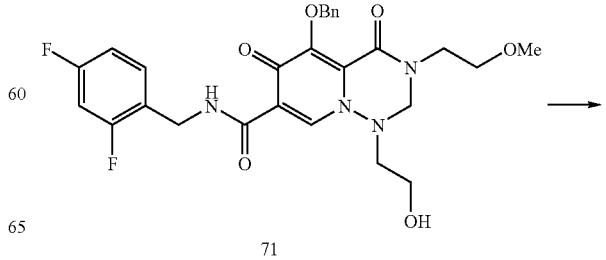

71

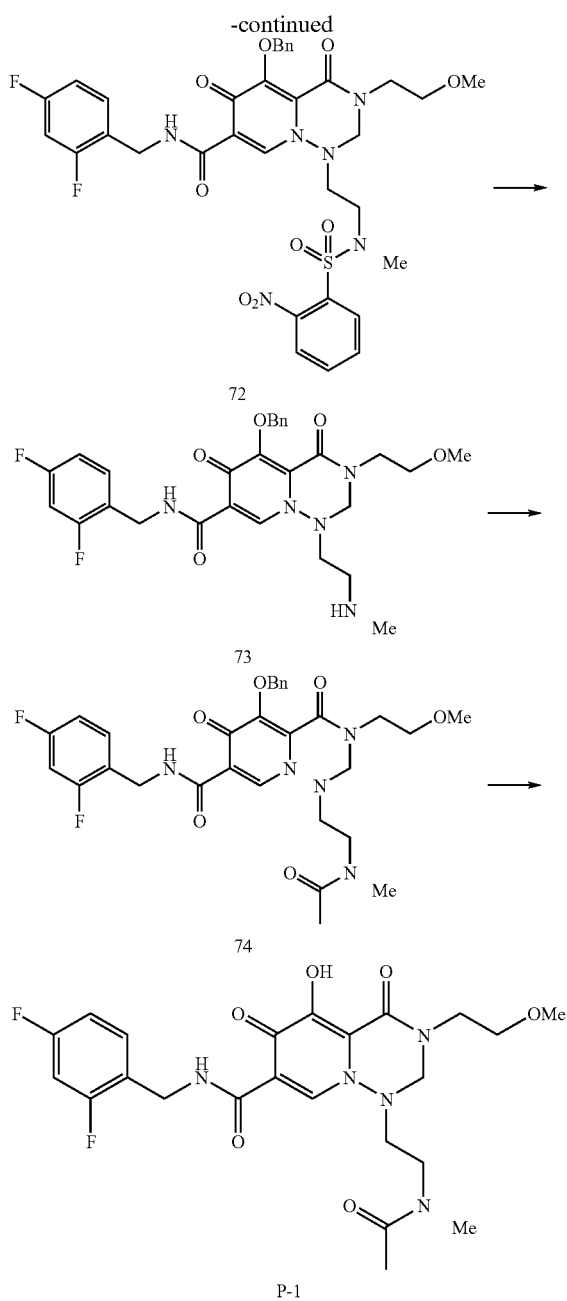

NMR (CDCl3) δ: 2.94 (3H, s), 3.13 (1H, br s), 3.34 (1H, br s), 3.37 (3H, s), 3.62 (6H, br s), 4.64 (2H, d, J=6.0 Hz), 4.72 (2H, s), 5.29 (1H, br s), 5.35 (1H, br s), 6.77-6.87 (2H, m), 7.30-7.42 (4H, m), 7.57 (2H, dd, J=1.5 Hz, 7.9 Hz), 7.64-7.70 (1H, m), 7.71-7.77 (2H, m), 8.08-8.05 (1H, m), 8.55 (1H, s), 10.40 (1H, t, J=6.0 Hz).

2) To a solution of Compound 72 (106.6 mg, 0.144 mmol) and potassium carbonate (99.5 mg, 0.72 mmol) in DMF (5 ml) was added benzenethiol (23.8 mg, 0.216 mmol) at room temperature, and the mixture was stirred for 16 hours. To the reaction solution was add water, and this was extracted with ethyl acetate, washed with water, and dried with magnesium sulfate. The solvent was distilled off, and the resulting residue was purified by subjecting to silica gel chromatography. From fractions eluting with chloroform-methanol (85:15 v/v), 39.1 mg (yield 49%) of 5-benzyloxy-7-[3-(2,4-difluoro-phenyl)-propyl]-3-(2-methoxy-ethyl)-1-(2-methylamino-ethyl)-2,3-dihydro-1H-pyrid[2,1-f][1,2,4]triazine-4,6-dione 73 was obtained as an oil.

NMR (CDCl3) δ: 2.56 (3H, s), 3.29 (2H, br s), 3.33 (3H, s), 3.65 (6H, br s), 4.62 (2H, d, J=6.6 Hz), 4.72 (2H, br s), 5.32 (2H, br s), 6.76-6.88 (2H, m), 7.29-7.40 (4H, m), 7.55-7.61 (2H, m), 8.61 (1H, s), 10.47 (1H, t, J=6.6 Hz).

3) To a solution of Compound 73 (45 mg, 0.081 mmol) in dichloromethane (5 ml) were added triethylamine (24.6 mg, 0.243 mmol) and acetic anhydride (16.5 mg, 0.162 mmol) under ice-cooling, and the mixture was stirred at room temperature for 30 minutes. The solvent was distilled off, and the resulting residue was purified by subjecting to silica gel chromatography. From fractions eluting with chloroform-methanol (95:5 v/v), 48.0 mg (yield 100%) of N-{2-[5-benzyloxy-7-[3-(2,4-difluoro-phenyl)-propyl]-3-(2-methoxy-ethyl)-4,6-dioxo-2,3,4,6-tetrahydro-pyrid[2,1-f][1,2,4]triazin-1-yl]-ethyl}-N-methyl-acetamide 74 was obtained as an oil.

NMR (CDCl3) δ: 2.14 (3H, s), 3.10 (3H, s), 3.34 (3H, s), 3.36 (4H, br s), 3.61 (2H, br s), 3.70 (2H, br s), 4.63 (2H, d, J=5.9 Hz), 4.73 (2H, s), 5.31 (2H, br s), 6.77-6.87 (2H, m), 7.29-7.41 (4H, m), 7.55-7.58 (2H, m), 10.43 (1H, t, J=5.9 Hz).

4) According to the method of synthesizing Example A-1, Example P-1 (46.1 mg, 75%) was obtained from Compound 74 (72.2 mg).

2.13 (3H, s), 3.09 (3H, s), 3.56 (3H, s), 3.64 (2H, t, J=4.8 Hz), 3.75 (2H, br s), 4.64 (2H, d, J=6.4 Hz), 4.89 (2H, s), 6.77-6.85 (2H, m), 7.32-7.40 (1H, m), 8.40 (1H, s), 10.38 (1H, t, J=6.4 Hz), 11.65 (1H, br s).

Example Q-1

5-hydroxy-1-(2-methoxy-acetyl)-3-(2-methoxy-ethyl)-4,6-dioxo-2,3,4,6-tetrahydro-1H-pyrid[2,1-f][1,2,4]triazine-7-carboxylic acid 2,4-difluoro-benzylamide

[Chemical formula 131]

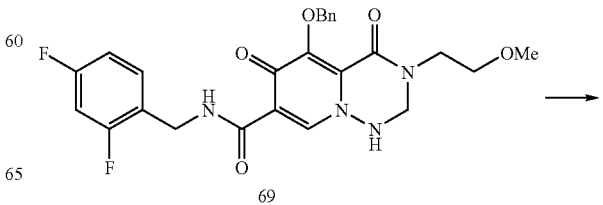

1) Using Compound 71 synthesized according to the method of synthesizing Compound 70, Compound 72 was synthesized by the following procedure.

To a solution of Compound 71 (200 mg, 0.369 mmol) in THF (10 ml) were added triphenylphosphine (145 mg, 0.553 mmol), a diethyl azodicarboxylate 40 wt % toluene solution (251 μl, 0.553 mmol), and N-methyl-o-nitrobenzenesulfonamide (120 mg, 0.553 mmol) under ice-cooling, and the mixture was stirred at room temperature for 2 hours. The solvent was distilled off, and the resulting residue was purified by subjecting to silica gel chromatography. From fractions eluting with hexane-ethyl acetate (1:19 v/v), 143 mg (yield 52%) of N-{2-[5-benzyloxy-7-[3-(2,4-difluoro-phenyl)-propyl]-3-(2-methoxy-ethyl)-4,6-dioxo-2,3,4,6-tetrahydro-pyrid[2,1-f][1,2,4]triazin-1-yl]-ethyl}-N-methyl-o-nitro-benzenesulfonamide 72 was obtained as an oil.

-continued

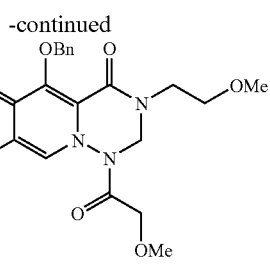

75

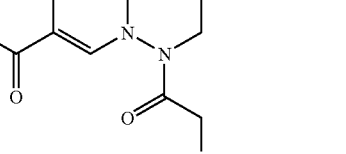

Q-1

1) To a solution of Compound 69 (150 mg, 0.301 mmol) in THF (2 ml) were added methoxyacetyl chloride (327 mg, 3.010 mmol) and pyridine (47.6 mg, 0.602 mmol) at room temperature, and the mixture was stirred at 60° C. for 30 minutes. This was quenched with an aqueous saturated sodium bicarbonate solution, extracted with ethyl acetate, washed with an aqueous saturated sodium chloride solution, and dried with sodium sulfate. The solvent was distilled off, and the resulting residue was purified by subjecting to silica gel chromatography. From fractions eluting with chloroform-methanol (97:3 v/v), 168.0 mg (yield 98%) of the title Compound 75 was obtained as an oil.

1H-NMR (CDCl3) δ: 3.37 (3H, s), 3.46 (3H, s), 3.60 (3H, br s), 3.86 (1H, br s), 4.27 (2H, br s), 4.67 (2H, d, J=6.04 Hz), 5.06-4.88 (2H, m), 5.51-5.20 (2H, m), 5.73-5.56 (1H, m), 6.92-6.79 (4H, m), 7.47-7.31 (4H, m), 7.64-7.57 (2H, m), 8.43 (1H, s), 10.28 (1H, t, J=5.96 Hz)

2) According to the method of synthesizing Example A-1, Example Q-1 (80 g, 57%) was obtained from Compound 75 (168 mg).

1H-NMR (CDCl3) δ: 3.42 (3H, s), 3.49 (3H, s), 3.49 (3H, s), 3.69-3.60 (2H, m) 3.87-3.70 (2H, m), 4.27 (2H, s), 4.69 (2H, d, J=5.88 Hz), 5.25-5.04 (1H, br m), 5.88-5.69 (1H, br m), 6.93-6.79 (2H, m), 7.48-7.35 (1H, m), 8.42 (1.3H, s), 10.23 (1H, br s), 11.55-11.27 (1H, m)

According to the same manner as that of Example Q-1, the following Example Compounds Q-2 to Q-15 were synthesized.

Example Q-2

1-Acetyl-3-(4-fluoro-benzyl)-5-hydroxy-4,6-dioxo-2,3,4,6-tetrahydro-1H-pyrid[2,1-f][1,2,4]triazine-7-carboxylic acid 2,4-difluoro-benzylamide NMR (DMSO-d₆) δ: 2.00 (3H, s), 4.45 (2H, d, J=5.7 Hz), 4.63 (1H, br s), 4.71 (1H, br s), 5.29 (1H, br s), 5.55 (1H, br s), 7.03-7.44 (7H, m), 8.26 (1H, s), 10.25 (1H, t, J=6.3 Hz), 11.23 (1H, br s).

Example Q-3

3-(4-Fluoro-benzyl)-5-hydroxy-1-(2-methoxy-acetyl)-4,6-dioxo-2,3,4,6-tetrahydro-1H-pyrid[2,1-f][1,2,4]triazine-7-carboxylic acid 2,4-difluoro-benzylamide NMR (DMSO-d₆) δ: 3.21 (3H, s), 4.02 (2H, m), 4.53 (2H, d, J=6.0 Hz), 4.72 (2H, m), 5.22 (1H, br s), 5.38 (1H, br s), 7.04-7.46 (7H, m), 8.11 (1H, s), 10.39 (1H, t, J=6.0 Hz).

Example Q-4

1-Benzoyl-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.05 (3H, s), 3.65-3.31 (4H, m), 4.69 (2H, d, J=4.87 Hz), 5.58-5.22 (2H, m), 6.93-6.79 (2H, m), 7.48-7.36 (2H, m), 7.67-7.56 (2H, m), 7.78-7.69 (2H, m), 7.88-7.76 (2H, m), 8.46 (1H, s), 10.28 (1H, brt, J=4.87 Hz), 11.58-11.34 (1H, m)

Example Q-5

5-Hydroxy-1-(4-methoxy-benzoyl)-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.04 (3H, s), 3.61-3.31 (4H, m), 3.92 (3H, s), 4.65 (1H, d, J=7.32 Hz), 5.55-5.27 (2H, m), 6.90-6.75 (2H, m), 7.03 (2H, d, J=8.69 Hz), 7.45-7.29 (1H, m), 7.76 (2H, d, J=8.69 Hz), 8.39 (1H, s), 10.29 (1H, br s), 11.61-11.30 (1H, m)

Example Q-6

1-(4-Fluoro-benzoyl)-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.09 (3H, s), 3.44 (2H, br s), 3.57 (2H, br s), 4.69 (0.9H, d, J=5.29 Hz), 5.49-5.34 (0.8H, m), 6.91-6.80 (2H, m), 7.35-7.26 (2H, m), 7.47-7.36 (1H, m), 7.92-7.79 (2H, m), 8.45 (1H, s), 10.27 (1H, t, J=5.29 Hz), 11.44 (1H, br s)

Example Q-7

5-Hydroxy-3-(2-methoxy-ethyl)-1-(4-methyl-benzoyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 2.51 (3H, s), 3.07 (2.9H, s), 3.46-3.36 (2H, m), 3.63-3.49 (2H, m), 4.69 (1H, d, J=6.04 Hz), 5.42 (1H, br s), 6.91-6.79 (1.1H, m), 7.40 (2H, d, J=8.23 Hz), 7.45-7.39 (1H, m), 7.70 (2H, d, J=8.23 Hz), 8.46 (1H, s), 10.31 (1H, t, J=6.04 Hz), 11.47 (1H, br s)

Example Q-8

5-Hydroxy-1-isobutyryl-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.29-1.19 (4H, m), 2.81 (1H, t, J=6.97 Hz), 3.41 (3H, s), 3.74-3.59 (3H, m), 3.96-3.82 (1H, m), 4.68 (2H, d, J=5.71 Hz), 5.09 (0H, d, J=10.91 Hz), 5.65 (1H, d, J=12.09 Hz), 6.93-6.80 (2H, m), 7.47-7.36 (1H, m), 8.44 (1H, s), 10.24 (1H, t, J=12.09 Hz), 11.39 (1H, br s)

Example Q-9

1-Cyclopropanecarbonyl-5-hydroxy-3-(2-methoxy-ethyl)-4,6-dioxo-2,3,4,6-tetrahydro-H-pyrid[2,1-f][1,2,4]triazine-7-carboxylic acid 2,4-difluoro-benzylamide 1H-NMR (CDCl3) δ: 1.17-0.96 (6H, m), 1.51 (1H, s), 3.40 (3H, s), 3.62 (3H, br s), 4.08-3.96 (1H, m), 4.69 (1H, d, J=7.39 Hz), 5.07-5.02 (1H, br m), 5.81-5.78 (1H, br m), 6.92-6.80 (2H, m), 7.48-7.36 (1H, m), 8.58 (1H, s), 10.25 (1H, t, J=7.39 Hz), 11.47 (1H, br s)

Example Q-10

1-(Flurane-2-carbonyl)-5-hydroxy-3-(2-methoxy-ethyl)-4,6-dioxo-2,3,4,6-tetrahydro-H-pyrid[2,1-f][1,2,4]triazine-7-carboxylic acid 2,4-difluoro-benzylamide 1H-NMR (CDCl3) δ: 3.16 (3H, s), 3.51 (2H, br s), 3.68 (2H, br s), 4.67 (2H, d, J=6.71 Hz), 5.36 (1H, br s), 6.02 (1H, br s), 6.68 (1H, s), 6.90-6.78 (2H, m), 7.46-7.34 (1H, m), 7.68 (1H, s), 8.43 (1H, s), 10.27 (1H, br s), 11.41 (1H, br s)

Example Q-11

5-Hydroxy-3-(2-methoxy-ethyl)-4,6-dioxo-1-(thiophene-2-carbonyl)-2,3,4,6-tetrahydro-1H-pyrid[2,1-f][1,2,4]triazine-7-carboxylic acid 2,4-difluoro-benzylamide 1H-NMR (CDCl3) δ: 3.12 (3H, s), 3.54-3.44 (2H, m), 3.69-3.61 (2H, m), 4.67 (2H, d, J=6.55 Hz), 5.53-5.25 (1H, m), 5.88-5.62 (1H, m), 6.94-6.76 (2H, m), 7.25 (1H, dd, J=5.04, 4.40 Hz), 7.45-7.34 (1H, m), 7.71 (1H, dd, J=4.40, 1.10 Hz), 7.81 (1H, dd, J=5.04, 1.10 Hz), 8.43 (1H, s), 10.30-10.24 (1H, m)

Example Q-12

5-Hydroxy-3-(2-methoxy-ethyl)-4,6-dioxo-1-(2-oxo-2-thiophen-2-yl-acetoxyl)-2,3,4,6-tetra hydro-1H-pyrid[2,1-f][1,2,4]triazine-7-carboxylic acid 2,4-difluoro-benzylamide 1H-NMR (CDCl3) δ: 3.11 (3H, s), 3.52 (2H, br s), 3.70 (1H, br s), 3.78 (1H, br s), 4.64 (2H, d, J=5.9 Hz), 5.28 (1H, br s), 5.75 (1H, br s), 6.77-6.87 (2H, m), 7.25-7.27 (1H, m), 7.33-7.41 (1H, m), 7.95 (1H, d, J=4.9 Hz), 8.04 (1H, br s), 8.44 (3H, s), 10.20 (1H, br s).

Example Q-13

5-Hydroxy-3-(2-methoxy-ethyl)-4,6-dioxo-2,3,4,6-tetrahydro-pyrid[2,1-f][1,2,4]triazine-1,7-dicarboxylic acid 7-(2,4-difluoro-benzylamide)-1-dimethylamide 1H-NMR (CDCl3) δ: 3.08 (6H, s), 3.35 (3H, s), 3.57 (2H, t, J=4.5 Hz), 3.69 (2H, br s), 4.63 (2H, d, J=5.7 Hz), 5.07 (2H, s), 6.76-6.85 (2H, m), 7.31-7.39 (1H, m), 8.30 (1H, s), 10.33 (1H, t, J=5.7 Hz), 11.40 (1H, br s).

Example Q-14

5-Hydroxy-1-methanesulfonyl-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 3.18 (3H, s), 3.38 (3H, s), 3.64 (2H, s), 3.70 (1H, br s), 3.87 (1H, m), 4.64 (2H, d, J=5.7 Hz), 5.15 (1H, d, J=13.2 Hz), 5.49 (1H, d, J=13.2 Hz), 6.77-6.86 (2H, m), 7.33-7.41 (1H, m), 8.55 (1H, s), 10.10 (1H, t, 5.7 Hz), 11.55 (1H, br s).

Example Q-15

1-Acetyl-5-hydroxy-3-(2-methoxy-ethyl)-4,6-dioxo-2,3,4,6-tetrahydro-1H-pyrid[2,1-f][1,2, 4]triazine-7-carboxylic acid 2,4-difluoro-benzylamide 1H-NMR (CDCl3) δ: 2.20 (3H, s), 3.37 (3H, s), 3.60 (2H, br s), 3.67 (1H, br s), 3.81 (1H, br s), 4.64 (2H, d, J=5.9 Hz), 5.02 (1H, br s), 5.61 (1H, br s), 6.77-6.86 (2H, m), 7.33-7.41 (1H, m), 8.43 (1H, s), 10.17 (1H, t, J=5.9 Hz), 11.39 (1H, br s).

The present invention further provides the following compounds.

[Chemical formula 132]

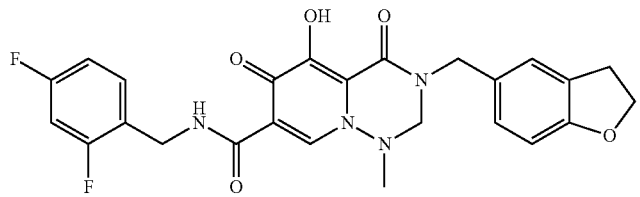

N-120

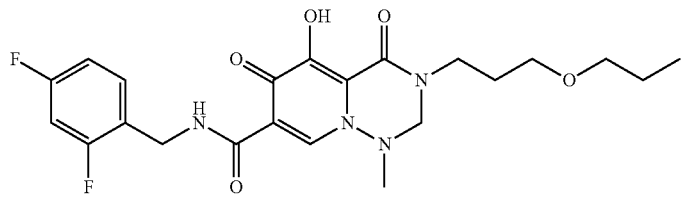

N-119

-continued
N-83
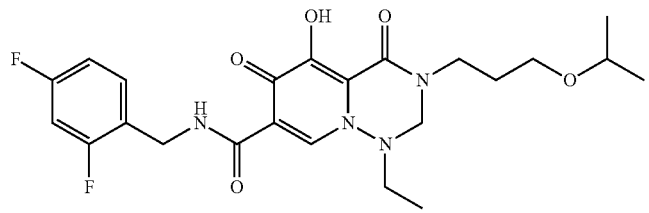
N-84
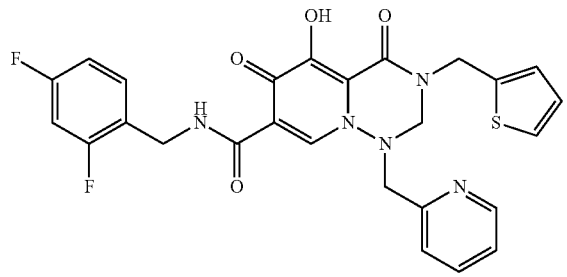
N-85
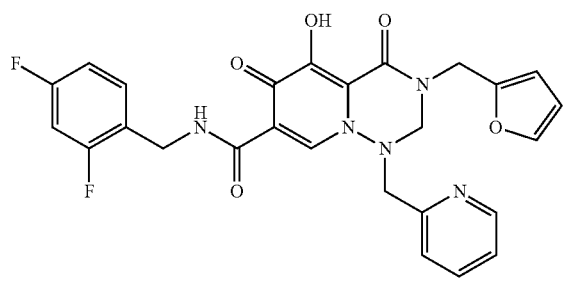
[Chemical formula 133]
N-122
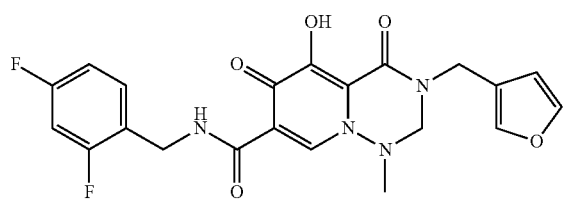
N-121
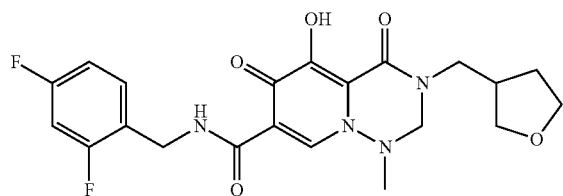
Q-16
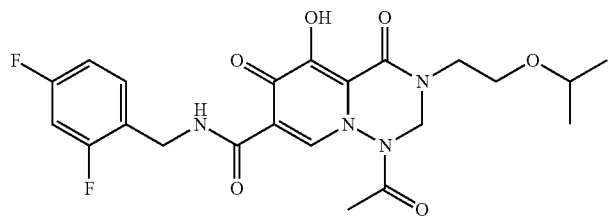

-continued
N-82
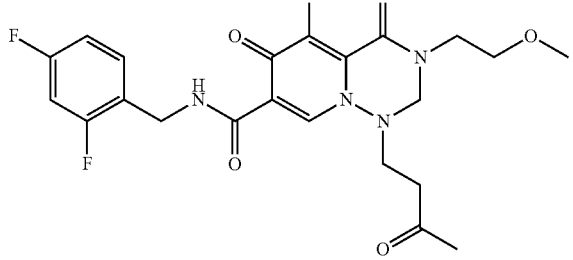
N-86
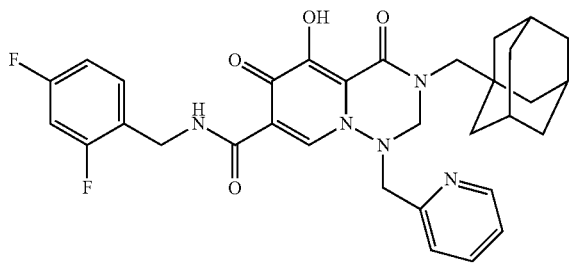
[Chemical formula 134]
N-87
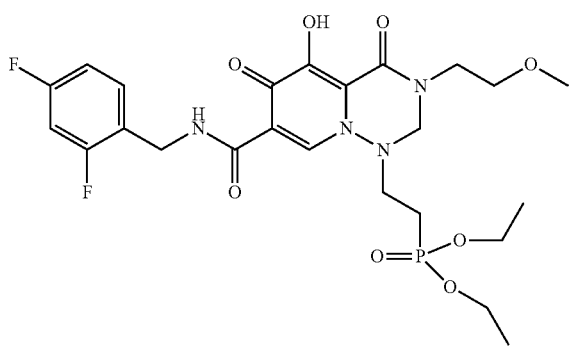
N-88
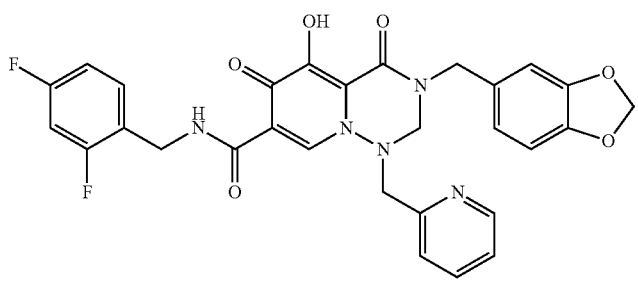
N-126
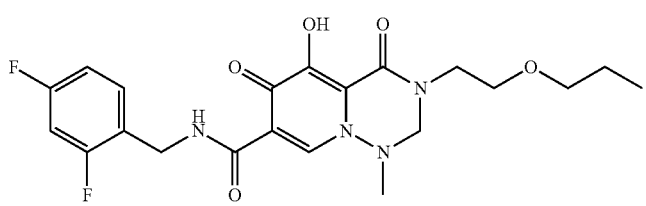
N-127
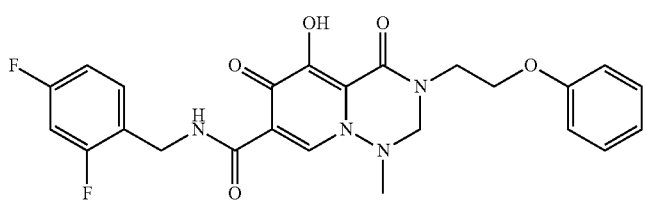

-continued
N-128
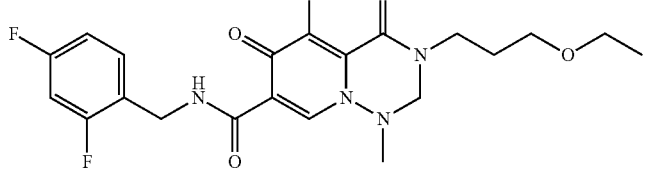
[Chemical formula 135]
N-124
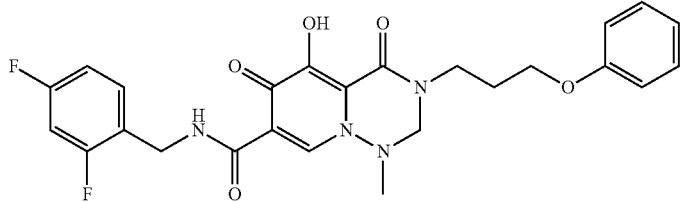
N-125
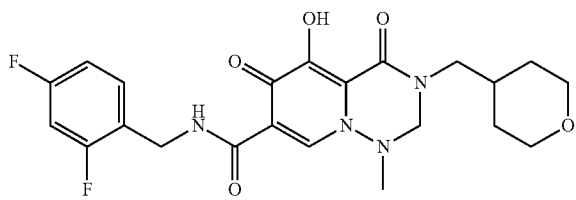
N-123
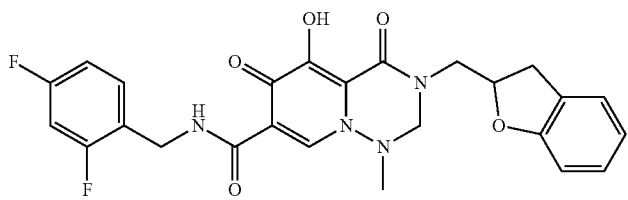
N-89
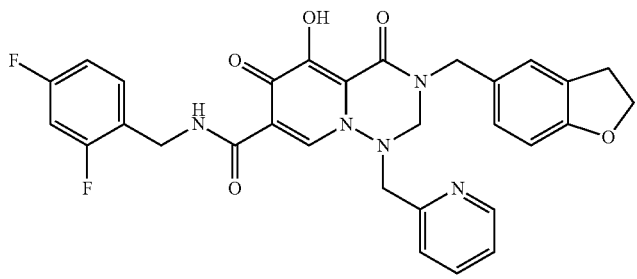
N-90
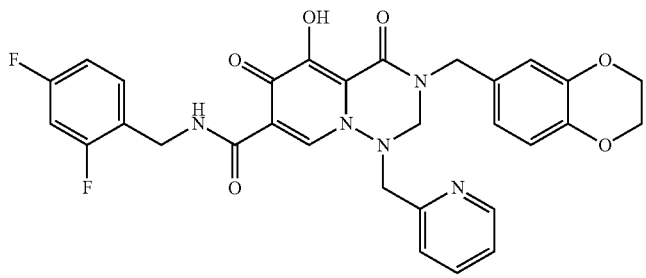

-continued
[Chemical formula 136]
N-91
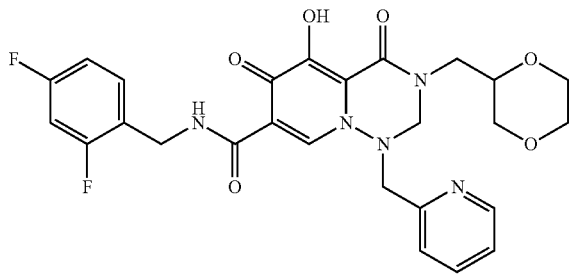
N-92
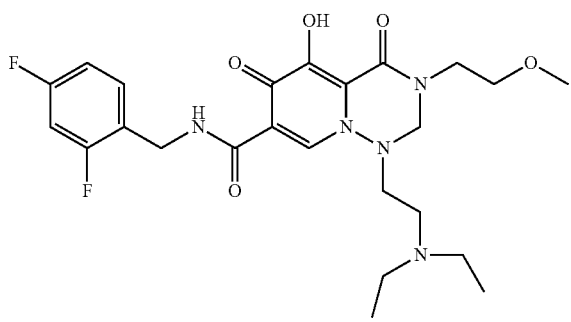
N-59-1
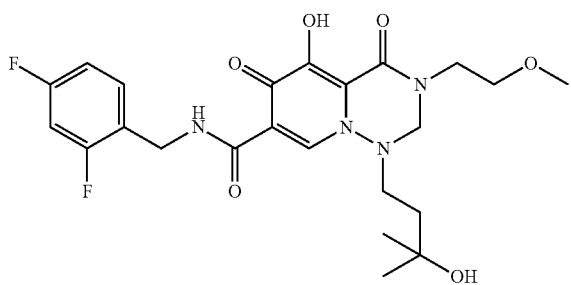
N-93
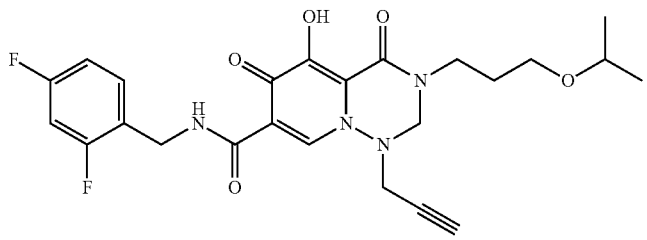
N-129
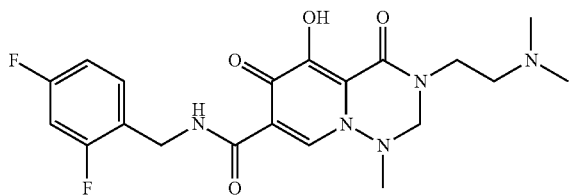

-continued
[Chemical formula 137]
N-94
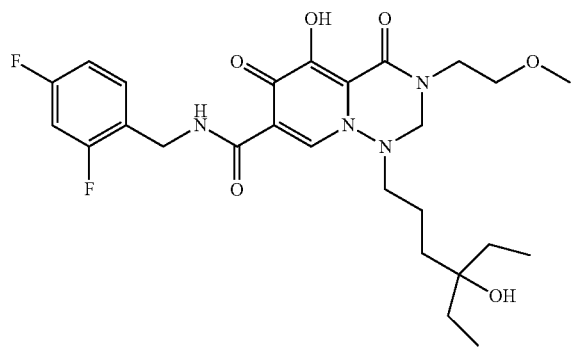
N-95
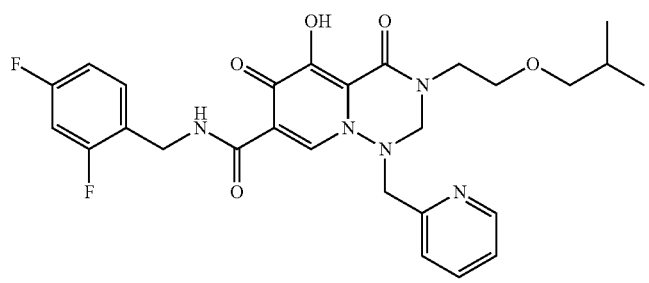
N-96
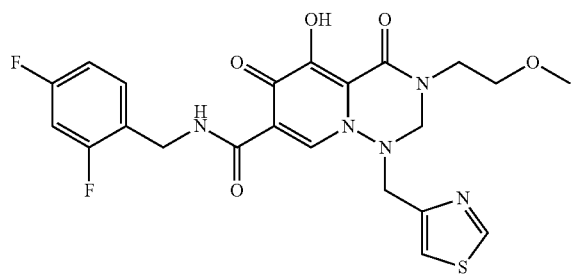
N-130
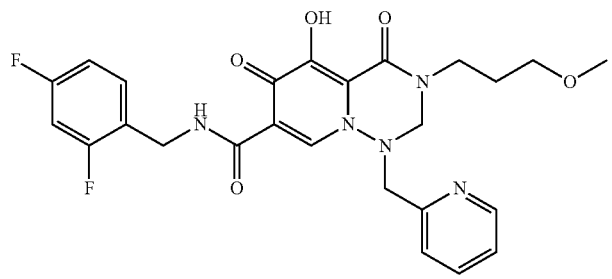
N-131
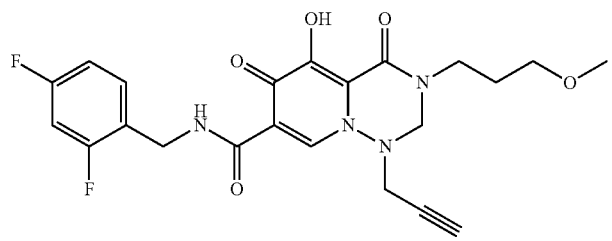

-continued
[Chemical formula 138]
Q-22
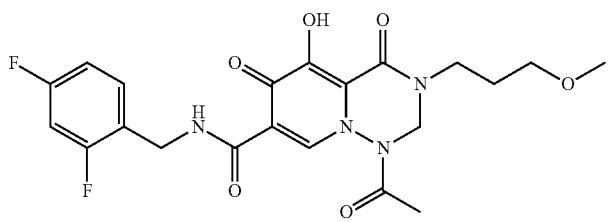
N-132
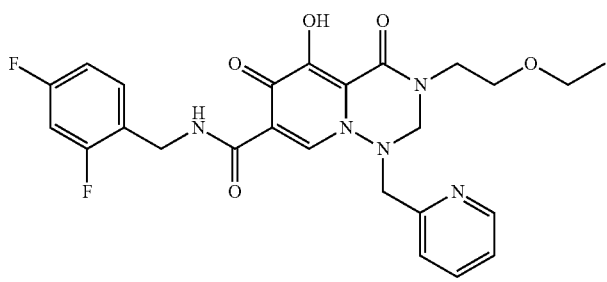
N-133
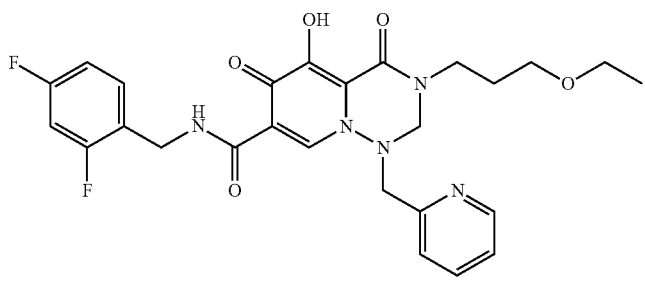
N-97
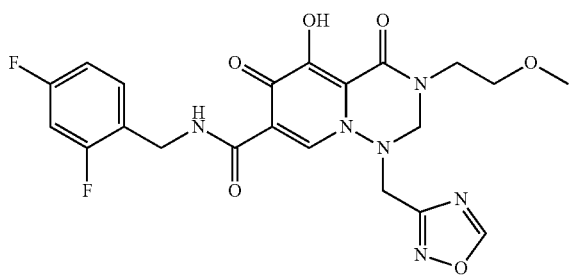
N-98
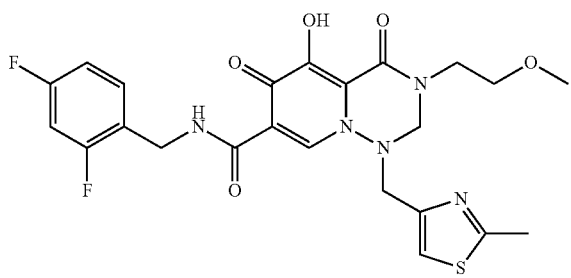

-continued
[Chemical formula 139]
N-99
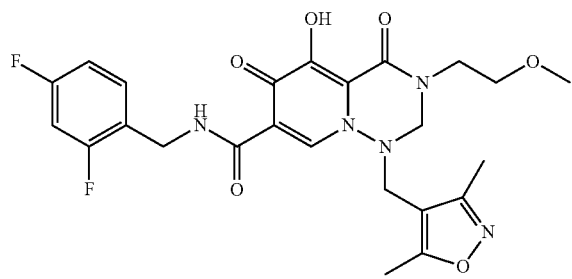
N-100
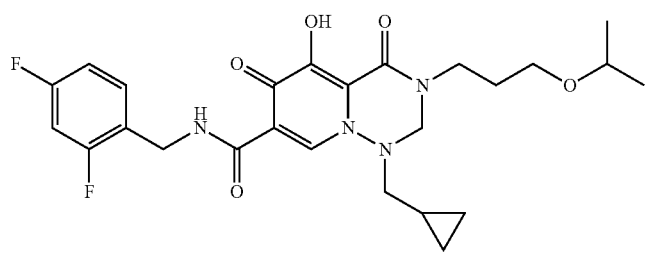
N-101
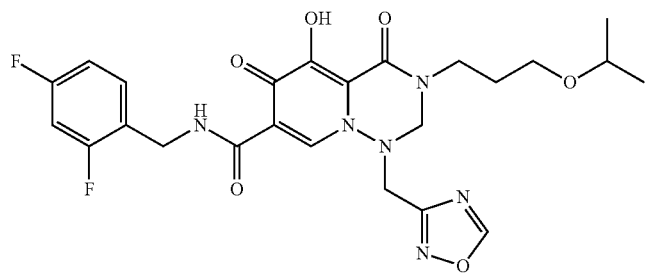
N-103
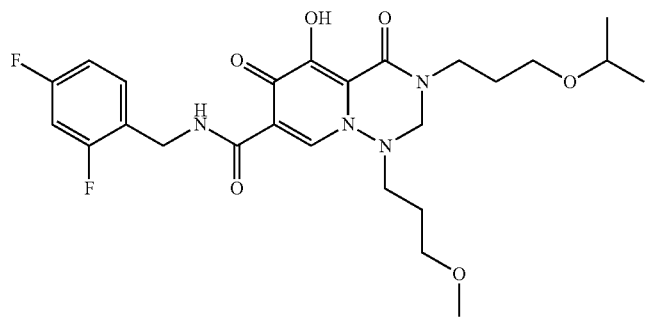
N-105
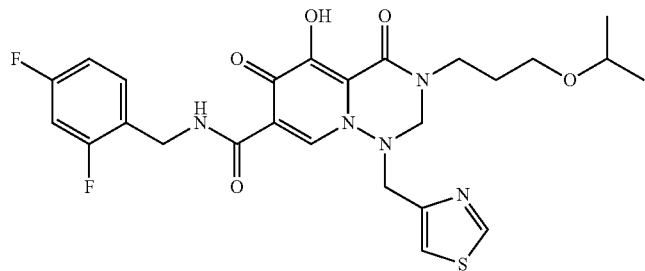

[Chemical formula 140]
N-134
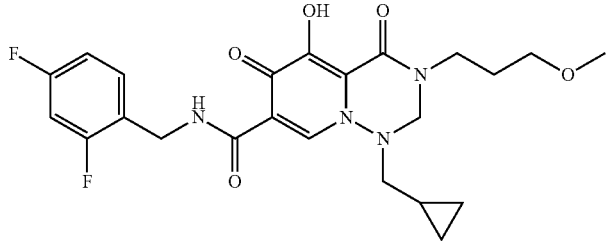
N-135
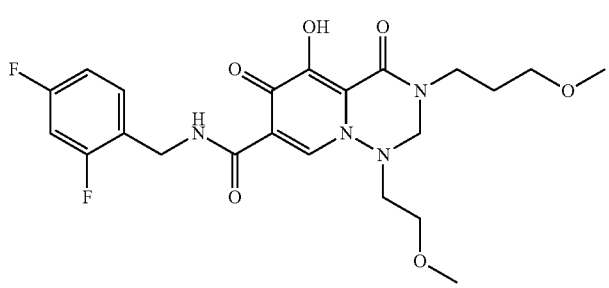
N-136
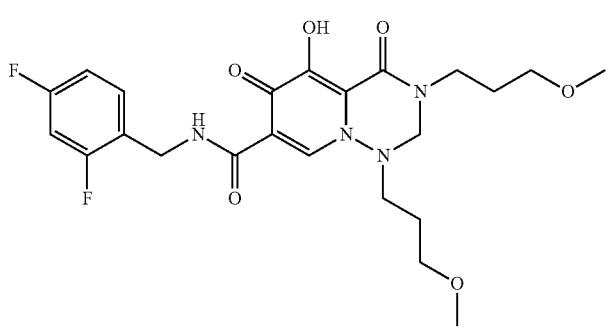
N-60-1
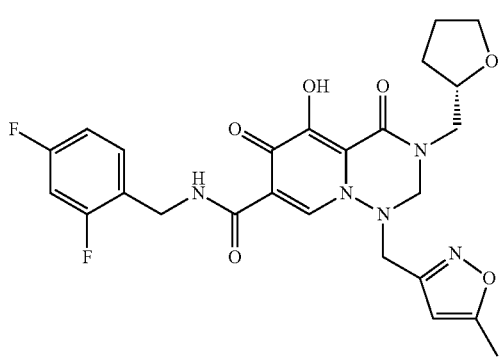
N-61
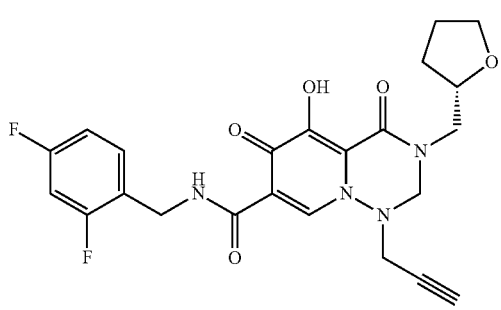

N-62
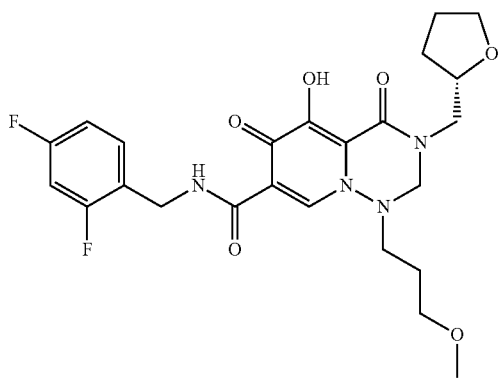
N-63
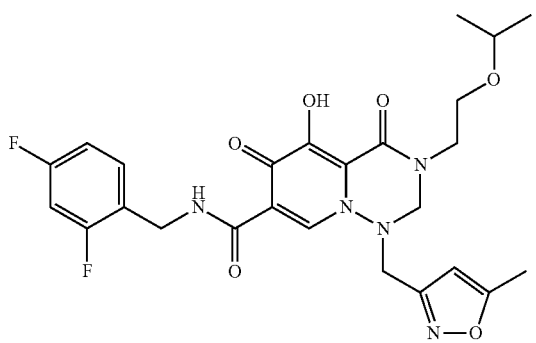
N-64
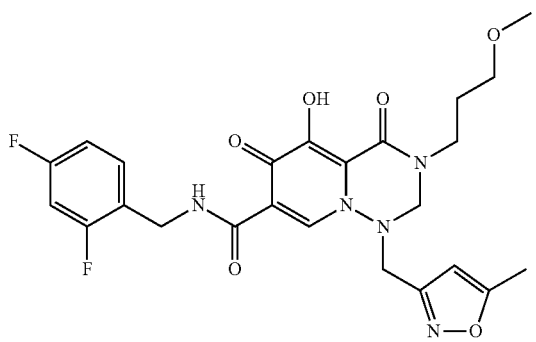
N-65
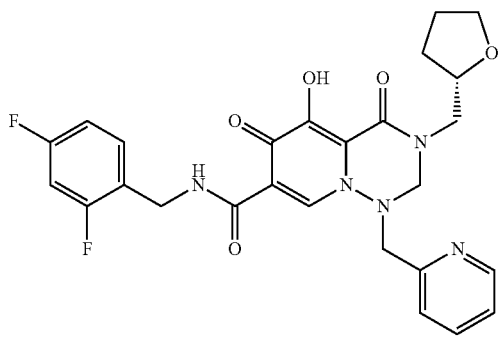

N-66
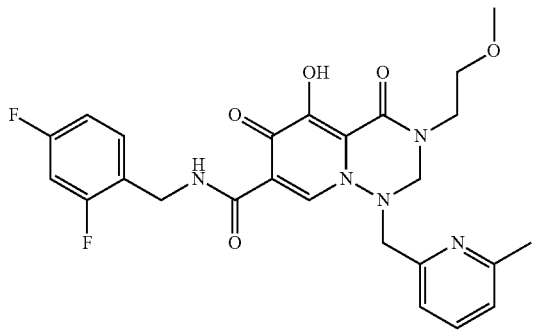
[Chemical formula 142]
N-137
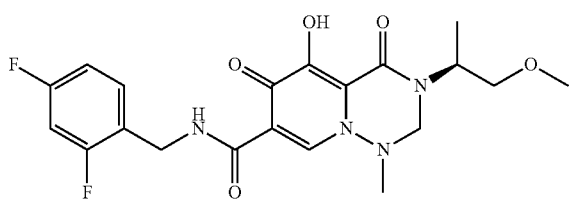
N-138
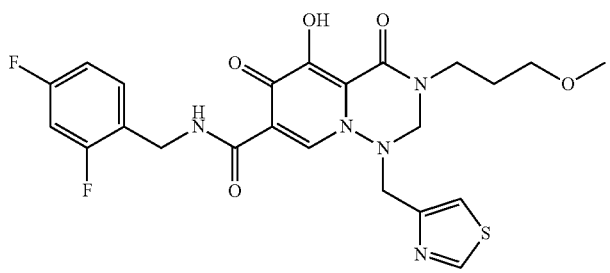
N-139
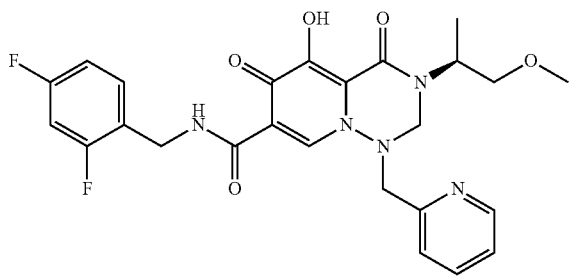
N-102
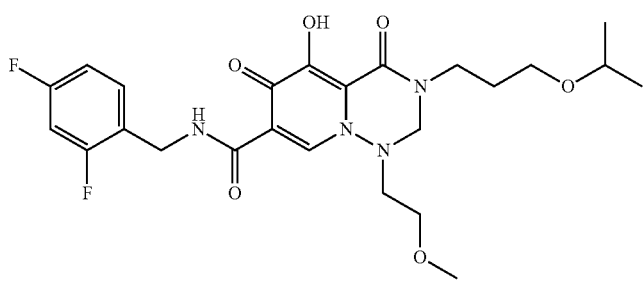

N-104
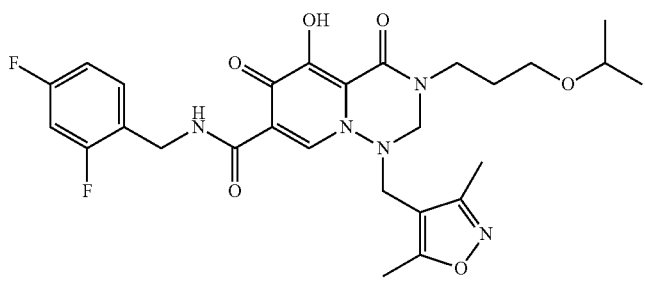
[Chemical formula 143]
Q-17
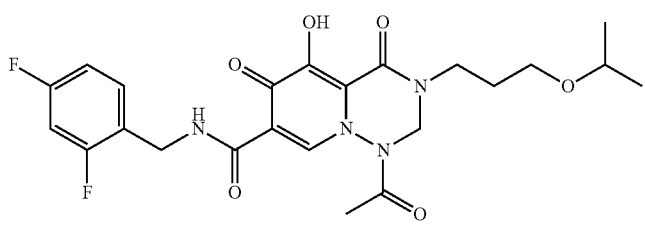
N-106
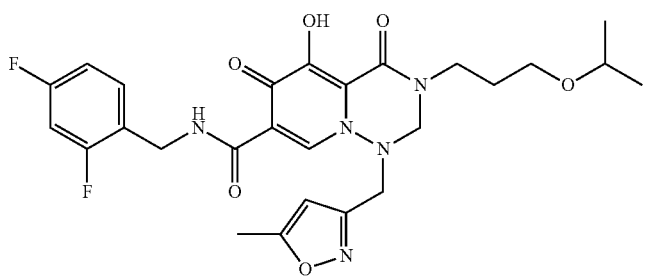
N-67
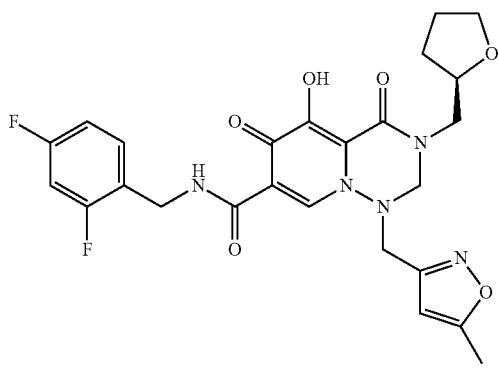
N-68
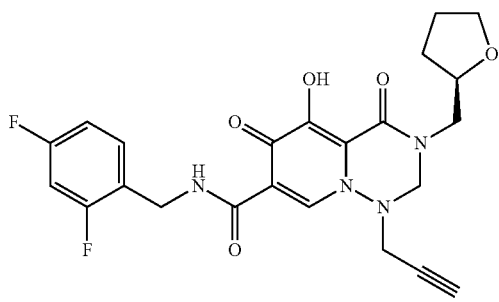

N-69
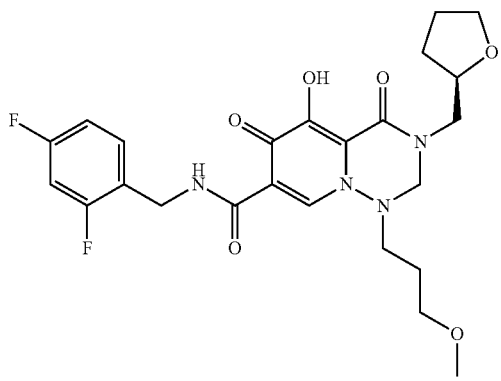
[Chemical formula 144]
N-70
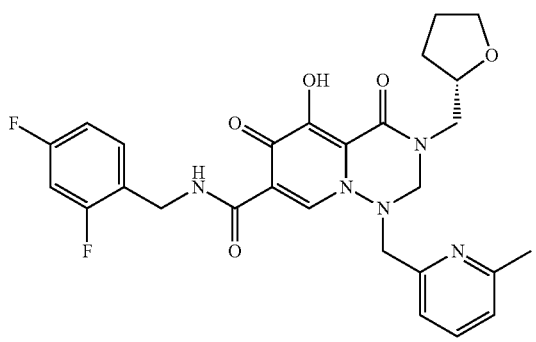
N-71
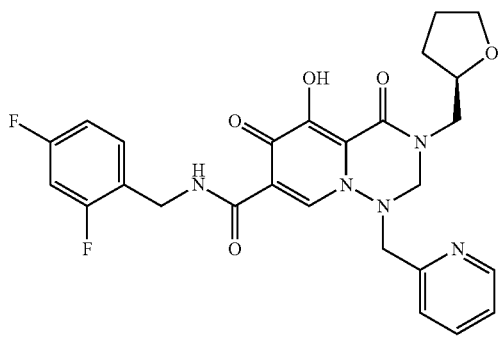
N-72
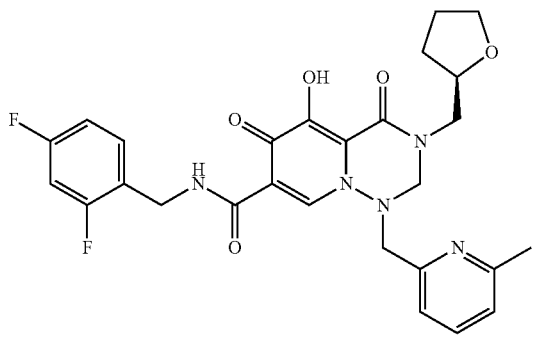

-continued
N-73
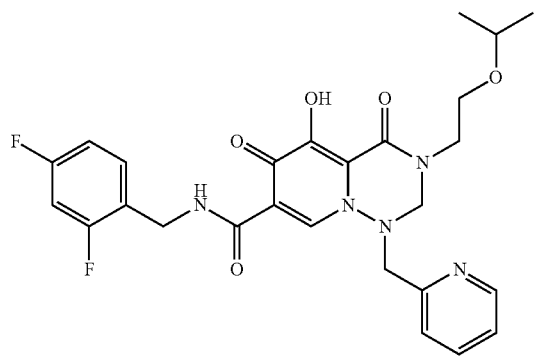
N-144
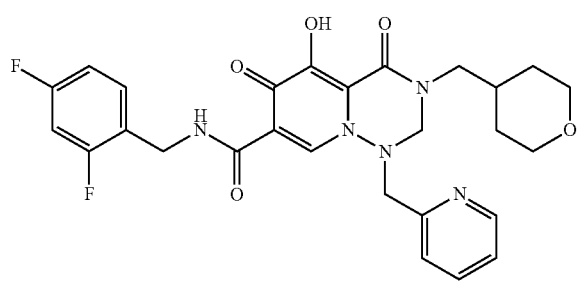
[Chemical formula 145]
Q-19
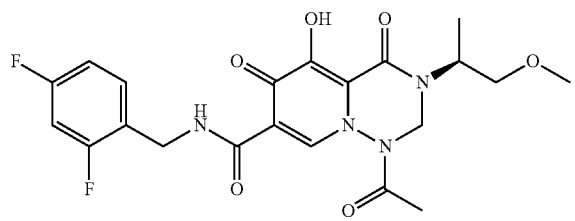
Q-20
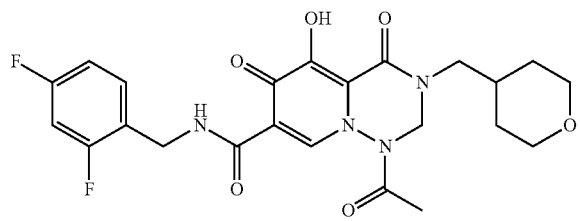
N-140
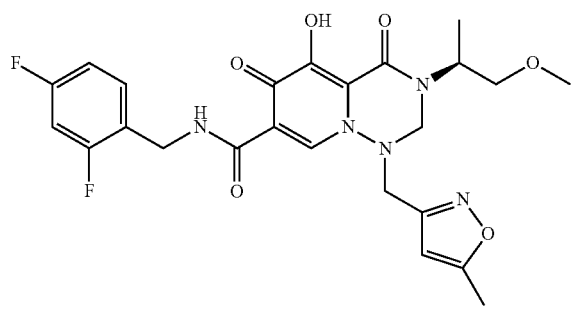

N-141
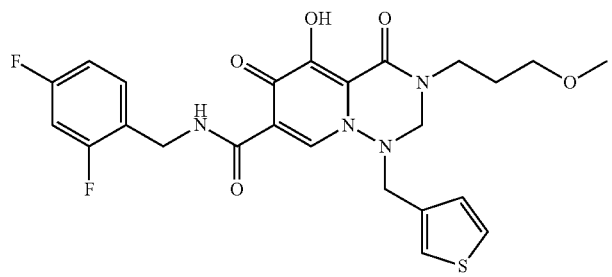
N-142
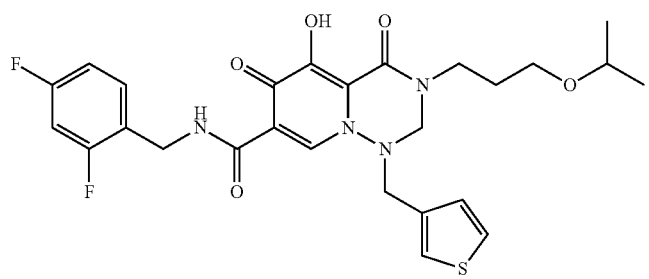
[Chemical formula 146]
N-143
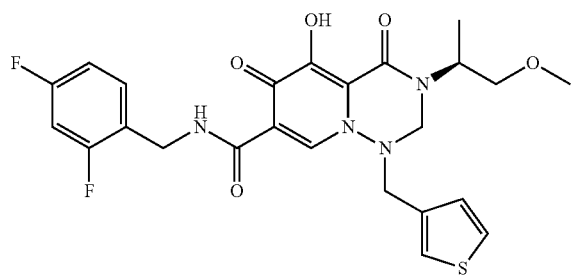
N-107
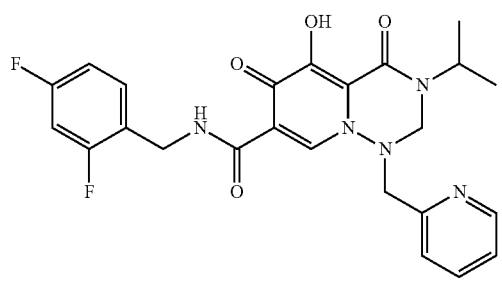
N-108
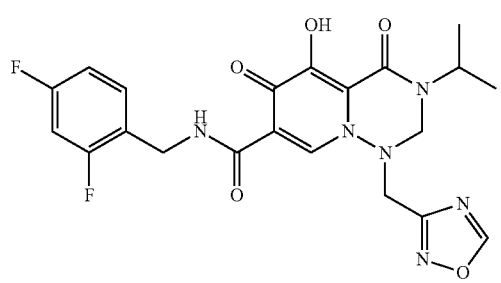

-continued
Q-18
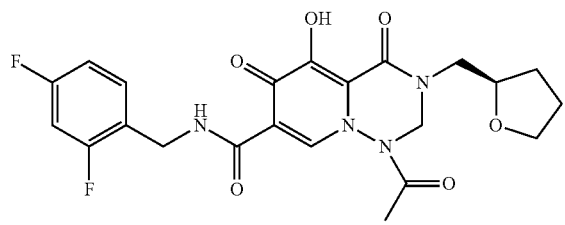
N-109
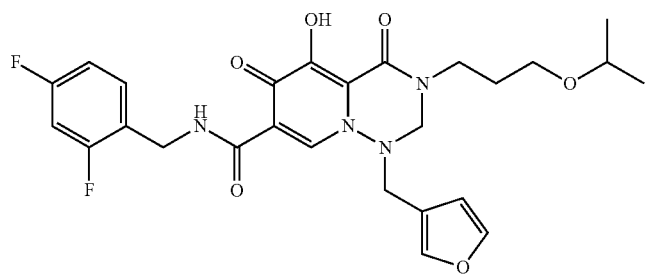
[Chemical formula 147]
N-110
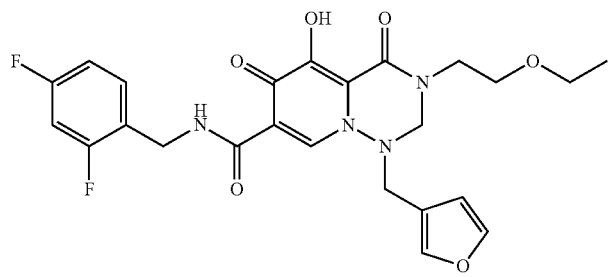
N-111
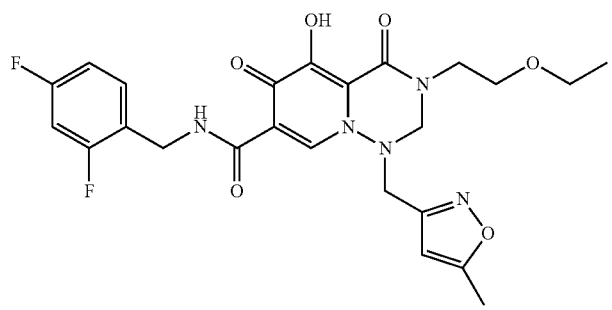
N-112
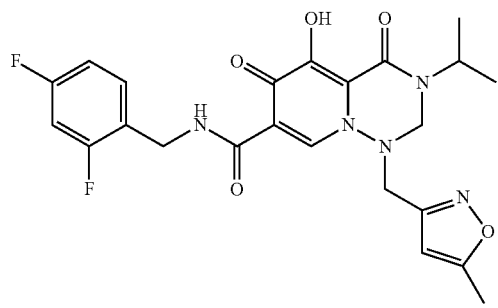

-continued
N-145
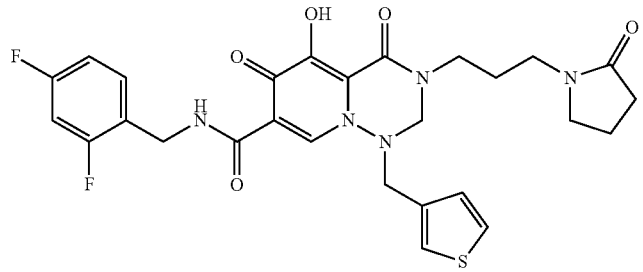
N-146
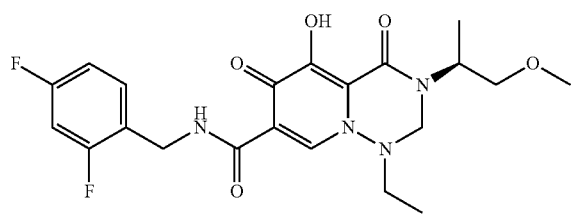
[Chemical formula 148]
N-147
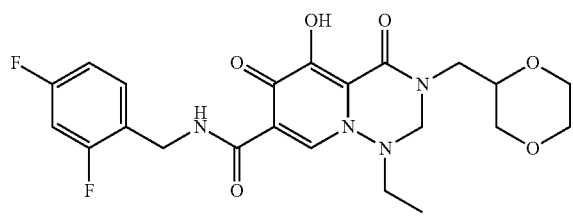
Q-21
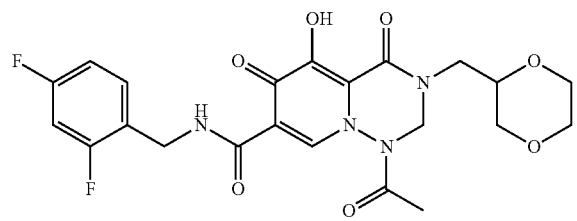
N-74
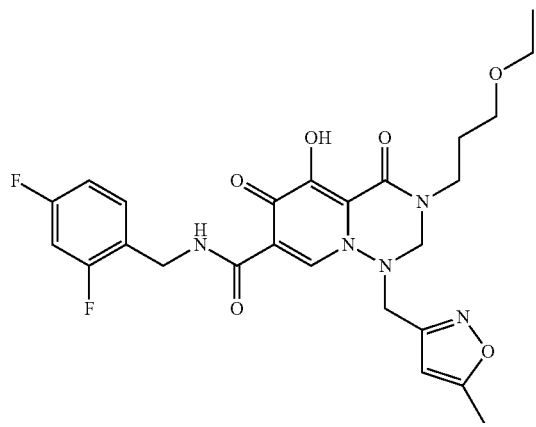

-continued
N-75
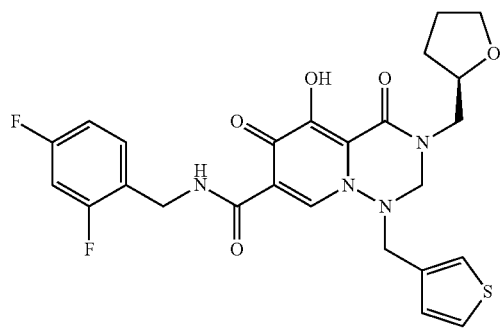
[Chemical formula 149]
N-76
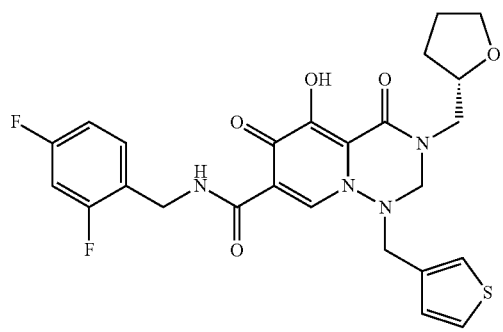
N-77
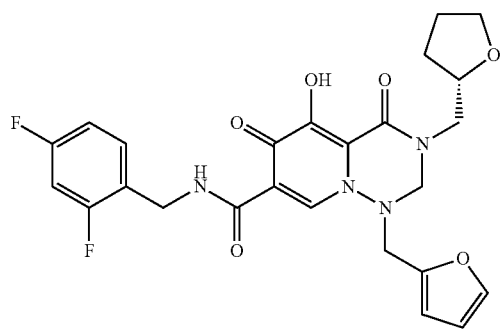
N-78
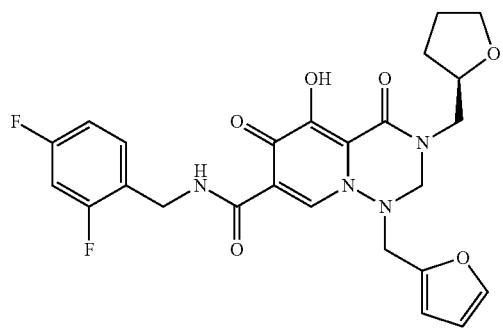

-continued
N-79
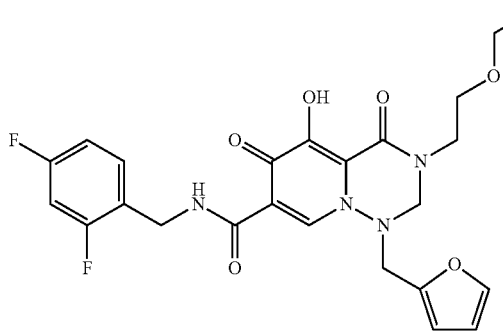
[Chemical formula 150]
N-80
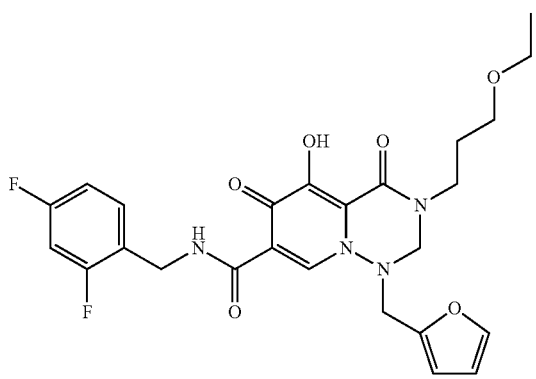
N-81
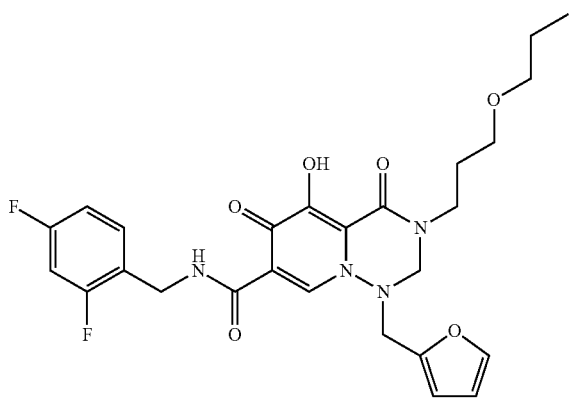
N-149
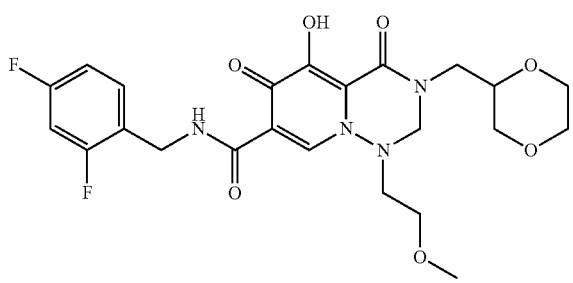

-continued
N-148
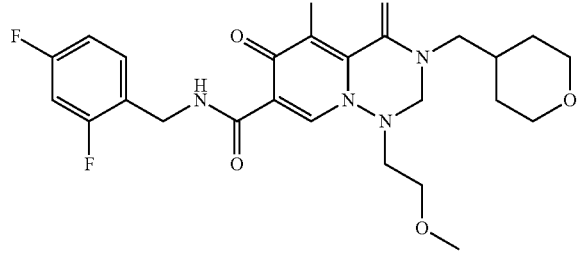
[Chemical formula 151]
N-151
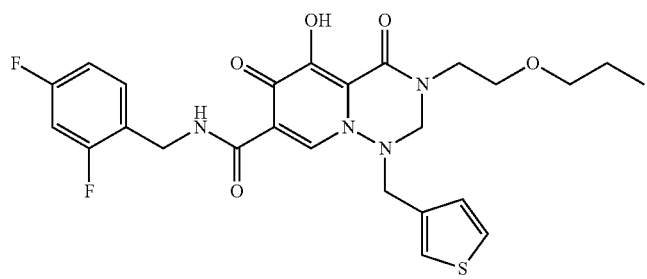
N-150
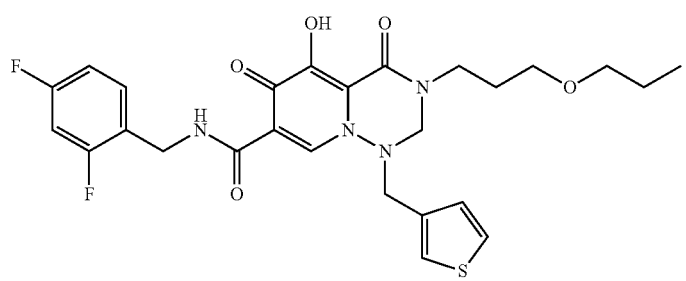
N-118
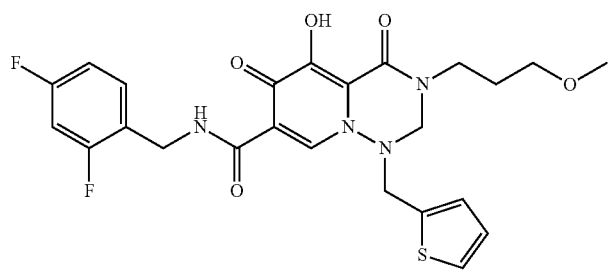
N-113
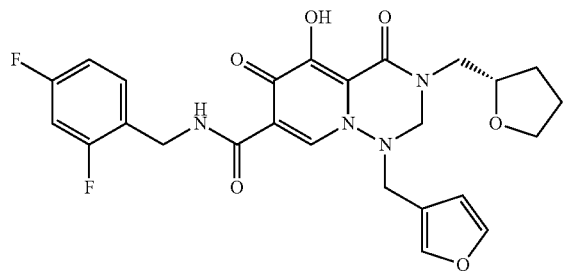
Q-23
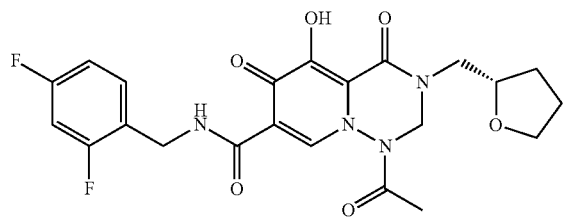

-continued
[Chemical formula 152]
N-115
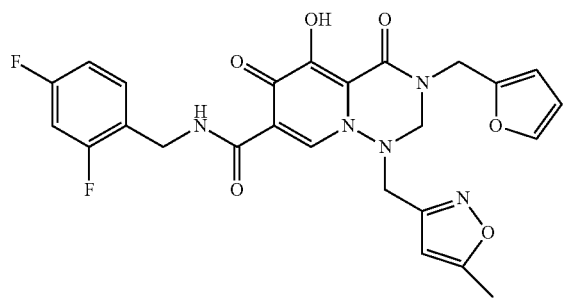
N-116
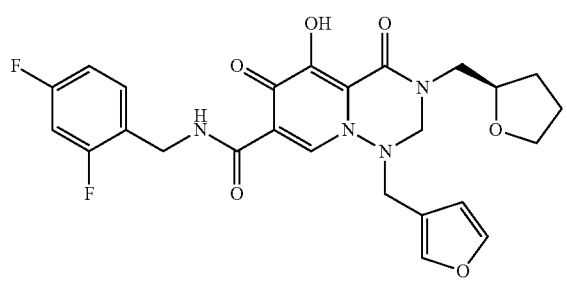
N-117
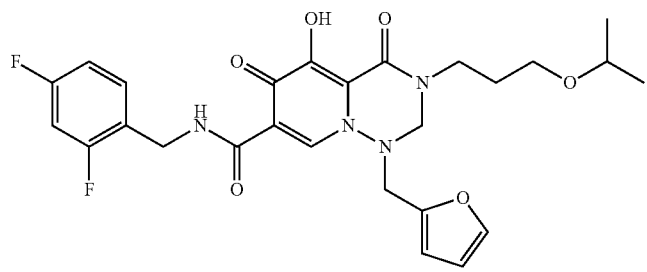
N-114
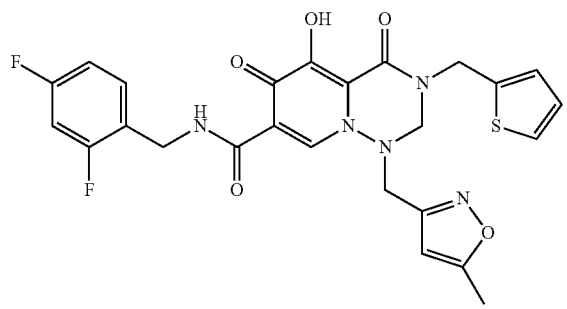
N-152
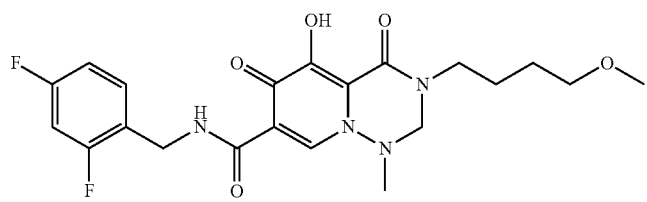

Chemical names and physical properties of above compounds are shown below.

Example N-59-1

5-Hydroxy-1-(3-hydroxy-3-methyl-butyl)-3-(2-methoxy-ethyl)-4,6-dioxo-2,3,4,6-tetrahydro-H-pyrid[2,1-f][1,2,4]triazine-7-carboxylic acid 2,4-difluoro-benzylamide 1H-NMR (CDCl3) δ: 1.28 (6.0H, s), 1.60-1.78 (2.0H, m), 3.27 (2.0H, br s), 3.41 (3.0H, s), 3.63-3.82 (4.0H, m), 4.68 (2.0H, d, J=5.71 Hz), 4.83 (2.0H, br s), 6.80-6.90 (2.0H, m), 7.38-7.45 (1.0H, m), 8.50 (1.0H, s), 10.41 (1.0H, t, J=5.62 Hz).

Example N-60-1

5-Hydroxy-1-(5-methyl-isoxazol-3-ylmethyl)-4,6-dioxo-3-[(S)-2-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.56-1.62 (1.0H, m), 1.92-2.01 (2.0H, m), 2.07-2.15 (1.0H, m), 2.50 (3.0H, s), 3.26 (1.0H, br s), 3.70-3.80 (1.0H, m), 3.82-3.92 (1.0H, m), 4.01-4.19 (3.0H, m), 4.30 (1.0H, br s), 4.66 (1.0H, br s), 4.67 (2.0H, d, J=5.37 Hz), 4.91 (1.0H, br s), 6.12 (1.0H, s), 6.79-6.90 (2.0H, m), 7.35-7.43 (1.0H, m), 8.44 (1.0H, s), 10.30-10.40 (1.0H, m), 11.70 (1.0H, br s).

Example N-61-1

5-Hydroxy-4,6-dioxo-1-prop-2-ynyl-3-[(S)-2-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.54-1.61 (1.0H, m), 1.92-2.01 (2.0H, m), 2.06-2.20 (1.0H, m), 2.51 (1.0H, t, J=2.47 Hz), 3.20 (2.0H, dd, J=13.73, 8.52 Hz), 3.75-3.83 (1.0H, m), 3.88-3.96 (2.0H, m), 4.03-4.20 (2.0H, m), 4.67 (2.0H, d, J=5.77 Hz), 4.87 (1.0H, d, J=13.46 Hz), 5.02 (1.0H, d, J=13.46 Hz), 6.78-6.88 (2.0H, m), 7.35-7.43 (1.0H, m), 8.58 (1.0H, s), 10.36 (1.0H, t, J=7.00 Hz).

Example N-62

5-Hydroxy-1-(3-methoxy-propyl)-4,6-dioxo-3-[(S)-2-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.55-1.63 (2.0H, m), 1.75-1.87 (1.0H, m), 1.90-2.00 (2.0H, m), 2.05-2.17 (1.0H, m), 3.17-3.28 (2.0H, m), 3.35 (3.0H, s), 3.70-4.15 (6.0H, m), 4.67 (2.0H, d, J=5.71 Hz), 4.78 (1.0H, br s), 4.93 (1.0H, br s), 6.79-6.90 (2.0H, m), 7.35-7.44 (1.0H, m), 8.47 (1.0H, s), 10.41 (1.0H, t, J=7.00 Hz)

Example N-63

5-Hydroxy-3-(2-isopropoxy-ethyl)-1-(5-methyl-isoxazol-3-ylmethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.15 (6.0H, d, J=6.04 Hz), 2.50 (3.0H, s), 3.48-3.55 (1.0H, m), 3.59-3.65 (2.0H, m), 3.65-3.72 (2.0H, m), 3.77 (1.0H, br s), 4.28 (1.0H, br s), 4.67 (2.0H, d, J=5.71 Hz), 4.67 (1.0H, br s), 4.79 (1.0H, br s), 6.12 (1.0H, s), 6.80-6.90 (2.0H, m), 7.37-7.42 (1.0H, m), 8.44 (1.0H, br s), 10.36 (1.0H, br s).

Example N-64

5-Hydroxy-3-(3-methoxy-propyl)-1-(5-methyl-isoxazol-3-ylmethyl)-4,6-dioxo-2,3,4,6-tetra hydro-1H-pyrid[2,1-f][1,2,4]triazine-7-carboxylic acid 2,4-difluoro-benzylamide 1H-NMR (CDCl3) δ: 1.93-2.01 (2.0H, m), 2.51 (3.0H, s), 3.33 (3.0H, s), 3.50 (2.0H, t, J=7.00 Hz), 3.69 (2.0H, br s), 4.26 (1.0H, br s), 4.60-4.70 (1.0H, m), 4.68 (2.0H, d, J=6.04 Hz), 6.14 (1.0H, s), 6.80-6.90 (2.0H, m), 7.35-7.46 (1.0H, m), 8.50 (1.0H, s), 10.37 (1.0H, br s), 11.80 (1.0H, br s).

Example N-65

5-Hydroxy-4,6-dioxo-1-pyridin-2-ylmethyl-3-[(S)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.92-2.01 (2.0H, m), 2.08-2.16 (1.0H, m), 3.31 (1.0H, br s), 3.75 (1.0H, q, J=7.50 Hz), 3.86 (1.0H, q, J=7.39 Hz), 4.05-4.21 (2.0H, m), 4.39 (1.0H, s), 4.64 (2.0H, d, J=5.71 Hz), 4.73-4.92 (2.0H, m), 4.95-5.06 (2.0H, m), 6.80-6.88 (2.0H, m), 7.28-7.42 (3.0H, m), 7.81 (1.0H, t, J=6.88 Hz), 8.26 (1.0H, s), 8.65 (1.0H, d, J=4.03 Hz), 10.32-10.35 (1.0H, m).

Example N-66

5-Hydroxy-3-(2-methoxy-ethyl)-1-(6-methyl-pyridin-2-ylmethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 2.62 (3.0H, s), 3.37 (3.0H, s), 3.69 (2.0H, t, J=4.62 Hz), 3.81 (2.0H, br s), 4.35 (2.0H, br s), 4.64 (2.0H, d, J=5.71 Hz), 4.90 (2.0H, br s), 6.81-6.88 (2.0H, m), 7.15 (1.0H, d, J=7.72 Hz), 7.23 (1.0H, d, J=7.72 Hz), 7.32-7.42 (1.0H, m), 7.69 (1.0H, t, J=7.81 Hz), 8.21 (1.0H, s), 10.33 (1.0H, s).

Example N-67

5-Hydroxy-1-(5-methyl-isoxazol-3-ylmethyl)-4,6-dioxo-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.56-1.62 (1.0H, m), 1.92-2.01 (2.0H, m), 2.07-2.15 (1.0H, m), 2.50 (3.0H, s), 3.26 (1.0H, br s), 3.70-3.80 (1.0H, m), 3.82-3.92 (1.0H, m), 4.01-4.19 (3.0H, m), 4.30 (1.0H, br s), 4.66 (1.0H, br s), 4.67 (2.0H, d, J=5.37 Hz), 4.91 (1.0H, br s), 6.12 (1.0H, s), 6.79-6.90 (2.0H, m), 7.35-7.43 (1.0H, m), 8.44 (1.0H, s), 10.30-10.40 (1.0H, m), 11.70 (1.0H, br s).

Example N-68

5-Hydroxy-4,6-dioxo-1-prop-2-ynyl-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.54-1.61 (1.0H, m), 1.92-2.01 (2.0H, m), 2.06-2.20 (1.0H, m), 2.51 (1.0H, t, J=2.47 Hz), 3.20 (2.0H, dd, J=13.73, 8.52 Hz), 3.75-3.83 (1.0H, m), 3.88-3.96 (2.0H, m), 4.03-4.20 (2.0H, m), 4.67 (2.0H, d, J=5.77 Hz), 4.87 (1.0H, d, J=13.46 Hz), 5.02 (1.0H, d, J=13.46 Hz), 6.78-6.88 (2.0H, m), 7.35-7.43 (1.0H, m), 8.58 (1.0H, s), 10.36 (1.0H, t, J=7.00 Hz).

Example N-69

5-Hydroxy-1-(3-methoxy-propyl)-4,6-dioxo-3-[(R) 1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.55-1.63 (2.0H, m), 1.75-1.87 (1.0H, m), 1.90-2.00 (2.0H, m), 2.05-2.17 (1.0H, m), 3.17-3.28 (2.0H, m), 3.35 (3.0H, s), 3.70-4.15 (6.0H, m), 4.67 (2.0H, d, J=5.71 Hz), 4.78 (1.0H, br s), 4.93 (1.0H, br s), 6.79-6.90 (2.0H, m), 7.35-7.44 (1.0H, m), 8.47 (1.0H, s), 10.41 (1.0H, t, J=7.00 Hz)

Example N-70

5-Hydroxy-1-(6-methyl-pyridin-2-ylmethyl)-4,6-dioxo-3-[(S)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.52-1.61 (1.0H, m), 1.90-2.00 (2.0H, m), 2.05-2.19 (1.0H, m), 2.57 (3.0H, s), 3.75 (1.0H, q, J=7.23 Hz), 3.85 (1.0H, q, J=7.42 Hz), 4.00-4.20 (2.0H, m), 4.34 (1.0H, br s), 4.62 (2.0H, d, J=5.77 Hz), 4.77-5.05 (4.0H, m), 6.78-6.86 (2.0H, m), 7.12 (1.0H, d, J=7.69 Hz), 7.18 (1.0H, d, J=7.97 Hz), 7.25-7.40 (1.0H, m), 7.64 (1.0H, t, J=7.83 Hz), 8.20 (1.0H, br s), 10.33 (1.0H, br s).

Example N-71

5-Hydroxy-4,6-dioxo-1-pyridin-2-ylmethyl-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.92-2.01 (2.0H, m), 2.08-2.16 (1.0H, m), 3.31 (1.0H, br s), 3.75 (1.0H, q, J=7.50 Hz), 3.86 (1.0H, q, J=7.39 Hz), 4.05-4.21 (2.0H, m), 4.39 (1.0H, s), 4.64 (2.0H, d, J=5.71 Hz), 4.73-4.92 (2.0H, m), 4.95-5.06 (2.0H, m), 6.80-6.88 (2.0H, m), 7.28-7.42 (3.0H, m), 7.81 (1.0H, t, J=6.88 Hz), 8.26 (1.0H, s), 8.65 (1.0H, d, J=4.03 Hz), 10.32-10.35 (1.0H, m).

Example N-72

5-Hydroxy-1-(6-methyl-pyridin-2-ylmethyl)-4,6-dioxo-3-[(R)-1-(tetrahydro-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.52-1.61 (1.0H, m), 1.90-2.00 (2.0H, m), 2.05-2.19 (1.0H, m), 2.57 (3.0H, s), 3.75 (1.0H, q, J=7.23 Hz), 3.85 (1.0H, q, J=7.42 Hz), 4.00-4.20 (2.0H, m), 4.34 (1.0H, br s), 4.62 (2.0H, d, J=5.77 Hz), 4.77-5.05 (4.0H, m), 6.78-6.86 (2.0H, m), 7.12 (1.0H, d, J=7.69 Hz), 7.18 (1.0H, d, J=7.97 Hz), 7.25-7.40 (1.0H, m), 7.64 (1.0H, t, J=7.83 Hz), 8.20 (1.0H, br s), 10.33 (1.0H, br s).

Example N-73

5-Hydroxy-3-(2-isopropoxy-ethyl)-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.13 (6.0H, d, J=6.21 Hz), 3.56-3.64 (1.0H, m), 3.68-3.71 (2.0H, m), 3.81 (2.0H, br s), 4.41 (2.0H, br s), 4.62 (2.0H, d, J=6.21 Hz), 4.92 (2.0H, br s), 6.79-6.86 (2.0H, m), 7.31-7.42 (3.0H, m), 7.83 (1.0H, t, J=7.97 Hz), 8.21 (1.0H, s), 8.65-8.67 (1.0H, m), 10.31 (1.0H, t, J=10.00 Hz).

Example N-74

3-(3-Ethoxy-propyl)-5-hydroxy-1-(5-methyl-isoxazol-3-ylmethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.14 (3.0H, t, J=6.97 Hz), 1.90-2.00 (2.0H, m), 2.50 (3.0H, s), 3.46 (2.0H, q, J=7.05 Hz), 3.53 (2.0H, t, J=5.62 Hz), 3.70 (2.0H, br s), 4.26 (2.0H, br s), 4.60-4.71 (2.0H, m), 4.66 (2.0H, d, J=6.04 Hz), 6.14 (1.0H, s), 6.78-6.88 (2.0H, m), 7.35-7.44 (1.0H, m), 8.49 (1.0H, br s), 10.39 (1.0H, br s).

Example N-75

5-Hydroxy-4,6-dioxo-3-[(R)-1-(tetrahydro-furan-2-yl)methyl]-1-thiophen-3-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.50-1.66 (1.0H, m), 1.89-2.03 (2.0H, m), 2.06-2.21 (1.0H, m), 3.20 (1.0H, br s), 3.78 (1.0H, dd, J=15.19, 6.97 Hz), 3.83-3.93 (1.0H, m), 3.97-4.18 (2.0H, m), 4.25 (2.0H, br s), 4.59-4.66 (1.0H, m), 4.65 (2.0H, d, J=5.54 Hz), 4.89 (1.0H, br s), 6.79-6.90 (2.0H, m), 7.13 (1.0H, d, J=5.04 Hz), 7.19 (1.0H, d, J=2.01 Hz), 7.33-7.41 (1.0H, m), 7.41-7.46 (1.0H, m), 8.25 (1.0H, br s), 10.30-10.34 (1.0H, br m), 11.69 (1.0H, br s).

Example N-76

5-Hydroxy-4,6-dioxo-3-[(S)-1-(tetrahydro-furan-2-yl)methyl]-1-thiophen-3-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.50-1.66 (1.0H, m), 1.89-2.03 (2.0H, m), 2.06-2.21 (1.0H, m), 3.20 (1.0H, br s), 3.78 (1.0H, dd, J=15.19, 6.97 Hz), 3.83-3.93 (1.0H, m), 3.97-4.18 (2.0H, m), 4.25 (2.0H, br s), 4.59-4.66 (1.0H, m), 4.65 (2.0H, d, J=5.54 Hz), 4.89 (1.0H, br s), 6.79-6.90 (2.0H, m), 7.13 (1.0H, d, J=5.04 Hz), 7.19 (1.0H, d, J=2.01 Hz), 7.33-7.41 (1.0H, m), 7.41-7.46 (1.0H, m), 8.25 (1.0H, br s), 10.30-10.34 (1.0H, br m), 11.69 (1.0H, br s).

Example N-77

1-Furan-2-ylmethyl-5-hydroxy-4,6-dioxo-3-[(S)-1-(tetrahyrdo-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.51-1.68 (1.0H, m), 1.91-2.02 (2.0H, m), 2.06-2.20 (1.0H, m), 3.22 (1.0H, s), 3.79 (1.0H, dd, J=15.36, 6.97 Hz), 3.85-3.95 (1.0H, m), 4.01-4.35 (4.0H, m), 4.64 (2.0H, d, J=5.87 Hz), 4.94 (2.0H, br s), 6.29 (1.0H, d, J=3.02 Hz), 6.35 (1.0H, d, J=1.85 Hz), 6.78-6.87 (2.0H, m), 7.32-7.42 (1.0H, m), 7.47 (1.0H, d, J=1.85 Hz), 8.20 (1.0H, s), 10.31 (1.0H, t, J=7.00 Hz).

Example N-78

1-Furan-2-ylmethyl-5-hydroxy-4,6-dioxo-3-[(R)-1-(tetrahyrdo-furan-2-yl)methyl]-2,3,4,6-tetrahydro-1H-pyrid[2,1-f][1,2,4]triazine-7-carboxylic acid 2,4-difluoro-benzylamide 1H-NMR (CDCl3) δ: 1.51-1.68 (1.0H, m), 1.91-2.02 (2.0H, m), 2.06-2.20 (1.0H, m), 3.22 (1.0H, s), 3.79 (1.0H, dd, J=15.36, 6.97 Hz), 3.85-3.95 (1.0H, m), 4.01-4.35 (4.0H, m), 4.64 (2.0H, d, J=5.87 Hz), 4.94 (2.0H, br s), 6.29 (1.0H, d, J=3.02 Hz), 6.35 (1.0H, d, J=1.85 Hz), 6.78-6.87 (2.0H, m), 7.32-7.42 (1.0H, m), 7.47 (1.0H, d, J=1.85 Hz), 8.20 (1.0H, s), 10.31 (1.0H, t, J=7.00 Hz).

Example N-79

3-(2-Ethoxy-ethyl)-1-furan-2-ylmethyl-5-hydroxy-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.22 (3.0H, t, J=6.97 Hz), 3.55 (2.0H, q, J=6.99 Hz), 3.68-3.84 (3.0H, m), 4.26 (2.0H, s), 4.65 (2.0H, d, J=5.88 Hz), 4.85 (2.0H, br s), 6.30 (1.0H, d, J=3.36 Hz), 6.38 (1.0H, t, J=2.43 Hz), 6.79-6.90 (2.0H, m), 7.33-7.43 (1.0H, m), 7.48 (1.0H, t, J=0.92 Hz), 8.22 (1.0H, s), 10.32 (1.0H, t, J=7.00 Hz), 11.66 (1.0H, br s).

Example N-80

3-(3-Ethoxy-propyl)-1-furan-2-ylmethyl-5-hydroxy-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.16 (3.0H, t, J=7.05 Hz), 1.90-2.01 (2.0H, m), 3.47 (2.0H, q, J=6.99 Hz), 3.54 (2.0H, t, J=5.62 Hz), 3.70 (2.0H, br s), 4.23 (2.0H, s), 4.65 (2.0H, d, J=5.54 Hz), 6.32 (1.0H, d, J=2.85 Hz), 6.38 (1.0H, dd, J=3.27, 1.76 Hz), 6.79-6.87 (2.0H, m), 7.32-7.44 (1.0H, m), 7.48 (1.0H, dd, J=1.93, 0.76 Hz), 8.29 (1.0H, s), 10.34 (1.0H, t, J=7.00 Hz).

Example N-81

1-Furan-2-ylmethyl-5-hydroxy-4,6-dioxo-3-(3-propoxy-propyl)-2,3,4,6-tetrahydro-1H-pyrid[2,1-f][1,2,4]triazine-7-carboxylic acid 2,4-difluoro-benzylamide 1H-NMR (CDCl3) δ: 0.92 (3.0H, t, J=7.39 Hz), 1.53-1.65 (2.0H, m), 1.92-2.03 (2.0H, m), 3.39 (2.0H, t, J=6.71 Hz), 3.55 (2.0H, t, J=5.54 Hz), 3.71 (2.0H, br s), 4.24 (2.0H, s), 4.61-4.85 (2.0H, m), 4.66 (2.0H, d, J=5.88 Hz), 6.33 (1.0H, d, J=3.36 Hz), 6.39 (1.0H, br s), 6.80-6.91 (2.0H, m), 7.33-7.44 (1.0H, m), 7.49 (1.0H, br s), 8.30 (1.0H, s), 10.33-10.36 (1.0H, br m).

Example N-82

5-Hydroxy-3-(2-methyl-ethyl)-4,6-dioxo-1-(3-oxo-butyl)-2,3,4,6-tetrahydro-1H-pyrid[2,1-f][1,2,4]triazine-7-carboxylic acid 2,4-difluoro-benzylamide 1H-NMR (CDCl3) δ: 2.22 (2H, t), 2.24 (3H, s), 2.74 (2H, br), 3.40 (3H, s), 3.68 (2H, t, J=3.68 Hz), 3.78 (2H, t, J=3.68 Hz), 4.68 (2H, s, J=5.71 Hz), 4.77 (2H, br), 6.77-6.91 (2H, m), 7.36 (1.0H, m), 8.40 (1.0H, s), 10.35 (1.0H, s), 11.66 (1.0H, br)

Example N-83

1-Ethyl-5-hydroxy-3-(3-isopropyl-propyl)-4,6-dioxo-2,3,4,6-tetrahydro-1H-pyrid]2,1-f][1,2,4]triazine-7-carboxylic acid 2,4-difluoro-benzylamide 1H-NMR (CDCl3) δ: 1.16 (6H, d, J=6.2 Hz), 1.21 (3H, t, J=7.22 Hz), 1.91-1.99 (2H, m), 3.15 (2H, q, J=7.16 Hz), 3.58 (2H, t, J=5.71 Hz), 3.59 (1H, q, J=6.2 Hz), 3.70 (2H, t, J=6.71 Hz), 4.71 (2H, d, J=5.88 Hz), 4.74 (2H, br), 6.81-6.90 (2H, m), 7.38-7.46 (1H, m), 8.50 (1.0H, s), 10.43 (1H, s), 11.74 (1H, s).

Example N-84

5-Hydroxy-4,6-dioxo-1-pyridin-2-ylmethyl-3-thiophen-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 4.21 (2H, s), 4.64 (2H, d, J=5.88 Hz), 4.79 (2H, s), 5.01 (1H, s), 6.82-6.86 (1.0H, m), 7.03 (1H, dd, J=5.20, 3.53 Hz), 7.11-7.12 (1H, m), 7.20 (1H, d, J=7.72 Hz), 7.36-7.38 (2.0H, m), 7.77 (1H, td, J=7.68, 1.73 Hz), 8.28 (1H, s), 8.65 (1H, d, J=5.04 Hz), 10.30 (1H, t, J=6.04 Hz).

Example N-85

3-Furan-2-ylmethyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 4.24 (2H, s), 4.64 (2H, d, J=5.88 Hz), 4.82 (2H, br), 4.85 (2H, s) 6.40 (1H, dd, J=3.27, 1.93 Hz), 6.45 (1H, d, J=3.36 Hz), 6.80-6.89 (2H, m), 7.27 (1H, d, J=7.72 Hz), 7.34-7.39 (2H, m), 7.41-7.42 (1H, m), 7.77 (1H, td, J=7.72, 1.68 Hz), 8.28 (1.0H, s), 8.65 (1H, d, J=4.70 Hz), 10.30 (0.6H, t, J=5.71 Hz).

Example N-86

3-Adamantan-1-ylmethyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.58-1.77 (15H, m), 2.03 (2H, s), 4.34 (2H, s), 4.64 (2H, d, J=5.88 Hz), 4.80 (2H, br), 6.79-6.88

(2H, m), 7.33-7.40 (3H, m), 7.78 (1H, dt, J=7.55, 1.68 Hz), 8.32 (1H, s), 8.63-8.66 (1H, m), 10.36 (1H, t, J=5.88 Hz), 11.73 (1H, br).

Example N-87

{2-[7-(2,4-Difluoro-benzylcarbamoyl)-5-hydroxy-3-(2-methoxy-ethyl)-4,6-dioxo-2,3,4,6-tetrahydro-pyrid[2,1-f][1,2,4]triazin-1-yl]-ethyl}-phosphonic Acid Diethyl Ester 1H-NMR (CDCl3) δ: 1.37 (6H, t, J=7.14 Hz), 2.00 (2H, s), 3.34 (2H, br) 3.41 (3H, s), 3.66 (2H, br), 3.74 (2H, br), 4.15 (4H, q, J=7.14 Hz), 4.67 (2H, d, J=6.04 Hz), 4.82 (2H, s), 6.79-6.88 (2.1H, m), 7.37-7.42 (1.0H, m), 8.51 (1.0H, s), 10.36 (1.0H, t, J=5.91 Hz), 11.58 (1H, br).

Example N-88

3-Benzo[1,3]dioxol-5-ylmethyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 4.18 (2H, s), 4.64 (2H, d, J=5.88 Hz), 4.69 (2H, br), 4.73 (2H, s), 6.01 (2H, s), 6.80 (1H, s), 6.83-6.88 (2H, m), 7.21 (1H, d, J=7.72 Hz), 7.32-7.45 (3H, m), 7.75 (1H, td, J=7.68, 1.79 Hz), 8.30 (1H, s), 8.63 (1H, d, J=5.04 Hz), 10.32 (1H, t, J=5.88 Hz).

Example N-89

3-(2,3-Dihydro-benzofuran-5-ylmethyl)-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 3.22 (2H, t, J=8.73 Hz), 4.19 (2H, s), 4.60 (2.0H, t, J=8.64 Hz), 4.73 (4H, s), 6.75 (1H, d, J=7.39 Hz), 6.78-6.87 (2H, m), 7.07 (1H, d, J=8.06 Hz), 7.17-7.22 (2H, m), 7.31-7.41 (2H, m), 7.78 (1H, t, J=7.30 Hz), 8.24 (1H, s), 8.63 (1H, d, J=4.70 Hz), 10.29 (1H, t, J=8.73 Hz), 11.78 (1H, br).

Example N-90

3-(2,3-Dihydro-benzo[1,4]dioxin-6-ylmethyl)-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 4.23 (3H, s), 4.27 (4H, s), 4.62 (2H, d, J=6.04 Hz), 4.71 (4H, s), 6.78-6.87 (5H, m), 7.22 (1H, d, J=7.72 Hz), 7.34-7.42 (2H, m), 7.79 (1H, d, J=6.71 Hz), 8.23 (1H, s), 8.65 (1H, d, J=4.87 Hz), 10.30 (1H, d, J=6.04 Hz), 11.81 (1H, br).

Example N-91

3-[1,4]Dioxan-2-ylmethyl-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 3.32-3.98 (9H, m), 4.43 (2H, br), 4.63 (2H, d, J=5.87 Hz), 4.94 (2H, br), 6.80-6.88 (2H, m), 7.32-7.45 (3H, m), 7.86 (1H, t, J=8.73 Hz), 8.27 (1H, s), 8.66 (1H, d, J=4.87 Hz), 10.30 (1.0H, d, J=5.87 Hz), 11.60 (1H, br).

Example N-92

1-(2-Diethylamino-ethyl)-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.03 (6.0H, t, J=7.05 Hz), 2.56 (4H, q, J=7.23 Hz), 2.66 (2H, t, J=4.89 Hz), 3.16 (2H, br), 3.38 (3H, s), 3.65 (2H, t, J=5.20 Hz), 3.76 (2H, br), 4.66 (2H, d, J=5.87 Hz), 4.90 (2H, s), 6.79-6.88 (2H, m), 7.35-7.43 (1H, m), 8.54 (1H, s), 10.40 (1.0H, t, J=5.79 Hz).

Example N-93

5-Hydroxy-3-(3-isopropyl-propyl)-4,6-dioxo-1-prop-2-ynyl-2,3,4,6-tetrahydro-1H-pyrid[2,1-f][1,2,4]triazine-7-carboxylic acid 2,4-difluoro-benzylamide 1H-NMR (CDCl3) δ: 1.13 (6H, d, J=6.04 Hz), 1.91-1.99 (2H, m), 2.55 (1H, t, J=2.52 Hz), 3.54 (2H, t, J=5.71 Hz), 3.58 (1H, t, J=6.21 Hz), 3.70 (2H, t, J=6.71 Hz), 3.94 (2H, d, J=2.35 Hz), 4.67 (2H, d, J=5.87 Hz), 4.85 (2H, s), 6.79-6.88 (2H, m), 7.36-7.44 (1H, m), 8.57 (1H, s), 10.38 (1H, br), 11.74 (1H, br).

Example N-94

1-(4-Ethyl-4-hydroxy-hexyl)-5-hydroxy-3-(2-methoxy-ethyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 0.89 (6H, t, J=7.39 Hz), 1.50 (4H, q, J=7.39 Hz), 1.46-1.57 (4H, m), 3.09 (2H, br), 3.39 (3H, s), 3.66 (2H, t, J=4.12 Hz), 3.74 (2H, br), 4.67 (2H, d, J=5.54 Hz), 4.80 (2H, br), 6.80-6.87 (2H, m), 7.36-7.43 (1H, m), 8.50 (1H, s), 10.41 (1.0H, t, J=5.54 Hz), 11.60 (1H, br).

Example N-95

5-Hydroxy-3-(3-isopropoxypropyl)-4,6-dioxo-1-pyridin-2-ylmethyl-2,3,4,6-tetrahydro-1H-pyrid[2,1-f][1,2,4]triazine-7-carboxylic acid 2,4-difluoro-benzylamide 1H-NMR (CDCl3) δ: 1.13 (6H, d, J=6.13 Hz), 1.92-2.01 (2H, m), 3.52-3.60 (3H, m), 3.75 (2H, br), 4.36 (2H, br), 4.66 (2H, d, J=5.88 Hz), 4.81 (2H, br), 6.81-6.90 (2.0H, m), 7.35-7.43 (3H, m), 7.77-7.84 (1H, m), 8.36 (1.0H, s), 8.66 (1H, d, J=4.03 Hz), 10.38 (1H, s), 11.87 (1H, br).

Example N-96

5-Hydroxy-3-(2-methoxyethyl)-4,6-dioxo-1-thiazol-4-ylmethyl-2,3,4,6-tetrahydro-1H-pyrid[2,1-f][1,2,4]triazine-7-carboxylic acid 2,4-difluorobenzylamide 1H-NMR (CDCl3) δ: 3.39 (3H, s), 3.70 (2H, t, J=4.53 Hz), 3.83 (2H, t, J=4.03 Hz), 4.43 (2H, br), 4.65 (2H, d, J=5.88 Hz), 4.90 (2H, br), 6.81-6.88 (2H, m), 7.34-7.42 (1H, m), 8.23 (1H, s), 8.90 (1H, d, J=1.51 Hz), 10.32 (1H, t, J=5.21 Hz), 11.68 (1H, br).

Example N-97

5-Hydroxy-3-(2-methoxyethyl)-1-[1,2,4]oxadiazol-3-ylmethyl-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 3.34 (3H, s), 3.66 (2H, t, J=4.50 Hz), 3.75 (2H, br), 4.44 (2H, br), 4.62 (2H, d, J=5.95 Hz), 4.89 (2H, br), 6.78-6.85 (2H, m), 7.31-7.38 (1H, m), 8.39 (1H, s), 8.80 (1H, s), 10.25 (1H, t, J=5.64 Hz).

Example N-98

5-Hydroxy-3-(2-methoxyethyl)-1-(2-methylthiazol-4-ylmethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 2.74 (3H, s), 3.35 (3H, s), 3.65 (2H, t, J=4.50 Hz), 3.76 (2H, t, J=4.27 Hz), 4.27 (2H, br), 4.60 (2H, d, J=5.80 Hz), 4.86 (2H, br), 6.76-6.85 (2H, m), 6.98 (1H, s), 7.29-7.37 (1H, m), 8.16 (1.0H, s), 10.26 (1H, t, J=5.95 Hz), 11.65 (1H, br).

Example N-99

1-(3,5-Dimethylisoxazol-4-ylmethyl)-5-hydroxy-3-(2-methoxyethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 2.26 (3H, s), 2.31 (3H, s), 3.35 (3H, s), 3.63 (3H, br), 3.97 (3H, br), 4.62 (2H, d, J=5.64 Hz), 4.75 (2H, br), 6.77-6.86 (2H, m), 7.31-7.39 (1H, m), 8.21 (1H, s), 10.22 (1H, t, J=5.64 Hz), 11.57 (1H, br).

Example N-100

1-Cyclopropylmethyl-5-hydroxy-3-(3-isopropoxypropyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 0.00 (2H, br), 0.58 (2H, br), 0.84-0.97 (1H, m), 1.10 (3H, s), 1.12 (3H, s), 1.86-1.94 (2H, m), 2.91 (2H, br), 3.47-3.57 (3H, m), 3.65 (2H, br), 4.64 (2H, d, J=5.80 Hz), 4.77 (2H, br), 6.76-6.85 (2H, m), 7.32-7.40 (1H, m), 8.52 (1H, s), 10.38 (1H, t, J=5.80 Hz), 11.70 (1H, br).

Example N-101

5-Hydroxy-3-(3-isopropoxypropyl) 1-[1,2,4]oxadiazol-3-ylmethyl-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.13 (6H, d, J=6.04 Hz), 1.93-2.01 (2H, m), 3.4-3.59 (3H, m), 3.75 (2H, br), 4.49 (2H, br), 4.67 (2H, d, J=5.54 Hz), 4.86 (2H, br), 6.82-6.89 (2H, m), 7.37-7.45 (1H, m), 8.48 (1H, s), 8.85 (1H, s), 10.32 (1H, br).

Example N-102

5-Hydroxy-3-(3-isopropoxypropyl)-1-(2-methoxyethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.13 (6H, d, J=6.04 Hz), 1.88-1.97 (2H, m), 3.25 (2H, br), 3.38 (3H, s), 3.52 (2H, t, J=5.54 Hz), 3.56-3.60 (2H, m), 3.67 (2H, br), 4.67 (2H, d, J=6.21 Hz), 4.82 (2H, br), 6.79-6.88 (2H, m), 7.35-7.43 (1H, m), 8.51 (1H, s), 10.42 (1H, t, J=6.04 Hz), 11.79 (1H, br).

Example N-103

5-Hydroxy-3-(3-isopropoxypropyl)-4,6-dioxo-1-thiazol-4-ylmethyl-2,3,4,6-tetrahydro-H-pyrid[2,1-f][1,2,4]triazine-7-carboxylic acid 2,4-difluorobenzylamide 1H-NMR (CDCl3) δ: 1.12 (6H, d, J=6.04 Hz), 1.91-2.00 (2H, m), 3.52-3.59 (3H, m), 3.74 (2H, br), 4.40 (2H, br), 4.64 (2H, d, J=5.71 Hz), 4.82 (2H, br), 6.80-6.87 (2H, m), 7.31-7.41 (1H, m), 8.26 (1H, s), 8.89 (1H, s), 10.34 (1H, t, J=5.71 Hz), 11.84 (1H, br).

Example N-104

1-(3,5-Dimethylisoxazol-4-ylmethyl)-5-hydroxy-3-(3-isopropoxypropyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.09 (6H, d, J=6.21 Hz), 1.87-1.95 (2H, m), 2.30 (3H, s), 3.34 (3H, s), 3.49-3.57 (3H, m), 3.99 (2H, br), 4.65 (2H, d, J=5.71 Hz), 4.65 (2H, br), 6.79-6.89 (2H, m), 7.34-7.42 (1H, m), 8.29 (1H, s), 10.29 (1H, t, J=5.71 Hz), 11.77 (1H, br).

Example N-105

5-Hydroxy-3-(3-isopropoxypropyl) 1-(3-methoxypropyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.14 (6H, d, J=6.04 Hz), 1.78 (2H, br), 1.88-1.97 (2H, m), 3.17 (2H, t, J=6.71 Hz), 3.35 (3H, s), 3.46-3.58 (5H, m), 3.68 (2H, br), 4.66 (2H, d, J=6.04 Hz), 4.71 (2H, br), 6.80-6.87 (2.4H, m), 7.36-7.44 (1H, m), 8.46 (1H, s), 10.41 (1H, t, J=6.71 Hz), 11.75 (1H, br).

Example N-106

5-Hydroxy-3-(3-isopropoxypropyl)-1-(5-methylisoxazol-3-ylmethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.10 (6H, d, J=6.04 Hz), 1.88-1.96 (2H, m), 2.50 (3H, s), 3.50-3.56 (3H, m), 3.71 (2H, br), 4.25

(2H, br), 4.66 (2H, d, J=6.21 Hz), 4.66 (2H, br), 6.79-6.89 (2H, m), 7.35-7.43 (1H, m), 8.48 (1H, s), 10.37 (1H, t, J=6.21 Hz), 11.85 (1H, br).

Example N-107

5-Hydroxy-3-isopropyl-4,6-dioxo-1-pyridin-2-ylmethyl-2,3,4,6-tetrahydro-1H-pyrid[2,1-f][1,2,4]triazine-7-carboxylic acid 2,4-difluorobenzylamide 1H-NMR (CDCl3) δ: 1.30 (6H, d, J=6.71 Hz), 4.27 (2H, br), 4.60 (2H, d, J=5.80 Hz), 4.76 (2H, s), 4.90 (1H, q, J=6.71 Hz), 6.75-6.84 (2H, m), 7.28-7.37 (3H, m), 7.77 (1H, dd, J=8.54, 6.86 Hz), 8.22 (1H, s), 8.61 (1H, d, J=4.12 Hz), 10.31 (1H, t, J=6.71 Hz), 11.89 (1H, br).

Example N-108

5-Hydroxy-3-isopropyl-1-[1,2,4]oxadiazol-3-ylmethyl-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.32 (6H, d, J=6.71 Hz), 4.35 (2H, br), 4.62 (2H, d, J=5.80 Hz), 4.78 (2H, br), 4.92 (1H, q, J=6.79 Hz), 6.76-6.85 (2H, m), 7.31-7.39 (1H, m), 8.43 (1H, s), 8.82 (1H, s), 10.27 (1H, t, J=6.79 Hz).

Example N-109

1-Furan-3-ylmethyl-5-hydroxy-3-(3-isopropoxypropyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.09 (6H, d, J=6.10 Hz), 1.83-1.91 (2H, m), 3.48-3.55 (3H, m), 3.62 (2H, br), 4.06 (2.5H, s), 4.62 (2H, d, J=5.80 Hz), 4.62 (2H, br), 6.45 (1H, s), 6.76-6.84 (2H, m), 7.31-7.39 (3H, m), 7.48 (1H, d, J=1.68 Hz), 8.38 (1H, s), 10.33 (1H, t, J=5.80 Hz), 11.75 (2H, br).

Example N-110

1-Furan-3-ylmethyl-5-hydroxy-3-(3-methoxypropyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.85-1.94 (2H, m), 3.30 (3H, s), 3.46 (2H, t, J=5.64 Hz), 3.61 (2H, br), 4.05 (2H, br), 4.62 (2H, d, J=5.80 Hz), 4.62 (2H, br), 6.45 (1H, d, J=1.07 Hz), 6.76-6.85 (2H, m), 7.30-7.40 (3H, m), 7.48 (1H, t, J=1.68 Hz), 8.37 (1H, s), 10.31 (1H, t, J=5.80 Hz), 11.70 (1H, br).

Example N-111

3-(2-Ethoxyethyl)-5-hydroxy-1-(5-methylisoxazol-3-ylmethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.15 (3.0H, t, J=7.02 Hz), 2.46 (3H, s), 3.48 (2.4H, q, J=7.02 Hz), 3.65 (2H, t, J=4.12 Hz), 3.75 (2H, br), 4.23 (2H, br), 4.63 (2H, d, J=5.95 Hz), 4.74 (2H, br), 6.09 (1H, s), 6.76-6.85 (2H, m), 7.31-7.39 (1H, m), 8.40 (1H, s), 10.31 (1H, t, J=5.95 Hz), 11.66 (1H, br).

Example N-112

5-Hydroxy-3-isopropyl-1-(5-methylisoxazol-3-ylemthy)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 1.33 (6H, d, J=7.22 Hz), 2.52 (3H, s), 4.22 (2H, br), 4.67 (2H, d, J=5.88 Hz), 4.67 (2H, br), 4.91 (1H, q, J=7.22 Hz), 6.15 (1H, s), 6.80-6.90 (2H, m), 7.36-7.44 (1H, m), 8.48 (1H, s), 10.38 (1H, t, J=5.54 Hz), 11.89 (1H, br).

Example N-113

1-Furan-3-ylmethyl-hydroxy-4,6-dioxo-3-[(S)-1-(tetrahydrofuran-2-yl)methyl]-2,3,4,6-tetrahydro-1H-pyrid[2,1-f][1,2,4]triazine-7-carboxylic acid 2,4-difluorobenzylamide 1H-NMR (CDCl3) δ: 1.93-2.03 (3H, m), 2.09-2.18 (1H, m), 3.19 (1H, br), 3.76-3.84 (1H, m), 3.87-3.94 (1H, m), 4.02-4.17 (4H, m), 4.66 (2H, d, J=5.54 Hz), 4.66 (1H, br), 4.89 (1H, br), 6.49 (1H, s), 6.80-6.89 (2H, m), 7.35-7.44 (2H, m), 7.54 (1H, s), 8.38 (1H, s), 10.35 (1H, br), 11.67 (1H, br).

Example N-114

5-Hydroxy-1-(5-methylisoxazol-3-ylmethyl)-4,6-dioxo-3-thiophen-2-ylmethyl-2,3,4,6-tetrahydro-1H-pyrid[2,1-f][1,2,4]triazine-7-carboxylic acid 2,4-difluorobenzylamide 1H-NMR (CDCl3) δ: 2.47 (3H, s), 4.12 (2H, br), 4.65 (2H, d, J=5.54 Hz), 4.65 (2H, br), 4.96 (2H, br), 6.01 (1H, s), 6.79-6.88 (2H, m), 7.01 (1H, dd, J=5.20, 3.36 Hz), 7.10 (1H, d, J=2.85 Hz), 7.21-7.41 (2H, m), 8.41 (1H, s), 10.31 (1H, br), 11.56 (1H, br).

Example N-115

3-Furan-2-ylmethyl-5-hydroxy-1-(5-methylisoxazol-3-ylmethyl)-4,6-dioxo-2,3,4,6-tetrahydro-1H-pyrid[2,1-f][1,2,4]triazine-7-carboxylic acid 2,4-difluorobenzylamide 1H-NMR (CDCl3) δ: 2.48 (3H, s), 4.17 (2H, br), 4.67 (2H, d, J=6.21 Hz), 4.73 (2H, br), 4.81 (2H, br), 6.07 (1. H, s), 6.40 (1H, dd, J=3.36, 1.85 Hz), 6.45 (1H, d, J=3.36 Hz), 6.81-6.90 (2H, m), 7.35-7.43 (2H, m), 8.44 (1H, s), 10.32 (1H, br), 11.58 (1H, br).

Example N-116

1-Furan-3-ylmethyl-5-hydroxy-4,6-dioxo-3-[(R)-1-(tetrahydrofuran-2-yl)methyl]-2,3,4,6-tetrahydro-1H-pyrid[2,1-f][1,2,4]triazine-7-carboxylic acid 2,4-difluorobenzylamide 1H-NMR (CDCl3) δ: 1.93-2.03 (3H, m), 2.09-2.18 (1H, m), 3.19 (1H, br), 3.76-3.84 (1H, m), 3.87-3.94 (1H, m), 4.02-4.17 (4H, m), 4.66 (2H, d, J=5.54 Hz), 4.66 (1H, br), 4.89 (1H, br), 6.49 (1H, s), 6.80-6.89 (2H, m), 7.35-7.44 (2H, m), 7.54 (1H, s), 8.38 (1H, s), 10.35 (1H, br), 11.67 (1H, br).

Example N-117

1-Furan-2-ylmethyl-5-hydroxy-3-(3-isopropoxypropyl)-4,6-dioxo-2,3,4,6-tetrahydro-H-pyrid[2,1-f][1,2,4]triazine-7-carboxylic acid 2,4-difluorobenzylamide 1H-NMR (CDCl3) δ: 1.12 (6H, d, J=6.04 Hz), 1.90-1.98 (2H, m), 3.51-3.59 (3H, m), 3.70 (2H, br), 4.24 (2H, s), 4.65 (2H, d, J=5.71 Hz), 4.70 (2H, br), 6.32 (1H, d, J=3.19 Hz), 6.37-6.39 (1H, m), 6.79-6.88 (2H, m), 7.34-7.42 (1H, m), 7.48 (1H, d, J=1.68 Hz), 8.30 (1H, s), 10.35 (1H, br), 11.80 (2H, br).

Example N-118

5-Hydroxy-3-(3-methoxy-propyl)-4,6-dioxo-1-thiophen-2-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 1.85 (2H, m), 3.24 (3H, s), 3.40 (2H, t, J=6.0 Hz), 3.54 (2H, t, J=7.2 Hz), 4.46 (2H, d), 4.47 (2H, s), 4.98 (2H, br s), 6.98-7.59 (6H, m), 7.81 (1H, s), 10.17 (1H, t, J=5.9 Hz), 11.86 (1H, s).

Example N-119

5-Hydroxy-1-methyl-4,6-dioxo-3-(3-propoxy-propyl)-2,3,4,6-tetrahydro-1H-pyrid[2,1-f][1,2,4]triazine-7-carboxylic acid 2,4-difluoro-benzylamide NMR (DMSO-$d_6$) δ: 0.85 (3H, t, J=7.3 Hz), 1.49 (2H, q, J=7.1 Hz), 1.82 (2H, t, J=6.7 Hz), 2.87 (3H, s), 3.29 (2H, t, J=10 Hz), 3.42 (2H, t, J=5.8 Hz), 3.51-3.55 (2H, m), 4.53 (2H, d, J=6.0 Hz), 4.80 (2H, s), 7.08 (1H, d, J=8.8 Hz), 7.24 (1H, s), 7.40 (1H, d, J=7.1 Hz), 8.27 (1H, s), 10.37 (1H, s).

Example N-120

3-(2,3-Dihydro-benzofuran-5-ylmethyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.69 (3H, s), 3.16 (2H, t, J=8.8 Hz), 4.54 (6H, m), 4.76 (2H, s), 6.73 (1H, d, J=8.06 Hz), 7.10 (2H, m), 7.23 (2H, m), 7.39 (1H, m), 8.22 (1H, s), 10.35 (1H, s).

Example N-121

5-Hydroxy-1-methyl-4,6-dioxo-3-(tetrahydro-furan-3-ylmethyl)-2,3,4,6-tetrahydro-1H-pyrid[2,1-f][1,2,4]triazine-7-carboxylic acid 2,4-difluoro-benzylamide NMR (DMSO-$d_6$) δ: 1.61 (1H, m), 1.91-2.01 (1H, m), 2.61 (1H, m), 2.88 (3H, s), 3.42-3.51 (6H, m), 4.54 (2H, d, J=5.7 Hz), 4.84 (2H, s), 7.04-7.10 (1H, m), 7.20-7.28 (1H, m), 7.41 (1H, m), 8.25 (1H, s), 10.38 (1H, s).

Example N-122

3-Furan-3-ylmethyl-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.72 (3H, s), 4.52 (2H, s), 4.56 (2H, s), 4.80 (1H, s), 6.54 (1H, s), 7.06 (1H, td, J=8.5, 2.6 Hz), 7.20-7.29 (1H, m), 7.40 (1.0H, dd, J=15.4, 8.6 Hz), 7.67 (1H, s), 7.75 (1H, s), 8.24 (1H, s), 10.30 (1H, t, J=6.0 Hz).

Example N-123

3-(2,3-Dihydro-benzofuran-2-ylmethyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.82 (3H, s), 3.01 (1H, dd, J=16.2, 6.6 Hz), 3.56-3.85 (2H, m), 4.50 (2H, d, J=5.7 Hz), 4.78-5.12 (4H, m), 6.77-6.86 (2H, m), 7.03-7.12 (2H, m), 7.24 (2H, m), 7.40 (1H, dd, J=15.3, 8.6 Hz), 8.21 (1H, s), 10.39 (1H, s), 11.59 (1H, br s).

Example N-124

5-Hydroxy-1-methyl-4,6-dioxo-3-(3-phenoxy-propyl)-2,3,4,6-tetrahydro-1H-pyrid[2,1-f][1,2,4]triazine-7-carboxylic acid 2,4-difluoro-benzylamide NMR (DMSO-$d_6$) δ: 2.06 (2H, dd, J=10.6, 4.0 Hz), 2.88 (3H, s), 3.65 (2H, t, J=7.0 Hz), 4.04 (2H, t, J=6.1 Hz), 4.53 (2H, d, J=5.9 Hz), 4.84 (2H, s), 6/90-7.30 (m, 8H), 8.26 (1H, s), 10.36 (1H, s).

Example N-125

5-Hydroxy-1-methyl-4,6-dioxo-3-(tetrahydro-pyran-4-ylmethyl)-2,3,4,6-tetrahydro-1H-pyrid[2,1-f][1,2,4]triazine-7-carboxylic acid 2,4-difluoro-benzylamide NMR (DMSO-$d_6$) δ: 1.24 (2H, m), 1.58 (1H, d, J=12.4 Hz), 1.91 (1H, m), 2.91 (3H, s), 3.36 (4H, m), 3.85 (2H, d, J=9.4 Hz), 4.53 (2H, d, J=5.5 Hz), 4.83 (2H, s), 7.06 (1H, dd, J=9.5, 7.1 Hz), 7.19-7.27 (1H, m), 7.40 (1H, dd, J=15.4, 8.6 Hz), 8.29 (1H, s), 10.35 (1H, t, J=5.5 Hz).

Example N-126

5-Hydroxy-1-methyl-4,6-dioxo-3-(2-propoxy-ethyl)-2,3,4,6-tetrahydro-1H-pyrid[2,1-f][1,2,4]triazine-7-carboxylic acid 2,4-difluoro-benzylamide NMR (DMSO-$d_6$) δ: 0.84 (3H, t, J=7.8 Hz), 1.48 (2H, m), 2.87 (3H, s), 3.35 (2H, m), 3.60 (2H, m), 4.53 (2H, d, J=5.7 Hz), 4.83 (2H, s), 7.09 (1H, m), 7.26 (1H, m), 7.41 (1H, m), 8.28 (1H, s), 10.34 (1H, t, J=5.7 Hz), 11.73 (1H, br s).

Example N-127

5-Hydroxy-1-methyl-4,6-dioxo-3-(2-phenoxy-ethyl)-2,3,4,6-tetrahydro-1H-pyrid[2,1-f][1,2,4]triazine-7-carboxylic acid 2,4-difluoro-benzylamide NMR (DMSO-$d_6$) δ: 2.87 (3H, s), 3.89 (2H, s), 4.21 (2H, t, J=4.7 Hz), 4.53 (2H, d, J=6.4 Hz), 4.95 (2H, s), 7.18 (8H, m), 8.31 (1H, s), 10.32 (1H, t, J=6.0 Hz).

Example N-128

3-(3-Ethoxy-propyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.08 (3H, t, J=6.9 Hz), 1.82 (2H, t, J=6.6 Hz), 2.87 (3H, s), 3.42 (4H, m), 3.53 (2H, t, J=7.2 Hz), 4.53 (2H, d, J=6.0 Hz), 4.82 (2H, s), 7.06 (1H, m), 7.24 (1H, m), 7.40 (1H, m), 8.30 (1H, s), 10.33 (1H, t, J=6.0 Hz).

Example N-129)

3-(2-Dimethylamino-ethyl)-5-hydroxy-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 2.10 (6H, s), 2.82 (3H, s), 3.59 (2H, s), 4.54 (2H, d, J=5.9 Hz), 4.85 (2H, s), 7.04-7.10 (1H, m), 7.25 (1H, m), 7.41 (1H, m), 8.31 (1H, s), 10.32 (1H, t, J=5.9 Hz), 11.81 (1H, br s).

Example N-130

5-Hydroxy-3-(3-methoxy-propyl)-4,6-dioxo-1-pyridin-2-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 1.81-1.90 (2H, m), 3.24 (3.6H, s), 3.39 (2H, t, J=7.13 Hz), 3.55 (2H, t, J=7.13 Hz), 4.35 (2H, s), 4.47 (2H, d, J=5.7 Hz), 4.93 (2H, s), 7.04-7.10 (1H, m), 7.19-7.36 (3H, m), 7.50 (1H, d, J=7.7 Hz), 7.81 (2H, td, J=7.6, 1.7 Hz), 8.49 (1H, dd, J=4.9, 0.8 Hz), 10.18 (1H, t, J=6.0 Hz), 11.80 (1H, br s).

Example N-131

5-Hydroxy-3-(3-methoxy-propyl)-4,6-dioxo-1-prop-2-ynyl-2,3,4,6-tetrahydro-1H-pyrid[2,1-f][1,2,4]triazine-7-carboxylic acid 2,4-difluoro-benzylamide NMR (DMSO-$d_6$) δ: 1.85 (2H, m), 3.22 (3H, s), 3.38 (2H, t, J=6.0 Hz), 3.51 (2H, t, J=7.5 Hz), 3.53 (1H, s), 4.12 (2H, s), 4.54 (2H, d, J=5.9 Hz), 4.93 (2H, s), 7.07 (1H, m), 7.20-7.28 (1H, m), 7.40 (1H, dd, J=15.36, 8.64 Hz), 8.34 (1H, s), 10.28 (1H, t, J=5.9 Hz), 11.79 (1H, br s).

Example N-132

3-(2-Ethoxy-ethyl)-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 1.07 (3H, t, J=7.1 Hz), 3.39-3.70 (6H, m), 4.36 (2H, s), 4.47 (2H, d, J=6.0 Hz), 4.97 (2H, s), 7.04-7.10 (1H, m), 7.19-7.36 (3H, m), 7.50 (1H, d, J=7.7 Hz), 7.77 (1H, s), 7.81 (1H, t, J=8.0, 2.2 Hz), 8.49 (1H, dd, J=4.9, 0.8 Hz), 10.16 (1H, t, J=5.9 Hz), 11.73 (1H, s).

Example N-133

3-(3-Ethoxy-propyl)-5-hydroxy-4,6-dioxo-1-pyridin-2-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 1.08 (3H, t, J=7.0 Hz), 1.80-1.89 (2H, m), 3.39-3.45 (4H, m), 3.56 (2H, t, J=7.1 Hz), 4.35 (2H, s), 4.46 (2H, d, J=5.8 Hz), 4.93 (1H, s), 7.06 (1H, dt, J=11.6, 4.3 Hz), 7.27 (3H, m), 7.49 (1H, d, J=7.8 Hz), 7.80 (2H, td, J=7.7, 1.8 Hz), 8.48 (1H, d, J=4.0 Hz), 10.17 (1H, t, J=5.9 Hz), 11.81 (1H, s).

Example N-134

1-Cyclopropylmethyl-5-hydroxy-3-(3-methoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 0.00 (2H, m), 0.37 (2H, s), 0.88 (1H, m), 1.76-1.85 (2H, m), 3.36 (3H, s), 3.49 (2H, dd, J=13.7, 6.4 Hz), 4.53 (2H, d, J=5.8 Hz), 4.89 (2H, s), 7.06 (1H, m), 7.24 (1H, m), 7.39 (1H, m), 8.30 (1H, s), 10.30 (1H, t, J=5.9 Hz).

Example N-135

5-Hydroxy-1-(2-methoxy-ethyl)-3-(3-methoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.76-1.85 (2H, m), 3.16 (3H, s), 3.21 (3H, s), 3.33 (6H, m), 3.49 (2H, dd, J=12.2, 5.0 Hz), 4.53 (2H, d, J=5.6 Hz), 4.84 (2H, s), 7.02-7.09 (1H, m), 7.20-7.27 (1H, m), 7.38 (1H, dd, J=15.3, 8.6 Hz), 8.20 (1H, s), 10.34 (1H, s).

Example N-136

5-Hydroxy-1,3-bis-(3-methoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.66 (2H, m), 1.76-1.85 (2H, m), 3.0 (2H, m), 3.18 (3H, s), 3.23 (3H, s), 3.35-3.62 (6H, m), 4.53 (2H, d, J=5.4 Hz), 4.87 (2H, s), 7.04-7.10 (1H, m), 7.21-7.28 (1H, m), 7.36-7.44 (1H, m), 8.19 (1H, s), 10.33 (1H, t, J=5.5 Hz).

Example N-137

5-Hydroxy-3-((S)-2-methoxy-1-methyl-ethyl)-1-methyl-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.15 (3H, d, J=6.9 Hz), 2.78 (3H, s), 3.25 (3H, s), 3.33-3.43 (3H, m), 4.52 (2H, d, J=5.7 Hz), 4.81

(2H, m), 7.05 (1H, td, J=8.3, 2.1 Hz), 7.23 (1H, dt, J=13.7, 5.2 Hz), 7.39 (1H, dd, J=15.3, 8.5 Hz), 8.23 (1H, s), 10.38 (1H, s), 11.82 (1H, s).

Example N-138

5-Hydroxy-3-(3-methoxy-propyl)-4,6-dioxo-1-thiazol-4-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 1.88 (2H, m), 3.24 (3H, s), 3.40 (2H, t, J=6.0 Hz), 3.56 (2H, t, J=7.1 Hz), 4.42 (s, 2H), 4.45 (2H, d, J=5.7 Hz), 4.96 (2H, s), 7.07 (1H, m), 7.19-7.27 (1H, m), 7.33 (1H, dd, J=15.3, 8.6 Hz), 7.68 (1H, s), 7.69 (1H, s), 9.10 (1H, d, J=1.7 Hz), 10.17 (1H, t, J=6.0 Hz), 11.84 (1H, s).

Example N-139

5-Hydroxy-3-((S)-2-methoxy-1-methyl-ethyl)-4,6-dioxo-1-pyridin-2-ylmethyl-2,3,4,6-tetra hydro-1H-pyrid[2,1-f][1,2,4]triazine-7-carboxylic acid 2,4-difluoro-benzylamide NMR (DMSO-d$_6$) δ: 1.20 (3H, br s), 3.25 (3H, s), 3.32 (2H, m), 3.44 (1H, m), 4.31 (1H, br s), 4.45 (2H, d, J=5.6 Hz), 4.79 (1H, m), 4.95 (2H, s), 7.04-7.09 (1H, m), 7.19-7.34 (3H, m), 7.48 (1H, d, J=7.6 Hz), 7.67 (1H, s), 7.80 (1H, td, J=7.6, 1.8 Hz), 8.48 (1H, d, J=4.0 Hz), 10.14 (1H, t, J=6.0 Hz), 11.88 (1H, s).

Example N-140

5-Hydroxy-3-((S)-2-methoxy-1-methyl-ethyl)-1-(5-methyl-isoxazol-3-ylmethyl)-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 1.18 (3H, br s), 2.38 (3H, s), 3.21 (3H, s), 3.42-3.54 (3H, m), 4.30 (2H, br s), 4.50 (2H, d, J=5.7 Hz), 4.82 (2H, m), 6.41 (1H, s), 7.04-7.09 (1H, m), 7.24 (1H, dt, J=13.7, 5.3 Hz), 7.37 (1H, dd, J=15.4, 8.7 Hz), 8.00 (1H, s), 10.19 (1H, t, J=6.0 Hz), 11.84 (1H, s).

Example N-141

5-Hydroxy-3-(3-methoxy-propyl)-4,6-dioxo-1-thiophen-3-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 1.84 (2H, m), 3.25 (3H, s), 3.40 (2H, t, J=6.1 Hz), 3.55 (2H, t, J=7.2 Hz), 4.27 (2H, s), 4.48 (2H, d, J=5.9 Hz), 4.84 (2H, br s), 7.04-7.39 (5H, m), 7.57 (1H, dd, J=4.9, 2.9 Hz), 7.79 (1H, s), 10.19 (1H, t, J=5.9 Hz), 11.85 (1H, s).

Example N-142

5-Hydroxy-3-(3-isopropoxy-propyl)-4,6-dioxo-1-thiophen-3-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 1.46 (6H, d, J=6.0 Hz), 1.76-1.84 (2H, m), 3.49 (4H, m), 4.26 (2H, s), 4.47 (2H, d, J=5.7 Hz), 4.83 (2H, m), 7.03-7.39 (6H, m), 7.56 (1H, dd, J=5.0, 2.9 Hz), 7.80 (1H, s), 10.19 (1H, t, J=5.9 Hz), 11.90 (1H, s).

Example N-143

5-Hydroxy-3-((S)-2-methoxy-1-methyl-ethyl)-4,6-dioxo-1-thiophen-3-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 1.19 (3H, s), 3.27 (3H, s), 3.37-3.62 (3H, m), 4.21 (2H, s), 4.46 (2H, d, J=6.0 Hz), 4.74-4.90 (2H, m), 7.02-7.35 (5H, m), 7.57 (1H, dd, J=5.0, 2.9 Hz), 7.68 (1H, s), 10.16 (1H, t, J=5.9 Hz), 11.92 (1H, s).

Example N-144

5-Hydroxy-4,6-dioxo-1-pyridin-2-ylmethyl-3-(tetrahydro-pyran-4-ylmethyl)-2,3,4,6-tetra hydro-1H-pyrid[2,1-f][1,2,4]triazine-7-carboxylic acid 2,4-difluoro-benzylamide NMR (DMSO-d$_6$) δ: 1.26 (2H, m), 1.61 (2H, d, J=12.4 Hz), 1.95 (1H, m), 3.23 (4H, m), 3.85 (2H, d, J=9.7 Hz), 4.37 (2H, s), 4.47 (2H, d, J=5.4 Hz), 4.96 (2H, br s), 7.07 (1H, t, J=7.7 Hz), 7.29 (3H, m), 7.54 (1H, d, J=7.7 Hz), 7.82 (1H, s), 7.85 (1H, s), 8.52 (1H, d, J=3.9 Hz), 10.18 (1H, t, J=6.0 Hz), 11.80 (1H, s).

Example N-145

5-Hydroxy-4,6-dioxo-3-[3-(2-oxo-1-yl)-propyl]-1-thiophen-3-ylmethyl-2,3,4,6-tetrahydro-1H-pyrid[2,1-f][1,2,4]triazine-7-carboxylic acid 2,4-difluoro-benzylamide NMR (DMSO-d$_6$) δ: 1.76-1.98 (4H, m), 2.22 (2H, t, J=8.1 Hz), 3.22-3.44 (6H, m), 4.28 (2H, s), 4.47 (2H, d, J=5.7 Hz), 4.95 (2H, br s), 7.02-7.38 (5H, m), 7.56 (1H, dd, J=5.0, 2.9 Hz), 7.76 (1H, s), 10.16 (1H, t, J=6.0 Hz), 11.82 (1H, s).

Example N-146

1-Ethyl-5-hydroxy-3-((S)-2-methoxy-1-methyl-ethyl)-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 1.06 (3H, t, J=6.9 Hz), 1.15 (3H, d, J=6.9 Hz), 3.05 (2H, m), 3.26 (3H, s), 3.43-3.56 (3H, m), 4.55 (2H, d, J=5.9 Hz), 4.75 (1H, m), 4.84 (2H, s), 7.08 (1H, td, J=8.6, 2.6 Hz), 7.21-7.29 (1H, m), 7.42 (1H, dd, J=15.4, 8.6 Hz), 8.23 (1H, d, J=13.6 Hz), 10.31 (1H, t, J=5.8 Hz), 11.85 (1H, s).

Example N-147

3-[1,4]Dioxan-2-ylmethyl-1-ethyl-5-hydroxy-4,6-dioxo-2,3,4,6-tetrahydro-1H-pyrid[2,1-f][1,2,4]triazine-7-carboxylic acid 2,4-difluoro-benzylamide NMR (DMSO-d$_6$) δ: 3.10-3.78 (3H, m), 3.07-3.75 (11H, m), 4.51 (2H, d, J=6.0 Hz), 4.84 (2H, s), 7.05-7.11 (1H, m), 7.21-7.28 (1H, m), 7.41 (1H, dd, J=15.4, 8.6 Hz), 8.20 (1H, s), 10.35 (1H, t, J=6.0 Hz).

Example N-148

5-Hydroxy-1-(2-methoxy-ethyl)-4,6-dioxo-3-(tetrahydro-pyran-4-ylemthyl)-2,3,4,6-tetrahydro-1H-pyrid[2,1-f][1,2,4]triazine-7-carboxylic acid 2,4-difluoro-benzylamide NMR (DMSO-$d_6$) δ: 1.15-1.29 (2H, m), 1.57 (2H, d, J=12.4 Hz), 1.91 (1H, m), 3.19 (3H, s), 3.25 (8H, m), 3.84 (2H, d, J=11.3 Hz), 4.51 (2H, d, J=5.7 Hz), 4.90 (2H, br s), 7.06 (1H, dt, J=11.6, 4.2 Hz), 7.20-7.27 (1H, m), 7.39 (1H, dd, J=15.4, 8.6 Hz), 8.26 (1H, s), 10.28 (1H, t, J=6.0 Hz), 11.73 (1H, s).

Example N-149

3-[1,4]Dioxan-2-ylemthyl-5-hydroxy-1-(2-methoxy-ethyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 3.20 (3H, s), 3.40-3.79 (13H, m), 4.53 (2H, d, J=5.7 Hz), 4.89 (2H, m), 7.03-7.44 (3H, m), 8.25 (1H, s), 10.28 (1H, t, J=6.0 Hz), 11.58 (1H, s).

Example N-150

5-Hydroxy-4,6-dioxo-3-(3-propoxy-propyl)-1-thiophen-3-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 0.84 (3H, t, J=7.4 Hz), 1.48 (2H, td, J=14.0, 7.2 Hz), 1.82 (2H, m), 3.31 (2H, t, J=6.6 Hz), 3.42 (2H, t, J=6.0 Hz), 3.55 (2H, s), 4.26 (2H, s), 4.47 (2H, d, J=5.6 Hz), 4.68-5.00 (2H, br s), 7.02-7.39 (5H, m), 7.56 (1H, dd, J=4.9, 2.9 Hz), 7.79 (1H, s), 10.18 (1H, t, J=6.0 Hz), 11.87 (1H, s).

Example N-151

5-Hydroxy-4,6-dioxo-3-(2-propoxy-ethyl)-1-thiophen-3-ylmethyl-2,3,4,6-tetrahydro-1H-pyrid[2,1-f][1,2,4]triazine-7-carboxylic acid 2,4-difluoro-benzylamide NMR (DMSO-$d_6$) δ: 0.84 (3H, s), 1.48 (2H, s), 3.64 (4H, m), 4.26 (2H, s), 4.47 (2H, s), 7.25-7.37 (5H, m), 7.56 (1H, s), 7.76 (1H, s), 10.17 (1H, s), 11.79 (1H, s).

Example Q-16

1-Acetyl-5-hydroxy-3-(2-isopropoxy-ethyl)-4,6-dioxo-2,3,4,6-tetrahydro-H-pyrid[2,1-f][1,2,4]triazine-7-carboxylic acid 2,4-difluoro-benzylamide 1H-NMR (CDCl3) δ: 1.18 (6.0H, d, J=6.21 Hz), 2.23 (3.0H, s), 3.59-3.67 (4.0H, m), 3.96 (1.0H, br s), 4.67 (2.0H, d, J=5.71 Hz), 4.95-5.11 (2.0H, m), 6.80-6.88 (2.0H, m), 7.35-7.45 (1.0H, m), 8.47 (1.0H, s), 10.21 (1.0H, t, J=7.00 Hz).

Example Q-17

1-Acetyl-5-hydroxy-3-(3-isopropoxypropyl)-4,6-dioxo-2,3,4,6-tetrahydro-1H-pyrid[2,1-f][1,2,4]triazine-7-carboxylic acid 2,4-difluoro-benzylamide 1H-NMR (CDCl3) δ: 1.12 (6H, d, J=6.21 Hz), 1.88-1.96 (2H, m), 2.15 (3H, s), 3.49-3.59 (3H, m), 3.58 (1H, br), 4.67 (2H, d, J=5.87 Hz), 4.93 (1H, br), 5.63 (1H, br), 6.81-6.89 (2H, m), 7.36-7.44 (1H, br), 8.51 (1H, s), 10.22 (1H, t, J=5.87 Hz), 11.62 (1H, br).

Example Q-18

1-Acetyl-5-hydroxy-4,6-dioxo-3-[(R)-1-(tetrahydrofuran-2-yl)methyl]-2,3,4,6-tetrahydro-1H-pyrid[2,1-f][1,2,4]triazine-7-carboxylic acid 2,4-difluoro-benzylamide NMR (DMSO-$d_6$) δ: 1.47-1.59 (1H, m), 1.79-1.99 (3H, m), 2.51 (3H, s), 3.40-3.49 (1H, m), 3.64-3.73 (2H, m), 3.77-3.85 (1H, m), 4.06 (1H, br), 4.55 (2H, d, J=5.64 Hz), 5.37 (1H, br), 5.63 (1H, br), 7.07 (1H, t, J=8.54 Hz), 7.25 (1H, dd, J=16.40, 6.02 Hz), 7.41 (1H, dd, J=15.56, 8.54 Hz), 8.32 (1H, s), 10.20 (1H, t, J=5.72 Hz), 11.38 (1H, br).

Example Q-19

1-Acetyl-5-hydroxy-3-((S)-2-methoxy-1-methylethyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.16 (3H, br s), 2.27 (3H, br s), 3.24 (3H, s), 3.38 (2H, m), 4.54 (2H, d, J=5.8 Hz), 4.67 (1H, br s), 5.12 (1H, br s), 5.68 (1H, br s), 7.03-7.44 (3H, m), 8.28 (1H, s), 10.28 (1H, s).

Example Q-20

1-Acetyl-5-hydroxy-4,6-dioxo-3-(tetrahydro-pyran-4-ylmethyl)-2,3,4,6-tetrahydro-1H-pyrid[2,1-f][1,2,4]triazine-7-carboxylic acid 2,4-difluoro-benzylamide NMR (DMSO-$d_6$) δ: 1.21 (2H, m), 1.52 (2H, m), 1.89 (1H, m), 2.25 (3H, br s), 3.21 (4H, m), 3.84 (2H, d, J=9.0 Hz), 4.54 (2H, d, J=5.88 Hz), 5.31-5.65 (2H, m), 7.04-7.10 (1H, m), 7.20-7.28 (1H, m), 7.41 (1H, dd, J=15.3, 8.6 Hz), 8.38 (1H, s), 10.22 (1H, t, J=5.8 Hz), 11.44 (1H, s).

Example Q-21

1-Acetyl-3-[1,4]dioxan-2-ylmethyl-5-hydroxy-4,6-dioxo-2,3,4,6-tetrahydro-H-pyrid[2,1-f][1,2,4]triazine-7-carboxylic acid 2,4-difluoro-benzylamide NMR (DMSO-$d_6$) δ: 2.30 (3H, s), 3.19-3.77 (9H, m), 4.54 (2H, d, J=5.7 Hz), 5.31-5.44 (2H, m), 7.04-7.45 (3H, m), 8.25 (1H, s), 10.27 (1H, s).

Example Q-22

1-Acetyl-5-hydroxy-3-(3-methoxy-propyl)-4,6-dioxo-2,3,4,6-tetrahydro-1H-pyrid[2,1-f][1,2,4]triazine-7-carboxylic acid 2,4-difluoro-benzylamide NMR (DMSO-$d_6$) δ: 1.79 (2H, m), 2.24 (3H, m), 3.21 (3H, s), 3.52 (2H, m), 4.54 (2H, d, J=5.5 Hz), 5.24-5.61 (2H, m), 7.06 (1H, m), 7.24 (1H, m), 7.41 (1H, m), 8.37 (1H, s), 10.26 (1H, s).

Example Q-23

1-Acetyl-5-hydroxy-4,6-dioxo-3-[(S)-1-(tetrahydro-furan-2-yl)methyl]-2,3,4,6-tetrahydro-1H-pyrid[2,1-f][1,2,4]triazine-7-carboxylic acid 2,4-difluoro-benzylamide NMR (DMSO-$d_6$) δ: 1.47-1.59 (1H, m), 1.79-1.99 (3H, m), 2.51 (3H, s), 3.40-3.49 (1H, m), 3.64-3.73 (2H, m), 3.77-3.85 (1H, m), 4.06 (1H, br), 4.55 (2H, d, J=5.64 Hz), 5.37 (1H, br), 5.63 (1H, br), 7.07 (1H, t, J=8.54 Hz), 7.25 (1H, dd, J=16.40, 6.02 Hz), 7.41 (1H, dd, J=15.56, 8.54 Hz), 8.32 (1H, s), 10.20 (1H, t, J=5.72 Hz), 11.38 (1H, br).

The present invention further provides the following compound.

[Chemical formula 153]

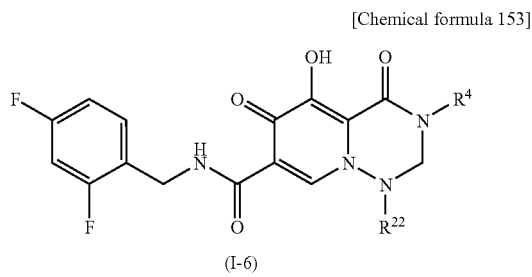

(I-6)

In Compound (I-6), $R^4$ and $R^{22}$ are selected from the following substituents, and the present invention provides all compounds which are formed from those combinations.

$R^4$:
methyl, ethyl, n-propyl, i-propyl, n-butyl, cyclopropyl, cyclopropylmethyl, 1-adamantylmethyl, 2-adamantylmethyl, dodecahedranemethyl, methoxyethyl, methoxypropyl, methoxyethyl, methoxypropyl, methoxybutyl, ethoxyethyl, ethoxypropyl, ethoxybutyl, propoxyethyl, propoxypropyl, propoxybutyl, phenyl, picolyl, piperonylmethyl, benzyl, dimethylanimoethyl, diethylaminoethyl, morpholinoethyl, phenoxyethyl, phenoxypropyl, cubanemethyl, thiophenemethyl, furanemethyl, tetrahydrofuranmethyl, dioxanemethyl, tetrahydropyranmethyl, pyridyl, thiazolemethyl, oxazolemethyl, 1,2,4-oxadiazolemethyl, 1,3,4-oxadiazolemethyl $R^{22}$:
methyl, ethyl, n-propyl, i-propyl, n-butyl, cyclopropyl, cyclopropylmethyl, 1-adamantylmethyl, 2-adamantylmethyl, dodecahedranemethyl, methoxyethyl, methoxypropyl, methoxyethyl, methoxypropyl, methoxybutyl, ethoxyethyl, ethoxypropyl, ethoxybutyl, propoxyethyl, propoxypropyl, propoxybutyl, phenyl, picolyl, piperonylmethyl, benzyl, dimethylaminoethyl, diethylaminoethyl, morpholinoethyl, phenoxyethyl, phenoxypropyl, cubanemethyl, thiophenemethyl, furanemethyl, tetrahydrofuranmethyl, dioxanemethyl, tetrahydrapyranmethyl, pyridyl, acetyl, methoxyacetyl, benzoyl, cyanomethyl, 2,2,2-trifluoromethyl, triazolemethyl, tetrazolemethyl, thiazolemethyl, oxazolemethyl, 1,2,4-oxadiazolemethyl, 1,3,4-oxadiazolemethyl, neopentyl, carboranemethyl, fluoromethyl, dimethylurea, methanesulfonyl, benzenesulfonyl, thiophenesulfonyl, acetamidoethyl, allyl, propargyl, isoxazolemethyl, dimethylthiourea, chrotyl, methoxymethyl, 18-crownethermethyl, imidazolemethyl, methylpyrrolemethyl

Experimental Example 1

The HIV integrase inhibitory activity was investigated based on the following assay method.
(1) Preparation of DNA Solution
By the same method as that described in Experimental Example 1 of WO 2004/024693, a substrate DNA solution (2 μmol/μl) and a target DNA solution (5 μmol/μl) were prepared. After each target DNA solution was once boiled, a temperature was slowly lowered to anneal complementary chains, which was used. Each sequence of a substrate DNA and a target DNA is as described in the same Experimental Example.

(2) Measurement of Inhibition Rate ($IC_{50}$ Value)
Streptavidin (manufactured by Vector Laboratories) was dissolved in a 0.1 M carbonate buffer solution (composition: 90 mM $Na_2CO_3$, 10 mM $NaHCO_3$) to a concentration of 40 μg/ml. Each 50 μl of this solution was added to a well of an immunoplate (manufactured by NUNC), and this is allowed to stand at 4° C. overnight to adsorb. Then, each well was washed with a phosphate buffer (composition: 13.7 mM NaCl, 0.27 mM KCl, 0.43 mM $Na_2HPO_4$, 0.14 mM $KH_2PO_4$) two times, and 300 μl of a phosphate buffer containing 1% skim milk was added to block it for 30 minutes. Further, each well was washed with a phosphate buffer two times, 50 ml of a substrate DNA solution (2 μmol/μl) was added to adsorb at room temperature for 30 minutes while shaking, and this was washed with a phosphate buffer two times and, then, distilled water once.

Then, to each well prepared as described above were added 12 μl of a buffer (composition: 150 mM MOPS (pH7.2), 75 mM $MnCl_2$, 50 mM 2-mercaptoethanol, 25% glycerol, 500 μg/ml bovine serum albumin-fraction V), and 51 μl of a reaction solution prepared from 39 ml of distilled water. Then, 9 μl of an integrase solution (30 μmol) was added, and the mixture was mixed well. To a well as a negative control (NC) was added 9 μl of a diluting solution (composition: 20 mM MOPS (pH7.2), 400 mM potassium glutamete, 1 mM EDTA, 0.1% NP-40, 20% glycerol, 1 mM DTT, 4 M urea), and this was mixed well using a plate mixer.

After the plate was incubated at 30° C. for 60 minutes, the reaction solution was discarded, followed by washing with 250 μl of a washing buffer (composition: 150 mM MOPS (pH7.2), 50 mM 2-mercaptoethanol, 25% glycerol, 500 μg/ml bovine serum albumin-fraction V) three times.

Then, to each well were added 12 μl of a buffer (composition: 150 mM MOPS (pH7.2), 75 mM $MgCl_2$, 50 mM 2-mercaptoethanol, 25% glycerol, 500 μg/ml bovine serum albumin-fraction V), and 53 μl of a reaction solution prepared from 41 μl of distilled water. Further, 6 μl of a solution of a test compound in DMSO was added to each well, and 6 μl of DMSO was added to a well as a positive control (PC), followed by mixing well using a plate mixer. After the plate was incubated at 30° C. for 30 minutes, 11 of a target DNA (5 μmol/μl) was added, and this was mixed well using a plate mixer.

After each plate was incubated at 30° C. for 10 minutes, the reaction solution was discarded, followed by washing with a phosphate buffer two times. Then, an anti-digoxigenin antibody labeled with alkaline phosphatase (sheep Fab fragment: manufactured by Boehringer) was diluted 2000-fold with an antibody diluting solution, 100 μl of the diluent was added to bind at 30° C. for 1 hour, and this was washed successively with a phosphate buffer containing 0.05% Tween20 two times, and a phosphate buffer once. Then, 150 μl of an alkaline phosphatase coloring buffer (composition: 10 mM paranitrophenyl phosphate (manufactured by Vector Laboratories), 5 mM $MgCl_2$, 100 mM NaCl, 100 mM Tris-HCl (pH 9.5)) was added to react at 30° C. for 2 hours, 50 μl of a 1N NaOH solution was added to stop the reaction, an absorbance (OD405 nm) of each well was measured, and an inhibition rate ($IC_{50}$) was obtained according to the following calculation equation.

Inhibition rate (%)=
100[1−{(C abs.−NC abs.)/(PC abs.−NC abs.)}]

C abs.; absorbance of well of compound
NC abs.: absorbance of NC
PC abs.: absorbance of PC The present compound showed the strong integrase inhibitory activity against HIV.

TABLE 1

| Ex No. | IC50 (nM) |
|---|---|
| O-07 | 4.8 |
| O-06 | 3.8 |
| N-15 | 3.3 |
| N-16 | 2.6 |

FORMULATION EXAMPLE

A term "active ingredient" means the present compound, a tautomer thereof, a pharmaceutically acceptable salt thereof, or a solvate thereof.

Formulation Example 1

A hard gelatin capsule is prepared using the following ingredients:

| | dose (mg/capsule) |
|---|---|
| Active ingredient | 250 |
| Starch (dried) | 200 |
| Magnesium stearate | 10 |
| Total | 460 mg |

Formulation Example 2

A tablet is prepared using the following ingredients:

| | dose (mg/tablet) |
|---|---|
| Active ingredient | 250 |
| Cellulose (microcrystalline) | 400 |
| Silicon dioxide (fumed) | 10 |
| Stearic acid | 5 |
| Total | 665 mg |

Ingredients are mixed, and compressed to obtain tablets, each weighing 665 mg.

The invention claimed is:

1. A compound of the formula:

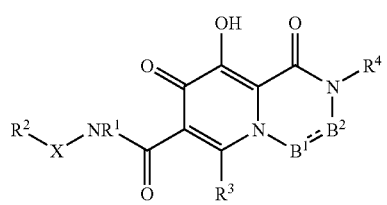

(I)

(wherein,
$R^1$ is hydrogen or lower alkyl;
X is a single bond, a heteroatom group selected from the group consisting of O, S, SO, $SO_2$ and NH, or lower alkylene or lower alkenylene each may be intervened by the heteroatom group;
$R^2$ is optionally substituted aryl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino,
$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from the group consisting of O, S, SO, $SO_2$, $NR^a$ ($R^a$ is hydrogen or lower alkyl), —N= and =N—));
the broken line represents the presence or absence of a bond;
one of $B^1$ and $B^2$ is $CR^{20}R^{21}$ and another is $NR^{22}$, where the broken line represents the absence of a bond; or
one of $B^1$ and $B^2$ is $CR^{23}$ and another is N, where the broken line represents the presence of a bond;
$R^{20}$, $R^{21}$, $R^{22}$ and $R^{23}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from the group consisting of O, S, SO, $SO_2$, $NR^5$ ($R^5$ is independently selected from the same substitution group as $R^4$), —N= and =N—), hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), or a pharmaceutically acceptable salt thereof.

2. A compound of the formula:

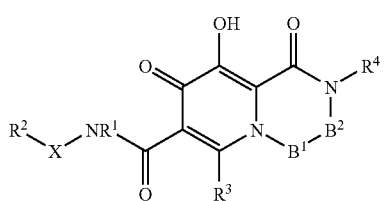

(I-6)

(wherein,

R$^1$ is hydrogen or lower alkyl;

X is a single bond, a heteroatom group selected from the group consisting of O, S, SO, SO$_2$ and NH, or lower alkylene or lower alkenylene each may be intervened by the heteroatom group;

R$^2$ is optionally substituted aryl;

R$^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

R$^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from the group consisting of O, S, SO, SO$_2$, NR$^a$ (R$^a$ is hydrogen or lower alkyl), —N= and =N—));

one of B$^1$ and B$^2$ is CR$^{20}$R$^{21}$ and another is NR$^{22}$;

R$^{20}$, R$^{21}$ and R$^{22}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkyl carbonyl, optionally substituted lower alkoxycarbonyl, optionally substituted aryl carbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, substituted thiourea or substituted sulfonyl), according to claim 1, or a pharmaceutically acceptable salt thereof.

3. The compound according to claim 2, or pharmaceutically acceptable salt thereof, wherein B$^1$ is CR$^{20}$R$^{21}$ and B$^2$ is NR$^{22}$ (R$^{20}$, R$^{21}$ and R$^{22}$ are the same as defined in claim 2).

4. The compound according to claim 2, or pharmaceutically acceptable salt thereof, wherein B$^1$ is NR$^{22}$ and B$^2$ is CR$^{20}$R$^{21}$ (R$^{20}$, R$^{21}$ and R$^{22}$ are the same as defined in claim 2).

5. The compound according to claim 2, or pharmaceutically acceptable salt thereof, wherein B$^1$ is NR$^{22}$ (R$^{22}$ is the same as defined in claim 2) and B$^2$ is CH$_2$.

6. The compound according to claim 2, or pharmaceutically acceptable salt thereof, wherein B$^1$ is NR$^{22}$ (R$^{22}$ is hydrogen, optionally substituted lower alkyl, lower alkenyl, optionally substituted cycloalkyl, optionally substituted cycloalkyl lower alkyl, optionally substituted aryl, optionally substituted aryl lower alkyl, optionally substituted heterocycle, optionally substituted heterocycle lower alkyl, optionally substituted lower alkylcarbonyl, optionally substituted aryl carbonyl, substituted thiourea or substituted sulfonyl), and B$^2$ is CH$_2$.

7. The compound according to claim 2, or pharmaceutically acceptable salt thereof, wherein R$^4$ is optionally substituted lower alkyl, optionally substituted cycloalkyl, optionally substituted cycloalkyl lower alkyl, optionally substituted aryl, optionally substituted aryl lower alkyl, optionally substituted heterocycle, or optionally substituted heterocycle lower alkyl.

8. The compound according to claim 2, or pharmaceutically acceptable salt thereof, wherein B$^1$ is NR$^{22}$ (R$^{22}$ is hydrogen, optionally substituted lower alkyl, optionally substituted cycloalkyl, optionally substituted cycloalkyl lower alkyl, optionally substituted aryl, optionally substituted aryl lower alkyl, optionally substituted heterocycle, optionally substituted heterocycle lower alkyl, optionally substituted lower alkylcarbonyl, optionally substituted aryl carbonyl, substituted thiourea or substituted sulfonyl), B$^2$ is CH$_2$ and R$^4$ is optionally substituted lower alkyl, optionally substituted cycloalkyl, optionally substituted cycloalkyl lower alkyl, optionally substituted aryl, optionally substituted aryl lower alkyl, optionally substituted heterocycle, or optionally substituted heterocycle lower alkyl.

9. The compound according to claim 2, or pharmaceutically acceptable salt thereof, wherein B$^1$ is NR$^{22}$ (R$^{22}$ is hydrogen, optionally substituted lower alkyl (substituent: amino, lower alkylamino, lower alkoxy, aryloxy, cyano, halogen, optionally substituted carbamoyl, acylamino lower alkynyl, hydroxy), cycloalkyl, cycloalkyl lower alkyl, optionally substituted phenyl, optionally substituted benzyl, optionally substituted 5- to 6-membered aromatic heterocycle, optionally substituted 5- to 6-membered heterocycle lower alkyl, optionally substituted lower alkylcarbonyl (substituent: lower alkoxy), optionally substituted benzoyl (substituent: lower alkoxy), substituted sulfonyl (substituent: lower alkyl, aryl, heterocycle)), B$^2$ is CH$_2$ and R$^4$ is optionally substituted lower alkyl (substituent: amino, lower alkylamino, lower alkoxy, aryloxy), cycloalkyl, cycloalkyl lower alkyl, optionally substituted phenyl, optionally substituted benzyl, optionally substituted 5- to 6-membered aromatic heterocycle, or optionally substituted 5- to 6-membered heterocycle lower alkyl).

10. The compound according to claim 1, or pharmaceutically acceptable salt thereof, wherein $R^1$ is hydrogen or lower alkyl.

11. The compound according to claim 1, or pharmaceutically acceptable salt thereof, wherein X is lower alkylene; $R^2$ is phenyl or phenyl substituted with at least halogen.

12. The compound according to claim 1, or pharmaceutically acceptable salt thereof, wherein $R^3$ is hydrogen.

13. The compound according to claim 1, or pharmaceutically acceptable salt thereof, wherein $R^1$ is hydrogen or lower alkyl; X is lower alkylene; $R^2$ is phenyl or phenyl substituted with 1 to 2 halogen; and $R^3$ is hydrogen.

14. A pharmaceutical composition comprising a compound according to claim 1, or a pharmaceutically acceptable salt thereof and a pharmaceutically acceptable carrier or diluent.

* * * * *